(12) United States Patent
Demko et al.

(10) Patent No.: US 8,501,790 B2
(45) Date of Patent: Aug. 6, 2013

(54) COMPOUNDS FOR THE TREATMENT OF PROLIFERATIVE DISORDERS

(75) Inventors: Zachary Demko, Somerville, MA (US); Christopher Borella, Bedford, MA (US); Shoujun Chen, Bedford, MA (US); Lijun Sun, Harvard, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 13/252,423

(22) Filed: Oct. 4, 2011

(65) Prior Publication Data

US 2012/0022118 A1   Jan. 26, 2012

Related U.S. Application Data

(63) Continuation of application No. 12/768,164, filed on Apr. 27, 2010, now abandoned, which is a continuation of application No. 11/492,692, filed on Jul. 24, 2006, now Pat. No. 7,781,462.

(60) Provisional application No. 60/702,237, filed on Jul. 25, 2005, provisional application No. 60/749,418, filed on Dec. 12, 2005, provisional application No. 60/780,488, filed on Mar. 8, 2006.

(51) Int. Cl.
*A61K 31/41* (2006.01)
*C07D 249/00* (2006.01)

(52) U.S. Cl.
USPC ........... 514/359; 514/449; 514/461; 514/463; 548/255; 549/200

(58) Field of Classification Search
USPC .... 514/359, 449, 461, 463; 548/255; 549/200
See application file for complete search history.

(56) References Cited

U.S. PATENT DOCUMENTS 7,781,462 B2 *   8/2010   Demko et al. ................ 514/359
2004/0152738 A1    8/2004   Gaster et al.

FOREIGN PATENT DOCUMENTS

| WO | WO 02/088097 A1 | 11/2002 |
|---|---|---|
| WO | WO 2004/002965 A1 | 1/2004 |
| WO | WO 2004-026307 A1 | 4/2004 |
| WO | WO 2005/000300 A1 | 1/2005 |

OTHER PUBLICATIONS

Pati, Hari N. et al., "Synthesis and Biological Evaluation of CIS-Combretastatin Analogs and Their Novel 1,2,3-Triazole Derivatives," *Heterocyclic Communications* 11(2):117-120 (2005).
Townes, J.A., et al., "The Development of New Bicyclic Pyrazole-Based Cytokine Synthesis Inhibitors," *Bioorganic & Med. Chem. Letters*, 14:4945-4948 (2004).
Biagi, et al,. "1,5-Diarylsubstituted 1,2,3-triazoles as potassium channel activators. VI", Il Farmaco, 2004, vol. 59, pp. 397-404.
Patini, et al,. "Bioisosterism: A Rational Approach in Drug Design", Chem. Rev., 1996, vol. 96, pp. 3147-3176.
Han, et al,. "The Potassium Ion Channel Opener NS1619 Inhibits Proliferation and Induces Apoptosis in A2780 Ovarian Cancer Cells", Biochem. And Biophys. Res Comm., 2008, vol. 375, pp. 205-209.
International Search Report and Written Opinion—(PCT/US2006/028801) Date of Mailing Dec. 18, 2006.

* cited by examiner

*Primary Examiner* — Susannah Chung
(74) *Attorney, Agent, or Firm* — McCarter & English, LLP; Steven G. Davis; Wei Song

(57) ABSTRACT

The invention relates to compounds of structural formula (I):

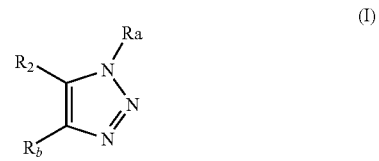

or a pharmaceutically acceptable salt, solvate, clathrate, and prodrug thereof, wherein $R_a$, $R_b$, and $R_2$ are defined herein. These compounds inhibit tubulin polymerization and/or target vasculature and are useful for treating proliferative disorders, such as cancer.

4 Claims, No Drawings

COMPOUNDS FOR THE TREATMENT OF PROLIFERATIVE DISORDERS

RELATED APPLICATIONS

This Application is a continuation application of U.S. patent application Ser. No. 12/768,164, filed Apr. 27, 2010, which is a continuation application of U.S. patent application Ser. No. 11/492,692, filed Jul. 24, 2006, which claims the benefit of U.S. Provisional Application 60/702,237, filed Jul. 25, 2005, U.S. Provisional Application 60/749,418, filed Dec. 12, 2005, and U.S. Provisional Application 60/780,488, filed Mar. 8, 2006, The entire contents of each of the aforementioned applications are incorporated herein by reference in their entirety.

FIELD OF THE INVENTION

This invention relates to biologically active chemical compounds, namely [1,2,3]triazole derivatives that may be used for treating or preventing proliferative disorders.

BACKGROUND OF THE INVENTION

Many chemotherapeutic methods are now available to be used in the treatment of cancer. One of the most successful methods is the use of anti-mitotic agents which interfere with the assembly or disassembly of microtubules. Since microtubule assemble and disassemble is necessary for mitosis, inhibition of either the assembly or disassembly of microtubules interferes with cell proliferation. Thus, compounds that inhibit the assembly of microtubule are useful in treating diseases or conditions which are caused or exasperated by rapid or abnormal cell proliferation, such as cancer. Several anti-mitotic agents have had considerable clinical success. For example, the following vinca alkaloids which inhibit microtubule assembly have proved clinically successful: Vincristine has been successfully used to treat hematological malignancies and non-small-cell lung carcinoma; Vinblastine has been successfully used to treat hematological malignancies, testicular carcinomas and non-small-cell lung carcinoma; and Vinorelbine has been successfully used to treat hematological malignancies, breast carcinomas and non-small-cell lung carcinoma. In addition, taxanes which inhibit microtubule disassemble have also proved to be clinically successful. For example, Paclitaxel has been successful in treating breast, ovarian and non-small-cell lung carcinomas; and Docetaxel has been successful in treating breast and non-small-cell lung carcinomas.

Despite these successes, available anti-mitotic agents are inadequate for a number of reasons. For example, paclitaxel, docetaxel and vincristine are associated with significant neuropathy which can limit their use in repeat courses of therapy. In addition, both the vinca alkaloids and taxanes are good substrates for the 170 kDa P-glycoprotein (Pgp) efflux pump found in most multi-drug resistant cells. This protein pumps a drug out of the tumor cells causing the tumor cells to become resistant to treatment. Once a patient's cancer has become multi-drug resistant, there is typically little that can be done to halt or retard further progression of the disease.

There is therefore still a need for new drugs which overcome one or more of the aforementioned shortcomings of drugs currently used in the treatment of cancer. Desirable properties of new anti-cancer drugs include a good therapeutic index, efficacy against tumors that are currently untreatable or poorly treatable, efficacy against multi-drug resistant tumors and/or reduced side effects.

SUMMARY OF THE INVENTION

This invention meets the above-mentioned needs by providing certain [1,2,3]triazole derivatives that inhibit tubulin polymerization. Compounds of the invention are also capable of vascular targeting, in particular, blocking, occluding, or otherwise disrupting blood flow in neovasculature. These compounds are particularly useful for treat or prevent proliferative disorders, such as cancer.

In one embodiment, the invention relates to compounds of formula (I):

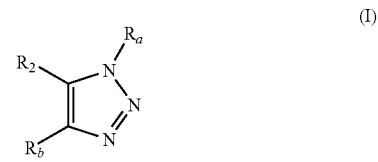

(I)

or a pharmaceutically acceptable salt, solvate, clathrate, or prodrug thereof, wherein:

one of $R_a$ or $R_b$ is —H and the other is an optionally substituted aryl or an optionally substituted heteroaryl. In one aspect of this embodiment, $R_a$ is not acridinyl; and $R_2$ is an optionally substituted aryl or an optionally substituted heteroaryl.

In one embodiment, the invention relates to compounds of formula (IA):

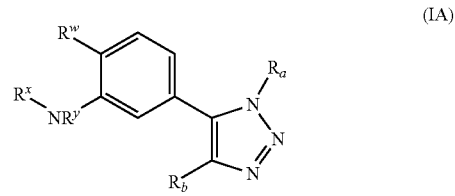

(IA)

or a pharmaceutically acceptable salt, solvate, clathrate, or prodrug thereof, wherein one of $R_a$ or $R_b$ is —H and the other is an optionally substituted aryl or an optionally substituted heteroaryl;

$R^x$ is $(R^{aa})_m$, —$R^{aa}$—C(O)(CH$_2$)$_n$C(O)OH, —C(O)(CH$_2$)$_n$C(O)OH, —C(O)YR$^z$, —C(O)NH—R$^{aa}$, or —(R$^{aa}$)$_q$C(O)(Y$_1$);

$R^y$ is —H or lower alkyl;

$R^w$ is —H, an alkyl, an alkenyl, an alkynyl, cyano, a haloalkyl, an alkoxy, a haloalkoxy, a halo, an amino, an alkylamino, a dialkylamino, —OP(O)(OR$_7$)$_2$, —SP(O)(OR$_7$)$_2$, nitro, an alkyl ester, or hydroxyl;

$R_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R^{aa}$ is an amino acid residue or an amino acid residue analog;

Y is CH$_2$, O, or NH;
R$^z$ is Alk-NH$_2$, Alk-C(O)OH, Het, or Y$_1$;
Alk is an optionally substituted alkylene;
Het is an optionally substituted heteroalkyl;
Y$_1$ is a water soluble polymer with a molecular weight less than 60,000 daltons;
n is 1, 2, 3, or 4;
m is an integer from 1 to 10; and
q is 0 or 1.

In another embodiment, in the compounds represented by formula (IA), neither R$_a$ or R$_b$ is acridinyl.

In one embodiment, the invention relates to compounds of formula (IB):

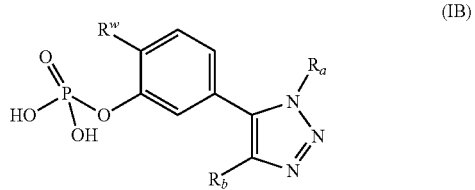

(IB)

or a pharmaceutically acceptable salt, solvate, clathrate, or prodrug thereof, wherein one of R$_a$ or R$_b$ is —H and the other is an optionally substituted aryl or an optionally substituted heteroaryl;

R$^w$ is —H, an alkyl, an alkenyl, an alkynyl, cyano, a haloalkyl, an alkoxy, a haloalkoxy, a halo, an amino, an alkylamino, a dialkylamino, —OP(O)(OR$_7$)$_2$, —SP(O)(OR$_7$)$_2$, nitro, an alkyl ester, or hydroxyl;

R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl. In another embodiment, in the compounds represented by formula (IB), neither R$_a$ or R$_b$ is acridinyl.

Compounds of the invention or pharmaceutically acceptable salts, solvates, clathrates, or prodrugs thereof are potent antimitotic agents which inhibiting tubulin polymerization, and thus can inhibit microtubule growth. In order for cells to undergo mitosis, microtubules must be able to assemble and disassemble, in a process known as dynamic instability. Thus, in one embodiment, the compounds of the invention can be used to inhibit tubulin polymerization in a cell by contacting the cell with an effective amount of a compound of the invention or a pharmaceutically acceptable salt, solvate, clathrate, or prodrug thereof.

In another embodiment, compounds of the invention can be used to inhibit tubulin polymerization in a subject by administering to the subject an effective amount of a compound of the invention or a pharmaceutically acceptable salt, solvate, clathrate, or prodrug thereof.

Compounds of the invention or pharmaceutically acceptable salts, solvates, clathrates, or prodrugs thereof are vascular targeting agents which can be used to block, occlude, or otherwise disrupt blood flow in neovasculature, and thus lead to destruction of vasculature. Thus in one embodiment, compounds of the invention can be used to block, occlude, or otherwise disrupt blood flow in neovasculature by contacting the neovasculature with an effective amount of a compound of the invention or a pharmaceutically acceptable salt, solvate, clathrate, or prodrug thereof.

In another embodiment, compounds of the invention can be used to block, occlude, or otherwise disrupt blood flow in neovasculature of a subject by administering to the subject an effective amount of a compound of the invention or a pharmaceutically acceptable salt, solvate, clathrate, or prodrug thereof.

Since the compounds of the invention, disrupt mitosis by inhibiting tubulin polymerization, they are particularly useful in treating or preventing proliferative disorders, such as cancer. Therefore, in one embodiment, compounds of the invention or pharmaceutically acceptable salts, solvates, clathrates, or prodrugs thereof can be used to treat or prevent a proliferative disorder in a subject by administering to the subject an effective amount of a compound of the invention or a pharmaceutically acceptable salt, solvate, clathrate, or prodrug thereof All of the methods of this invention may be practice with a compound of the invention alone, or in combination with other agents, such as other anti-cancer agents.

As will be described in detail below, compounds of the invention overcome or ameliorated some of the limitation of known anti-mitotic agents. In particular, compounds of the invention are cytotoxic in multidrug resistant cells, and thus may be useful for treating cancers that have become resistant to other therapies.

DETAILED DESCRIPTION OF THE INVENTION

Definitions

Unless otherwise specified, the below terms used herein are defined as follows:

As used herein, the term "aryl" means a monocyclic or polycyclic-aromatic ring or ring radical comprising carbon and hydrogen atoms. Typically, aryl groups have about 6 to about 14 carbon atom ring members. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylsulfanyl (preferably, lower alkylsulfanyl), cyano, halo, amino, and nitro. In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethyl pentyl, 2-methyl-3-ethylpentyl, 2-methyl-4-ethyl pentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents. Examples of substituents include, but are not limited to, amino, alkylamino, alkoxy, alkylsulfanyl, oxo, halo, acyl, nitro, hydroxyl, cyano, aryl, alkylaryl, aryloxy, arylsulfanyl, arylamino, carbocyclyl, carbocyclyloxy, carbocyclylthio, carbocyclylamino, heterocyclyl, heterocyclyloxy, heterocyclylamino, heterocyclylthio, and the like. In addition, any carbon in the alkyl segment may be substituted with oxygen (=O), sulfur (=S), or nitrogen (=NR$^{32}$, wherein R$^{32}$ is —H, an alkyl, acetyl, or aralkyl). Lower alkyls are typically preferred for the compounds of this invention.

The term alkylene refers to an alkyl group or a cycloalkyl group that has two points of attachment to two moieties (e.g., {—CH$_2$—}, —{CH$_2$CH$_2$—},

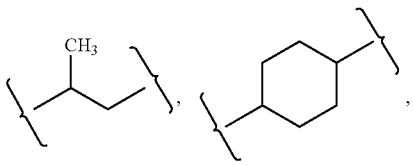

etc., wherein the brackets indicate the points of attachment). Alkylene groups may be optionally substituted with one or more substituents.

An aralkyl group refers to an aryl group that is attached to another moiety via an alkylene linker. Aralkyl groups can be optionally substituted with one or more substituents.

The term "alkoxy," as used herein, refers to an alkyl group which is linked to another moiety though an oxygen atom. Preferred alkoxy groups are methoxy, ethoxy, isopropoxy, n-propoxy, and the like. The alkyl portion of an alkoxy group can be optionally substituted with one or more substituents.

The term "alkylsulfanyl," as used herein, refers to an alkyl group which is linked to another moiety though a divalent sulfur atom. Preferred, alkylsulfanyl groups are methylsulfanyl and ethylsulfanyl. The alkyl portion of an alkylsulfanyl group can be optionally substituted with one or more substituents.

The term "arylsulfanyl," as used herein, refers to an aryl group which is linked to another moiety though a divalent sulfur atom (e.g., phenylsulfanyl). The aryl portion of an arylsulfanyl groups can be optionally substituted with one or more substituents.

The term "alkyl ester" or "alkoxycarbonyl," as used herein, refers to a group represented by the formula —C(O)OR$_{32}$, wherein R$_{32}$ is an alkyl group. A "lower alkyl ester" or a "lower alkoxycarbonyl" is a group represented by the formula —C(O)OR$_{32}$, wherein R$_{32}$ is a lower alkyl group.

The term "heteroalkyl," as used herein, refers to an alkyl group which has one or more carbons in the alkyl chain replaced with an —O—, —S— or —NR$_{33}$—, wherein R$_{33}$ is H or a lower alkyl. Heteroalkyl groups can be optionally substituted with one or more substituents.

The term "alkylamino," as used herein, refers to an amino group in which one hydrogen atom attached to the nitrogen has been replaced by an alkyl group. The term "dialkylamino," as used herein, refers to an amino group in which two hydrogen atoms attached to the nitrogen have been replaced by alkyl groups, in which the alkyl groups can be the same or different. The alkyl portion of alkylamino groups and dialkylamino groups can be optionally substituted with one or more substituents.

As used herein, the term "alkenyl" means a straight chain or branched, hydrocarbon radical typically having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups can be optionally substituted with one or more substituents.

As used herein, the term "alkynyl" means a straight chain or branched, hydrocarbon radical typically having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl,-1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be optionally substituted with one or more substituents.

As used herein, the term "cycloalkyl" means a saturated, mono- or polycyclic alkyl radical typically having from 3 to 14 carbon atoms. Representative cycloalkyls include cyclopropyl, cyclobutyl, cyclopentyl, cyclohexyl, cycloheptyl, cyclooctyl, cyclononyl, cyclodecyl, adamantly, decahydronaphthyl, octahydropentalene, bicycle[1.1.1]pentanyl, and the like. Cycloalkyl groups can be optionally substituted with one or more substituents.

As used herein, the term "cycloalkenyl" means a cyclic non-aromatic alkenyl radical having at least one carbon-carbon double bond in the cyclic system and typically having from 3 to 14 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like. Cycloalkenyl groups can be optionally substituted with one or more substituents.

As used herein, the term "heterocycle" or "heterocyclyl" means a monocyclic or polycyclic heterocyclic ring (typically having 3- to 14-members) which is either a saturated ring or an unsaturated non-aromatic ring. A 3-membered heterocycle can contain from 1 to 3 heteroatoms, and a 4- to 14-membered heterocycle can contain from 1 to about 8 heteroatoms. Each heteroatom is independently selected from nitrogen, which can be quaternized; oxygen; and sulfur, including sulfoxide and sulfone. The heterocyclyl may be attached via any heteroatom or carbon atom. Representative heterocyclyls include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, 4H-pyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halo, an alkyl, a haloalkyl, or aryl). Only stable isomers of such substituted heterocyclic groups are contemplated in this definition.

As used herein, the term "heteroaryl" means a monocyclic or polycyclic aromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzo[1,3]dioxolyl, 2,3-dihydro-benzo[1,4]dioxinyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo[b]thienyl and the like. Heteroaryl groups may be optionally substituted with one or more substituents A heteroaralkyl group refers to a heteroaryl group that is attached to another moiety via an alkylene linker. Heteroaralkyl groups can be substituted or unsubstituted with one or more substituents.

As used herein, the term "halogen" or "halo" means —F, —Cl, —Br or —I.

As used herein, the term "haloalkyl" means an alkyl group in which one or more —H is replaced with a halo group. Examples of haloalkyl groups include —$CF_3$, —$CHF_2$, —$CCl_3$, —$CH_2CH_2Br$, —$CH_2CH(CH_2CH_2Br)CH_3$, —$CHICH_3$, and the like.

As used herein, the term "haloalkoxy" means an alkoxy group in which one or more —H is replaced with a halo group. Examples of haloalkoxy groups include —$OCF_3$ and —$OCHF_2$.

An "amino acid" is compound represented by $NH_2$—CH($R_{21}$)—COOH, wherein $R_{21}$ is H or an amino acid sidechain. A "naturally-occurring amino acid" is found in nature. Examples include alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. Examples of naturally occurring amino acid sidechains include methyl (alanine), isopropyl (valine), sec-butyl (isoleucine), —$CH_2CH(CH_3)_2$ (leucine), benzyl (phenylalanine), p-hydroxybenzyl (tyrosine), —$CH_2OH$ (serine), —$CH(OH)CH_3$ (threonine), —$CH_2$-3-indoyl (tryptophan), —$CH_2COOH$ (aspartic acid), —$CH_2CH_2COOH$ (glutamic acid), —$CH_2C(O)NH_2$ (asparagine), —$CH_2CH_2C(O)NH_2$ (glutamine), —$CH_2SH$, (cysteine), —$CH_2CH_2SCH_3$ (methionine), —$(CH_2)_4NH_2$ (lysine), —$(CH_2)_3NH_2$ (ornithine), —$(CH_2)_3NHC(=NH)NH_2$ (arginine) and —$CH_2$-3-imidazoyl (histidine).

The side-chains of alanine, valine, leucine and isoleucine are aliphatic, i.e., contain only carbon and hydrogen, and are each referred to herein as "the aliphatic side-chain of a naturally occurring amino acid."

The side-chains of other naturally-occurring amino acids comprise a heteroatom-containing functional group, e.g., an alcohol (serine, tyrosine, hydroxyproline and threonine), an amine (lysine, ornithine, histidine and arginine), a thiol (cysteine) or a carboxylic acid (aspartic acid and glutamic acid). When the heteroatom-containing functional group is modified to include a protecting group, the side-chain is referred to as the "protected sidechain" of an amino acid.

The selection of a suitable protecting group depends upon the functional group being protected, the conditions to which the protecting group is being exposed and to other functional groups which may be present in the molecule. Suitable protecting groups for the functional groups discussed above are described in Greene and Wuts, "Protective Groups in Organic Synthesis", John Wiley & Sons (1991), the entire teachings of which are incorporated into this application by reference. The skilled artisan can select, using no more than routine experimentation, suitable protecting groups for use in the disclosed synthesis, including protecting groups other than those described below, as well as conditions for applying and removing the protecting groups.

Examples of suitable alcohol protecting groups include benzyl, allyl, trimethylsilyl, tert-butyldimethylsilyl, acetate, and the like. Benzyl is a preferred alcohol protecting group.

Examples of suitable amino protecting groups include benzyloxycarbonyl, tert-butoxycarbonyl, tert-butyl, benzyl and fluorenylmethyloxycarbonyl (Fmoc). Tert-butoxycarbonyl is a preferred amine protecting group.

Examples of suitable carboxylic acid protecting groups include tert-butyl, Fmoc, methyl, methoxylmethyl, trimethylsilyl, benzyloxymethyl, tert-butyldimethylsilyl and the like. Tert-butyl is a preferred carboxylic acid protecting group.

Examples of suitable thiol protecting groups include S-benzyl, S-tert-butyl, S-acetyl, S-methoxymethyl and the like.

The terms "bioisostere" and "bioisosteric replacement" have the same meanings as those generally recognized in the art. Bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

As used herein, the terms "subject", "patient" and "animal", are used interchangeably and include, but are not limited to, a cow, monkey, horse, sheep, pig, mini pig, chicken, turkey, quail, cat, dog, mouse, rat, rabbit, guinea pig and human. The preferred subject, patient or animal is a human.

As used herein, the term "lower" refers to a group having up to four carbon atoms. For example, a "lower alkyl" refers to an alkyl radical having from 1 to 4 carbon atoms, and a "lower alkenyl" or "lower alkynyl" refers to an alkenyl or alkynyl radical having from 2 to 4 carbon atoms, respectively. A lower alkoxy or a lower alkylsulfanyl refers to an alkoxy or an alkylsulfanyl having from 1 to 4 carbon atoms. Lower substituents are typically preferred.

Where a particular substituent, such as an alkyl substituent, occurs multiple times in a given structure or moiety, the identity of the substituent is independent in each case and may be the same as or different from other occurrences of that substituent in the structure or moiety. Furthermore, individual substituents in the specific embodiments and exemplary compounds of this invention are preferred in combination with other such substituents in the compounds of this invention, even if such individual substituents are not expressly noted as being preferred or not expressly shown in combination with other substituents.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Suitable substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroaralkyl include an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)NR$_{34}$R$_{35}$, —NR$_{36}$C(O)R$_{37}$, halo, —OR$_{36}$, cyano, nitro, haloalkoxy, —C(O)R$_{36}$, —NR$_{34}$R$_{35}$, —SR$_{36}$, —C(O)OR$_{36}$, —OC(O)R$_{36}$, —NR$_{36}$C(O)NR$_{34}$R$_{35}$, —NR$_{36}$C(N—R$_{38}$)NR$_{34}$R$_{35}$, —OC(O)NR$_{34}$R$_{35}$, —NR$_{36}$C(O)OR$_{37}$, —OP(O)(OR$_{36}$)$_2$, —SP(O)(OR$_{36}$)$_2$, —OS(O)$_2$(OR$_{36}$), —S(O)$_p$R$_{36}$, or —S(O)$_p$NR$_{34}$R$_{35}$, wherein R$_{34}$ and R$_{35}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{34}$ and R$_{35}$ taken together with the nitrogen to which they are attached is an optionally substituted heterocyclyl or an optionally substituted heteroaryl; R$_{36}$ and R$_{37}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; and R$_{38}$ is H, an optionally substituted alkyl, —C(O)R$_{36}$, —C(O)OR$_{36}$, or an optionally substituted aralkyl.

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, =S, =N—R$_{32}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds of the invention containing reactive functional groups (such as, without limitation, carboxy, hydroxy, and amino moieties) also include protected derivatives thereof. "Protected derivatives" are those compounds in which a reactive site or sites are blocked with one or more protecting groups. Suitable protecting groups for carboxy moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl, trimethyl silyl (TMS) and the like. Other suitable protecting groups are well known to those of ordinary skill in the art and include those found in T. W. Greene, Protecting Groups in Organic Synthesis, John Wiley & Sons, Inc. 1981, the entire teachings of which are incorporated herein by reference.

As used herein, the term "compound(s) of this invention" and similar terms refers to a compound of any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof and also include protected derivatives thereof.

As used herein, the term "amino acid residue" refers to what is left of an amino acid (losing a H$^+$ from the nitrogenous side, an OH$^-$ from the carboxylic side, or a H$^+$ from the nitrogenous side and an OH$^-$ from the carboxylic side) in the formation of a peptide bond(s). An "amino acid analog" includes D or L amino acids having the following formula: NH$_2$—CHR—C(O)OH, wherein R is an optionally substituted alkyl group, an optionally substituted heteroalkyl group, an optionally substituted aromatic group, or an optionally substituted heteroaromatic group, and wherein R does not correspond to the side chain of a naturally-occurring amino acid. An "amino acid residue analog" refers to what is left of an amino acid analog (losing a H$^+$ from the nitrogenous side, an OH$^-$ from the carboxylic side, or a H$^+$ from the nitrogenous side and an OH$^-$ from the carboxylic side) in the formation of a peptide bond(s).

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, but they may have activity in their unreacted forms. Examples of prodrugs contemplated in this invention include, but are not limited to, analogs or derivatives of compounds of any one of formulas (I) through (XIX), (IA) through (XIA), (XVIIA) through (XIXA), (IB) through (XIB), (XVIIB) through (XIXB), or Table 1, that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of formulas (I) through (XIX), (IA) through (XIA), (XVIIA) through (XIXA), (IB) through (XIB), (XVIIB) through (XIXB), or Table 1, that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed), the entire teachings of which are incorporated herein by reference.

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines. Examples of biohydrolyzable phosphate analogues include —OP(O)(OR$_{12}$)$_2$ and —SP(O)(OR$_{12}$)$_2$, wherein R$_{12}$ for each occurrence is independently H or a lower alkyl.

As used herein, the term "pharmaceutically acceptable salt," is a salt formed from an acid and a basic group of one of the compounds of any one of formulas (I) through (XIX), (IA) through (XIA), (XVIIA) through (XIXA), (IB) through (XIB), (XVIIB) through (XIXB), or Table 1. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of formulas (I) through (XIX), (IA) through (XIA), (XVIIA) through (XIXA), (IB) through (XIB), (XVIIB) through (XIXB), or Table 1, having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound of any one of formulas (I) through (XIX), (IA) through (XIA), (XVIIA) through (XIXA), (IB) through (XIB), (XVIIB) through (XIXB), or Table 1, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more solvent molecules to one or more molecules of a compound of any one of formulas (I) through (XIX), (IA) through (XIA), (XVIIA) through (XIXA), (IB) through (XIB), (XVIIB) through (XIXB), or Table 1. The term solvate includes hydrates (e.g., hemi-hydrate, mono-hydrate, dihydrate, trihydrate, tetrahydrate, and the like).

As used herein, the term "clathrate" means a compound of the present invention or a salt thereof in the form of a crystal lattice that contains spaces (e.g., channels) that have a guest molecule (e.g., a solvent or water) trapped within.

Inhibition of tubulin polymerization can be determined by any method known to those skilled in the art, such as the method described herein in Example 4 or 5. In addition the amount of a tubulin polymerization inhibitor that inhibits 50% of tubulin polymerization that occurs in the absence of the inhibitor (i.e., the IC$_{50}$) can be determined by pre-incubating purified tubulin with various amounts of an inhibitor for 15 minutes at 37° C. The mixture is then cooled to room temperature and GTP is added to induce tubulin polymerization. The polymerization can be monitored in a spectrophotometer at 350 nm. A typical reaction mixtures (0.25 mL) contains 1.5 mg/mL tubulin, 0.6 mg/mL microtubule-associated proteins (MAPs), 0.5 mM GTP, 0.5 mIM MgCl.sub.2, 4% DMSO and 0.1M 4-morpholineethanesulfonate buffer (MES, pH 6.4).

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy (e.g., diabetic retinopathy or other retinopathies), choroidal neovascularisation (e.g., macular degeneration), cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, and desmoid tumors.

Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

In a preferred embodiment, the proliferative disorder is cancer. Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1(murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1(acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B.C. Decker Inc. (2000). The entire teachings of the preceding references are incorporated herein by reference.

In one embodiment, the compounds of the invention are believed to be particularly effective in treating subject with hematological malignancies (e.g., Hodgkin's disease, Non-Hodgkin lymphoma, acute lymphoblastic leukemia, acute myelogenous leukemia, chronic myelogenous leukemia, chronic lymphocytic leukemia, and multiple myeloma). In another embodiment, the compounds of the invention are believed to be particularly useful in treating solid tumors.

In one embodiment, the compounds of the invention are particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

In another embodiment the compound of the invention are particularly useful in treating solid tumors.

An "effective amount" is the quantity of compound in which a beneficial outcome is achieved when the compound is administered to a subject or alternatively, the quantity of compound that possess a desired activity in vivo or in vitro. In the case of proliferative disorders, a beneficial clinical outcome includes reduction in the extent or severity of the symptoms associated with the disease or disorder and/or an increase in the longevity and/or quality of life of the subject compared with the absence of the treatment. For example, for a subject with cancer, a "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of proliferative disorder. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 1 gram/mm$^2$.

In one embodiment, compounds of the invention are vascular targeting agents. In one aspect, compounds of the invention are effective for blocking, occluding, or otherwise disrupting blood flow in "neovasculature." In one aspect, the invention provides a novel treatment for diseases involving the growth of new blood vessels ("neovasculature"), including, but not limited to: cancer; infectious diseases; autoimmune disorders; benign tumors, e.g. hemangiomas, acoustic neuromas, neurofibromas, trachomas, and pyogenic granulomas; artheroscleric plaques; ocular angiogenic diseases, e.g., diabetic retinopathy, retinopathy of prematurity, macular degeneration, corneal graft rejection, neovascular glaucoma, retrolental fibroplasia, rubeosis, retinoblastoma, persistent hyperplastic vitreous syndrome, choroidal neovascularization, uvietis and Pterygia (abnormal blood vessel growth) of the eye; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; HHT; transplant arteriopathy; restinosis; obesity; myocardial angiogenesis; coronary collaterals; cerebral collaterals; arteriovenous malformations; ischemic limb angiogenesis; primary pulmonary hypertension; asthma; nasal polyps; inflammatory bowel disease; periodontal disease; ascites; peritoneal adhesions; Osler-Webber Syndrome; plaque neovascularization; telangiectasia; hemophiliac joints; synovitis; osteomyelitis; osteophyte formation; angiofibroma; fibromuscular dysplasia; wound granulation; Crohn's disease; and atherosclerosis.

Vascular targeting can be demonstrated by any method known to those skilled in the art, such as the method described herein in Example 7.

The compounds of the invention may contain one or more chiral centers and/or double bonds and, therefore, may exist as stereoisomers, such as double-bond isomers (i.e., geometric isomers), enantiomers, or diastereomers. According to this

Specific Embodiments

The invention relates to compounds and pharmaceutical compositions that are useful for inhibiting tubulin polymerization and are particularly useful in treating or preventing proliferative disorders, such as cancer. The invention also relates to compounds and pharmaceutical compositions that are useful as vascular targeting agents, particularly, in blocking, occluding, or otherwise disrupting blood flow in neovasculature.

In one embodiment, the invention relates to compounds of formula (I):

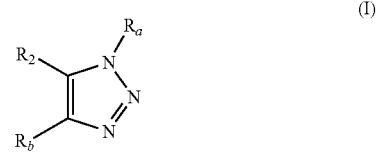

(I)

or a pharmaceutically acceptable salt, solvate, clathrate, or prodrug thereof, wherein $R_a$, $R_b$, and $R_2$ are defined as above. In another embodiment, in the compounds represented by formula (I), $R_a$ is not acridinyl.

In another embodiment, the invention relates to compounds of formula (II):

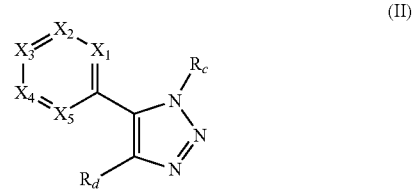

(II)

or a pharmaceutically acceptable salt, solvate, clathrate, or prodrug thereof, wherein:
one of $R_c$ or $R_d$ is —H and the other is

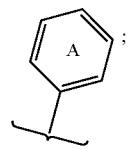

;

ring A is optionally substituted; and
$X_1$, $X_2$, $X_3$, $X_4$, and $X_5$ are each, independently, N or $CR_{14}$, provided that at least two of $X_1$, $X_2$, $X_3$, $X_4$, and $X_5$ are $CR_{14}$; and
$R_{14}$ is —H or a substituent.

In another embodiment, the invention relates to compounds of formula (III):

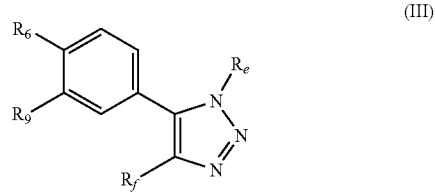

(III)

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a composition that is "substantially free" of a compound means that the composition contains less than about 20% by weight, more preferably less than about 10% by weight, even more preferably less than about 5% by weight, and most preferably less than about 3% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of any one of formulas (I) through (XIX), (IA) through (XIA), (XVIIA) through (XIXA), (IB) through (XIB), (XVIIB) through (XIXB), or Table 1.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When administered to a patient, e.g., to a non-human animal for veterinary use or for improvement of livestock, or to a human for clinical use, the compounds of the invention are typically administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single compound of the invention by weight of the isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

or a pharmaceutically acceptable salt, solvate, clathrate, or prodrug thereof, wherein:

one of $R_e$ or $R_f$ is —H and the other is

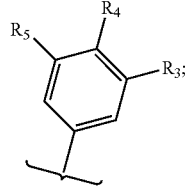

$R_3$, $R_4$, $R_5$, and $R_6$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

$R_9$ is —H, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

$R_7$, $R_8$, $R_{10}$, $R_{11}$, and p are defined as above.

In another embodiment, the invention relates to compounds represented by formulae (IIa) through (IIe):

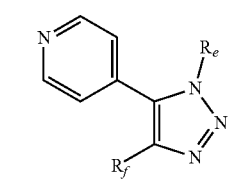

(IIa)

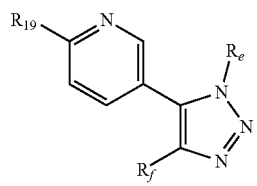

(IIb)

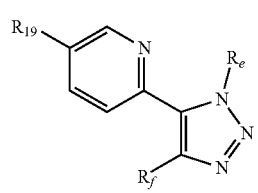

(IIc)

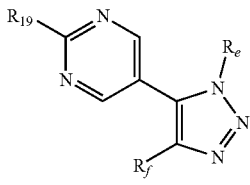

(IId)

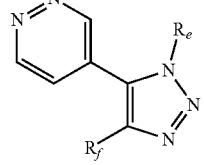

(IIe)

or a pharmaceutically acceptable salt, solvate, clathrate, or prodrug thereof, wherein:

$R_e$ and $R_f$ are defined as above;

$R_{19}$ is —H, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; and $R_7$, $R_8$, $R_{10}$, $R_{11}$, and p are defined as above.

In another embodiment, the invention relates to compounds of formula (IV):

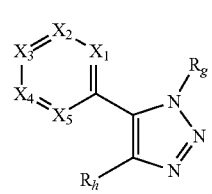

(IV)

or a pharmaceutically acceptable salt, solvate, clathrate, or prodrug thereof, wherein:

one of $R_g$ or $R_h$ is —H and the other is

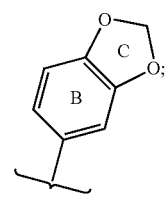

$X_1$, $X_2$, $X_3$, and $X_4$ are each, independently, N or CR$_{14}$, provided that at least two of $X_1$, $X_2$, $X_3$, $X_4$, and $X_5$ are CR$_{14}$;

Ring B is optionally substituted with one to three substituents;

Ring C is optionally substituted with one or two substituents; and $R_{14}$ is defined as above.

In another embodiment, the invention relates to compounds of formula (V):

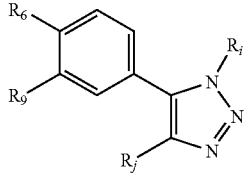
(V)

or a pharmaceutically acceptable salt, solvate, clathrate, or prodrug thereof, wherein:

one of $R_i$ or $R_j$ is —H and the other is

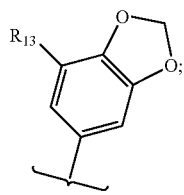

$R_6$ and $R_9$ are defined as above; and $R_{13}$ is —H, an alkyl, an alkoxy, a halo, nitro, cyano, —OH, —NH$_2$, an alkyl amino, or a dialkyl amino.

In another embodiment, the invention relates to compounds of formulae:

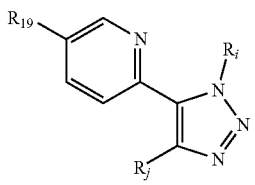
(IVa)

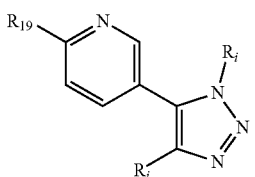
(IVb)

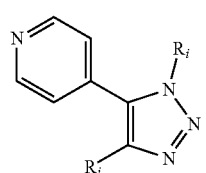
(IVc)

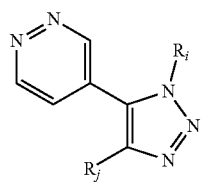
(IVd)

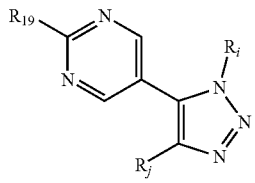
(IVe)

or a pharmaceutically acceptable salt, solvate, clathrate, or prodrug thereof, wherein $R_i$, $R_j$, and $R_{19}$ are defined as above.

In another embodiment, the invention relates to compounds of formula (XIX):

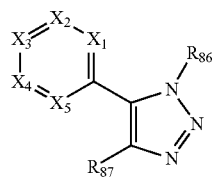
(XIX)

or a pharmaceutically acceptable salt, solvate, clathrate, or prodrug thereof, wherein:

one of $R_{86}$ or $R_{87}$ is —H and the other is

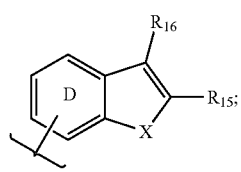

Ring D is optionally substituted one to three substituents;

$X_1$, $X_2$, $X_3$, $X_4$, and $X_5$ are each, independently, N or $CR_{14}$, provided that at least two of $X_1$, $X_2$, $X_3$, $X_4$, and $X_5$ are $CR_{14}$; and X, $R_{14}$, $R_{15}$, and $R_{16}$ are defined as above.

In another embodiment, the invention relates to compounds of formula (VI):

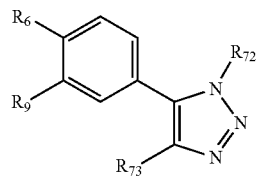
(VI)

or a pharmaceutically acceptable salt, solvate, clathrate, or prodrug thereof, wherein:

one of $R_{72}$ or $R_{73}$ is —H and the other is

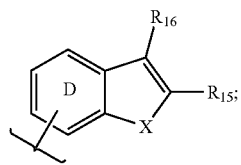

Ring D, X, $R_6$, $R_9$, $R_{15}$ and $R_{16}$ are defined as above.

In another embodiment, the invention relates to compounds of formula (VII):

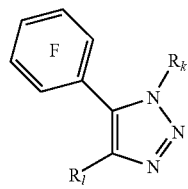
(VII)

or a pharmaceutically acceptable salt, solvate, clathrate, or prodrug thereof, wherein:
one of $R_k$ or $R_l$ is —H and the other is

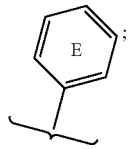

one of rings E or F is substituted with three or four substituents and the other is substituted with one or more substituents. In another embodiment, in the compounds represented by formula (VII), when $R_k$ is —H, then Ring E is not 4-aminophenyl.

In another embodiment, the invention relates to compounds of formula (VIII):

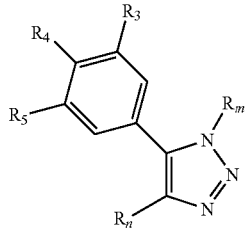
(VIII)

or a pharmaceutically acceptable salt, solvate, clathrate, or prodrug thereof, wherein:
one of $R_m$ or $R_n$ is —H and the other is

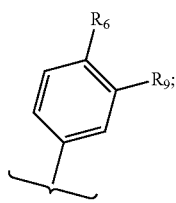

$R_3$, $R_4$, $R_5$, $R_6$ and $R_9$ are defined as above.

In another embodiment, the invention relates to compounds of formula (IX):

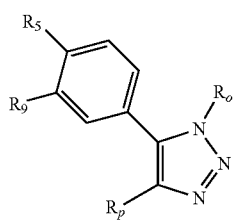
(IX)

a pharmaceutically acceptable salt, solvate, clathrate, or prodrug thereof, wherein:

one of $R_o$ or $R_p$ is —H and the other is

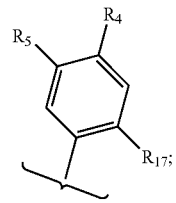

$R_{17}$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —$OR_7$, —$NR_{10}R_{11}$, —$C(O)R_7$, —$C(O)OR_7$, —$OC(O)R_7$, —$C(O)NR_{10}R_{11}$, —$NR_8C(O)R_7$, —$OP(O)(OR_7)_2$, —$SP(O)(OR_7)_2$, —$SR_7$, —$S(O)_pR_7$, —$OS(O)_pR_7$, —$S(O)_pOR_7$, —$NR_8S(O)_pR_7$, or —$S(O)_pNR_{10}R_{11}$; and $R_4$, $R_5$, $R_6$, $R_7$, $R_8$, $R_9$, $R_{10}$, $R_{11}$ and p are defined as above.

In another embodiment, the invention relates to compounds of formula (X):

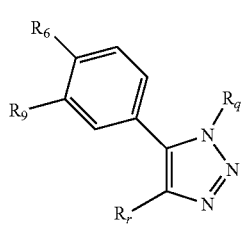
(X)

a pharmaceutically acceptable salt, solvate, clathrate, or prodrug thereof, wherein:
one of $R_q$ or $R_r$ is —H and the other is

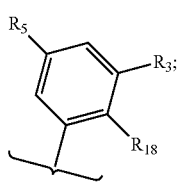

$R_{18}$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —$OR_7$, —$NR_{10}R_{11}$, —$C(O)R_7$, —$C(O)OR_7$, —$OC(O)R_7$, —$C(O)NR_{10}R_{11}$, —$NR_8C(O)R_7$, —$OP(O)(OR_7)_2$, —$SP(O)(OR_7)_2$, —$SR_7$, —$S(O)_pR_7$, —$OS(O)_pR_7$, —$S(O)_pOR_7$, —$NR_8S(O)_pR_7$, or —$S(O)_pNR_{10}R_{11}$; and $R_3$, $R_5$, $R_6$, $R_7$, $R_8$, $R_9$, $R_{10}$, $R_{11}$ and p are defined as above.

In another embodiment, the invention relates to compounds of formula (XI):

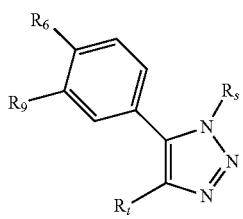

(XI)

a pharmaceutically acceptable salt, solvate, clathrate, or prodrug thereof, wherein:
one of $R_s$ or $R_t$ is —H and the other is

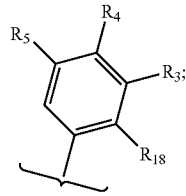

$R_3$, $R_4$, $R_5$, $R_6$, $R_9$, and $R_{18}$ are defined as above.

In another embodiment, the invention relates to compounds of formula (XII):

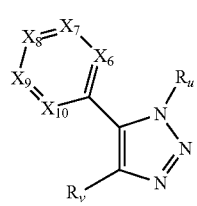

(XII)

or a pharmaceutically acceptable salt, solvate, clathrate, or prodrug thereof, wherein:
one of $R_u$ or $R_v$ is —H and the other is

ring G is substituted with three to five substituents;
$X_6$, $X_7$, $X_8$, $X_9$, and $X_{10}$ are each, independently, N or $CR_{14}$, provided that at least one of $X_6$, $X_7$, $X_8$, $X_9$, or $X_{10}$ is N and at least two of $X_6$, $X_7$, $X_8$, $X_9$, and $X_{10}$ are $CR_{14}$; and
$R_{14}$ is defined as above.

In another embodiment, the invention relates to compounds of formula (XIV):

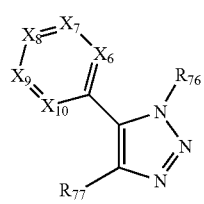

(XIV)

or a pharmaceutically acceptable salt, solvate, clathrate, or prodrug thereof, wherein:

one of $R_{76}$ or $R_{77}$ is —H and the other is

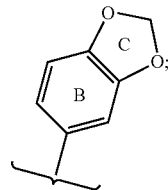

$X_6$, $X_7$, $X_8$, $X_9$, and $X_{10}$ are each, independently, N or $CR_{14}$, provided that at least one of $X_6$, $X_7$, $X_8$, $X_9$, or $X_{10}$ is N and at least two of $X_6$, $X_7$, $X_8$, $X_9$, and $X_{10}$ are $CR_{14}$;
Ring B is optionally substituted with one to three substituents;
Ring C is optionally substituted with one or two substituents; and
$R_{14}$ is defined as above.

In another embodiment, the invention relates to compounds of formula (XV):

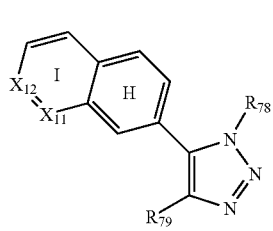

(XV)

or a pharmaceutically acceptable salt, solvate, clathrate, or prodrug thereof, wherein:
one of $R_{78}$ or $R_{79}$ is —H and the other is

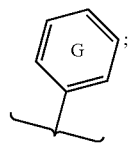

ring G is optionally substituted with one to five substituents;
ring H is optionally substituted with one to three substituents;
ring I is optionally substituted with one or two substituents;
$X_{11}$, and $X_{12}$ are each, independently, N or $CR_{14}$, provided that at least one $X_9$, or $X_{10}$ is N; and
$R_{14}$ is defined as above.

In another embodiment, the invention relates to compounds of formula (XVI):

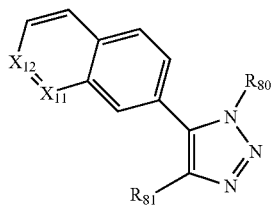

(XVI)

or a pharmaceutically acceptable salt, solvate, clathrate, or prodrug thereof, wherein;

one of R$_{80}$ or R$_{81}$ is —H and the other is

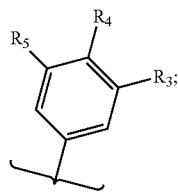

X$_{11}$, X$_{12}$, R$_3$, R$_4$, and R$_5$ are defined as above.

In another embodiment, the invention relates to compounds of formula (XVII):

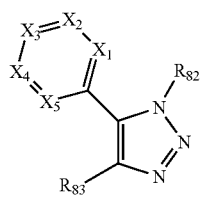

(XVII)

a pharmaceutically acceptable salt, solvate, clathrate, or prodrug thereof, wherein:

one of R$_{82}$ or R$_{83}$ is —H and the other is

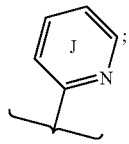

ring J is substituted with three or four substituents;

X$_1$, X$_2$, X$_3$, X$_4$, and X$_5$ are each, independently, N or CR$_{14}$, provided that at least two of X$_1$, X$_2$, X$_3$, X$_4$, and X$_5$ are CR$_{14}$; and R$_{14}$ is defined as above.

In another embodiment, the invention relates to compounds of formula (XVIII):

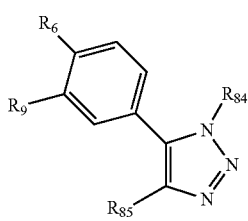

(XVIII)

or a pharmaceutically acceptable salt, solvate, clathrate, or prodrug thereof, wherein:

one of R$_{84}$ or R$_{85}$ is —H and the other is

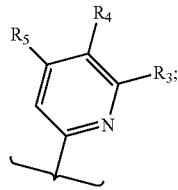

R$_3$, R$_4$, R$_5$, R$_6$ and R$_9$ are defined as above.

In one embodiment, the invention relates to compounds of formula (IA):

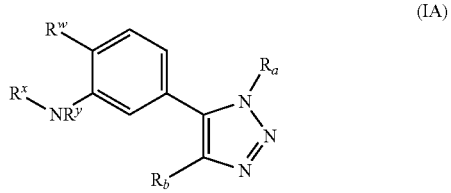

(IA)

or a pharmaceutically acceptable salt, solvate, clathrate, or prodrug thereof, wherein one of R$_a$ or R$_b$ is —H and the other is an optionally substituted aryl or an optionally substituted heteroaryl;

R$^x$ is (R$^{aa}$)$_m$, —R$^{aa}$—C(O)(CH$_2$)$_n$C(O)OH, —C(O)(CH$_2$)$_n$C(O)OH, —C(O)YR$^z$, —C(O)NH—R$^{aa}$, or —(R$^{aa}$)$_q$C(O)(Y$_1$);

R$^y$ is —H or lower alkyl;

R$^w$ is —H, an alkyl, an alkenyl, an alkynyl, cyano, a haloalkyl, an alkoxy, a haloalkoxy, a halo, an amino, an alkylamino, a dialkylamino, —OP(O)(OR$_7$)$_2$, —SP(O)(OR$_7$)$_2$, nitro, an alkyl ester, or hydroxyl;

R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$^{aa}$ is an amino acid residue or an amino acid residue analog;

Y is CH$_2$, O, or NH;

R$^z$ is Alk-NH$_2$, Alk-C(O)OH, Het, or Y$_1$;

Alk is an optionally substituted alkylene;

Het is an optionally substituted heteroalkyl;

Y$_1$ is a water soluble polymer with a molecular weight less than 60,000 daltons;

n is 1, 2, 3, or 4;

m is an integer from 1 to 10; and q is 0 or 1.

In another embodiment, in the compounds represented by formula (IA), neither R$_a$ or R$_b$ is acridinyl.

In another embodiment, the invention relates to compounds of formula (IIA):

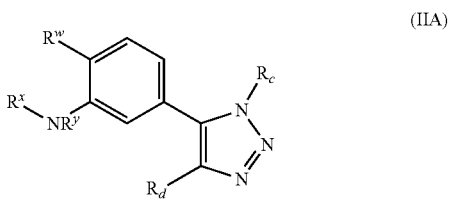

(IIA)

or a pharmaceutically acceptable salt, solvate, clathrate, or prodrug thereof, wherein:

one of $R_c$ or $R_d$ is —H and the other is

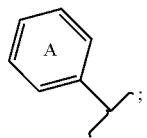

ring A is optionally substituted; and
$R^x$, $R^y$, and $R^w$ are defined as above.

In another embodiment, the invention relates to compounds of formula (IIIA):

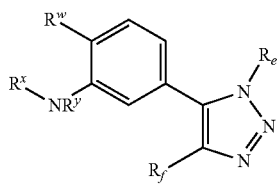

(IIIA)

or a pharmaceutically acceptable salt, solvate, clathrate, or prodrug thereof, wherein:
one of $R_e$ or $R_f$ is —H and the other is

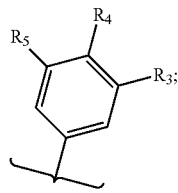

$R_3$, $R_4$, and $R_5$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; and
$R^x$, $R^y$, $R^w$, $R_7$, $R_8$, $R_{10}$, $R_{11}$, and p are defined as above.

In another embodiment, the invention relates to compounds of formula (IVA):

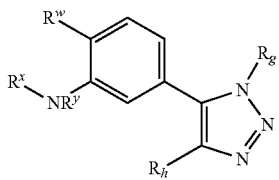

(IVA)

or a pharmaceutically acceptable salt, solvate, clathrate, or prodrug thereof, wherein:

one of $R_g$ or $R_h$ is —H and the other is

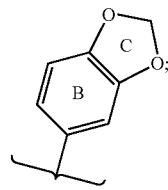

Ring B is optionally substituted with one to three substituents;
Ring C is optionally substituted with one or two substituents; and
$R^x$, $R^y$, and $R^w$ are defined as above.

In another embodiment, the invention relates to compounds of formula (VA):

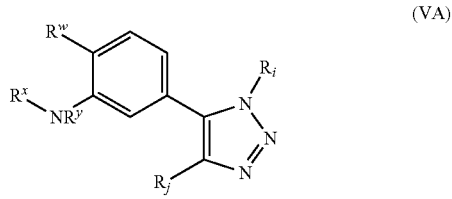

(VA)

or a pharmaceutically acceptable salt, solvate, clathrate, or prodrug thereof, wherein:
one of $R_i$ or $R_j$ is —H and the other is

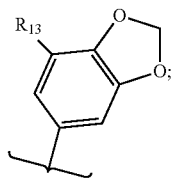

$R^x$, $R^y$, and $R^w$ are defined as above; and
$R_{13}$ is —H, an alkyl, an alkoxy, a halo, nitro, cyano, —OH, —NH$_2$, an alkyl amino, or a dialkyl amino.

In another embodiment, the invention relates to compounds of formula (VIIA):

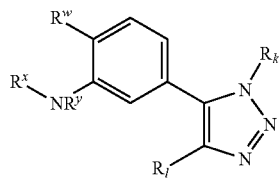

(VIIA)

or a pharmaceutically acceptable salt, solvate, clathrate, or prodrug thereof, wherein:

one of $R_k$ or $R_l$ is —H and the other is

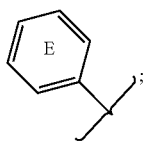

Ring E is substituted with one or more substituents.

In another embodiment, the invention relates to compounds of formula (XIXA):

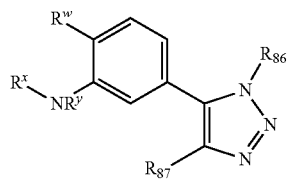

(XIXA)

or a pharmaceutically acceptable salt, solvate, clathrate, or prodrug thereof, wherein:
one of $R_{86}$ or $R_{87}$ is —H and the other is

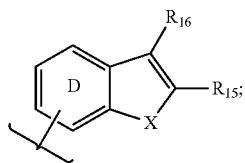

Ring D is optionally substituted one to three substituents; and
$R^x$, $R^y$, $R^w$, X, $R_{15}$, and $R_{16}$ are defined as above.

In another embodiment, the invention relates to compounds of formula (VIIIA):

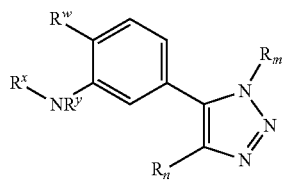

(VIIIA)

or a pharmaceutically acceptable salt, solvate, clathrate, or prodrug thereof, wherein
one of $R_m$ or $R_n$ is —H and the other is

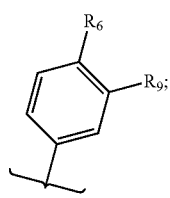

$R^x$, $R^y$, $R^w$, $R_6$ and $R_9$ are defined as above.

In another embodiment, the invention relates to compounds of formula (IXA):

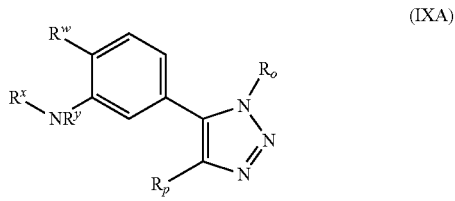

(IXA)

or a pharmaceutically acceptable salt, solvate, clathrate, or prodrug thereof, wherein:
one of $R_o$ or $R_p$ is —H and the other is

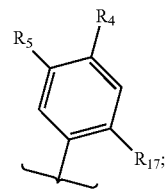

$R_{17}$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —$OR_7$, —$NR_{10}R_{11}$, —C(O)$R_7$, —C(O)O$R_7$, —OC(O)$R_7$, —C(O)$NR_{10}R_{11}$, —$NR_8$C(O)$R_7$, —OP(O)(O$R_7$)$_2$, —SP(O)(O$R_7$)$_2$, —S$R_7$, —S(O)$_p R_7$, —OS(O)$_p R_7$, —S(O)$_p$O$R_7$, —$NR_8$S(O)$_p R_7$, or —S(O)$_p$N$R_{10}R_{11}$; and
$R_4$, $R_5$, $R^x$, $R^y$, $R^w$, $R_7$, $R_8$, $R_{10}$, $R_{11}$ and p are defined as above.

In another embodiment, the invention relates to compounds of formula (XA):

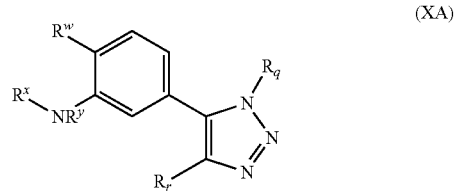

(XA)

or a pharmaceutically acceptable salt, solvate, clathrate, or prodrug thereof, wherein:
one of $R_q$ or $R_r$ is —H and the other is

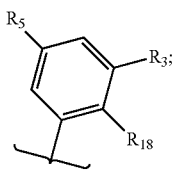

$R_{18}$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; and R$_3$, R$_5$, R$^x$, R$^y$, R$^w$, R$_7$, R$_8$, R$_9$, R$_{10}$, R$_{11}$ and p are defined as above.

In another embodiment, the invention relates to compounds of formula (XIA):

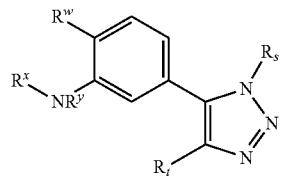

(XIA)

or a pharmaceutically acceptable salt, solvate, clathrate, or prodrug thereof, wherein:
one of R$_s$ or R$_t$ is —H and the other is

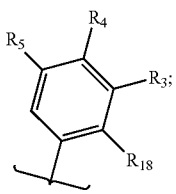

R$_3$, R$_4$, R$_5$, R$^x$, R$^y$, R$^w$ and R$_{18}$ are defined as above.

In another embodiment, the invention relates to compounds of formula (XVIIA):

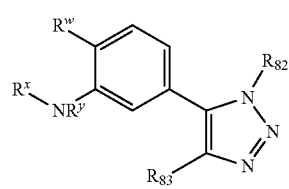

(XVIIA)

or a pharmaceutically acceptable salt, solvate, clathrate, or prodrug thereof, wherein:
one of R$_{82}$ or R$_{83}$ is —H and the other is

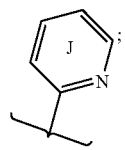

ring J is substituted with three or four substituents; and
R$^x$, R$^y$, R$^w$, and R$_{14}$ are defined as above.

In another embodiment, the invention relates to compounds of formula (XVIIIA):

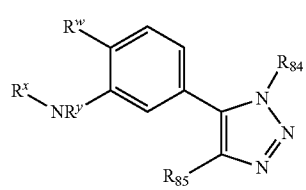

(XVIIIA)

or a pharmaceutically acceptable salt, solvate, clathrate, or prodrug thereof, wherein:
one of R$_{84}$ or R$_{85}$ is —H and the other is

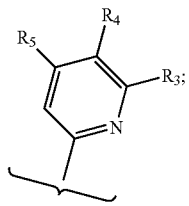

R$_3$, R$_4$, R$_5$, R$^x$, R$^y$, and R$^w$ are defined as above.

In one embodiment, the invention relates to compounds of formula (IB):

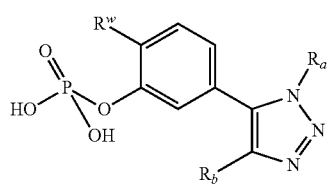

(IB)

or a pharmaceutically acceptable salt, solvate, clathrate, or prodrug thereof, wherein
one of R$_a$ or R$_b$ is —H and the other is an optionally substituted aryl or an optionally substituted heteroaryl;
R$^w$ is —H, an alkyl, an alkenyl, an alkynyl, cyano, a haloalkyl, an alkoxy, a haloalkoxy, a halo, an amino, an alkylamino, a dialkylamino, —OP(O)(OR$_7$)$_2$, —SP(O)(OR$_7$)$_2$, nitro, an alkyl ester, or hydroxyl;
R$_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl.

In another embodiment, in the compounds represented by formula (IB), neither R$_a$ or R$_b$ is acridinyl.

In another embodiment, the invention relates to compounds of formula (IIB):

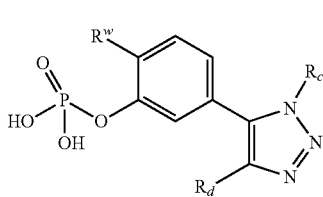

(IIB)

or a pharmaceutically acceptable salt, solvate, clathrate, or prodrug thereof, wherein:
one of R$_c$ or R$_d$ is —H and the other is

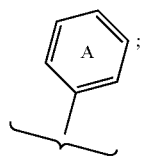

ring A is optionally substituted; and
R$^x$, R$^y$, and R$^w$ are defined as above.

In another embodiment, the invention relates to compounds of formula (IIIB):

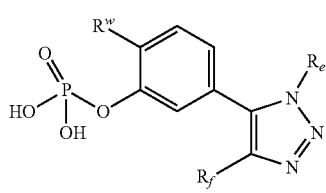

(IIIB)

or a pharmaceutically acceptable salt, solvate, clathrate, or prodrug thereof, wherein:
one of $R_e$ or $R_f$ is —H and the other is

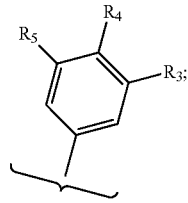

$R_3$, $R_4$, $R_5$, and $R_6$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —$OR_7$, —$NR_{10}R_{11}$, —$C(O)R_7$, —$C(O)OR_7$, —$OC(O)R_7$, —$C(O)NR_{10}R_{11}$, —$NR_8C(O)R_7$, —$OP(O)(OR_7)_2$, —$SP(O)(OR_7)_2$, —$SR_7$, —$S(O)_pR_7$, —$OS(O)_pR_7$, —$S(O)_pOR_7$, —$NR_8S(O)_pR_7$, or —$S(O)_pNR_{10}R_{11}$; and
$R^x$, $R^y$, $R^w$, $R_7$, $R_8$, $R_{10}$, $R_{11}$, and p are defined as above.

In another embodiment, the invention relates to compounds of formula (IVB):

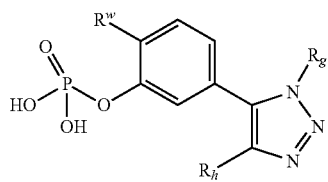

(IVB)

or a pharmaceutically acceptable salt, solvate, clathrate, or prodrug thereof, wherein:
one of $R_g$ or $R_h$ is —H and the other is

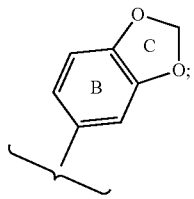

Ring B is optionally substituted with one to three substituents;
Ring C is optionally substituted with one or two substituents; and
$R^x$, $R^y$, and $R^w$ are defined as above.

In another embodiment, the invention relates to compounds of formula (VB):

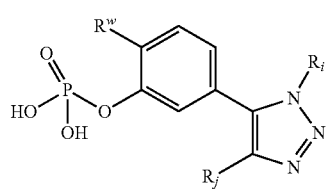

(VB)

or a pharmaceutically acceptable salt, solvate, clathrate, or prodrug thereof, wherein:
one of $R_i$ or $R_j$ is —H and the other is

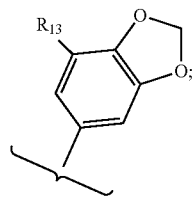

$R^x$, $R^y$, and $R^w$ are defined as above; and
$R_{13}$ is —H, an alkyl, an alkoxy, a halo, nitro, cyano, —OH, —$NH_2$, an alkyl amino, or a dialkyl amino.

In another embodiment, the invention relates to compounds of formula (VIIB):

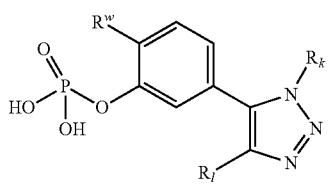

(VIIB)

or a pharmaceutically acceptable salt, solvate, clathrate, or prodrug thereof, wherein:
one of $R_k$ or $R_l$ is —H and the other is

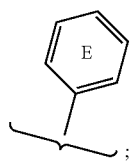

one of rings E or F is substituted with three or four substituents and the other is substituted with one or more substituents.

In another embodiment, the invention relates to compounds of formula (XIXB):

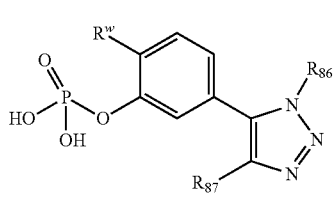

(XIXB)

or a pharmaceutically acceptable salt, solvate, clathrate, or prodrug thereof, wherein:
one of $R_{86}$ or $R_{87}$ is —H and the other is

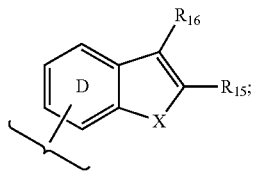

Ring D is optionally substituted one to three substituents; and
$R^x$, $R^y$, $R^w$, X, $R_{15}$, and $R_{16}$ are defined as above.
In another embodiment, the invention relates to compounds of formula (VIIIB):

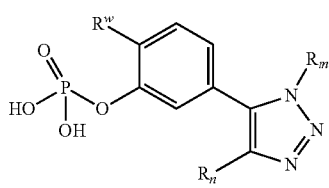

(VIIIB)

or a pharmaceutically acceptable salt, solvate, clathrate, or prodrug thereof, wherein:
one of $R_m$ or $R_n$ is —H and the other is

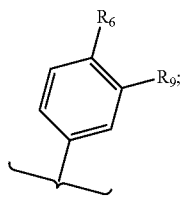

$R^x$, $R^y$, $R^w$ $R_6$ and $R_9$ are defined as above.
In another embodiment, the invention relates to compounds of formula (IXB):

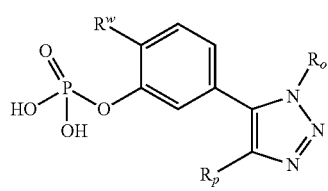

(IXB)

or a pharmaceutically acceptable salt, solvate, clathrate, or prodrug thereof, wherein:
one of $R_o$ or $R_p$ is —H and the other is

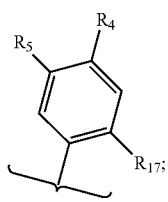

$R_{17}$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —$OR_7$, —$NR_{10}R_{11}$, —C(O)$R_7$, —C(O)$OR_7$, —OC(O)$R_7$, —C(O)$NR_{10}R_{11}$, —$NR_8$C(O)$R_7$, —OP(O)($OR_7$)$_2$, —SP(O)($OR_7$)$_2$, —$SR_7$, —S(O)$_p$$R_7$, —OS(O)$_p$$R_7$, —S(O)$_p$$OR_7$, —$NR_8$S(O)$_p$$R_7$, or —S(O)$_p$$NR_{10}R_{11}$; and
$R_4$, $R_5$, $R^x$, $R^y$, $R^w$, $R_7$, $R_8$, $R_{10}$, $R_{11}$ and p are defined as above.
In another embodiment, the invention relates to compounds of formula (XB):

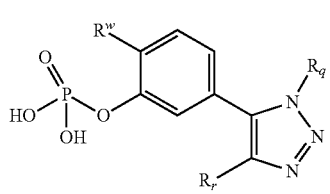

(XB)

or a pharmaceutically acceptable salt, solvate, clathrate, or prodrug thereof, wherein:
one of $R_q$ or $R_r$ is —H and the other is

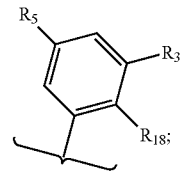

$R_{18}$ are each, independently, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —$OR_7$, —$NR_{10}R_{11}$, —C(O)$R_7$, —C(O)$OR_7$, —OC(O)$R_7$, —C(O)$NR_{10}R_{11}$, —$NR_8$C(O)$R_7$, —OP(O)($OR_7$)$_2$, —SP(O)($OR_7$)$_2$, —$SR_7$, —S(O)$_p$$R_7$, —OS(O)$_p$$R_7$, —S(O)$_p$$OR_7$, —$NR_8$S(O)$_p$$R_7$, or —S(O)$_p$$NR_{10}R_{11}$; and
$R_3$, $R_5$, $R^x$, $R^y$, $R^w$, $R_7$, $R_8$, $R_9$, $R_{10}$, $R_{11}$ and p are defined as above.
In another embodiment, the invention relates to compounds of formula (XIB):

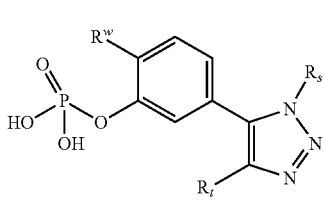

(XIB)

or a pharmaceutically acceptable salt, solvate, clathrate, or prodrug thereof, wherein:

one of $R_s$ or $R_t$ is —H and the other is

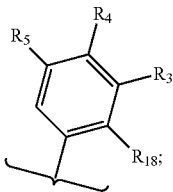

$R_3$, $R_4$, $R_5$, $R^x$, $R^y$, $R^w$ and $R_{18}$ are defined as above.

In another embodiment, the invention relates to compounds of formula (XVIIB):

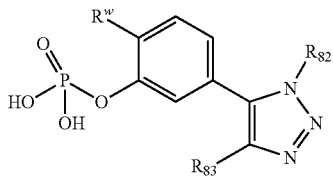

(XVIIB)

or a pharmaceutically acceptable salt, solvate, clathrate, or prodrug thereof, wherein:
one of $R_{82}$ or $R_{83}$ is —H and the other is

ring J is substituted with three or four substituents; and $R^x$, $R^y$, $R^w$, and $R_{14}$ are defined as above.

In another embodiment, the invention relates to compounds of formula (XVIIIB):

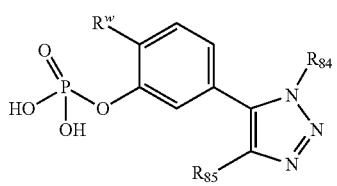

(XVIIIB)

or a pharmaceutically acceptable salt, solvate, clathrate, or prodrug thereof, wherein:
one of $R_{84}$ or $R_{85}$ is —H and the other is

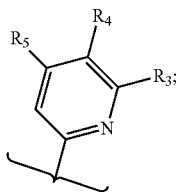

$R_3$, $R_4$, $R_5$, $R^x$, $R^y$, and $R^w$ are defined as above.

In some embodiments, $R_a$ and $R_2$ in formula (I) are each independently a substituted or unsubstituted phenyl. In some embodiments, $R_b$ and $R_2$ in formula (I) are each independently a substituted or unsubstituted phenyl.

In some embodiments, $R_a$ in formula (I), (IA), or (IB) is —H. In some embodiments, $R_b$ in formula (I), (IA), or (IB) is —H.

In some embodiments, $R_3$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) is a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and $R_{21}$ is H or an amino acid sidechain. In some embodiments, $R_3$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) is methyl, ethyl, or methoxy; preferably, $R_3$ is methoxy.

In some embodiments, $R_4$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) is a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and $R_{21}$ is H or an amino acid sidechain. In some embodiments, $R_4$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) is methyl, ethyl, or methoxy; preferably, $R_4$ is methoxy.

In some embodiments, $R_5$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) is a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and $R_{21}$ is H or an amino acid sidechain. In some embodiments, $R_5$ of formula (III), (IIIA), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) is methyl, ethyl, or methoxy; preferably, $R_3$ is methoxy.

In some embodiments, $R_6$ of formula (III), (V), (VI), (VIII), (IX), (X), (XI), or (XVIII) is a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and $R_{21}$ is H or an amino acid sidechain. In some embodiments, $R_6$ of formula (III), (V), (VI), (VIII), (IX), (X), (XI), or (XVIII) is methyl, ethyl, or methoxy; preferably, $R_3$ is methoxy. In some embodiments, $R_6$ of formula (III), (V), (VI), (VIII), (IX), (X), (XI), or (XVIII) is a lower alkyl, lower alkoxy, lower alkylsulfanyl, —OH, —SH, —NH$_2$, lower dialkyl amino, lower alkyl amino, nitro, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, or —NHC(O)R$_{12}$; preferably, R$_6$ is methoxy, dimethyl amino, methyl amino, hydroxy, —NHC(O)CH(R$_{21}$)NH$_2$, —OS(O)$_2$OR$_{12}$, —SP(O)(OR$_{12}$)$_2$, or —OP(O)(OR$_{12}$)$_2$; more preferably, R$_3$ is methoxy.

In some embodiments, R$_3$, R$_4$, and R$_5$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) are each, independently, a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and R$_{21}$ is H or an amino acid sidechain. In some embodiments, R$_3$, R$_4$, and R$_5$ of formula (III), (IIIA), (IIIB), (IIa), (IIb), (IIc), (IId), (IIe), (VIII), (VIIIA), (VIIIB), (X), (XA), (XB), (XI), (XIA), (XIB), (XVI), (XVIII), (VIIIA), or (XVIIIB) are each, independently, methyl, ethyl, or methoxy; preferably, R$_3$, R$_4$, and R$_5$ are each methoxy.

In some embodiments, R$_3$, R$_4$, R$_5$, and R$_6$ of formula (III), (VIII), (XI), or (XVIII) are each, independently, a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and R$_{21}$ is H or an amino acid sidechain. In some embodiments, R$_3$, R$_4$, R$_5$, and R$_6$ of formula (III), (VIII), (XI), or (XVIII) are each, independently, methyl, ethyl, or methoxy; preferably, R$_3$, R$_4$, R$_5$ and R$_6$ are methoxy. In some embodiments, R$_3$, R$_4$, and R$_5$ of formula (III), (VIII), (XI), or (XVIII) are each, independently, methyl, ethyl, or methoxy, and R$_6$ of formula (III), (VIII), (XI), or (XVIII) is a lower alkyl, lower alkoxy, lower alkylsulfanyl, —OH, —SH, —NH$_2$, halo, lower dialkyl amino, lower alkyl amino, nitro, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, or —NHC(O)R$_{12}$; preferably, R$_6$ is methoxy, dimethyl amino, methyl amino, hydroxy, —NHC(O)CH(R$_{21}$)NH$_2$, —OS(O)$_2$OR$_{12}$, —SP(O)(OR$_{12}$)$_2$, or —OP(O)(OR$_{12}$)$_2$; preferably, R$_3$, R$_4$, R$_5$ and R$_6$ are methoxy.

In some embodiments, R$_4$, R$_5$, and R$_6$ of formula (IX) are each, independently, a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and R$_{21}$ is H or an amino acid sidechain. In some embodiments, R$_4$, R$_5$, and R$_6$ of formula (IX) are each, independently, methyl, ethyl, or methoxy; preferably, R$_4$, R$_5$ and R$_6$ are methoxy. In some embodiments, R$_4$ and R$_5$ of formula (IX) are each, independently, methyl, ethyl, or methoxy, and R$_6$ of formula (IX) is a lower alkyl, lower alkoxy, lower alkylsulfanyl, —OH, —SH, —NH$_2$, halo, lower dialkyl amino, lower alkyl amino, nitro, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, or —NHC(O)R$_{12}$; preferably, R$_6$ is methoxy, dimethyl amino, methyl amino, hydroxy, —NHC(O)CH(R$_{21}$)NH$_2$, —OS(O)$_2$OR$_{12}$, —SP(O)(OR$_{12}$)$_2$, or —OP(O)(OR$_{12}$)$_2$; preferably, R$_4$, R$_5$ and R$_6$ are methoxy.

In some embodiments, R$_3$, R$_5$, and R$_6$ of formula (X) are each, independently, a lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and R$_{21}$ is H or an amino acid sidechain. In some embodiments, R$_3$, R$_5$, and R$_6$ of formula (X) are each, independently, methyl, ethyl, or methoxy; preferably, R$_3$, R$_5$ and R$_6$ are methoxy. In some embodiments, R$_3$ and R$_5$ of formula (X) are each, independently, methyl, ethyl, or methoxy, and R$_6$ of formula (X) is a lower alkyl, lower alkoxy, lower alkylsulfanyl, —OH, —SH, —NH$_2$, halo, lower dialkyl amino, lower alkyl amino, nitro, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, or —NHC(O)R$_{12}$; preferably, R$_6$ is methoxy, dimethyl amino, methyl amino, hydroxy, —NHC(O)CH(R$_{21}$)NH$_2$, —OS(O)$_2$OR$_{12}$, —SP(O)(OR$_{12}$)$_2$, or —OP(O)(OR$_{12}$)$_2$; preferably, R$_3$, R$_5$ and R$_6$ are methoxy.

In some embodiments, R$_9$ of formula (III), (V), (VI), (VIII), (VIIIA), (VIIIB), (IX), (X), (XI), or (XVIII) is —H, halo, —OH, —SH, —NH$_2$, carboxy, —OP(O)(OR$_{12}$)$_2$, —SP(O)(OR$_{12}$)$_2$, —NHC(O)R$_{12}$, —NHC(O)CH(R$_{21}$)NH$_2$, —OS(O)$_2$(OR$_{12}$), lower alkoxycarbonyl, or lower alkoxy; preferably, R$_9$ is —H, amino, hydroxy, —NHC(O)CH(R$_{21}$)NH$_2$, or —OP(O)(OR$_{12}$)$_2$.

In some embodiments, R$_{13}$ of formula (V), (VA), (VB), (IVa), (IVb), (IVc), (IVd) or (IVe) is —H or a lower alkoxy.

In some embodiments, ring A of formula (II), (IIA), or (IIB) is optionally substituted with one to five substituents independently selected from the group consisting of an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)NR$_{34}$R$_{35}$, —NR$_{36}$C(O)R$_{37}$, halo, —OR$_{36}$, cyano, nitro, haloalkoxy, —C(O)R$_{36}$, —NR$_{34}$R$_{35}$, —SR$_{36}$, —C(O)OR$_{36}$, —OC(O)R$_{36}$, —NR$_{36}$C(O)NR$_{34}$R$_{35}$, —NR$_{36}$C(N—R$_{38}$)NR$_{34}$R$_{35}$, —OC(O)NR$_{34}$R$_{35}$, —NR$_{36}$C(O)OR$_{37}$, —OP(O)(OR$_{36}$)$_2$, —SP(O)(OR$_{36}$)$_2$, —OS(O)$_2$(OR$_{36}$), —S(O)$_p$R$_{36}$, or —S(O)$_p$NR$_{34}$R$_{35}$, wherein R$_{34}$ and R$_{35}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{34}$ and R$_{35}$ taken together with the nitrogen to which they are attached is an optionally substituted heterocyclyl or an optionally substituted heteroaryl; R$_{36}$ and R$_{37}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; and $R_{38}$ is H, an optionally substituted alkyl, —C(O)$R_{36}$, —C(O)O$R_{36}$, or an optionally substituted aralkyl.

In some embodiments, ring B of formula (IV), (IVA), or (IVB) is optionally substituted with one to three substituents independently selected from the group consisting of an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)N$R_{34}R_{35}$, —N$R_{36}$C(O)$R_{37}$, halo, —O$R_{36}$, cyano, nitro, haloalkoxy, —C(O)$R_{36}$, —N$R_{34}R_{35}$, —S$R_{36}$, —C(O)O$R_{36}$, —OC(O)$R_{36}$, —N$R_{36}$C(O)N$R_{34}R_{35}$, —N$R_{36}$C(N—$R_{38}$)N$R_{34}R_{35}$, —OC(O)N$R_{34}R_{35}$, —N$R_{36}$C(O)O$R_{37}$, —OP(O)(O$R_{36}$)$_2$, —SP(O)(O$R_{36}$)$_2$, —OS(O)$_2$(O$R_{36}$), —S(O)$_p$$R_{36}$, or —S(O)$_p$N$R_{34}R_{35}$.

In some embodiments, ring C of formula (IV), (IVA), or (IVB) is optionally substituted with one or two substituents independently selected from the group consisting of an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)N$R_{34}R_{35}$, —N$R_{36}$C(O)$R_{37}$, halo, —O$R_{36}$, cyano, nitro, haloalkoxy, —C(O)$R_{36}$, —N$R_{34}R_{35}$, —S$R_{36}$, —C(O)O$R_{36}$, —OC(O)$R_{36}$, —N$R_{36}$C(O)N$R_{34}R_{35}$, —N$R_{36}$C(N—$R_{38}$)N$R_{34}R_{35}$, —OC(O)N$R_{34}R_{35}$, —N$R_{36}$C(O)O$R_{37}$, —OP(O)(O$R_{36}$)$_2$, —SP(O)(O$R_{36}$)$_2$, —OS(O)$_2$(O$R_{36}$), —S(O)$_p$$R_{36}$, —S(O)$_p$N$R_{34}R_{35}$, =O, =S, =N$R_{38}$.

In some embodiments, ring D of formula (XIX), (XIXA), (XIXB), or (VI) are optionally substituted with one to three substituents independently selected from the group consisting of an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)N$R_{34}R_{35}$, —N$R_{36}$C(O)$R_{37}$, halo, —O$R_{36}$, cyano, nitro, haloalkoxy, —C(O)$R_{36}$, —N$R_{34}R_{35}$, —S$R_{36}$, —C(O)O$R_{36}$, —OC(O)$R_{36}$, —N$R_{36}$C(O)N$R_{34}R_{35}$, —N$R_{36}$C(N—$R_{38}$)N$R_{34}R_{35}$, —OC(O)N$R_{34}R_{35}$, —N$R_{36}$C(O)O$R_{37}$, —OP(O)(O$R_{36}$)$_2$, —SP(O)(O$R_{36}$)$_2$, —OS(O)$_2$(O$R_{36}$), —S(O)$_p$$R_{36}$, or —S(O)$_p$N$R_{34}R_{35}$. Preferably, ring D of formula (XIX) or (VI) is optionally substituted with one to five substituents independently selected from the group consisting of halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —O$R_7$, —N$R_{10}R_{11}$, —C(O)$R_7$, —C(O)O$R_7$, —OC(O)$R_7$, —C(O)N$R_{10}R_{11}$, —N$R_8$C(O)$R_7$, —OP(O)(O$R_7$)$_2$, —SP(O)(O$R_7$)$_2$, —S$R_7$, —S(O)$_p$$R_7$, —OS(O)$_p$$R_7$, —S(O)$_p$O$R_7$, —N$R_8$S(O)$_p$$R_7$, or —S(O)$_p$N$R_{10}R_{11}$; and $R_{15}$ and $R_{16}$ are independently selected from the group consisting of —H or a halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —O$R_7$, —N$R_{10}R_{11}$, —C(O)$R_7$, —C(O)O$R_7$, —OC(O)$R_7$, —C(O)N$R_{10}R_{11}$, —N$R_8$C(O)$R_7$, —OP(O)(O$R_7$)$_2$, —SP(O)(O$R_7$)$_2$, —S$R_7$, —S(O)$_p$$R_7$, —OS(O)$_p$$R_7$, —S(O)$_p$O$R_7$, —N$R_8$S(O)$_p$$R_7$, or —S(O)$_p$N$R_{10}R_{11}$.

In some embodiments, ring E and/or ring F of formula (VII) are optionally substituted with one to five substituents independently selected from the group consisting of an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)N$R_{34}R_{35}$, —N$R_{36}$C(O)$R_{37}$, halo, —O$R_{36}$, cyano, nitro, haloalkoxy, —C(O)$R_{36}$, —N$R_{34}R_{35}$, —S$R_{36}$, —C(O)O$R_{36}$, —OC(O)$R_{36}$, —N$R_{36}$C(O)N$R_{34}R_{35}$, —N$R_{36}$C(N—$R_{38}$)N$R_{34}R_{35}$, —OC(O)N$R_{34}R_{35}$, —N$R_{36}$C(O)O$R_{37}$, —OP(O)(O$R_{36}$)$_2$, —SP(O)(O$R_{36}$)$_2$, —OS(O)$_2$(O$R_{36}$), —S(O)$_p$$R_{36}$, or —S(O)$_p$N$R_{34}R_{35}$.

In some embodiments, ring E of formula (VIIA) or (VIIB) is optionally substituted with one to five substituents independently selected from the group consisting of an optionally substituted alkyl, an optionally substituted alkoxy, an optionally substituted alkylsulfanyl, an optionally substituted alkylamino, an optionally substituted dialkylamino, an optionally substituted alkenyl; an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)N$R_{34}R_{35}$, —N$R_{36}$C(O)$R_{37}$, halo, —O$R_{36}$, cyano, nitro, haloalkoxy, —C(O)$R_{36}$, —N$R_{34}R_{35}$, —S$R_{36}$, —C(O)O$R_{36}$, —OC(O)$R_{36}$, —N$R_{36}$C(O)N$R_{34}R_{35}$, —N$R_{36}$C(N—$R_{38}$)N$R_{34}R_{35}$, —OC(O)N$R_{34}R_{35}$, —N$R_{36}$C(O)O$R_{37}$, —OP(O)(O$R_{36}$)$_2$, —SP(O)(O$R_{36}$)$_2$, —OS(O)$_2$(O$R_{36}$), —S(O)$_p$$R_{36}$, or —S(O)$_p$N$R_{34}R_{35}$.

In some embodiments, $R_{14}$, for each occurrence, is independently selected from the group consisting of —H, an optionally substituted alkyl, an optionally substituted alkoxy, an optionally substituted alkylsulfanyl, an optionally substituted alkylamino, an optionally substituted dialkylamino, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, an optionally substituted haloalkyl, —C(O)N$R_{34}R_{35}$, —N$R_{36}$C(O)$R_{37}$, halo, —O$R_{36}$, cyano, nitro, haloalkoxy, —C(O)$R_{36}$, —N$R_{34}R_{35}$, —S$R_{36}$, —C(O)O$R_{36}$, —OC(O)$R_{36}$, —N$R_{36}$C(O)N$R_{34}R_{35}$, —N$R_{36}$C(N—$R_{38}$)N$R_{34}R_{35}$, —OC(O)N$R_{34}R_{35}$, —N$R_{36}$C(O)O$R_{37}$, —OP (O)(OR$_{36}$)$_2$, —SP(O)(OR$_{36}$)$_2$, —OS(O)$_2$(OR$_{36}$), —S(O)$_p$R$_{36}$, or —S(O)$_p$NR$_{34}$R$_{35}$. Preferably, R$_{14}$ is —H, a lower alkyl, a lower alkoxy, a lower alkyl sulfanyl, a amino, a lower alkyl amino, a lower dialkyl amino, hydroxy, —NHC(O)CH(R$_{21}$)NH$_2$, —OP(O)(OR$_{12}$)$_2$, halo, —SH, carboxy, —SP(O)(OR$_{12}$)$_2$, —NHC(O)R$_{12}$, —OS(O)$_2$(OR$_{12}$), lower alkoxycarbonyl, or lower alkoxy; preferably, R$_{14}$ is —H, amino, hydroxy, —NHC(O)CH(R$_{21}$)NH$_2$, or —OP(O)(OR$_{12}$)$_2$.

In some embodiments, in the compounds represented by formula (VIIA) or VIIIB), R$_6$ is lower alkyl, lower alkoxy, lower alkylsulfanyl, —OH, —SH, —NH$_2$, halo, lower dialkyl amino, lower alkyl amino, nitro, cyano, pyridinyl, carboxy, lower alkoxycarbonyl, oxazolyl, —SP(O)(OR$_{12}$)$_2$, —OP(O)(OR$_{12}$)$_2$, —OC(O)R$_{12}$, —OS(O)$_2$(OR$_{12}$), tetrazolyl, 1-methyl-tetrazolyl, —NHC(O)R$_{12}$, or —NHC(O)CH(R$_{21}$)NH$_2$, wherein R$_{12}$ for each occurrence is independently, —H or a lower alkyl; and R$_{21}$ is H or an amino acid sidechain; and R$_9$ is —H, halo, —OH, —SH, —NH$_2$, carboxy, —OP(O)(OR$_{12}$)$_2$, —SP(O)(OR$_{12}$)$_2$, —NHC(O)R$_{12}$, —NHC(O)CH(R$_{21}$)NH$_2$, —OS(O)$_2$(OR$_{12}$), lower alkoxycarbonyl, or lower alkoxy.

In some embodiments, in the compounds represented by formula (IXA) or (IXB), R$_4$, R$_5$, and R$_{17}$ are each, independently, a lower alkyl, a lower alkoxy, or —OH.

In some embodiments, in the compounds represented by formula (XA) or (XB), R$_3$, R$_5$, and R$_{18}$ are each, independently, a lower alkyl, a lower alkoxy, or —OH.

In some embodiments, in the compounds represented by formula (XIA) or (XIB), R$_3$, R$_4$, R$_5$, and R$_{18}$ are each, independently, a lower alkyl, a lower alkoxy, or —OH.

In one embodiment, in formula (VI), (XIX), (XIXA), or (XIXB), X is NR$_{20}$; Ring D is unsubstituted; R$_{20}$ is —H or a lower alkyl; and R$_{15}$ and R$_{16}$ are —H.

In one embodiment, in formula (VI), (XIX), (XIXA), or (XIXB), X is O; Ring D is unsubstituted; and R$_{15}$ and R$_{16}$ are —H.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^x$ is R$^{aa}$, —C(O)YR$^z$, or —C(O)NH—R$^{aa}$. In one aspect, R$^x$ is R$^{aa}$. In another aspect, R$^x$ is —C(O)YR$^z$. R$^{aa}$, R$^z$, and Y are defined as for formula (IA).

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^x$ is R$^{aa}$ and R$^{aa}$ is defined as for formula (IA). In one aspect, R$^{aa}$ is glycine, serine, alanine, phenylalanine, leucine, or methionine.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^x$ is R$^{aa}$ and R$^y$ is —H, wherein R$^{aa}$ is defined as for formula (IA). In one aspect, R$^{aa}$ is glycine, alanine, valine, leucine, isoleucine, serine, threonine, cysteine, methionine, phenylalanine, tyrosine, tryptophan, aspartic acid, asparagine, glutamic acid, glutamine, arginine, histidine, lysine, or proline. In another aspect, R$^{aa}$ is glycine, serine, alanine, phenylalanine, leucine, or methionine.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^x$ is R$^{aa}$ and R$^{aa}$ is a D-amino acid residue or a D-amino acid residue analog. In one aspect, R$^{aa}$ is D-alanine, D-valine, D-leucine, D-isoleucine, D-serine, D-threonine, D-cysteine, D-methionine, D-phenylalanine, D-tyrosine, D-tryptophan, D-aspartic acid, D-asparagine, D-glutamic acid, D-glutamine, D-arginine, D-histidine, D-lysine, or D-proline.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^x$ is R$^{aa}$ and R$^{aa}$ is an L-amino acid residue or an L-amino acid residue analog. In one aspect, R$^{aa}$ is L-alanine, L-valine, L-leucine, L-isoleucine, L-serine, L-threonine, L-cysteine, L-methionine, L-phenylalanine, L-tyrosine, L-tryptophan, L-aspartic acid, L-asparagine, L-glutamic acid, L-glutamine, L-arginine, L-histidine, L-lysine, or L-proline.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^x$ is —C(O)YR$^z$ and Y and R$^z$ are defined as for formula (IA). In one aspect, Y is CH$_2$. In another aspect, Y is O. In another aspect, Y is NH. In one aspect, R$^z$ is Y$_1$ and Y$_1$ is defined as for formula (IA). In another aspect, R$^z$ is Alk-NH$_2$. In another aspect, R$^z$ is Alk-C(O)OH. In another aspect, R$^z$ is Het. Alk and Het and defined as for formula (IA).

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), m is 1, 2 or 3.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), Y$_1$ is PEG, HPMA copolymer-methacryloyl-Gly-Phe-Leu-Gly-ethylenediamine, or HPMA copolymer-methacryloyl-Gly-Phe-Leu-Gly-OH. In one aspect, Y$_1$ is PEG.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^y$ is —H.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), R$^y$ is a lower alkyl.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), Y$_1$ has a molecular weight greater than 20,000 daltons. In one aspect, Y$_1$ has a molecular weight of less than 40,000 daltons, but greater than 25,000 daltons.

In some embodiments, in the compounds represented by formula (IA), (IIA), (IIIA), (IVA), (VA), (VIIA), (VIIIA), (IXA), (XA), (XIA), (XVIIA), (XVIIIA) or (XIXA), Alk is an optionally substituted lower alkylene.

In some embodiments, in the compounds represented by formula (IA), (IIA), (IIIA), (IVA), (VA), (VIIA), (VIIIA), (IXA), (XA), (XVIIA), (XVIIIA) or (XIXA), Het is an optionally substituted lower heteroalkyl.

In some embodiments, in the compounds represented by formula (IIIA), R$_3$, R$_4$, and R$_5$ are each methoxy. In one aspect, R$^x$ is R$^{aa}$. In another aspect, R$^x$ is (R$^{aa}$)$_m$. In another aspect, R$^x$ is —R$^{aa}$—C(O)(CH$_2$)$_n$C(O)OH. In another aspect, R$^x$ is —C(O)(CH$_2$)$_n$C(O)OH. In another aspect, R$^x$ is —C(O)YR$^z$. In another aspect, R$^x$ is —C(O)NH—R$^{aa}$. In another aspect, R$^x$ is —(R$^{aa}$)$_q$C(O)(Y$_1$). R$^{aa}$, Y, R$^z$, Y$_1$, m, n, and q are defined as for formula (IA).

In some embodiments, in the compounds represented by formula (IIIA), R$_3$, R$_4$, and R$_5$ are each methoxy. In one aspect, R$^x$ is R$^{aa}$ and R$^w$ is alkoxy. In another aspect, R$^x$ is R$^{aa}$ and R$^y$ is —H. In another aspect, R$^x$ is R$^{aa}$, R$^w$ is alkoxy, and R$^y$ is —H. In another aspect, R$^x$ is R$^{aa}$, R$^w$ is alkoxy, and R$^y$ is —H. In another aspect, $R^x$ is $R^{aa}$, $R^w$ is methoxy, and $R^y$ is —H. $R^{aa}$ is defined as for formula (IA).

In some embodiments, in the compounds represented by formula (IIIB), $R_3$, $R_4$, and $R_5$ are each methoxy; and $R^w$ is alkoxy. In one aspect, $R^w$ is methoxy.

In some embodiments, in the compounds represented by formula (IA or B), (IIA or B), (IIIA or B), (IVA or B), (VA or B), (VIIA or B), (VIIIA or B), (IXA or B), (XA or B), (XIA or B), (XVIIA or B), (XVIIIA or B), or (XIXA or B), Fr is alkoxy. In one aspect, $R^w$ is methoxy.

In another embodiment, the invention relates to compounds selected from the group consisting of:

1-(3,4,5-trimethoxy-phenyl)-5-(4-bromo-phenyl)-1H-[1,2,3]triazole;
1-(2-hydroxy-4-methoxy-5-ethyl-phenyl)-5-(naphthylen-2-yl)-1H-[1,2,3]triazole;
1-(3,4,5-trimethoxy-phenyl)-5-(4-methoxy-phenyl)-1H-[1,2,3]triazole;
1-(2-hydroxy-4-methoxy-5-ethyl-phenyl)-5-(4-iodo-phenyl)-1H-[1,2,3]triazole;
1-(3,4,5-trimethoxy-phenyl)-5-[4-(N,N-dimethylamino)-phenyl]-1H-[1,2,3]triazole;
1-(2-hydroxy-4-methoxy-5-ethyl-phenyl)-5-(4-bromo-phenyl)-1H-[1,2,3]triazole;
1-(2-hydroxy-4-methoxy-5-(2,3-dihydro-benzo[1,4]dioxin-6-yl)-5-(4-bromo-phenyl)-1H-[1,2,3]triazole;
1-(3,4,5-hydroxy-phenyl)-5-(4-hyoxy-phenyl)-1H-[1,2,3]triazole;
1-(3,4,5-trimethoxy-phenyl)-5-(4-iodo-phenyl)-1H-[1,2,3]triazole;
1-(3,4,5-trimethoxy-phenyl)-5-(3-fluoro-4-methoxy-phenyl)-1H-[1,2,3]triazole;
1-(3,4,5-trimethoxy-phenyl)-5-(4-nitro-phenyl)-1H-[1,2,3]triazole;
1-(3,4,5-trimethoxy-phenyl)-5-(4-amino-phenyl)-1H-[1,2,3]triazole;
1-(3,4,5-trimethoxy-phenyl)-5-(4'-methoxy-biphenyl-4-yl)-1H-[1,2,3]triazole;
1-(3,4,5-trimethoxy-phenyl)-5-[4-(pyridin-3-yl)-phenyl]-1H-[1,2,3]triazole;
1-(3,4,5-trimethoxy-phenyl)-5-[4-(pyridin-4-yl)-phenyl]-1H-[1,2,3]triazole;
1-(3,4,5-trimethoxy-phenyl)-5-[4-(pyridin-2-yl)-phenyl]-1H-[1,2,3]triazole;
1-(3,4,5-trimethoxy-phenyl)-5-(quinolin-7-yl)-1H-[1,2,3]triazole;
1-(3,4,5-trimethoxy-phenyl)-5-(pyridine-4-yl)-1H-[1,2,3]triazole;
1-(3,4,5-trimethoxy-phenyl)-5-(isoquinolin-7-yl)-1H-[1,2,3]triazole;
1-(3,4,5-trimethoxy-phenyl)-5-(1-methyl-1H-indol-5-yl)-1H-[1,2,3]triazole;
1-(benzo[1,3]dioxol-5-yl)-5-(4-methoxy-phenyl)-1H-[1,2,3]triazole,
1-(1-ethyl-1H-indol-6-yl)-5-(4-methoxy-phenyl)-1H-[1,2,3]triazole;
1-(3,4,5-trimethoxy-phenyl)-5-(4-carboxy-phenyl)-1H-[1,2,3]triazole;
1-(3,4,5-trimethoxy-phenyl)-5-(4-carbomethoxy-phenyl)-1H-[1,2,3]triazole;
1-(3,4,5-trimethoxy-phenyl)-5-[4-(oxazol-2-yl)-phenyl]-1H-[1,2,3]triazole;
1-(3,4,5-triethyl-phenyl)-5-(4-methoxy-phenyl)-1H-[1,2,3]triazole;
1-(3,4,5-triethyl-phenyl)-5-(4-iodo-phenyl)-1H-[1,2,3]triazole;
1-(3,4,5-triethyl-phenyl)-5-(3-fluoro-4-methoxy-phenyl)-1H-[1,2,3]triazole;
1-(3,4,5-triethyl-phenyl)-5-(4-nitro-phenyl)-1H-[1,2,3]triazole;
1-(3,4,5-triethyl-phenyl)-5-[4-(N,N-dimethylamino)-phenyl]-1H-[1,2,3]triazole;
1-(3,4,5-trimethyl-phenyl)-5-(4-methoxy-phenyl)-1H-[1,2,3]triazole;
1-(3,4,5-triethyl-phenyl)-5-[4-(pyridine-3-yl)-phenyl]-1H-[1,2,3]triazole;
1-(3,4,5-triethyl-phenyl)-5-[4-(pyridine-4-yl)-phenyl]-1H-[1,2,3]triazole;
1-(3,4,5-triethyl-phenyl)-5-[4-(pyridine-2-yl)-phenyl]-1H-[1,2,3]triazole;
1-(3,4,5-triethyl-phenyl)-5-(quinolin-7-yl)-1H-[1,2,3]triazole;
1-(3,4,5-triethyl-phenyl)-5-(pyridine-4-yl)-1H-[1,2,3]triazole;
1-(3,4,5-triethyl-phenyl)-5-(isoquinolin-7-yl)-1H-[1,2,3]triazole;
1-(3,4,5-triethyl-phenyl)-5-(1H-indol-5-yl)-1H-[1,2,3]triazole;
1-(benzo[1,3]dioxol-5-yl)-5-(4-methoxy-phenyl)-1H-[1,2,3]triazole;
1-(1-isopropyl-1H-indol-6-yl)-5-(4-methoxy-phenyl)-1H-[1,2,3]triazole;
1-(2,3,4-trimethoxy-phenyl)-5-(4-methoxy-phenyl)-1H-[1,2,3]triazole;
1-(3,4,5-trimethoxy-phenyl)-5-(3-hydroxy-4-methoxy-phenyl)-1H-[1,2,3]triazole;
O-ethyl-O-{2-methoxy-5-[1-(3,4,5-trimethoxy-phenyl)-1H-[1,2,3]triazol-5-yl]-phenyl}-phosphate;
1-(2-hydroxy-4-methoxy-5-ethyl-phenyl)-5-(4-methoxy-phenyl)-1H-[1,2,3]triazole;
1-(3,4,5-trimethoxy-phenyl)-5-(4-isopropyl-phenyl)-1H-[1,2,3]triazole;
1-(3,4,5-trimethoxy-phenyl)-5-(2,3-dihydro-benzo[1,4]dioxine-6-yl)-1H-[1,2,3]triazole;
1-(3,4,5-trimethoxy-phenyl)-5-(4-ethyl-phenyl)-1H-[1,2,3]triazole;
1-(3,4,5-trimethoxy-phenyl)-5-(5-methoxy-pyridine-2-yl)-1H-[1,2,3]triazole;
1-(4,5,6-trimethoxy-pyridin-2-yl)-5-(4-methoxy-phenyl)-1H-[1,2,3]triazole;
1-(3,5-dimethoxy-4-carbomethoxy-phenyl)-5-(4-methoxy-phenyl)-1H-[1,2,3]triazole;
1-(3,5-diacetoxy-phenyl)-5-(4-methoxy-phenyl)-1H-[1,2,3]triazole;
1-(3,4,5-trimethoxy-phenyl)-5-(2-methoxy-pyridine-5-yl)-1H-[1,2,3]triazole;
1-(1-methyl-5-methoxy-1H-indol-7-yl)-5-(4-methoxy-phenyl)-1H-[1,2,3]triazole;
1-(1-methyl-1H-indol-7-yl)-5-(4-methoxy-phenyl)-1H-[1,2,3]triazole;
1-(Benzo[1,3]dioxol-4-yl)-5-(4-methoxy-phenyl)-1H-[1,2,3]triazole;
1-(3,4,5-trimethoxy-phenyl)-5-(2-hydroxy-4-methoxy-phenyl)-1H-[1,2,3]triazole;
O-ethyl-O-{5-methoxy-2-[1-(3,4,5-trimethoxy-phenyl)-1H-[1,2,3]triazol-5-yl]-phenyl}-phosphate;
1-(3,4,5-trimethoxy-phenyl)-5-(pyridazin-4-yl)-1H-[1,2,3]triazole;
1-(3,4,5-trimethoxy-phenyl)-5-(pyrimidin-5-yl)-1H-[1,2,3]triazole;
1-(3,4,5-trimethoxy-phenyl)-5-(pyridin-2-yl)-1H-[1,2,3]triazole, hydrochloric acid salt;

1-(3,4,5-trimethoxy-phenyl)-5-(2-mercapto-4-methoxy-phenyl)-1H-[1,2,3]triazole;
S-{2-methoxy-5-[1-(3,4,5-trimethoxy-phenyl)-1H-[1,2,3]triazol-5-yl]-phenyl}-thiophosphate, disodium salt;
1-(3,4,5-trimethoxy-phenyl)-5-(3-acetamido-4-methoxy-phenyl)-1H-[1,2,3]triazole;
1-(3,4,5-trimethoxy-phenyl)-5-(3-amino-4-methoxy-phenyl)-1H-[1,2,3]triazole, hydrochloric acid salt;
1-(3,4,5-trimethoxy-phenyl)-5-(2-hydroxy-4-methoxy-phenyl)-1H-[1,2,3]triazole;
1-(3,4,5-trimethoxy-phenyl)-5-(2-methoxy-pyridin-5-yl)-1H-[1,2,3]triazole;
1-(3,4,5-trimethoxy-phenyl)-5-(5-methoxy-pyridin-2-yl)-1H-[1,2,3]triazole;
1-(3,4,5-trimethoxy-phenyl)-5-(3-carboxy-4-methoxy-phenyl)-1H-[1,2,3]triazole, sodium salt;
1-(3,4,5-trimethoxy-phenyl)-5-(3-methoxycarbonyl-4-methoxy-phenyl)-1H-[1,2,3]triazole;
1-(3,4,5-trimethoxy-phenyl)-5-(3-sulfooxy-4-methoxy-phenyl)-1H-[1,2,3]triazole, sodium salt;
1-(3,4,5-trimethoxy-phenyl)-5-(2-amino-4-methoxy-phenyl)-1H-[1,2,3]triazole;
1-(3,4,5-trimethoxy-phenyl)-5-(3-phosphonooxy-4,5-dimethoxy-phenyl)-1H-[1,2,3]triazole, disodium salt;
1-(3,4,5-trimethoxy-phenyl)-5-(2-phosphonooxy-4-methoxy-phenyl)-1H-[1,2,3]triazole, disodium salt;
1-(3,4,5-trimethoxy-phenyl)-5-(4-methylsulfanyl-phenyl)-1H-[1,2,3]triazole;
1-(3,4,5-trimethoxy-phenyl)-5-(3-phosphonooxy-4-methylsulfanyl-phenyl)-1H-[1,2,3]-triazole, disodium salt;
1-(3,4,5-trimethoxy-phenyl)-5-(3-amino-4-methylsulfanyl-phenyl)-1H-[1,2,3]triazole;
1-(3,4,5-trimethoxy-phenyl)-5-(2,3-dihydro-benzofuran-6-yl)-1H-[1,2,3]triazole;
1-(3,4,5-trimethoxy-phenyl)-5-(4-hydroxy-phenyl)-1H-[1,2,3]triazole, sodium salt;
1-(3,4,5-trimethoxy-phenyl)-5-(4-phosphonooxy-phenyl)-1H-[1,2,3]triazole, disodium salt;
1-(3,4,5-trimethoxy-phenyl)-5-[4-(tetrazol-5-yl)-phenyl]-1H-[1,2,3]triazole;
1-(3,4,5-trimethoxy-phenyl)-5-[4-(1-methyl-tetrazol-5-yl)-phenyl]-1H-[1,2,3]triazole;
1-(3,4,5-trimethoxy-phenyl)-5-(1-methyl-1H-indol-5-yl)-1H-[1,2,3]triazole;
1-(7-methoxy-benzo[1,3]dioxol-5-yl)-5-(pyridazin-4-yl)-1H-[1,2,3]triazole;
1-(7-methoxy-benzo[1,3]dioxol-5-yl)-5-(pyrimidin-5-yl)-1H-[1,2,3]triazole;
1-(7-methoxy-benzo[1,3]dioxol-5-yl)-5-(pyridine-3-yl)-1H-[1,2,3]triazole, hydrochloric acid salt;
1-(7-methoxy-benzo[1,3]dioxol-5-yl)-5-(3-mercapto-4-methoxy-phenyl)-1H-[1,2,3]triazole;
S-{2-methoxy-5-[1-(7-methoxy-benzo[1,3]dioxol-5-yl)-1H-[1,2,3]triazol-5-yl]-phenyl}-thiophosphate, disodium salt;
1-(7-methoxy-benzo[1,3]dioxol-5-yl)-5-(3-acetamindo-4-methoxy-phenyl)-1H-[1,2,3]triazole;
1-(7-methoxy-benzo[1,3]dioxol-5-yl)-5-(3-amino-4-methoxy-phenyl)-1H-[1,2,3]triazole, hydrochloric acid salt;
1-(7-methoxy-benzo[1,3]dioxol-5-yl)-5-(2-hydroxy-4-methoxy-phenyl)-1H-[1,2,3]triazole;
1-(7-methoxy-benzo[1,3]dioxol-5-yl)-5-(2-methoxy-pyridin-5-yl)-1H-[1,2,3]triazole,
1-(7-methoxy-benzo[1,3]dioxol-5-yl)-5-(5-methoxy-pyridin-2-yl)-1H-[1,2,3]triazole;
1-(7-methoxy-benzo[1,3]dioxol-5-yl)-5-(3-carboxy-4-methoxy-phenyl)-1H-[1,2,3]triazole;
1-(7-methoxy-benzo[1,3]dioxol-5-yl)-5-(3-methoxycarbonyl-4-methoxy-phenyl)-1H-[1,2,3]triazole,
1-(7-methoxy-benzo[1,3]dioxol-5-yl)-5-(3-sulfooxy-4-methoxy-phenyl)-1H-[1,2,3]triazole, sodium salt;
1-(7-methoxy-benzo[1,3]dioxol-5-yl)-5-(2-amino-4-methoxy-phenyl)-1H-[1,2,3]triazole;
1-(7-methoxy-benzo[1,3]dioxol-5-yl)-5-(3-phosphonyl-4,5-dimethoxy-phenyl)-1H-[1,2,3]triazole, disodium salt;
1-(7-methoxy-benzo[1,3]dioxol-5-yl)-5-(2-phosphonyl-4-methoxy-phenyl)-1H-[1,2,3]triazole, sodium salt;
1-(7-methoxy-benzo[1,3]dioxol-5-yl)-5-(4-methylsulfanyl-phenyl)-1H-[1,2,3]triazole;
1-(7-methoxy-benzo[1,3]dioxol-5-yl)-5-(3-phosphonyl-4-methylsulfanyl-phenyl)-1H-[1,2,3]triazole, disodium salt;
1-(7-methoxy-benzo[1,3]dioxol-5-yl)-5-(3-amino-4-methylsulfanyl-phenyl)-1H-[1,2,3]triazole;
1-(7-methoxy-benzo[1,3]dioxol-5-yl)-5-(2,3-dihydro-benzofuran-6-yl)-1H-[1,2,3]triazole;
1-(7-methoxy-benzo[1,3]dioxol-5-yl)-5-(4-hydroxy-phenyl)-1H-[1,2,3]triazole, sodium salt;
1-(7-methoxy-benzo[1,3]dioxol-5-yl)-5-(4-phosphonooxy-phenyl)-1H-[1,2,3]triazole, disodium salt;
1-(7-methoxy-benzo[1,3]dioxol-5-yl)-5-[1H-tetrazol-5-yl)-phenyl]-1H-[1,2,3]triazole;
1-(7-methoxy-benzo[1,3]dioxol-5-yl)-5-(1-methyl-1H-tetrazol-5-yl)-phenyl)-1H-[1,2,3]triazole;
1-(7-methoxy-benzo[1,3]dioxol-5-yl)-5-(1-methyl-1H-indol-5-yl)-1H-[1,2,3]triazole;
1-(1-methyl-1H-indol-5-yl)-5-(3,4,5-trimethoxy-phenyl)-1H-[1,2,3]triazole;
1-(3-phosphonooxy-4-methoxy-phenyl)-5-(3,4,5-trimethoxy-phenyl)-1H-[1,2,3]triazole, disodium salt;
1-[4-(N,N-dimethylamino)-phenyl]-5-(3,4,5-trimethoxy-phenyl)-1H-[1,2,3]triazole;
1-(3-amino-4-methoxy-phenyl)-5-(3,4,5-trimethoxy-phenyl)-1H-[1,2,3]triazole, hydrochloric acid salt;
2-hydroxy-1-{2-methoxy-5-[5-(3,4,5-trimethoxy-phenyl)-[1,2,3]triazol-1-yl]-phenylcarbamoyl}-ethyl-ammonium chloride;
1-(2,4,5-trimethoxy-phenyl)-5-(4-methoxy-phenyl)-1H-[1,2,3]triazole;
1-(2,4,5-trimethoxy-phenyl)-5-(4-methyl-phenyl)-1H-[1,2,3]triazole;
1-(2,4,5-trimethoxy-phenyl)-5-(4-ethoxy-phenyl)-1H-[1,2,3]triazole;
1-(2,4,5-trimethoxy-phenyl)-5-(4-ethyl-phenyl)-1H-[1,2,3]triazole;
1-(2,4,5-trimethoxy-phenyl)-5-(4-propoxy-phenyl)-1H-[1,2,3]triazole;
1-(2,4,5-trimethoxy-phenyl)-5-(4-propyl-phenyl)-1H-[1,2,3]triazole;
1-(2,4,5-trimethoxy-phenyl)-5-(4-butoxy-phenyl)-1H-[1,2,3]triazole;
1-(2,4,5-trimethoxy-phenyl)-5-(4-butyl-phenyl)-1H-[1,2,3]triazole;
1-(2,4,5-trimethoxy-phenyl)-5-(4-bromo-phenyl)-1H-[1,2,3]triazole;
1-(2,4,5-trimethoxy-phenyl)-5-(4-chloro-phenyl)-1H-[1,2,3]triazole;
1-(2,4,5-trimethoxy-phenyl)-5-(4-fluoro-phenyl)-1H-[1,2,3]triazole;
1-(2,4,5-trimethoxy-phenyl)-5-(4-nitro-phenyl)-1H-[1,2,3]triazole;
1-(2,4,5-trimethoxy-phenyl)-5-[4-(N,N-dimethylamino)-phenyl]-1H-[1,2,3]triazole;
1-(2,4,5-trimethoxy-phenyl)-5-(3,4-dimethoxy-phenyl)-1H-[1,2,3]triazole;

1-(2,4,5-trimethoxy-phenyl)-5-(3-hydroxy-4-methoxy-phenyl)-1H-[1,2,3]triazole;
1-(2,4,5-trimethoxy-phenyl)-5-(3,4,5-trimethoxy-phenyl)-1H-[1,2,3]triazole;
1-(2,3,5-trimethoxy-phenyl)-5-(4-methoxy-phenyl)-1H-[1,2,3]triazole;
1-(2,3,5-trimethoxy-phenyl)-5-(4-methyl-phenyl)-1H-[1,2,3]triazole;
1-(2,3,5-trimethoxy-phenyl)-5-(4-ethoxy-phenyl)-1H-[1,2,3]triazole,
1-(2,3,5-trimethoxy-phenyl)-5-(4-ethyl-phenyl)-1H-[1,2,3]triazole;
1-(2,3,5-trimethoxy-phenyl)-5-(4-propoxy-phenyl)-1H-[1,2,3]triazole;
1-(2,3,5-trimethoxy-phenyl)-5-(4-propyl-phenyl)-1H-[1,2,3]triazole;
1-(2,3,5-trimethoxy-phenyl)-5-(4-butoxy-phenyl)-1H-[1,2,3]triazole;
1-(2,3,5-trimethoxy-phenyl)-5-(4-butyl-phenyl)-1H-[1,2,3]triazole;
1-(2,3,5-trimethoxy-phenyl)-5-(4-bromo-phenyl)-1H-[1,2,3]triazole;
1-(2,3,5-trimethoxy-phenyl)-5-(4-chloro-phenyl)-1H-[1,2,3]triazole;
1-(2,3,5-trimethoxy-phenyl)-5-(4-fluoro-phenyl)-1H-[1,2,3]triazole;
1-(2,3,5-trimethoxy-phenyl)-5-(4-nitro-phenyl)-1H-[1,2,3]triazole;
1-(2,3,5-trimethoxy-phenyl)-5-[4-(N,N-dimethylamino)-phenyl]-1H-[1,2,3]triazole;
1-(2,3,5-trimethoxy-phenyl)-5-(3,4-dimethoxy-phenyl)-1H-[1,2,3]triazole;
1-(2,3,5-trimethoxy-phenyl)-5-(3-hydroxy-4-methoxy-phenyl)-1H-[1,2,3]triazole;
1-(2,3,5-trimethoxy-phenyl)-5-(3,4,5-trimethoxy-phenyl)-1H-[1,2,3]triazole;
1-(4-methoxy-phenyl)-5-(2,3,4,5-tetramethoxy-phenyl)-1H-[1,2,3]triazole;
1-(4-methyl-phenyl)-5-(2,3,4,5-tetramethoxy-phenyl)-1H-[1,2,3]triazole;
1-(4-ethoxy-phenyl)-5-(2,3,4,5-tetramethoxy-phenyl)-1H-[1,2,3]triazole;
1-(4-ethyl-phenyl)-5-(2,3,4,5-tetramethoxy-phenyl)-1H-[1,2,3]triazole;
1-(4-propoxy-phenyl)-5(2,3,4,5-tetramethoxy-phenyl)-1H-[1,2,3]triazole;
1-(4-propyl-phenyl)-5-(2,3,4,5-tetramethoxy-phenyl)-1H[1,2,3]triazole;
1-(4-butoxy-phenyl)-5-(2,3,4,5-tetramethoxy-phenyl)-1H-[1,2,3]triazole;
1-(4-butyl-phenyl)-5(2,3,4,5-tetramethoxy-phenyl)-1H-[1,2,3]triazole;
1-(4-bromo-phenyl)-5-(2,3,4,5-tetramethoxy-phenyl)-1H-[1,2,3]triazole;
1-(4-chloro-phenyl)-5(2,3,4,5-tetramethoxy-phenyl)-1H-[1,2,3]triazole;
1-(4-fluoro-phenyl)-5-(2,3,4,5-tetramethoxy-phenyl)-1H-[1,2,3]triazole;
1-(4-nitro-phenyl)-5-(2,3,4,5-tetramethoxy-phenyl)-1H-[1,2,3]triazole;
1-[4-(N,N-dimethylamino)-phenyl]-5-(2,3,4,5-tetramethoxy-phenyl)-1H-[1,2,3]triazole;
1-(3,4-dimethoxy-phenyl)-5-(2,3,4,5-tetramethoxy-phenyl)-1H-[1,2,3]triazole;
1-(3-hydroxy-4-methoxy-phenyl)-5-(2,3,4,5-tetramethoxy-phenyl)-1H-[1,2,3]triazole;
1-(3,4,5-trimethoxy-phenyl)-5-(2,3,4,5-tetramethoxy-phenyl)-1H-[1,2,3]triazole;
1-(3,4-trimethoxy-phenyl)-5-(2,3-dihydro-benzo[1,4]dioxin-6-yl)-1H-[1,2,3]triazole;
1-(2-hydroxy-4-methoxy-5-ethyl-phenyl)-5-(3,4-dimethyl-phenyl)-1H-[1,2,3]triazole;
1-(2-hydroxy-4-methoxy-5-ethyl-phenyl)-5-(4-chloro-phenyl)-1H-[1,2,3]triazole;
1-(2-hydroxy-4-methoxy-5-propyl-phenyl)-5-phenyl-1H-[1,2,3]triazole;
1-(2-hydroxy-4-methoxy-5-ethyl-phenyl)-5-(4-methyl-phenyl)-1H-[1,2,3]triazole;
1-(2-hydroxy-4-methoxy-5-ethyl-phenyl)-5-(4-amino-phenyl)-1H-[1,2,3]triazole;
1-(2-hydroxy-4-methoxy-5-ethyl-phenyl)-5-(4-trifluoromethyl-phenyl)-1H-[1,2,3]-triazole;
1-(2-hydroxy-4-methoxy-5-ethyl-phenyl)-5-(4-methoxy-phenyl)-1H-[1,2,3]triazole;
1-(4-bromo-phenyl)-5-(3,4,5-trimethoxy-phenyl)-1H-[1,2,3]triazole;
or pharmaceutically acceptable salts, solvates, clathrates, or prodrugs thereof.

In another embodiment, the invention relates to compounds selected from the group consisting of:
2-amino-N-(2-methoxy-5-(1-(3,4,5-trimethoxyphenyl)-1H-1,2,3-triazol-5-yl)phenyl)acetamide hydrochloride;
2-amino-3-hydroxy-N-(2-methoxy-5-(1-(3,4,5-trimethoxyphenyl)-1H-1,2,3-triazol-5-yl)phenyl)propanamide hydrochloride;
2-amino-N-(2-methoxy-5-(1-(3,4,5-trimethoxyphenyl)-1H-1,2,3-triazol-5-yl)phenyl)propanamide;
2-amino-N-(2-methoxy-5-(1-(3,4,5-trimethoxyphenyl)-1H-1,2,3-triazol-5-yl)phenyl)-4-(methylthio)butanamide hydrochloride;
2-amino-N-(2-methoxy-5-(1-(3,4,5-trimethoxyphenyl)-1H-1,2,3-triazol-5-yl)phenyl)butanamide hydrochloride;
2-amino-N-(2-methoxy-5-(1-(3,4,5-trimethoxyphenyl)-1H-1,2,3-triazol-5-yl)phenyl)-3-phenylpropanamide hydrochloride;
2-amino-N-(2-methoxy-5-(1-(3,4,5-trimethoxyphenyl)-1H-1,2,3-triazol-5-yl)phenyl)-4-methylpentanamide hydrochloride;
2-amino-N-(2-methoxy-5-(1-(3,4,5-trimethoxyphenyl)-1H-1,2,3-triazol-5-yl)phenyl)-3-(4-methoxyphenyl)propanamide hydrochloride;
1-(2-methoxy-5-(1-(3,4,5-trimethoxyphenyl)-1H-1,2,3-triazol-5-yl)phenylamino)-3-methyl-1-oxobutan-2-aminium chloride;
1-(2-methoxy-5-(1-(3,4,5-trimethoxyphenyl)-1H-1,2,3-triazol-5-yl)phenylamino)-3-methyl-1-oxopentan-2-aminium chloride;
3-hydroxy-1-(2-methoxy-5-(1-(3,4,5-trimethoxyphenyl)-1H-1,2,3-triazol-5-yl)phenylamino)-1-oxobutan-2-aminium chloride;
3-(4-hydroxyphenyl)-1-(2-methoxy-5-(1-(3,4,5-trimethoxyphenyl)-1H-1,2,3-triazol-5-yl)phenylamino)-1-oxopropan-2-aminium chloride;
2-(2-methoxy-5-(1-(3,4,5-trimethoxyphenyl)-1H-1,2,3-triazol-5-yl)phenylamino)-2-oxo-1-phenylethanaminium chloride;
3-(1H-indol-2-yl)-1-(2-methoxy-5-(1-(3,4,5-trimethoxyphenyl)-1H-1,2,3-triazol-5-yl)phenylamino)-1-oxopropan-2-aminium chloride;
3-(benzofuran-2-yl)-1-(2-methoxy-5-(1-(3,4,5-trimethoxyphenyl)-1H-1,2,3-triazol-5-yl)phenylamino)-1-oxopropan-2-aminium chloride;

3-carboxy-1-(2-methoxy-5-(1-(3,4,5-trimethoxyphenyl)-1H-1,2,3-triazol-5-yl)phenylamino)-1-oxopropan-2-aminium chloride;
4-carboxy-1-(2-methoxy-5-(1-(3,4,5-trimethoxyphenyl)-1H-1,2,3-triazol-5-yl)phenylamino)-1-oxobutan-2-aminium chloride;
5-amino-1-(2-methoxy-5-(1-(3,4,5-trimethoxyphenyl)-1H-1,2,3-triazol-5-yl)phenylamino)-1,5-dioxopentan-2-aminium chloride;
4-amino-1-(2-methoxy-5-(1-(3,4,5-trimethoxyphenyl)-1H-1,2,3-triazol-5-yl)phenylamino)-1,4-dioxobutan-2-aminium chloride;
3-(1H-imidazol-5-yl)-1-(2-methoxy-5-(1-(3,4,5-trimethoxyphenyl)-1H-1,2,3-triazol-5-yl)phenylamino)-1-oxopropan-2-aminium chloride;
6-amino-1-(2-methoxy-5-(1-(3,4,5-trimethoxyphenyl)-1H-1,2,3-triazol-5-yl)phenylamino)-1-oxohexan-2-aminium chloride;
5-guanidino-1-(2-methoxy-5-(1-(3,4,5-trimethoxyphenyl)-1H-1,2,3-triazol-5-yl)phenylamino)-1-oxopentan-2-aminium chloride;
4-(2-methoxy-5-(1-(3,4,5-trimethoxyphenyl)-1H-1,2,3-triazol-5-yl)phenylamino)-4-oxobutanoic acid;
5-(2-methoxy-5-(1-(3,4,5-trimethoxyphenyl)-1H-1,2,3-triazol-5-yl)phenylamino)-5-oxopentanoic acid;
3-(2-methoxy-5-(1-(3,4,5-trimethoxyphenyl)-1H-1,2,3-triazol-5-yl)phenylamino)-3-oxopropan-1-aminium chloride;
N-(2-methoxy-5-(1-(3,4,5-trimethoxyphenyl)-1H-1,2,3-triazol-5-yl)phenyl)-3-(2-methoxyethoxy)propanamide;
3-(2-PEG)-N-(2-methoxy-5-(1-(3,4,5-trimethoxyphenyl)-1H-1,2,3-triazol-5-yl)phenyl)butyramide;
N-(2-methoxy-5-(1-(3,4,5-trimethoxyphenyl)-1H-1,2,3-triazol-5-yl)phenyl)-3-(2-(methylamino)ethylamino)propanamide;
3-PEG-N-(2-methoxy-5-(1-(3,4,5-trimethoxyphenyl)-1H-1,2,3-triazol-5-yl)phenylamino)-2-oxoethyl)butyramide;
4-(2-(2-methoxy-5-(1-(3,4,5-trimethoxyphenyl)-1H-1,2,3-triazol-5-yl)phenylamino)-2-oxoethylamino)-4-oxobutanoic acid;
2-methoxyethyl 2-methoxy-5-(1-(3,4,5-trimethoxyphenyl)-1H-1,2,3-triazol-5-yl)phenylcarbamate;
PEG-2-methoxy-5-(1-(3,4,5-trimethoxyphenyl)-1H-1,2,3-triazol-5-yl)phenylcarbamate;
3-amino-4-(2-((R)-5-guanidino-1-(2-methoxy-5-(1-(3,4,5-trimethoxyphenyl)-1H-1,2,3-triazol-5-yl)phenylamino)-1-oxopentan-2-ylamino)-2-oxoethylamino)-4-oxobutanoic acid; and
2-amino-N-(2-methoxy-5-(1-(3,4,5-trimethoxyphenyl)-1H-1,2,3-triazol-5-yl)phenyl)propanamide hydrochloride;
or pharmaceutically acceptable salts, solvates, clathrates, or prodrugs thereof.

In another embodiment, the invention relates to compounds selected from the group consisting of:
4-(3,4,5-trimethoxy-phenyl)-5-(4-bromo-phenyl)-1H-[1,2,3]triazole;
4-ethyl-5-methoxy-2-(5-(naphthalen-2-yl)-1H-1,2,3-triazol-4-yl)phenol;
5-(4-methoxyphenyl)-4-(3,4,5-trimethoxyphenyl)-1H-1,2,3-triazole;
4-ethyl-2-(5-(4-iodophenyl)-1H-1,2,3-triazol-4-yl)-5-methoxyphenol;
N,N-dimethyl-4-(4-(3,4,5-trimethoxyphenyl)-1H-1,2,3-triazol-5-yl)aniline;
2-(5-(4-bromophenyl)-1H-1,2,3-triazol-4-yl)-4-ethyl-5-methoxyphenol;
2-(5-(2,3-dihydrobenzo[b][1,4]dioxin-6-yl)-1H-1,2,3-triazol-4-yl)-5-methoxy-4-propylphenol;
5-(5-(4-hydroxyphenyl)-1H-1,2,3-triazol-4-yl)benzene-1,2,3-triol;
5-(4-iodophenyl)-4-(3,4,5-trimethoxyphenyl)-1H-1,2,3-triazole;
5-(3-fluoro-4-methoxyphenyl)-4-(3,4,5-trimethoxyphenyl)-1H-1,2,3-triazole;
5-(4-nitrophenyl)-4-(3,4,5-trimethoxyphenyl)-1H-1,2,3-triazole;
4-(4-(3,4,5-trimethoxyphenyl)-1H-1,2,3-triazol-5-yl)aniline;
5-(4'-methoxybiphenyl-4-yl)-4-(3,4,5-trimethoxyphenyl)-1H-1,2,3-triazole;
3-(4-(4-(3,4,5-trimethoxyphenyl)-1H-1,2,3-triazol-5-yl)phenyl)pyridine;
4-(4-(4-(3,4,5-trimethoxyphenyl)-1H-1,2,3-triazol-5-yl)phenyl)pyridine,
2-(4-(4-(3,4,5-trimethoxyphenyl)-1H-1,2,3-triazol-5-yl)phenyl)pyridine;
7-(4-(3,4,5-trimethoxyphenyl)-1H-1,2,3-triazol-5-yl)quinoline;
4-(4-(3,4,5-trimethoxyphenyl)-1H-1,2,3-triazol-5-yl)pyridine;
7-(4-(3,4,5-trimethoxyphenyl)-1H-1,2,3-triazol-5-yl)isoquinoline;
1-methyl-5-(4-(3,4,5-trimethoxyphenyl)-1H-1,2,3-triazol-5-yl)-1H-indole;
4-(benzo[d][1,3]dioxol-5-yl)-5-(4-methoxyphenyl)-1H-1,2,3-triazole;
1-ethyl-6-(5-(4-methoxyphenyl)-1H-1,2,3-triazol-4-yl)-1H-indole;
4-(4-(3,4,5-trimethoxyphenyl)-1H-1,2,3-triazol-5-yl)benzoic acid;
methyl 4-(4-(3,4,5-trimethoxyphenyl)-1H-1,2,3-triazol-5-yl)benzoate;
2-(4-(4-(3,4,5-trimethoxyphenyl)-1H-1,2,3-triazol-5-yl)phenyl)oxazole;
5-(4-methoxyphenyl)-4-(3,4,5-triethylphenyl)-1H-1,2,3-triazole;
5-(4-iodophenyl)-4-(3,4,5-triethylphenyl)-1H-1,2,3-triazole;
5-(3-fluoro-4-methoxyphenyl)-4-(3,4,5-triethylphenyl)-1H-1,2,3-triazole;
5-(4-nitrophenyl)-4-(3,4,5-triethylphenyl)-1H-1,2,3-triazole;
N,N-dimethyl-4-(4-(3,4,5-triethylphenyl)-1H-1,2,3-triazol-5-yl)aniline;
5-(4-methoxyphenyl)-4-(3,4,5-trimethylphenyl)-1H-1,2,3-triazole;
3-(4-(4-(3,4,5-triethylphenyl)-1H-1,2,3-triazol-5-yl)phenyl)pyridine;
4-(4-(4-(3,4,5-triethylphenyl)-1H-1,2,3-triazol-5-yl)phenyl)pyridine;
2-(4-(4-(3,4,5-triethylphenyl)-1H-1,2,3-triazol-5-yl)phenyl)pyridine;
7-(4-(3,4,5-triethylphenyl)-1H-1,2,3-triazol-5-yl)quinoline;
4-(4-(3,4,5-triethylphenyl)-1H-1,2,3-triazol-5-yl)pyridine;
7-(4-(3,4,5-triethylphenyl)-1H-1,2,3-triazol-5-yl)isoquinoline;
5-(4-(3,4,5-triethylphenyl)-1H-1,2,3-triazol-5-yl)-1H-indole;
4-(benzo[d][1,3]dioxol-5-yl)-5-(4-methoxyphenyl)-1H-1,2,3-triazole;
1-isopropyl-6-(5-(4-methoxyphenyl)-1H-1,2,3-triazol-4-yl)-1H-indole;
5-(4-methoxyphenyl)-4-(2,3,4-trimethoxyphenyl)-1H-1,2,3-triazole;

2-methoxy-5-(4-(3,4,5-trimethoxyphenyl)-1H-1,2,3-triazol-5-yl)phenol;
ethyl 2-methoxy-5-(4-(3,4,5-trimethoxyphenyl)-1H-1,2,3-triazol-5-yl)phenyl hydrogen phosphate;
4-ethyl-2-(5-(4-methoxyphenyl)-1H-1,2,3-triazol-4-yl)-5-methoxyphenol;
5-(4-isopropylphenyl)-4-(3,4,5-trimethoxyphenyl)-1H-1,2,3-triazole;
5-(2,3-dihydrobenzo[b][1,4]dioxin-6-yl)-4-(3,4,5-trimethoxyphenyl)-1H-1,2,3-triazole;
5-(4-ethylphenyl)-4-(3,4,5-trimethoxyphenyl)-1H-1,2,3-triazole;
5-methoxy-2-(4-(3,4,5-trimethoxyphenyl)-1H-1,2,3-triazol-5-yl)pyridine;
6-(5-(4-methoxyphenyl)-1H-1,2,3-triazol-4-yl)-2,3,4-trimethoxypyridine;
methyl 2,6-dimethoxy-4-(5-(4-methoxyphenyl)-1H-1,2,3-triazol-4-yl)benzoate;
5-(5-(4-methoxyphenyl)-1H-1,2,3-triazol-4-yl)-1,3-phenylene diacetate;
2-methoxy-5-(4-(3,4,5-trimethoxyphenyl)-1H-1,2,3-triazol-5-yl)pyridine;
5-methoxy-7-(5-(4-methoxyphenyl)-1H-1,2,3-triazol-4-yl)-1-methyl-1H-indole;
1-ethyl-7-(5-(4-methoxyphenyl)-1H-1,2,3-triazol-4-yl)-1H-indole;
4-(benzo[d][1,3]dioxol-4-yl)-5-(4-methoxyphenyl)-1H-1,2,3-triazole;
5-methoxy-2-(4-(3,4,5-trimethoxyphenyl)-1H-1,2,3-triazol-5-yl)phenol;
ethyl 5-methoxy-2-(4-(3,4,5-trimethoxyphenyl)-1H-1,2,3-triazol-5-yl)phenyl hydrogen phosphate;
4-(4-(3,4,5-trimethoxyphenyl)-1H-1,2,3-triazol-5-yl)pyridazine;
5-(4-(3,4,5-trimethoxyphenyl)-1H-1,2,3-triazol-5-yl)pyrimidine;
3-(4-(3,4,5-trimethoxyphenyl)-1H-1,2,3-triazol-5-yl)pyridine hydrochloride;
2-methoxy-5-(4-(3,4,5-trimethoxyphenyl)-1H-1,2,3-triazol-5-yl)benzenethiol;
sodium S-2-methoxy-5-(4-(3,4,5-trimethoxyphenyl)-1H-1,2,3-triazol-5-yl)phenyl phosphorothioate;
N-(2-methoxy-5-(4-(3,4,5-trimethoxyphenyl)-1H-1,2,3-triazol-5-yl)phenyl)acetamide;
2-methoxy-5-(4-(3,4,5-trimethoxyphenyl)-1H-1,2,3-triazol-5-yl)benzenaminium chloride;
5-methoxy-2-(4-(3,4,5-trimethoxyphenyl)-1H-1,2,3-triazol-5-yl)phenol;
2-methoxy-5-(4-(3,4,5-trimethoxyphenyl)-1H-1,2,3-triazol-5-yl)pyridine;
5-methoxy-2-(4-(3,4,5-trimethoxyphenyl)-1H-1,2,3-triazol-5-yl)pyridine;
sodium 2-methoxy-5-(4-(3,4,5-trimethoxyphenyl)-1H-1,2,3-triazol-5-yl)benzoate;
methyl 2-methoxy-5-(4-(3,4,5-trimethoxyphenyl)-1H-1,2,3-triazol-5-yl)benzoate;
sodium 2-methoxy-5-(4-(3,4,5-trimethoxyphenyl)-1H-1,2,3-triazol-5-yl)phenyl sulfate;
5-methoxy-2-(4-(3,4,5-trimethoxyphenyl)-1H-1,2,3-triazol-5-yl)aniline;
sodium 2,3-dimethoxy-5-(4-(3,4,5-trimethoxyphenyl)-1H-1,2,3-triazol-5-yl)phenyl phosphate;
sodium 5-methoxy-2-(4-(3,4,5-trimethoxyphenyl)-1H-1,2,3-triazol-5-yl)phenyl phosphate;
5-(4-(methylthio)phenyl)-4-(3,4,5-trimethoxyphenyl)-1H-1,2,3-triazole;
sodium 2-(methylthio)-5-(4-(3,4,5-trimethoxyphenyl)-1H-1,2,3-triazol-5-yl)phenyl phosphate;
2-(methylthio)-5-(4-(3,4,5-trimethoxyphenyl)-1H-1,2,3-triazol-5-yl)aniline;
5-(2,3-dihydrobenzofuran-6-yl)-4-(3,4,5-trimethoxyphenyl)-1H-1,2,3-triazole;
sodium 4-(4-(3,4,5-trimethoxyphenyl)-1H-1,2,3-triazol-5-yl)phenolate;
monosodium monosodium(II) mono(4-(4-(3,4,5-trimethoxyphenyl)-1H-1,2,3-triazol-5-yl)phenyl phosphate);
5-(4-(4-(3,4,5-trimethoxyphenyl)-1H-1,2,3-triazol-5-yl)phenyl)-1H-tetrazole;
1-methyl-5-(4-(4-(3,4,5-trimethoxyphenyl)-1H-1,2,3-triazol-5-yl)phenyl)-1H-tetrazole;
1-methyl-5-(4-(3,4,5-trimethoxyphenyl)-1H-1,2,3-triazol-5-yl)-1H-indole;
4-(4-(7-methoxybenzo[d][1,3]dioxol-5-yl)-1H-1,2,3-triazol-5-yl)pyridazine;
5-(4-(7-methoxybenzo[d][1,3]dioxol-5-yl)-1H-1,2,3-triazol-5-yl)pyrimidine;
3-(4-(7-methoxybenzo[d][1,3]dioxol-5-yl)-1H-1,2,3-triazol-5-yl)pyridine hydrochloride;
2-methoxy-5-(4-(7-methoxybenzo[d][1,3]dioxol-5-yl)-1H-1,2,3-triazol-5-yl)benzenethiol;
sodium S-2-methoxy-5-(4-(7-methoxybenzo[d][1,3]dioxol-5-yl)-1H-1,2,3-triazol-5-yl)phenyl phosphorothioate;
N-(2-methoxy-5-(4-(7-methoxybenzo[d][1,3]dioxol-5-yl)-1H-1,2,3-triazol-5-yl)phenyl)acetamide;
2-methoxy-5-(4-(7-methoxybenzo[d][1,3]dioxol-5-yl)-1H-1,2,3-triazol-5-yl)benzenaminium chloride;
5-methoxy-2-(4-(7-methoxybenzo[d][1,3]dioxol-5-yl)-1H-1,2,3-triazol-5-yl)phenol;
2-methoxy-5-(4-(7-methoxybenzo[d][1,3]dioxol-5-yl)-1H-1,2,3-triazol-5-yl)pyridine;
5-methoxy-2-(4-(7-methoxybenzo[d][1,3]dioxol-5-yl)-1H-1,2,3-triazol-5-yl)pyridine;
sodium 2-methoxy-5-(4-(7-methoxybenzo[d][1,3]dioxol-5-yl)-1H-1,2,3-triazol-5-yl)benzoate;
methyl 2-methoxy-5-(4-(7-methoxybenzo[d][1,3]dioxol-5-yl)-1H-1,2,3-triazol-5-yl)benzoate;
sodium 2-methoxy-5-(4-(7-methoxybenzo[d][1,3]dioxol-5-yl)-1H-1,2,3-triazol-5-yl)phenyl sulfate;
5-methoxy-2-(4-(7-methoxybenzo[d][1,3]dioxol-5-yl)-1H-1,2,3-triazol-5-yl)aniline;
sodium 2,3-dimethoxy-5-(4-(7-methoxybenzo[d][1,3]dioxol-5-yl)-1H-1,2,3-triazol-5-yl)phenyl phosphate;
sodium 5-methoxy-2-(4-(7-methoxybenzo[d][1,3]dioxol-5-yl)-1H-1,2,3-triazol-5-yl)phenyl phosphate;
4-(7-methoxybenzo[d][1,3]dioxol-5-yl)-5-(4-(methylthio)phenyl)-1H-1,2,3-triazole;
sodium 5-(4-(7-methoxybenzo[d][1,3]dioxol-5-yl)-1H-1,2,3-triazol-5-yl)-2-(methylthio)phenyl phosphate;
5-(4-(7-methoxybenzo[d][1,3]dioxol-5-yl)-1H-1,2,3-triazol-5-yl)-2-(methylthio)aniline;
5-(2,3-dihydrobenzofuran-6-yl)-4-(7-methoxybenzo[d][1,3]dioxol-5-yl)-1H-1,2,3-triazole;
sodium 4-(4-(7-methoxybenzo[d][1,3]dioxol-5-yl)-1H-1,2,3-triazol-5-yl)phenolate;
sodium 4-(4-(7-methoxybenzo[d][1,3]dioxol-5-yl)-1H-1,2,3-triazol-5-yl)phenyl phosphate;
5-(4-(4-(7-methoxybenzo[d][1,3]dioxol-5-yl)-1H-1,2,3-triazol-5-yl)phenyl)-1H-tetrazole;
5-(4-(4-(7-methoxybenzo[d][1,3]dioxol-5-yl)-1H-1,2,3-triazol-5-yl)phenyl)-1-methyl-1H-tetrazole;
5-(4-(7-methoxybenzo[d][1,3]dioxol-5-yl)-1H-1,2,3-triazol-5-yl)-1-methyl-1H-indole;

1-methyl-5-(5-(3,4,5-trimethoxyphenyl)-1H-1,2,3-triazol-4-yl)-1H-indole;
monosodium monosodium(II) mono(2-methoxy-5-(5-(3,4,5-trimethoxyphenyl)-1H-1,2,3-triazol-4-yl)phenyl phosphate);
N,N-dimethyl-4-(5-(3,4,5-trimethoxyphenyl)-1H-1,2,3-triazol-4-yl)aniline;
2-methoxy-5-(5-(3,4,5-trimethoxyphenyl)-1H-1,2,3-triazol-4-yl)benzenaminium chloride;
3-hydroxy-1-(2-methoxy-5-(5-(3,4,5-trimethoxyphenyl)-1H-1,2,3-triazol-4-yl)phenylamino)-1-oxopropan-2-aminium chloride;
5-(4-methoxyphenyl)-4-(2,4,5-trimethoxyphenyl)-1H-1,2,3-triazole;
5-p-tolyl-4-(2,4,5-trimethoxyphenyl)-1H-1,2,3-triazole;
5-(4-ethoxyphenyl)-4-(2,4,5-trimethoxyphenyl)-1H-1,2,3-triazole;
5-(4-ethylphenyl)-4-(2,4,5-trimethoxyphenyl)-1H-1,2,3-triazole;
5-(4-propoxyphenyl)-4-(2,4,5-trimethoxyphenyl)-1H-1,2,3-triazole;
5-(4-propylphenyl)-4-(2,4,5-trimethoxyphenyl)-1H-1,2,3-triazole;
5-(4-butoxyphenyl)-4-(2,4,5-trimethoxyphenyl)-1H-1,2,3-triazole;
5-(4-butylphenyl)-4-(2,4,5-trimethoxyphenyl)-1H-1,2,3-triazole;
5-(4-bromophenyl)-4-(2,4,5-trimethoxyphenyl)-1H-1,2,3-triazole;
5-(4-chlorophenyl)-4-(2,4,5-trimethoxyphenyl)-1H-1,2,3-triazole;
5-(4-fluorophenyl)-4-(2,4,5-trimethoxyphenyl)-1H-1,2,3-triazole;
5-(4-nitrophenyl)-4-(2,4,5-trimethoxyphenyl)-1H-1,2,3-triazole;
N,N-dimethyl-4-(4-(2,4,5-trimethoxyphenyl)-1H-1,2,3-triazol-5-yl)aniline;
5-(3,4-dimethoxyphenyl)-4-(2,4,5-trimethoxyphenyl)-1H-1,2,3-triazole;
2-methoxy-5-(4-(2,4,5-trimethoxyphenyl)-1H-1,2,3-triazol-5-yl)phenol;
4-(2,4,5-trimethoxyphenyl)-5-(3,4,5-trimethoxyphenyl)-1H-1,2,3-triazole;
5-(4-methoxyphenyl)-4-(2,3,5-trimethoxyphenyl)-1H-1,2,3-triazole;
5-p-tolyl-4-(2,3,5-trimethoxyphenyl)-1H-1,2,3-triazole;
5-(4-ethoxyphenyl)-4-(2,3,5-trimethoxyphenyl)-1H-1,2,3-triazole;
5-(4-ethylphenyl)-4-(2,3,5-trimethoxyphenyl)-1H-1,2,3-triazole;
5-(4-propoxyphenyl)-4-(2,3,5-trimethoxyphenyl)-1H-1,2,3-triazole;
5-(4-propylphenyl)-4-(2,3,5-trimethoxyphenyl)-1H-1,2,3-triazole;
5-(4-butoxyphenyl)-4-(2,3,5-trimethoxyphenyl)-1H-1,2,3-triazole;
5-(4-butylphenyl)-4-(2,3,5-trimethoxyphenyl)-1H-1,2,3-triazole;
5-(4-bromophenyl)-4-(2,3,5-trimethoxyphenyl)-1H-1,2,3-triazole;
5-(4-chlorophenyl)-4-(2,3,5-trimethoxyphenyl)-1H-1,2,3-triazole;
5-(4-fluorophenyl)-4-(2,3,5-trimethoxyphenyl)-1H-1,2,3-triazole;
5-(4-nitrophenyl)-4-(2,3,5-trimethoxyphenyl)-1H-1,2,3-triazole;
N,N-dimethyl-4-(4-(2,3,5-trimethoxyphenyl)-1H-1,2,3-triazol-5-yl)aniline;
5-(3,4-dimethoxyphenyl)-4-(2,3,5-trimethoxyphenyl)-1H-1,2,3-triazole;
2-methoxy-5-(4-(2,3,5-trimethoxyphenyl)-1H-1,2,3-triazol-5-yl)phenol;
4-(2,3,5-trimethoxyphenyl)-5-(3,4,5-trimethoxyphenyl)-1H-1,2,3-triazole;
4-(4-methoxyphenyl)-5-(2,3,4,5-tetramethoxyphenyl)-1H-1,2,3-triazole;
5-(2,3,4,5-tetramethoxyphenyl)-4-p-tolyl-1H-1,2,3-triazole;
4-(4-ethoxyphenyl)-5-(2,3,4,5-tetramethoxyphenyl)-1H-1,2,3-triazole;
4-(4-ethylphenyl)-5-(2,3,4,5-tetramethoxyphenyl)-1H-1,2,3-triazole;
4-(4-propoxyphenyl)-5-(2,3,4,5-tetramethoxyphenyl)-1H-1,2,3-triazole;
4-(4-propylphenyl)-5-(2,3,4,5-tetramethoxyphenyl)-1H-1,2,3-triazole;
4-(4-butoxyphenyl)-5-(2,3,4,5-tetramethoxyphenyl)-1H-1,2,3-triazole;
4-(4-butylphenyl)-5-(2,3,4,5-tetramethoxyphenyl)-1H-1,2,3-triazole;
4-(4-bromophenyl)-5-(2,3,4,5-tetramethoxyphenyl)-1H-1,2,3-triazole;
4-(4-chlorophenyl)-5-(2,3,4,5-tetramethoxyphenyl)-1H-1,2,3-triazole;
4-(4-fluorophenyl)-5-(2,3,4,5-tetramethoxyphenyl)-1H-1,2,3-triazole;
4-(4-nitrophenyl)-5-(2,3,4,5-tetramethoxyphenyl)-1H-1,2,3-triazole;
N,N-dimethyl-4-(5-(2,3,4,5-tetramethoxyphenyl)-1H-1,2,3-triazol-4-yl)aniline;
4-(3,4-dimethoxyphenyl)-5-(2,3,4,5-tetramethoxyphenyl)-1H-1,2,3-triazole;
2-methoxy-5-(5-(2,3,4,5-tetramethoxyphenyl)-1H-1,2,3-triazol-4-yl)phenol;
5-(2,3,4,5-tetramethoxyphenyl)-4-(3,4,5-trimethoxyphenyl)-1H-1,2,3-triazole;
5-(2,3-dihydrobenzo[b][1,4]dioxin-6-yl)-4-(3,4-dimethoxyphenyl)-1H-1,2,3-triazole;
2-(5-(3,4-dimethylphenyl)-1H-1,2,3-triazol-4-yl)-4-ethyl-5-methoxyphenol;
2-(5-(4-chlorophenyl)-1H-1,2,3-triazol-4-yl)-4-ethyl-5-methoxyphenol;
5-methoxy-2-(5-phenyl-1H-1,2,3-triazol-4-yl)-4-propylphenol;
4-ethyl-5-methoxy-2-(5-p-tolyl-1H-1,2,3-triazol-4-yl)phenol;
2-(5-(4-aminophenyl)-1H-1,2,3-triazol-4-yl)-4-ethyl-5-methoxyphenol;
4-ethyl-5-methoxy-2-(5-(4-(trifluoromethyl)phenyl)-1H-1,2,3-triazol-4-yl)phenol;
4-ethyl-5-methoxy-2-(5-(4-methoxyphenyl)-1H-1,2,3-triazol-4-yl)phenol; or
4-(4-bromophenyl)-5-(3,4,5-trimethoxyphenyl)-1H-1,2,3-triazole;
or pharmaceutically acceptable salts, solvates, clathrates, or prodrugs thereof.

In another embodiment, the invention relates to compounds selected from the group consisting of:
2-amino-N-(2-methoxy-5-(4-(3,4,5-trimethoxyphenyl)-1H-1,2,3-triazol-5-yl)phenyl)acetamide hydrochloride;
2-amino-3-hydroxy-N-(2-methoxy-5-(4-(3,4,5-trimethoxyphenyl)-1H-1,2,3-triazol-5-yl)phenyl)propanamide hydrochloride;

2-amino-N-(2-methoxy-5-(4-(3,4,5-trimethoxyphenyl)-1H-1,2,3-triazol-5-yl)phenyl)propanamide;
2-amino-N-(2-methoxy-5-(4-(3,4,5-trimethoxyphenyl)-1H-1,2,3-triazol-5-yl)phenyl)-4-(methylthio)butanamide hydrochloride;
2-amino-N-(2-methoxy-5-(4-(3,4,5-trimethoxyphenyl)-1H-1,2,3-triazol-5-yl)phenyl)butanamide hydrochloride;
2-amino-N-(2-methoxy-5-(4-(3,4,5-trimethoxyphenyl)-1H-1,2,3-triazol-5-yl)phenyl)-3-phenylpropanamide hydrochloride;
2-amino-N-(2-methoxy-5-(4-(3,4,5-trimethoxyphenyl)-1H-1,2,3-triazol-5-yl)phenyl)-4-methylpentanamide hydrochloride;
2-amino-N-(2-methoxy-5-(4-(3,4,5-trimethoxyphenyl)-1H-1,2,3-triazol-5-yl)phenyl)-4-methylpentanamide hydrochloride;
1-(2-methoxy-5-(4-(3,4,5-trimethoxyphenyl)-1H-1,2,3-triazol-5-yl)phenylamino)-3-methyl-1-oxobutan-2-aminium chloride;
1-(2-methoxy-5-(4-(3,4,5-trimethoxyphenyl)-1H-1,2,3-triazol-5-yl)phenylamino)-3-methyl-1-oxopentan-2-aminium chloride;
3-hydroxy-1-(2-methoxy-5-(4-(3,4,5-trimethoxyphenyl)-1H-1,2,3-triazol-5-yl)phenylamino)-1-oxobutan-2-aminium chloride;
3-(4-hydroxyphenyl)-1-(2-methoxy-5-(4-(3,4,5-trimethoxyphenyl)-1H-1,2,3-triazol-5-yl)phenylamino)-1-oxopropan-2-aminium chloride;
2-(2-methoxy-5-(4-(3,4,5-trimethoxyphenyl)-1,2,3-triazol-5-yl)phenylamino)-2-oxo-1-phenylethanaminium chloride;
3-(1H-indol-2-yl)-1-(2-methoxy-5-(4-(3,4,5-trimethoxyphenyl)-1H-1,2,3-triazol-5-yl)phenylamino)-1-oxopropan-2-aminium chloride;
3-(benzofuran-2-yl)-1-(2-methoxy-5-(4-(3,4,5-trimethoxyphenyl)-1H-1,2,3-triazol-5-yl)phenylamino)-1-oxopropan-2-aminium chloride;
3-carboxy-1-(2-methoxy-5-(4-(3,4,5-trimethoxyphenyl)-1H-1,2,3-triazol-5-yl)phenylamino)-1-oxopropan-2-aminium chloride;
4-carboxy-1-(2-methoxy-5-(4-(3,4,5-trimethoxyphenyl)-1H-1,2,3-triazol-5-yl)phenylamino)-1-oxobutan-2-aminium chloride;
5-amino-1-(2-methoxy-5-(4-(3,4,5-trimethoxyphenyl)-1H-1,2,3-triazol-5-yl)phenylamino)-1,5-dioxopentan-2-aminium chloride;
4-amino-1-(2-methoxy-5-(4-(3,4,5-trimethoxyphenyl)-1H-1,2,3-triazol-5-yl)phenylamino)-1,4-dioxobutan-2-aminium chloride;
3-(1H-imidazol-5-yl)-1-(2-methoxy-5-(4-(3,4,5-trimethoxyphenyl)-1H-1,2,3-triazol-5-yl)phenylamino)-1-oxopropan-2-aminium chloride;
6-amino-1-(2-methoxy-5-(4-(3,4,5-trimethoxyphenyl)-1H-1,2,3-triazol-5-yl)phenylamino)-1-oxohexan-2-aminium chloride;
5-guanidino-1-(2-methoxy-5-(4-(3,4,5-trimethoxyphenyl)-1H-1,2,3-triazol-5-yl)phenylamino)-1-oxopentan-2-aminium chloride;
4-(2-methoxy-5-(4-(3,4,5-trimethoxyphenyl)-1H-1,2,3-triazol-5-yl)phenylamino)-4-oxobutanoic acid;
5-(2-methoxy-5-(4-(3,4,5-trimethoxyphenyl)-1H-1,2,3-triazol-5-yl)phenylamino)-5-oxopentanoic acid;
3-(2-methoxy-5-(4-(3,4,5-trimethoxyphenyl)-1H-1,2,3-triazol-5-yl)phenylamino)-3-oxopropan-1-aminium chloride;
N-(2-methoxy-5-(4-(3,4,5-trimethoxyphenyl)-1H-1,2,3-triazol-5-yl)phenyl)-3-(2-methoxyethoxy)propanamide;
3-(2-PEG)-N-(2-methoxy-5-(4-(3,4,5-trimethoxyphenyl)-1H-1,2,3-triazol-5-yl)phenyl)butyramide;
N-(2-methoxy-5-(4-(3,4,5-trimethoxyphenyl)-1H-1,2,3-triazol-5-yl)phenyl)-3-(2-(methylamino)ethylamino)propanamide;
3-PEG-N-(2-methoxy-5-(4-(3,4,5-trimethoxyphenyl)-1H-1,2,3-triazol-5-yl)phenylamino)-2-oxoethyl)butyramide;
4-(2-(2-methoxy-5-(4-(3,4,5-trimethoxyphenyl)-1H-1,2,3-triazol-5-yl)phenylamino)-2-oxoethylamino)-4-oxobutanoic acid;
2-methoxyethyl 2-methoxy-5-(4-(3,4,5-trimethoxyphenyl)-1H-1,2,3-triazol-5-yl)phenylcarbamate;
PEG-2-methoxy-5-(4-(3,4,5-trimethoxyphenyl)-1H-1,2,3-triazol-5-yl)phenylcarbamate;
3-amino-4-(2-(5-guanidino-1-(2-methoxy-5-(4-(3,4,5-trimethoxyphenyl)-1H-1,2,3-triazol-5-yl)phenylamino)-1-oxopentan-2-ylamino)-2-oxoethylamino)-4-oxobutanoic acid; or
2-amino-N-(2-methoxy-5-(4-(3,4,5-trimethoxyphenyl)-1H-1,2,3-triazol-5-yl)phenyl)propanamide hydrochloride;
  or pharmaceutically acceptable salts, solvates, clathrates, or prodrugs thereof.

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values for variables (e.g., values shown in the exemplary compounds disclosed herein) in any chemical formula disclosed herein can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features, embodiments or substituents.

In another embodiment, the invention relates to pharmaceutical compositions that comprise a compound of any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof, as an active ingredient, and a pharmaceutically acceptable carrier or vehicle. The compositions are useful for treating or preventing proliferative disorders such as cancer or macular degeneration.

In another embodiment, the invention relates to methods for inhibiting tubulin polymerization in a cell comprising contacting the cell with an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof.

In another embodiment, the invention relates to methods for promoting microtubule depolymerization in a cell comprising contacting the cell with an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof.

In another embodiment, the invention relates to methods for treating or preventing a proliferative disorder in a subject in need thereof comprising administering an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof.

In another embodiment, the invention relates to methods for treating cancer in a subject in need thereof comprising administering an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof. In one aspect of this embodiment, the method involves treating a subject with multidrug resistant cancer. In another aspect of this embodiment, the method involves treating a subject having a solid tumor. In another aspect of this embodiment, the method involves treating a subject having a hematological malignancy.

In another embodiment, the invention relates to methods for treating cancer in a subject in need thereof comprising administering an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof, and an additional therapeutic agent. In one aspect of this embodiment, the additional therapeutic agent is another anti-cancer agent.

In another embodiment, the invention relates to methods for blocking, occluding, or otherwise disrupting blood flow in neovasculature, comprising contacting the neovasculature with an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof, and an additional therapeutic agent.

In another embodiment, the invention relates to methods blocking, occluding, or otherwise disrupting blood flow in neovasculature in a subject, comprising administering to the subject an effective amount of a compound represented by any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, or prodrug thereof, and an additional therapeutic agent.

Exemplary Compounds of the Invention

Exemplary compounds of the invention are depicted in Table 1 below.

TABLE 1

| Compound No. | Structure | Chemical Name |
|---|---|---|
| 1 | 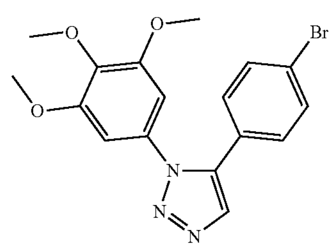 [SMILES: COc1cc(-n2nncc2-c2ccc(Br)cc2)cc(OC)c1OC] | 1-(3,4,5-trimethoxy-phenyl)-5-(4-bromo-phenyl)-1H-[1,2,3]triazole |
| 2 | 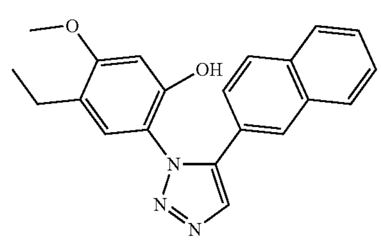 [SMILES: CCc1cc(-n2nncc2-c2ccc3ccccc3c2)c(O)cc1OC] | 1-(2-hydroxy-4-methoxy-5-ethyl-phenyl)-5-(naphthylen-2-yl)-1H-[1,2,3]triazole |
| 3 | 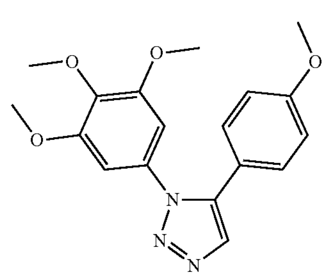 [SMILES: COc1ccc(-c2cnnn2-c2cc(OC)c(OC)c(OC)c2)cc1] | 1-(3,4,5-trimethoxy-phenyl)-5-(4-methoxy-phenyl)-1H-[1,2,3]triazole |

TABLE 1-continued

| Compound No. | Structure | Chemical Name |
|---|---|---|
| 4 | 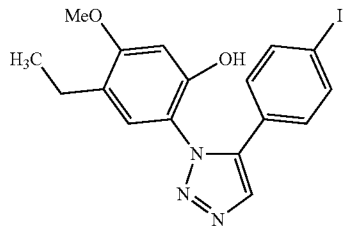 [SMILES: CCc1cc(-n2nncc2-c2ccc(I)cc2)c(O)cc1OC] | 1-(2-hydroxy-4-methoxy-5-ethyl-phenyl)-5-(4-iodo-phenyl)-1H-[1,2,3]triazole |
| 5 | 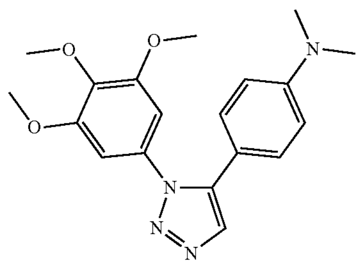 | 1-(3,4,5-trimethoxy-phenyl)-5-[4-(N,N-dimethylamino)-phenyl]-1H-[1,2,3]triazole |
| 6 | 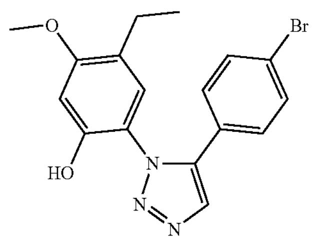 [SMILES: CCc1cc(-n2nncc2-c2ccc(Br)cc2)c(O)cc1OC] | 1-(2-hydroxy-4-methoxy-5-ethyl-phenyl)-5-(4-bromo-phenyl)-1H-[1,2,3]triazole |
| 7 | 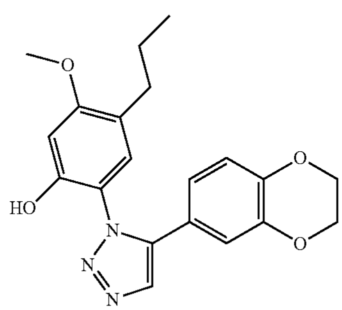 [SMILES: CCCc1cc(-n2nncc2-c2ccc3c(c2)OCCO3)c(O)cc1OC] | 1-(2-hydroxy-4-methoxy-5-(2,3-dihydro-benzo[1,4]dioxin-6-yl)-5-(4-bromo-phenyl)-1H-[1,2,3]triazole |
| 8 | 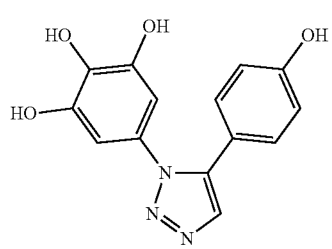 [SMILES: Oc1ccc(-c2cnnn2-c2cc(O)c(O)c(O)c2)cc1] | 1-(3,4,5-hydroxy-phenyl)-5-(4-hyoxy-phenyl)-1H-[1,2,3]triazole |
| 9 | 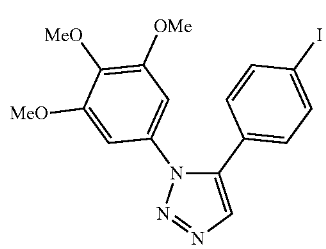 [SMILES: COc1cc(-n2nncc2-c2ccc(I)cc2)cc(OC)c1OC] | 1-(3,4,5-trimethoxy-phenyl)-5-(4-iodo-phenyl)-1H-[1,2,3]triazole |

TABLE 1-continued

| Compound No. | Structure | Chemical Name |
|---|---|---|
| 10 | 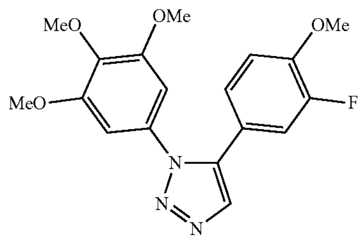 [SMILES: COc1ccc(-c2cnnn2-c2cc(OC)c(OC)c(OC)c2)cc1F] | 1-(3,4,5-trimethoxy-phenyl)-5-(3-fluoro-4-methoxy-phenyl)-1H-[1,2,3]triazole |
| 11 | 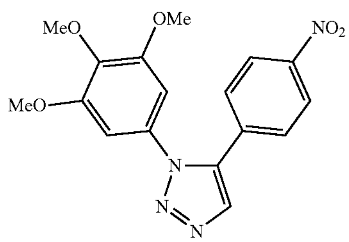 | 1-(3,4,5-trimethoxy-phenyl)-5-(4-nitro-phenyl)-1H-[1,2,3]triazole |
| 12 | 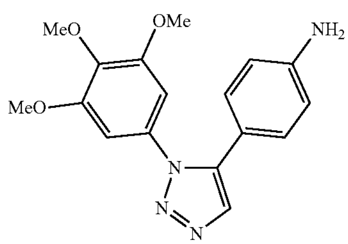 [SMILES: COc1cc(-n2nncc2-c2ccc([N+](=O)[O-])cc2)cc(OC)c1OC] | 1-(3,4,5-trimethoxy-phenyl)-5-(4-amino-phenyl)-1H-[1,2,3]triazole |
| 13 | 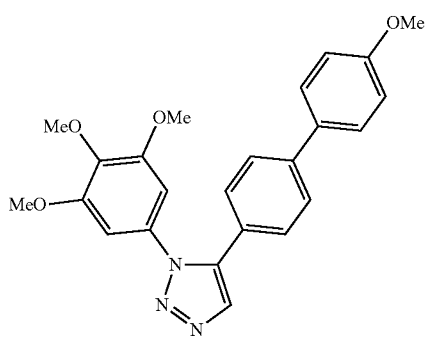 [SMILES: COc1ccc(-c2ccc(-c3cnnn3-c3cc(OC)c(OC)c(OC)c3)cc2)cc1] | 1-(3,4,5-trimethoxy-phenyl)-5-(4'-methoxy-biphenyl-4-yl)-1H-[1,2,3]triazole |
| 14 | 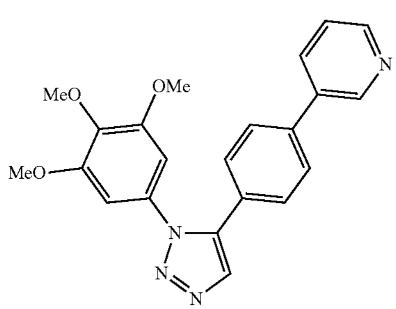 [SMILES: COc1cc(-n2nncc2-c2ccc(-c3cccnc3)cc2)cc(OC)c1OC] | 1-(3,4,5-trimethoxy-phenyl)-5-[4-(pyridin-3-yl)-phenyl]-1H-[1,2,3]triazole |

TABLE 1-continued

| Compound No. | Structure | Chemical Name |
|---|---|---|
| 15 | 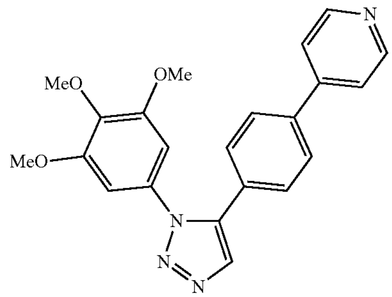 [SMILES: COc1cc(-n2nncc2-c2ccc(-c3ccncc3)cc2)cc(OC)c1OC] | 1-(3,4,5-trimethoxy-phenyl)-5-[4-(pyridin-4-yl)-phenyl]-1H-[1,2,3]triazole |
| 16 | 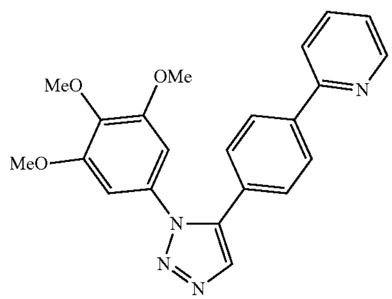 [SMILES: COc1cc(-n2nncc2-c2ccc(-c3ccccn3)cc2)cc(OC)c1OC] | 1-(3,4,5-trimethoxy-phenyl)-5-[4-(pyridin-2-yl)-phenyl]-1H-[1,2,3]triazole |
| 17 | 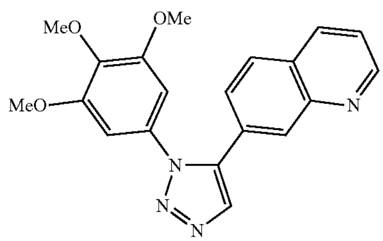 [SMILES: COc1cc(-n2nncc2-c2ccc3cccnc3c2)cc(OC)c1OC] | 1-(3,4,5-trimethoxy-phenyl)-5-(quinolin-7-yl)-1H-[1,2,3]triazole |
| 18 | 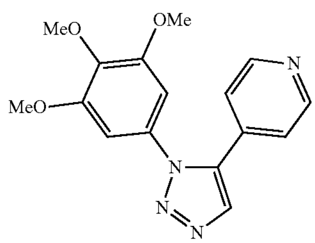 [SMILES: COc1cc(-n2nncc2-c2ccncc2)cc(OC)c1OC] | 1-(3,4,5-trimethoxy-phenyl)-5-(pyridine-4-yl)-1H-[1,2,3]triazole |
| 19 | 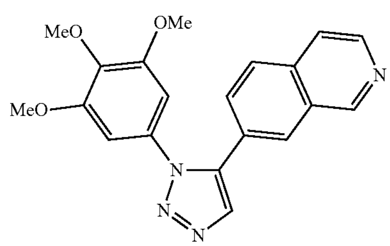 [SMILES: COc1cc(-n2nncc2-c2ccc3ccncc3c2)cc(OC)c1OC] | 1-(3,4,5-trimethoxy-phenyl)-5-(isoquinolin-7-yl)-1H-[1,2,3]triazole |
| 20 | 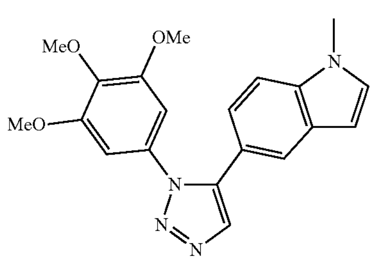 [SMILES: COc1cc(-n2nncc2-c2ccc3c(ccn3C)c2)cc(OC)c1OC] | 1-(3,4,5-trimethoxy-phenyl)-5-(1-methyl-1H-indol-5-yl)-1H-[1,2,3]triazole |

TABLE 1-continued

| Compound No. | Structure | Chemical Name |
|---|---|---|
| 21 | 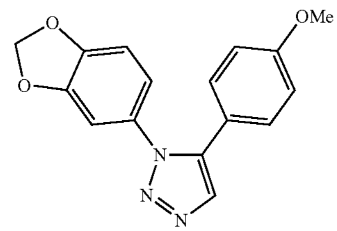 [SMILES: COc1ccc(-c2cnnn2-c2ccc3c(c2)OCO3)cc1] | 1-(benzo[1,3]dioxol-5-yl)-5-(4-methoxy-phenyl)-1H-[1,2,3]triazole |
| 22 | 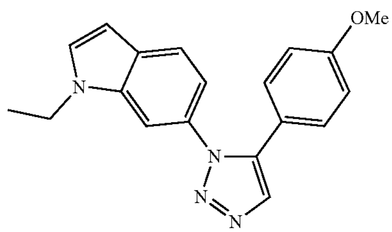 [SMILES: CCn1ccc2ccc(-n3nncc3-c3ccc(OC)cc3)cc21] | 1-(1-ethyl-1H-indol-6-yl)-5-(4-methoxy-phenyl)-1H-[1,2,3]triazole |
| 23 | 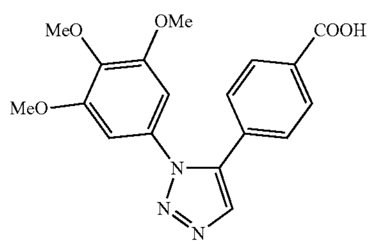 [SMILES: COc1cc(-n2nncc2-c2ccc(C(=O)O)cc2)cc(OC)c1OC] | 1-(3,4,5-trimethoxy-phenyl)-5-(4-carboxy-phenyl)-1H-[1,2,3]triazole |
| 24 | 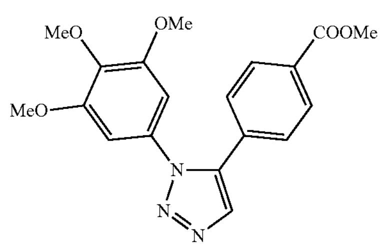 [SMILES: COC(=O)c1ccc(-c2cnnn2-c2cc(OC)c(OC)c(OC)c2)cc1] | 1-(3,4,5-trimethoxy-phenyl)-5-(4-carbomethoxy-phenyl)-1H-[1,2,3]triazole |
| 25 | 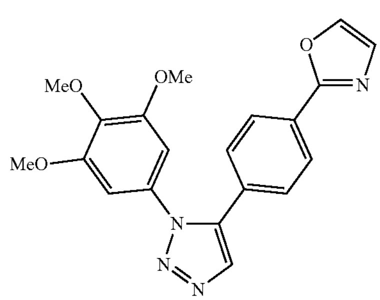 [SMILES: COc1cc(-n2nncc2-c2ccc(-c3ncco3)cc2)cc(OC)c1OC] | 1-(3,4,5-trimethoxy-phenyl)-5-[4-(oxazol-2-yl)-phenyl]-1H-[1,2,3]triazole |
| 26 | 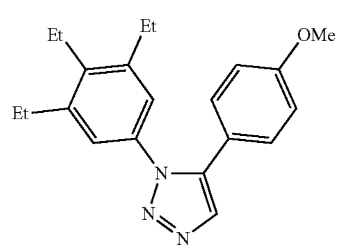 [SMILES: CCc1cc(-n2nncc2-c2ccc(OC)cc2)cc(CC)c1CC] | 1-(3,4,5-triethyl-phenyl)-5-(4-methoxy-phenyl)-1H-[1,2,3]triazole |

TABLE 1-continued

| Compound No. | Structure | Chemical Name |
|---|---|---|
| 27 | 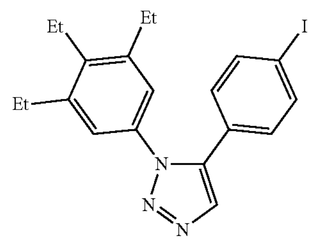 [SMILES: CCc1cc(-n2nncc2-c2ccc(I)cc2)cc(CC)c1CC] | 1-(3,4,5-triethyl-phenyl)-5-(4-iodo-phenyl)-1H-[1,2,3]triazole |
| 28 | 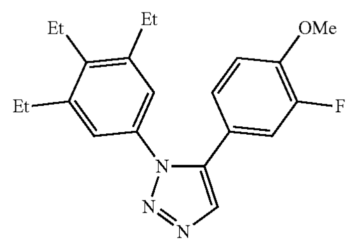 [SMILES: CCc1cc(-n2nncc2-c2ccc(OC)c(F)c2)cc(CC)c1CC] | 1-(3,4,5-triethyl-phenyl)-5-(3-fluoro-4-methoxy-phenyl)-1H-[1,2,3]triazole |
| 29 | 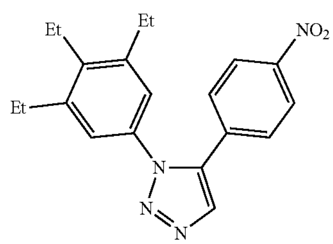 [SMILES: CCc1cc(-n2nncc2-c2ccc([N+](=O)[O-])cc2)cc(CC)c1CC] | 1-(3,4,5-triethyl-phenyl)-5-(4-nitro-phenyl)-1H-[1,2,3]triazole |
| 30 | 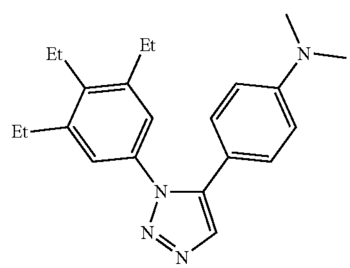 [SMILES: CCc1cc(-n2nncc2-c2ccc(N(C)C)cc2)cc(CC)c1CC] | 1-(3,4,5-triethyl-phenyl)-5-[4-(N,N-dimethylamino)-phenyl]-1H-[1,2,3]triazole |
| 31 | 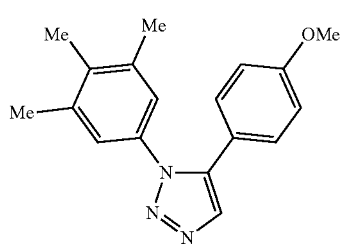 [SMILES: COc1ccc(-c2cnnn2-c2cc(C)c(C)c(C)c2)cc1] | 1-(3,4,5-trimethyl-phenyl)-5-(4-methoxy-phenyl)-1H-[1,2,3]triazole |
| 32 | 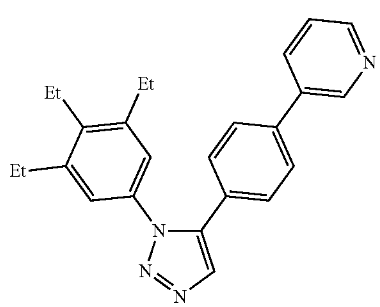 [SMILES: CCc1cc(-n2nncc2-c2ccc(-c3cccnc3)cc2)cc(CC)c1CC] | 1-(3,4,5-triethyl-phenyl)-5-[4-(pyridin-3-yl)-phenyl]-1H-[1,2,3]triazole |

TABLE 1-continued

| Compound No. | Structure | Chemical Name |
|---|---|---|
| 33 | 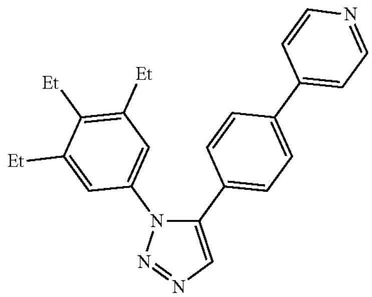 [SMILES: CCc1cc(-n2nncc2-c2ccc(-c3ccncc3)cc2)cc(CC)c1CC] | 1-(3,4,5-triethyl-phenyl)-5-[4-(pyridine-4-yl)-phenyl]-1H-[1,2,3]triazole |
| 34 | 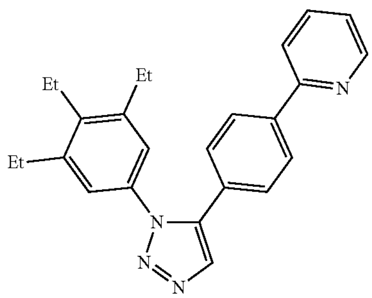 [SMILES: CCc1cc(-n2nncc2-c2ccc(-c3ccccn3)cc2)cc(CC)c1CC] | 1-(3,4,5-triethyl-phenyl)-5-[4-(pyridine-2-yl)-phenyl]-1H-[1,2,3]triazole |
| 35 | 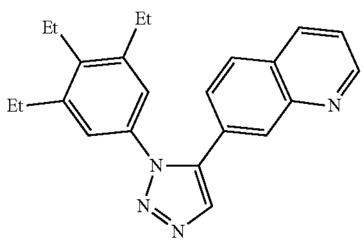 [SMILES: CCc1cc(-n2nncc2-c2ccc3cccnc3c2)cc(CC)c1CC] | 1-(3,4,5-triethyl-phenyl)-5-(quinolin-7-yl)-1H-[1,2,3]triazole |
| 36 | 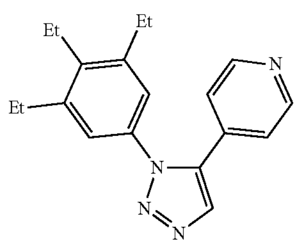 [SMILES: CCc1cc(-n2nncc2-c2ccncc2)cc(CC)c1CC] | 1-(3,4,5-triethyl-phenyl)-5-(pyridine-4-yl)-1H-[1,2,3]triazole |
| 37 | 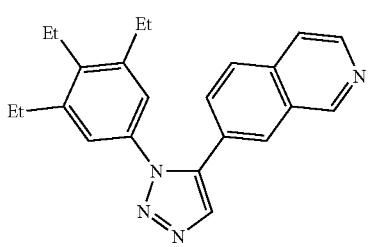 [SMILES: CCc1cc(-n2nncc2-c2ccc3ccncc3c2)cc(CC)c1CC] | 1-(3,4,5-triethyl-phenyl)-5-(isoquinolin-7-yl)-1H-[1,2,3]triazole |
| 38 | 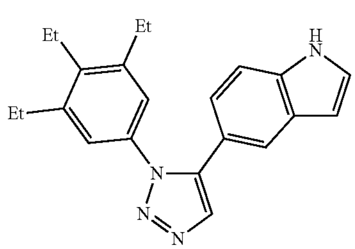 [SMILES: CCc1cc(-n2nncc2-c2ccc3[nH]ccc3c2)cc(CC)c1CC] | 1-(3,4,5-triethyl-phenyl)-5-(1H-indol-5-yl)-1H-[1,2,3]triazole |

TABLE 1-continued

| Compound No. | Structure | Chemical Name |
|---|---|---|
| 39 | 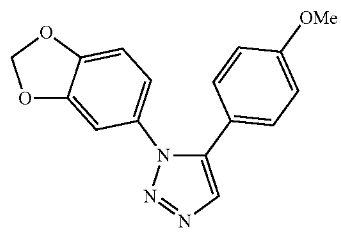 [SMILES: COc1ccc(-c2cnnn2-c2ccc3c(c2)OCO3)cc1] | 1-(benzo[1,3]dioxol-5-yl)-5-(4-methoxy-phenyl)-1H-[1,2,3]triazole |
| 40 | 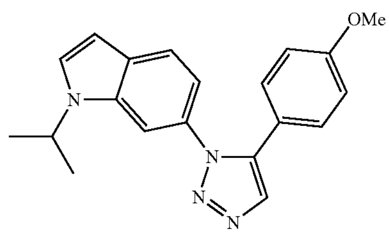 [SMILES: COc1ccc(-c2cnnn2-c2ccc3ccn(C(C)C)c3c2)cc1] | 1-(1-isopropyl-1H-indol-6-yl)-5-(4-methoxy-phenyl)-1H-[1,2,3]triazole |
| 41 | 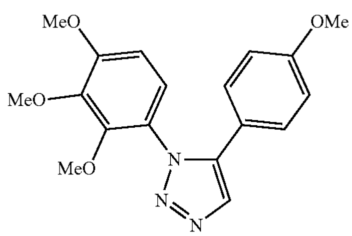 [SMILES: COc1ccc(-c2cnnn2-c2ccc(OC)c(OC)c2OC)cc1] | 1-(2,3,4-trimethoxy-phenyl)-5-(4-methoxy-phenyl)-1H-[1,2,3]triazole |
| 42 | 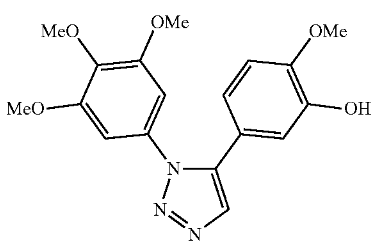 [SMILES: COc1ccc(-c2cnnn2-c2cc(OC)c(OC)c(OC)c2)cc1O] | 1-(3,4,5-trimethoxy-phenyl)-5-(3-hydroxy-4-methoxy-phenyl)-1H-[1,2,3]triazole |
| 43 | 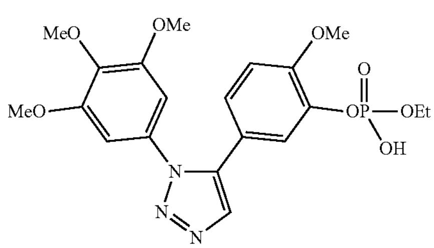 | O-ethyl-O-{2-methoxy-5-[1-(3,4,5-trimethoxy-phenyl)-1H-[1,2,3]triazol-5-yl]-phenyl}-phosphate |
| 44 | 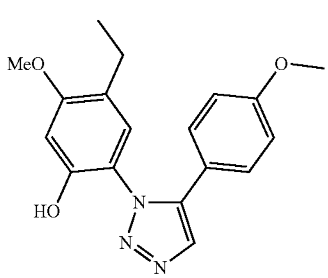 [SMILES: CCc1cc(-n2nncc2-c2ccc(OC)cc2)c(O)cc1OC] | 1-(2-hydroxy-4-methoxy-5-ethyl-phenyl)-5-(4-methoxy-phenyl)-1H-[1,2,3]triazole |

TABLE 1-continued

| Compound No. | Structure | Chemical Name |
| --- | --- | --- |
| 45 | 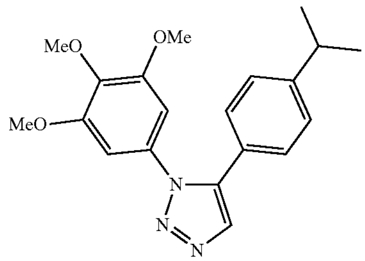 [SMILES: COc1cc(-n2nncc2-c2ccc(C(C)C)cc2)cc(OC)c1OC] | 1-(3,4,5-trimethoxy-phenyl)-5-(4-isopropyl-phenyl)-1H-[1,2,3]triazole |
| 46 | 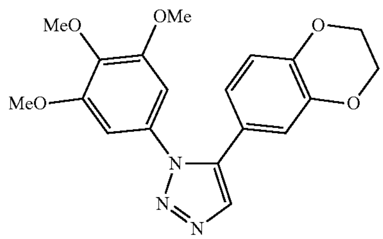 [SMILES: COc1cc(-n2nncc2-c2ccc3c(c2)OCCO3)cc(OC)c1OC] | 1-(3,4,5-trimethoxy-phenyl)-5-(2,3-dihydro-benzo[1,4]dioxine-6-yl)-1H-[1,2,3]triazole |
| 47 | 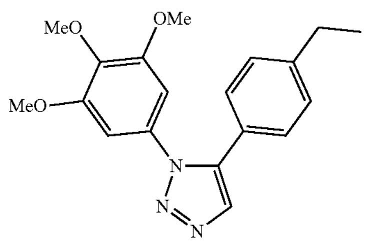 [SMILES: CCc1ccc(-c2cnnn2-c2cc(OC)c(OC)c(OC)c2)cc1] | 1-(3,4,5-trimethoxy-phenyl)-5-(4-ethyl-phenyl)-1H-[1,2,3]triazole |
| 48 | 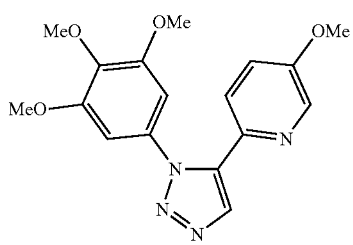 [SMILES: COc1ccc(-c2cnnn2-c2cc(OC)c(OC)c(OC)c2)nc1] | 1-(3,4,5-trimethoxy-phenyl)-5-(5-methoxy-pyridine-2-yl)-1H-[1,2,3]triazole |
| 49 | 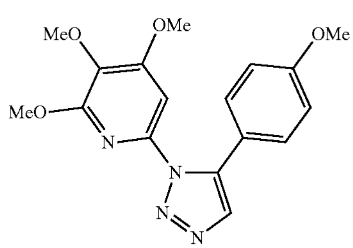 [SMILES: COc1ccc(-c2cnnn2-c2cc(OC)c(OC)c(OC)n2)cc1] | 1-(4,5,6-trimethoxy-pyridin-2-yl)-5-(4-methoxy-phenyl)-1H-[1,2,3]triazole |
| 50 | 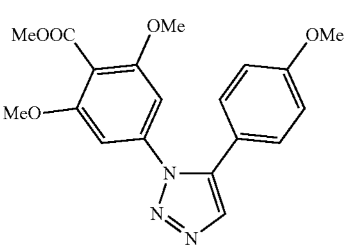 [SMILES: COC(=O)c1c(OC)cc(-n2nncc2-c2ccc(OC)cc2)cc1OC] | 1-(3,5-dimethoxy-4-carbomethoxy-phenyl)-5-(4-methoxy-phenyl)-1H-[1,2,3]triazole |

TABLE 1-continued

| Compound No. | Structure | Chemical Name |
| --- | --- | --- |
| 51 | 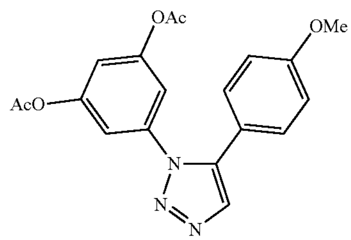 [SMILES: COc1ccc(-c2cnnn2-c2cc(OC(C)=O)cc(OC(C)=O)c2)cc1] | 1-(3,5-diacetoxy-phenyl)-5-(4-methoxy-phenyl)-1H-[1,2,3]triazole |
| 52 | 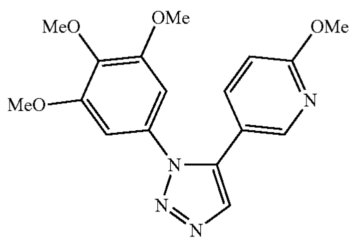 [SMILES: COc1ccc(-c2cnnn2-c2cc(OC)c(OC)c(OC)c2)cn1] | 1-(3,4,5-trimethoxy-phenyl)-5-(2-methoxy-pyridine-5-yl)-1H-[1,2,3]triazole |
| 53 | 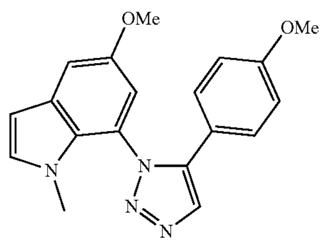 [SMILES: COc1ccc(-c2cnnn2-c2cc(OC)cc3ccn(C)c23)cc1] | 1-(1-methyl-5-methoxy-1H-indol-7-yl)-5-(4-methoxy-phenyl)-1H-[1,2,3]triazole |
| 54 | 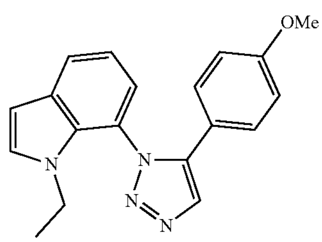 [SMILES: CCn1ccc2cccc(-n3nncc3-c3ccc(OC)cc3)c21] | 1-(1-methyl-1H-indol-7-yl)-5-(4-methoxy-phenyl)-1H-[1,2,3]triazole |
| 55 | 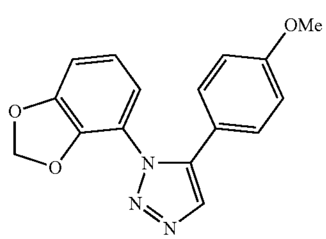 [SMILES: COc1ccc(-c2cnnn2-c2cccc3c2OCO3)cc1] | 1-(Benzo[1,3]dioxol-4-yl)-5-(4-methoxy-phenyl)-1H-[1,2,3]triazole |
| 56 | 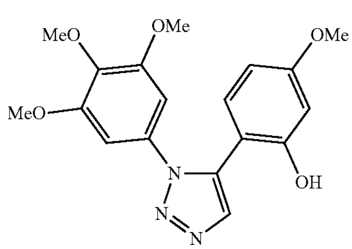 [SMILES: COc1ccc(-c2cnnn2-c2cc(OC)c(OC)c(OC)c2)c(O)c1] | 1-(3,4,5-trimethoxy-phenyl)-5-(2-hydroxy-4-methoxy-phenyl)-1H-[1,2,3]triazole |

TABLE 1-continued

| Compound No. | Structure | Chemical Name |
|---|---|---|
| 57 | 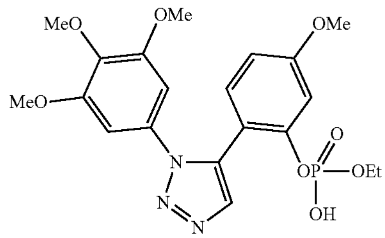 | O-ethyl-O-{5-methoxy-2-[1-(3,4,5-trimethoxy-phenyl)-1H-[1,2,3]triazol-5-yl]-phenyl}-phosphate |
| 58 | 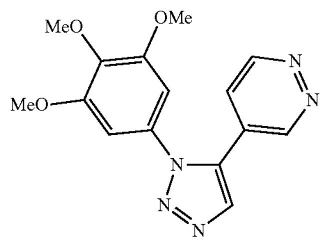 [SMILES: COc1cc(-n2nncc2-c2ccnnc2)cc(OC)c1OC] | 1-(3,4,5-trimethoxy-phenyl)-5-(pyridazin-4-yl)-1H-[1,2,3]triazole |
| 59 | 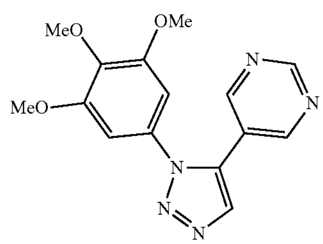 [SMILES: COc1cc(-n2nncc2-c2cncnc2)cc(OC)c1OC] | 1-(3,4,5-trimethoxy-phenyl)-5-(pyrimidin-5-yl)-1H-[1,2,3]triazole |
| 60 | 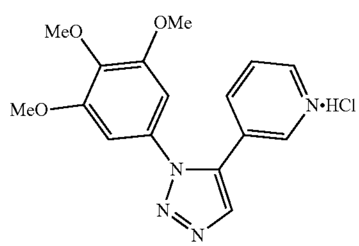 | 1-(3,4,5-trimethoxy-phenyl)-5-(pyridin-2-yl)-1H-[1,2,3]triazole, hydrochloric acid salt |
| 61 | 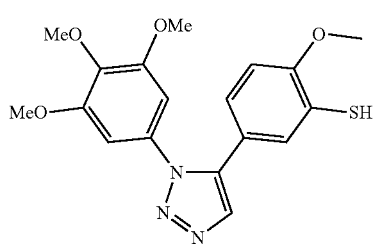 [SMILES: COc1ccc(-c2cnnn2-c2cc(OC)c(OC)c(OC)c2)cc1S] | 1-(3,4,5-trimethoxy-phenyl)-5-(2-mercapto-4-methoxy-phenyl)-1H-[1,2,3]triazole |
| 62 | 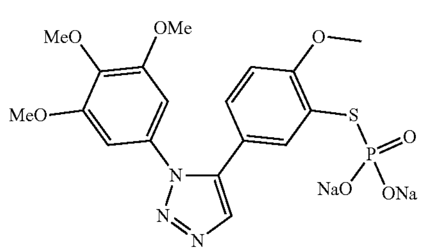 | S-{2-methoxy-5-[1-(3,4,5-trimethoxy-phenyl)-1H-[1,2,3]triazol-5-yl]-phenyl}-thiophosphate, disodium salt |

| Compound No. | Structure | Chemical Name |
|---|---|---|
| 63 | 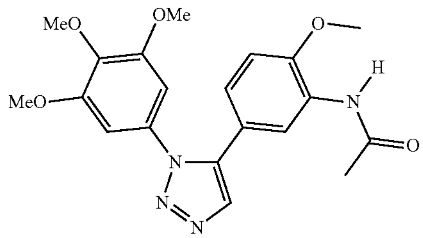 [SMILES: COc1ccc(-c2cnnn2-c2cc(OC)c(OC)c(OC)c2)cc1NC(C)=O] | 1-(3,4,5-trimethoxy-phenyl)-5-(3-acetamido-4-methoxy-phenyl)-1H-[1,2,3]triazole |
| 64 | 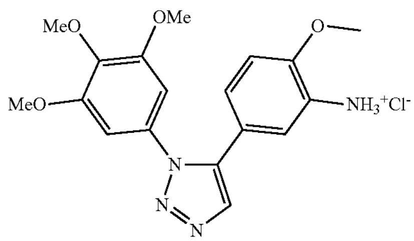 | 1-(3,4,5-trimethoxy-phenyl)-5-(3-amino-4-methoxy-phenyl)-1H-[1,2,3]triazole, hydrochloric acid salt |
| 65 | 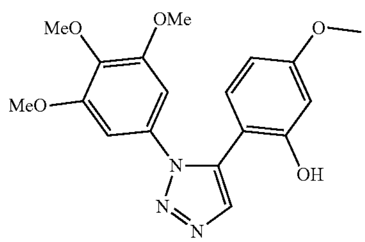 [SMILES: COc1ccc(-c2cnnn2-c2cc(OC)c(OC)c(OC)c2)c(O)c1] | 1-(3,4,5-trimethoxy-phenyl)-5-(2-hydroxy-4-methoxy-phenyl)-1H-[1,2,3]triazole |
| 66 | 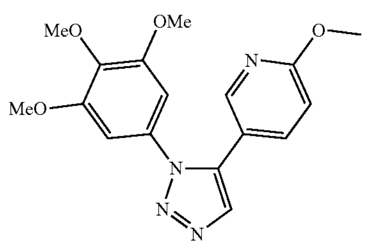 [SMILES: COc1ccc(-c2cnnn2-c2cc(OC)c(OC)c(OC)c2)cn1] | 1-(3,4,5-trimethoxy-phenyl)-5-(2-methoxy-pyridin-5-yl)-1H-[1,2,3]triazole |
| 67 | 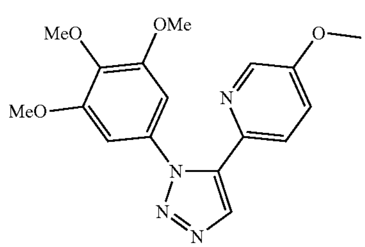 [SMILES: COc1ccc(-c2cnnn2-c2cc(OC)c(OC)c(OC)c2)nc1] | 1-(3,4,5-trimethoxy-phenyl)-5-(5-methoxy-pyridin-2-yl)-1H-[1,2,3]triazole |
| 68 | 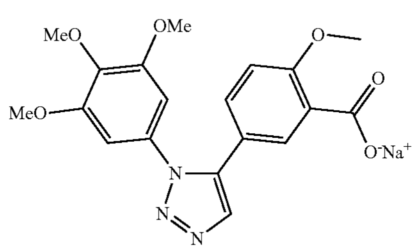 | 1-(3,4,5-trimethoxy-phenyl)-5-(3-carboxy-4-methoxy-phenyl)-1H-[1,2,3]triazole, sodium salt |

TABLE 1-continued

| Compound No. | Structure | Chemical Name |
|---|---|---|
| 69 | 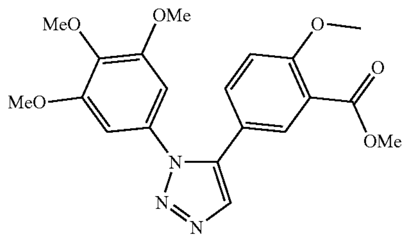 [SMILES: COC(=O)c1cc(-c2cnnn2-c2cc(OC)c(OC)c(OC)c2)ccc1OC] | 1-(3,4,5-trimethoxy-phenyl)-5-(3-methoxycarbonyl-4-methoxy-phenyl)-1H-[1,2,3]triazole |
| 70 | 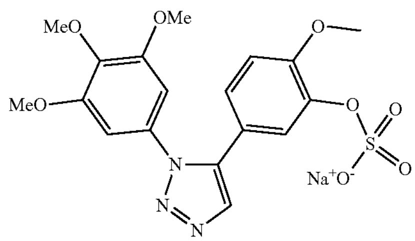 | 1-(3,4,5-trimethoxy-phenyl)-5-(3-sulfooxy-4-methoxy-phenyl)-1H-[1,2,3]triazole, sodium salt |
| 71 | 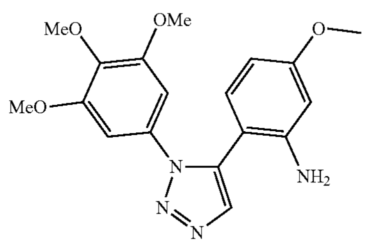 [SMILES: COc1ccc(-c2cnnn2-c2cc(OC)c(OC)c(OC)c2)c(N)c1] | 1-(3,4,5-trimethoxy-phenyl)-5-(2-amino-4-methoxy-phenyl)-1H-[1,2,3]triazole |
| 72 | 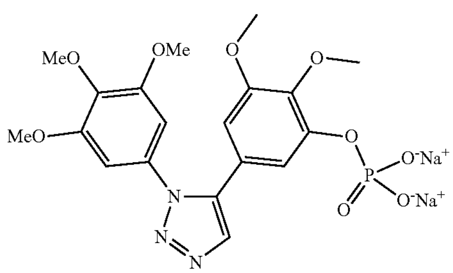 | 1-(3,4,5-trimethoxy-phenyl)-5-(3-phosphonooxy-4,5-dimethoxy-phenyl)-1H-[1,2,3]triazole, disodium salt |
| 73 | 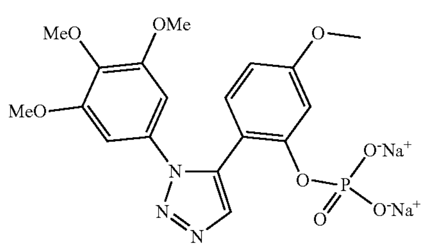 | 1-(3,4,5-trimethoxy-phenyl)-5-(2-phosphonooxy-4-methoxy-phenyl)-1H-[1,2,3]triazole, disodium salt |
| 74 | 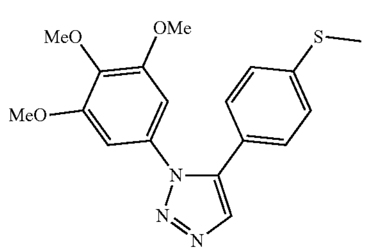 [SMILES: COc1cc(-n2nncc2-c2ccc(SC)cc2)cc(OC)c1OC] | 1-(3,4,5-trimethoxy-phenyl)-5-(4-methylsulfanyl-phenyl)-1H-[1,2,3]triazole |

TABLE 1-continued

| Compound No. | Structure | Chemical Name |
|---|---|---|
| 75 | 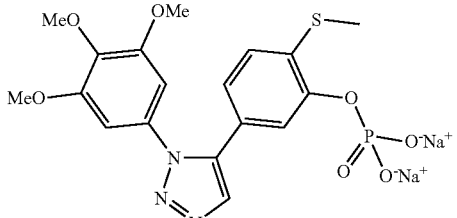 | 1-(3,4,5-trimethoxy-phenyl)-5-(3-phosphonooxy-4-methylsulfanyl-phenyl)-1H-[1,2,3]triazole, disodium salt |
| 76 | 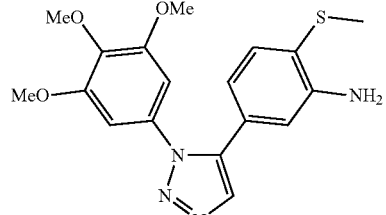 | 1-(3,4,5-trimethoxy-phenyl)-5-(3-amino-4-methylsulfanyl-phenyl)-1H-[1,2,3]triazole |
| 77 | 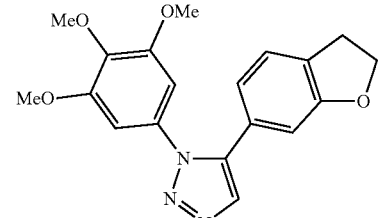 | 1-(3,4,5-trimethoxy-phenyl)-5-(2,3-dihydro-benzofuran-6-yl)-1H-[1,2,3]triazole |
| 78 | 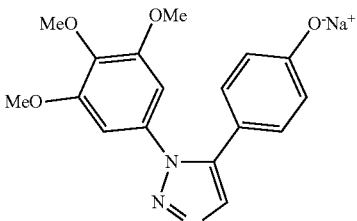 | 1-(3,4,5-trimethoxy-phenyl)-5-(4-hydroxy-phenyl)-1H-[1,2,3]triazole, sodium salt |
| 79 | 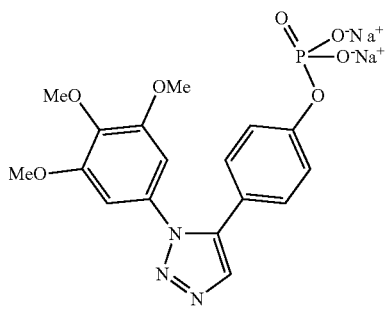 | 1-(3,4,5-trimethoxy-phenyl)-5-(4-phosphonooxy-phenyl)-1H-[1,2,3]triazole, disodium salt |
| 80 | 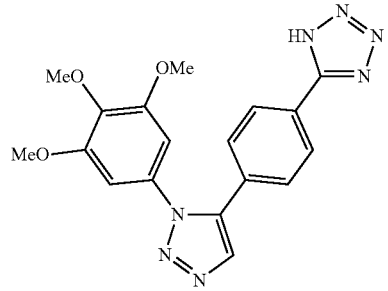 [SMILES: COc1cc(-n2nncc2-c2ccc(-c3nnn[nH]3)cc2)cc(OC)c1OC] | 1-(3,4,5-trimethoxy-phenyl)-5-[4-(tetrazol-5-yl)-phenyl]-1H-[1,2,3]triazole |

TABLE 1-continued

| Compound No. | Structure | Chemical Name |
|---|---|---|
| 81 | 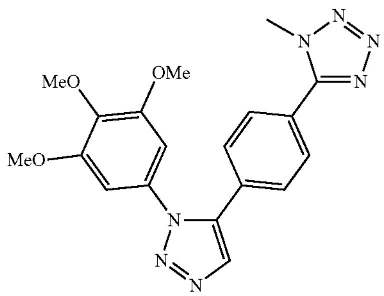 [SMILES: COc1cc(-n2nncc2-c2ccc(-c3nnnn3C)cc2)cc(OC)c1OC] | 1-(3,4,5-trimethoxy-phenyl)-5-[4-(1-methyl-tetrazol-5-yl)-phenyl]-1H-[1,2,3]triazole |
| 82 | 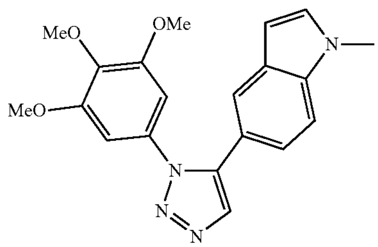 [SMILES: COc1cc(-n2nncc2-c2ccc3c(ccn3C)c2)cc(OC)c1OC] | 1-(3,4,5-trimethoxy-phenyl)-5-(1-methyl-1H-indol-5-yl)-1H-[1,2,3]triazole |
| 83 | 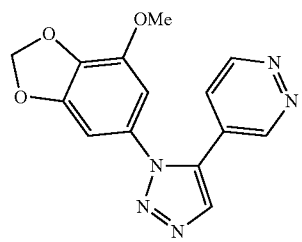 [SMILES: COc1cc(-n2nncc2-c2ccnnc2)cc2c1OCO2] | 1-(7-methoxy-benzo[1,3]dioxol-5-yl)-5-(pyridazin-4-yl)-1H-[1,2,3]triazole |
| 84 | 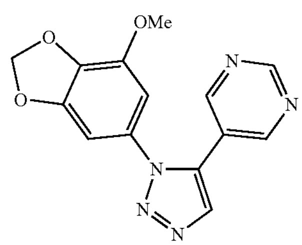 [SMILES: COc1cc(-n2nncc2-c2cncnc2)cc2c1OCO2] | 1-(7-methoxy-benzo[1,3]dioxol-5-yl)-5-(pyrimidin-5-yl)-1H-[1,2,3]triazole |
| 85 | 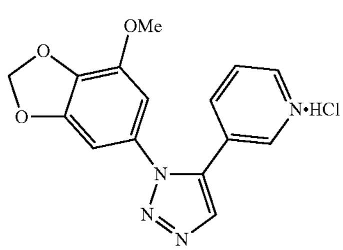 | 1-(7-methoxy-benzo[1,3]dioxol-5-yl)-5-(pyridin-3-yl)-1H-[1,2,3]triazole, hydrochloric acid salt |
| 86 | 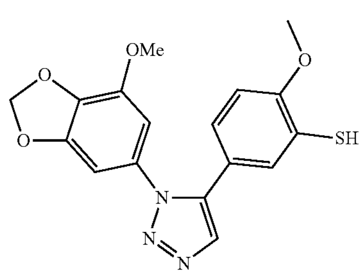 [SMILES: COc1ccc(-c2cnnn2-c2cc(OC)c3c(c2)OCO3)cc1S] | 1-(7-methoxy-benzo[1,3]dioxol-5-yl)-5-(3-mercapto-4-methoxy-phenyl)-1H-[1,2,3]triazole |

TABLE 1-continued

| Compound No. | Structure | Chemical Name |
|---|---|---|
| 87 | 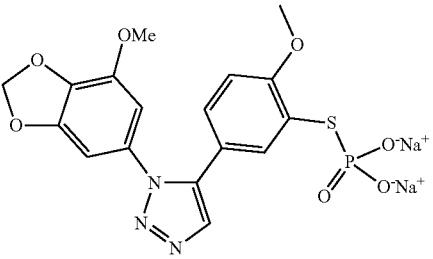 | S-{2-methoxy-5-[1-(7-methoxy-benzo[1,3]dioxol-5-yl)-1H-[1,2,3]triazol-5-yl]-phenyl}-thiophosphate, disodium salt |
| 88 | 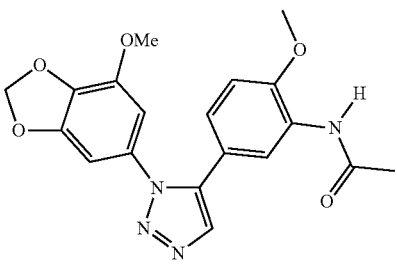 [SMILES: COc1ccc(-c2cnnn2-c2cc(OC)c3c(c2)OCO3)cc1NC(C)=O] | 1-(7-methoxy-benzo[1,3]dioxol-5-yl)-5-(3-acetamido-4-methoxy-phenyl)-1H-[1,2,3]triazole |
| 89 | 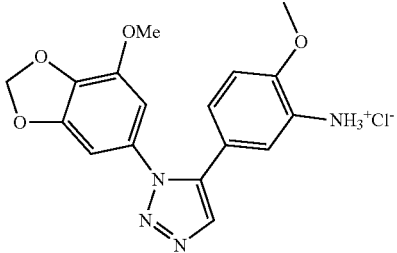 | 1-(7-methoxy-benzo[1,3]dioxol-5-yl)-5-(3-amino-4-methoxy-phenyl)-1H-[1,2,3]triazole, hydrochloric acid salt |
| 90 | 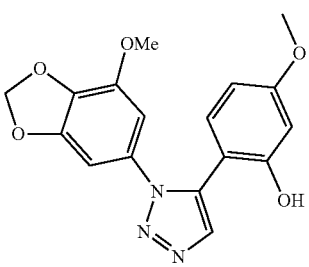 [SMILES: COc1ccc(-c2cnnn2-c2cc(OC)c3c(c2)OCO3)c(O)c1] | 1-(7-methoxy-benzo[1,3]dioxol-5-yl)-5-(2-hydroxy-4-methoxy-phenyl)-1H-[1,2,3]triazole |
| 91 | 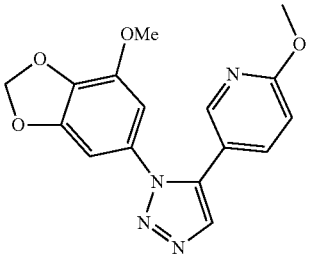 [SMILES: COc1ccc(-c2cnnn2-c2cc(OC)c3c(c2)OCO3)cn1] | 1-(7-methoxy-benzo[1,3]dioxol-5-yl)-5-(2-methoxy-pyridin-5-yl)-1H-[1,2,3]triazole |

TABLE 1-continued

| Compound No. | Structure | Chemical Name |
|---|---|---|
| 92 | 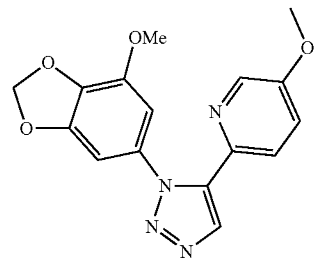 [SMILES: COc1ccc(-c2cnnn2-c2cc(OC)c3c(c2)OCO3)nc1] | 1-(7-methoxy-benzo[1,3]dioxol-5-yl)-5-(5-methoxy-pyridin-2-yl)-1H-[1,2,3]triazole |
| 93 | 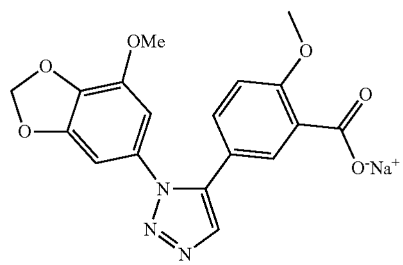 | 1-(7-methoxy-benzo[1,3]dioxol-5-yl)-5-(3-carboxy-4-methoxy-phenyl)-1H-[1,2,3]triazole |
| 94 | 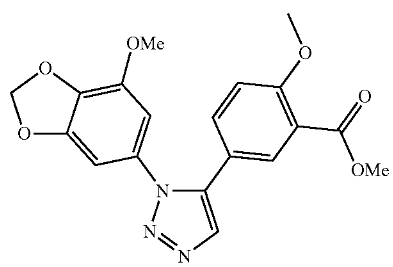 [SMILES: COC(=O)c1cc(-c2cnnn2-c2cc(OC)c3c(c2)OCO3)ccc1OC] | 1-(7-methoxy-benzo[1,3]dioxol-5-yl)-5-(3-methoxycarbonyl-4-methoxy-phenyl)-1H-[1,2,3]triazole |
| 95 | 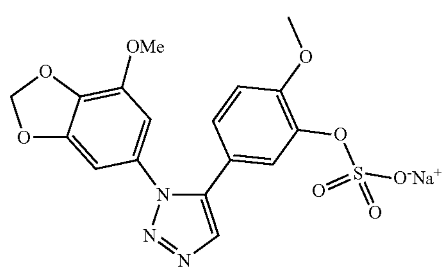 | 1-(7-methoxy-benzo[1,3]dioxol-5-yl)-5-(3-sulfooxy-4-methoxy-phenyl)-1H-[1,2,3]triazole, sodium salt |
| 96 | 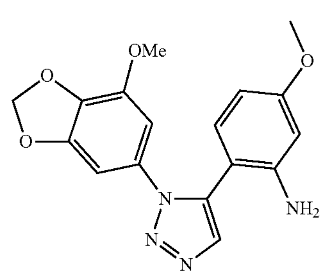 [SMILES: COc1ccc(-c2cnnn2-c2cc(OC)c3c(c2)OCO3)c(N)c1] | 1-(7-methoxy-benzo[1,3]dioxol-5-yl)-5-(2-amino-4-methoxy-phenyl)-1H-[1,2,3]triazole |

TABLE 1-continued

| Compound No. | Structure | Chemical Name |
|---|---|---|
| 97 | 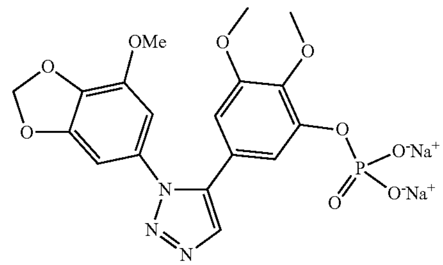 | 1-(7-methoxy-benzo[1,3]dioxol-5-yl)-5-(3-phosphonyl-4,5-dimethoxy-phenyl)-1H-[1,2,3]triazole, disodium salt |
| 98 | 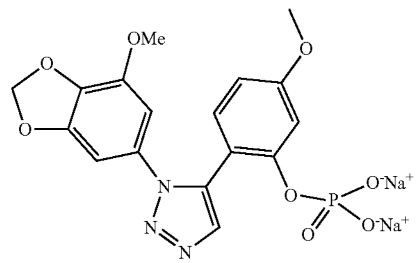 | 1-(7-methoxy-benzo[1,3]dioxol-5-yl)-5-(2-phosphonyl-4-methoxy-phenyl)-1H-[1,2,3]triazole, sodium salt |
| 99 | 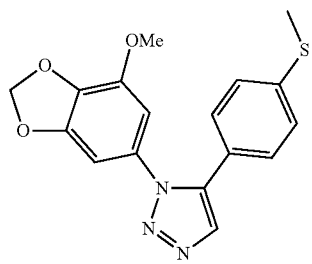 [SMILES: COc1cc(-n2nncc2-c2ccc(SC)cc2)cc2c1OCO2] | 1-(7-methoxy-benzo[1,3]dioxol-5-yl)-5-(4-methylsulfanyl-phenyl)-1H-[1,2,3]triazole |
| 100 | 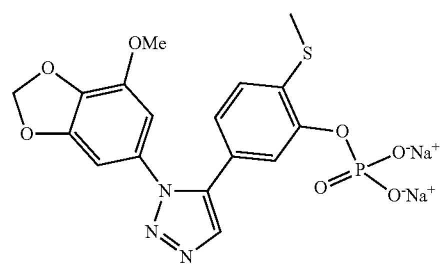 | 1-(7-methoxy-benzo[1,3]dioxol-5-yl)-5-(3-phosphonyl-4-methylsulfanyl-phenyl)-1H-[1,2,3]triazole, disodium salt |
| 101 | 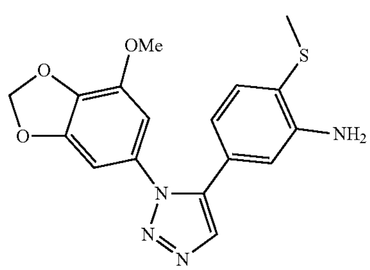 [SMILES: COc1cc(-n2nncc2-c2ccc(SC)c(N)c2)cc2c1OCO2] | 1-(7-methoxy-benzo[1,3]dioxol-5-yl)-5-(3-amino-4-methylsulfanyl-phenyl)-1H-[1,2,3]triazole |
| 102 | 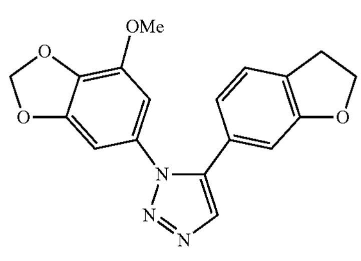 [SMILES: COc1cc(-n2nncc2-c2ccc3c(c2)OCC3)cc2c1OCO2] | 1-(7-methoxy-benzo[1,3]dioxol-5-yl)-5-(2,3-dihydro-benzofuran-6-yl)-1H-[1,2,3]triazole |

TABLE 1-continued
| Compound No. | Structure | Chemical Name |
|---|---|---|
| 103 | 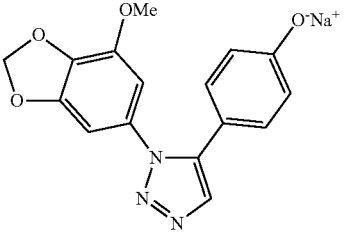 | 1-(7-methoxy-benzo[1,3]dioxol-5-yl)-5-(4-hydroxy-phenyl)-1H-[1,2,3]triazole, sodium salt |
| 104 | 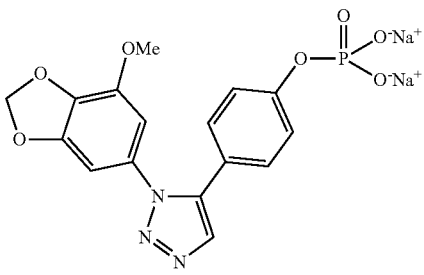 | 1-(7-methoxy-benzo[1,3]dioxol-5-yl)-5-(4-phosphonooxy-phenyl)-1H-[1,2,3]triazole, disodium salt |
| 105 | 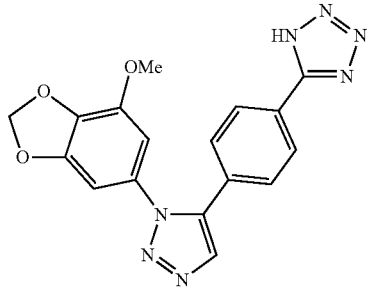 [SMILES: COc1cc(-n2nncc2-c2ccc(-c3nnn[nH]3)cc2)cc2c1OCO2] | 1-(7-methoxy-benzo[1,3]dioxol-5-yl)-5-[1H-tetrazol-5-yl)-phenyl]-1H-[1,2,3]triazole |
| 106 | 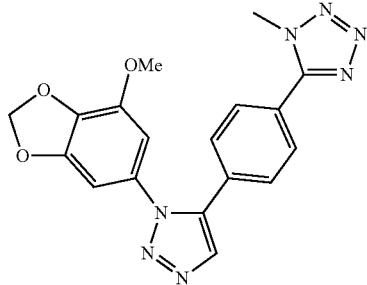 [SMILES: COc1cc(-n2nncc2-c2ccc(-c3nnnn3C)cc2)cc2c1OCO2] | 1-(7-methoxy-benzo[1,3]dioxol-5-yl)-5-[1-methyl-1H-tetrazol-5-yl)-phenyl]-1H-[1,2,3]triazole |
| 107 | 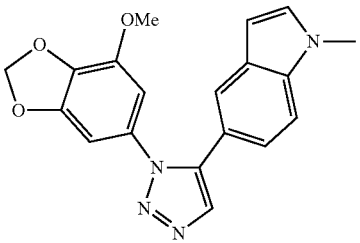 [SMILES: COc1cc(-n2nncc2-c2ccc3c(ccn3C)c2)cc2c1OCO2] | 1-(7-methoxy-benzo[1,3]dioxol-5-yl)-5-(1-methyl-1H-indol-5-yl)-1H-[1,2,3]triazole |

TABLE 1-continued

| Compound No. | Structure | Chemical Name |
|---|---|---|
| 108 | 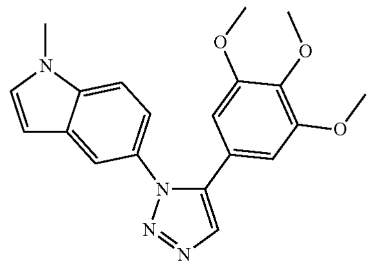 [SMILES: COc1cc(-c2cnnn2-c2ccc3c(ccn3C)c2)cc(OC)c1OC] | 1-(1-methyl-1H-indol-5-yl)-5-(3,4,5-trimethoxy-phenyl)-1H-[1,2,3]triazole |
| 109 | 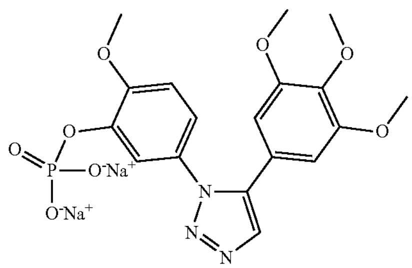 | 1-(3-phosphonooxy-4-methoxy-phenyl)-5-(3,4,5-trimethoxy-phenyl)-1H-[1,2,3]triazole, disodium salt |
| 110 | 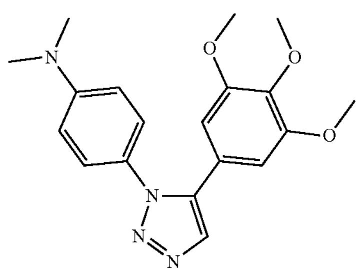 | 1-[4-(N,N-dimethylamino)-phenyl]-5-(3,4,5-trimethoxy-phenyl)-1H-[1,2,3]triazole |
| 111 | 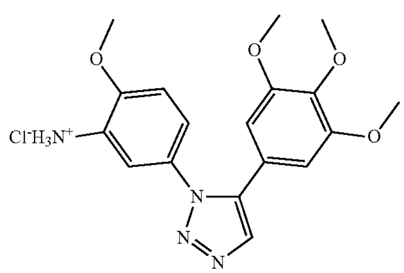 | 1-(3-amino-4-methoxy-phenyl)-5-(3,4,5-trimethoxy-phenyl)-1H-[1,2,3]triazole, hydrochloric acid salt |
| 112 | 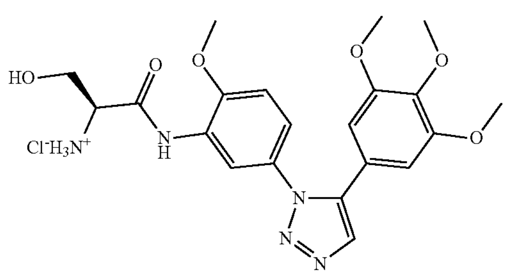 | 2-hydroxy-1-{2-methoxy-5-[5-(3,4,5-trimethoxy-phenyl)-[1,2,3]triazol-1-yl]-phenylcarbamoyl}-ethyl-ammonium chloride |

TABLE 1-continued

| Compound No. | Structure | Chemical Name |
|---|---|---|
| 113 | 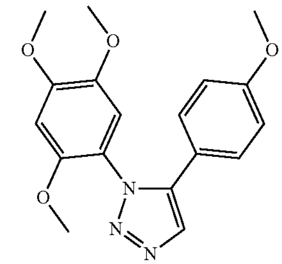 [SMILES: COc1ccc(-c2cnnn2-c2cc(OC)c(OC)cc2OC)cc1] | 1-(2,4,5-trimethoxy-phenyl)-5-(4-methoxy-phenyl)-1H-[1,2,3]triazole |
| 114 | 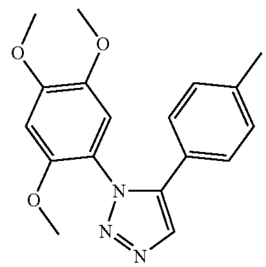 [SMILES: COc1cc(OC)c(-n2nncc2-c2ccc(C)cc2)cc1OC] | 1-(2,4,5-trimethoxy-phenyl)-5-(4-methyl-phenyl)-1H-[1,2,3]triazole |
| 115 | 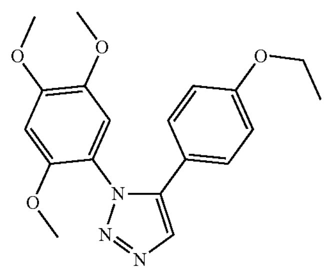 [SMILES: CCOc1ccc(-c2cnnn2-c2cc(OC)c(OC)cc2OC)cc1] | 1-(2,4,5-trimethoxy-phenyl)-5-(4-ethoxy-phenyl)-1H-[1,2,3]triazole |
| 116 | 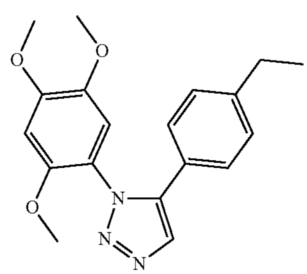 [SMILES: CCc1ccc(-c2cnnn2-c2cc(OC)c(OC)cc2OC)cc1] | 1-(2,4,5-trimethoxy-phenyl)-5-(4-ethyl-phenyl)-1H-[1,2,3]triazole |
| 117 | 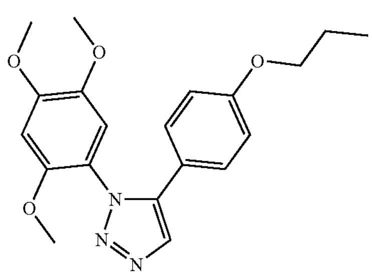 [SMILES: CCCOc1ccc(-c2cnnn2-c2cc(OC)c(OC)cc2OC)cc1] | 1-(2,4,5-trimethoxy-phenyl)-5-(4-propoxy-phenyl)-1H-[1,2,3]triazole |

TABLE 1-continued

| Compound No. | Structure | Chemical Name |
| --- | --- | --- |
| 118 | 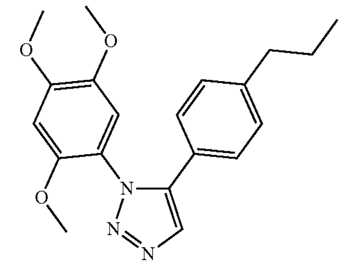 [SMILES: CCCc1ccc(-c2cnnn2-c2cc(OC)c(OC)cc2OC)cc1] | 1-(2,4,5-trimethoxy-phenyl)-5-(4-propyl-phenyl)-1H-[1,2,3]triazole |
| 119 | 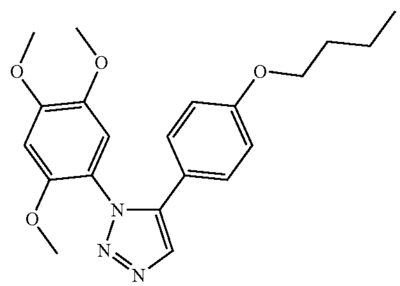 [SMILES: CCCCOc1ccc(-c2cnnn2-c2cc(OC)c(OC)cc2OC)cc1] | 1-(2,4,5-trimethoxy-phenyl)-5-(4-butoxy-phenyl)-1H-[1,2,3]triazole |
| 120 | 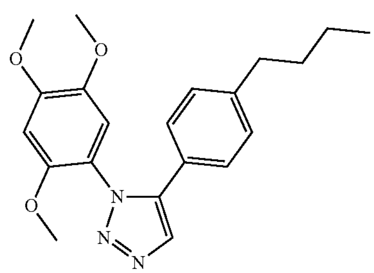 [SMILES: CCCCc1ccc(-c2cnnn2-c2cc(OC)c(OC)cc2OC)cc1] | 1-(2,4,5-trimethoxy-phenyl)-5-(4-butyl-phenyl)-1H-[1,2,3]triazole |
| 121 | 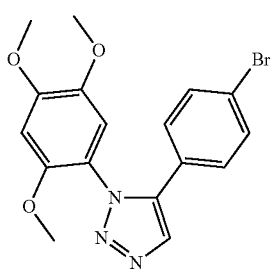 [SMILES: COc1cc(OC)c(-n2nncc2-c2ccc(Br)cc2)cc1OC] | 1-(2,4,5-trimethoxy-phenyl)-5-(4-bromo-phenyl)-1H-[1,2,3]triazole |
| 122 | 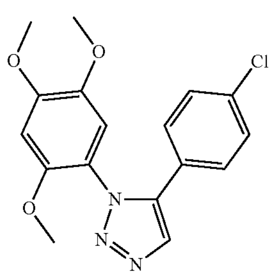 [SMILES: COc1cc(OC)c(-n2nncc2-c2ccc(Cl)cc2)cc1OC] | 1-(2,4,5-trimethoxy-phenyl)-5-(4-chloro-phenyl)-1H-[1,2,3]triazole |

TABLE 1-continued

| Compound No. | Structure | Chemical Name |
|---|---|---|
| 123 | 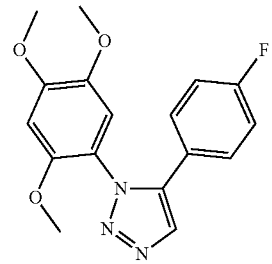 [SMILES: COc1cc(OC)c(-n2nncc2-c2ccc(F)cc2)cc1OC] | 1-(2,4,5-trimethoxy-phenyl)-5-(4-fluoro-phenyl)-1H-[1,2,3]triazole |
| 124 | 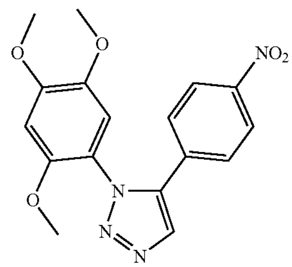 [SMILES: COc1cc(OC)c(-n2nncc2-c2ccc([N+](=O)[O-])cc2)cc1OC] | 1-(2,4,5-trimethoxy-phenyl)-5-(4-nitro-phenyl)-1H-[1,2,3]triazole |
| 125 | 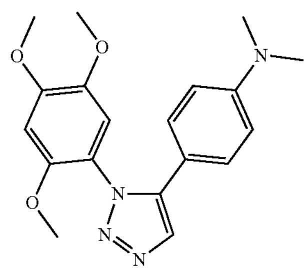 [SMILES: COc1cc(OC)c(-n2nncc2-c2ccc(N(C)C)cc2)cc1OC] | 1-(2,4,5-trimethoxy-phenyl)-5-[4-(N,N-diethylamino)-phenyl]-1H-[1,2,3]triazole |
| 126 | 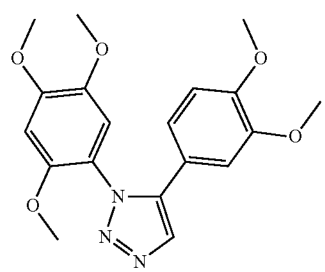 [SMILES: COc1ccc(-c2cnnn2-c2cc(OC)c(OC)cc2OC)cc1OC] | 1-(2,4,5-trimethoxy-phenyl)-5-(3,4-dimethoxy-phenyl)-1H-[1,2,3]triazole |
| 127 | 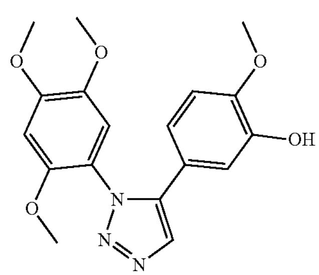 [SMILES: COc1ccc(-c2cnnn2-c2cc(OC)c(OC)cc2OC)cc1O] | 1-(2,4,5-trimethoxy-phenyl)-5-(3-hydroxy-4-methoxy-phenyl)-1H-[1,2,3]triazole |

TABLE 1-continued

| Compound No. | Structure | Chemical Name |
|---|---|---|
| 128 | 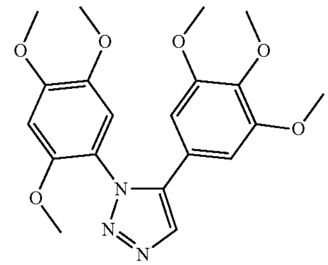 [SMILES: COc1cc(OC)c(-n2nncc2-c2cc(OC)c(OC)c(OC)c2)cc1OC] | 1-(2,4,5-trimethoxy-phenyl)-5-(3,4,5-trimethoxy-phenyl)-1H-[1,2,3]triazole |
| 129 | 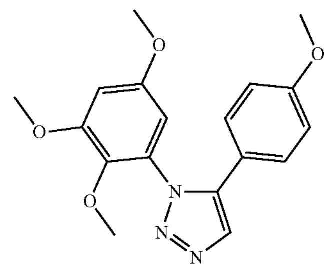 [SMILES: COc1ccc(-c2cnnn2-c2cc(OC)cc(OC)c2OC)cc1] | 1-(2,3,5-trimethoxy-phenyl)-5-(4-methoxy-phenyl)-1H-[1,2,3]triazole |
| 130 | 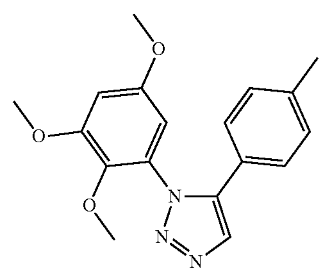 | 1-(2,3,5-trimethoxy-phenyl)-5-(4-methyl-phenyl)-1H-[1,2,3]triazole |
| 131 | 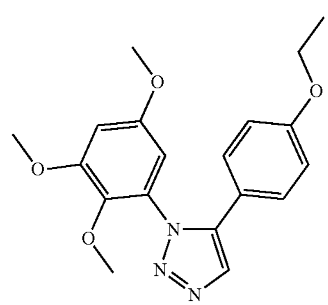 [SMILES: CCOc1ccc(-c2cnnn2-c2cc(OC)cc(OC)c2OC)cc1] | 1-(2,3,5-trimethoxy-phenyl)-5-(4-ethoxy-phenyl)-1H-[1,2,3]triazole |
| 132 | 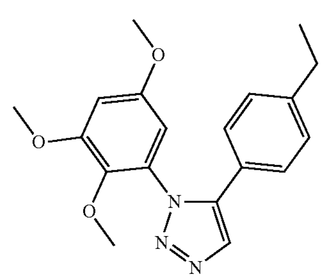 [SMILES: CCc1ccc(-c2cnnn2-c2cc(OC)cc(OC)c2OC)cc1] | 1-(2,3,5-trimethoxy-phenyl)-5-(4-ethyl-phenyl)-1H-[1,2,3]triazole |

TABLE 1-continued

| Compound No. | Structure | Chemical Name |
|---|---|---|
| 133 | 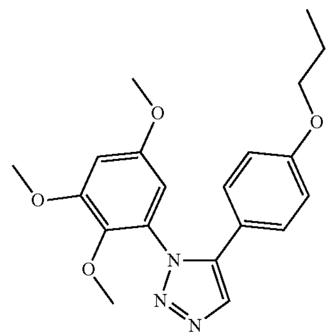 [SMILES: CCCOc1ccc(-c2cnnn2-c2cc(OC)cc(OC)c2OC)cc1] | 1-(2,3,5-trimethoxy-phenyl)-5-(4-propoxy-phenyl)-1H-[1,2,3]triazole |
| 134 | 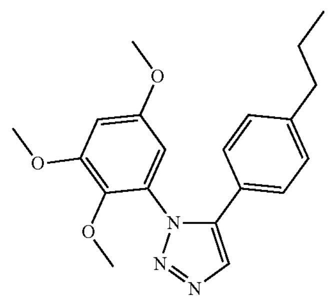 [SMILES: CCCc1ccc(-c2cnnn2-c2cc(OC)cc(OC)c2OC)cc1] | 1-(2,3,5-trimethoxy-phenyl)-5-(4-propyl-phenyl)-1H-[1,2,3]triazole |
| 135 | 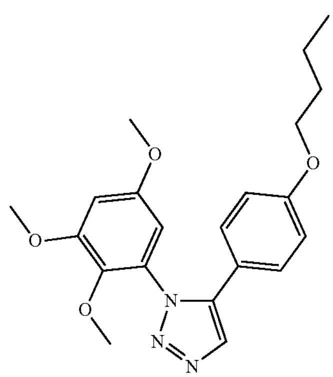 [SMILES: CCCCOc1ccc(-c2cnnn2-c2cc(OC)cc(OC)c2OC)cc1] | 1-(2,3,5-trimethoxy-phenyl)-5-(4-butoxy-phenyl)-1H-[1,2,3]triazole |
| 136 | 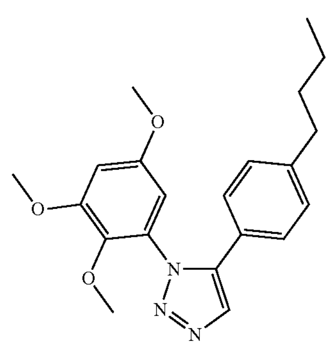 [SMILES: CCCCc1ccc(-c2cnnn2-c2cc(OC)cc(OC)c2OC)cc1] | 1-(2,3,5-trimethoxy-phenyl)-5-(4-butyl-phenyl)-1H-[1,2,3]triazole |

TABLE 1-continued

| Compound No. | Structure | Chemical Name |
|---|---|---|
| 137 | 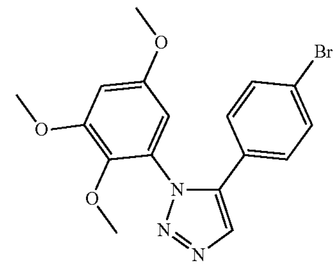 [SMILES: COc1cc(OC)c(OC)c(-n2nncc2-c2ccc(Br)cc2)c1] | 1-(2,3,5-trimethoxy-phenyl)-5-(4-bromo-phenyl)-1H-[1,2,3]triazole |
| 138 | 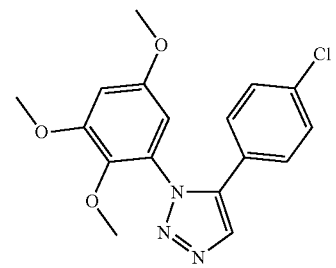 [SMILES: COc1cc(OC)c(OC)c(-n2nncc2-c2ccc(Cl)cc2)c1] | 1-(2,3,5-trimethoxy-phenyl)-5-(4-chloro-phenyl)-1H-[1,2,3]triazole |
| 139 | 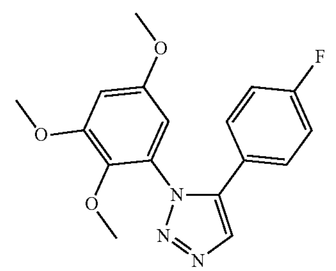 [SMILES: COc1cc(OC)c(OC)c(-n2nncc2-c2ccc(F)cc2)c1] | 1-(2,3,5-trimethoxy-phenyl)-5-(4-fluoro-phenyl)-1H-[1,2,3]triazole |
| 140 | 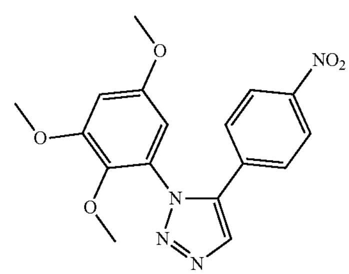 [SMILES: COc1cc(OC)c(OC)c(-n2nncc2-c2ccc([N+](=O)[O-])cc2)c1] | 1-(2,3,5-trimethoxy-phenyl)-5-(4-nitro-phenyl)-1H-[1,2,3]triazole |
| 141 | 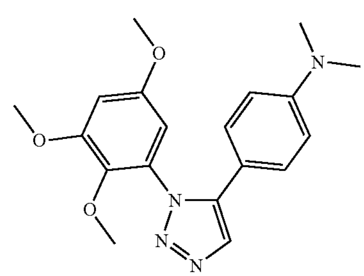 | 1-(2,3,5-trimethoxy-phenyl)-5-[4-(N,N-dimethylamino)-phenyl]-1H-[1,2,3]triazole |

TABLE 1-continued

| Compound No. | Structure | Chemical Name |
|---|---|---|
| 142 | 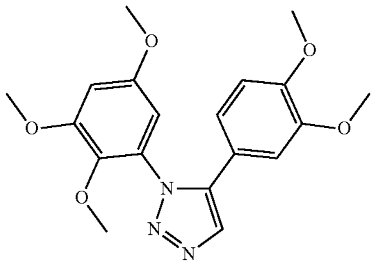 | 1-(2,3,5-trimethoxy-phenyl)-5-(3,4-dimethoxy-phenyl)-1H-[1,2,3]triazole |
| 143 | 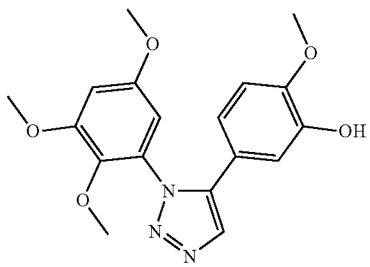 [SMILES: COc1cc(OC)c(OC)c(-n2nncc2-c2ccc(OC)c(O)c2)c1] | 1-(2,3,5-trimethoxy-phenyl)-5-(3-hydroxy-4-methoxy-phenyl)-1H-[1,2,3]triazole |
| 144 | 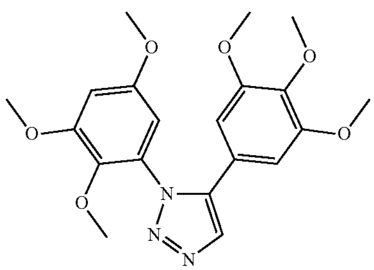 | 1-(2,3,5-trimethoxy-phenyl)-5-(3,4,5-trimethoxy-phenyl)-1H-[1,2,3]triazole |
| 145 | 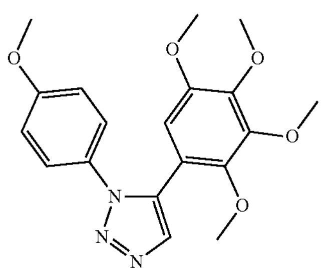 [SMILES: COc1ccc(-n2nncc2-c2cc(OC)c(OC)c(OC)c2OC)cc1] | 1-(4-methoxy-phenyl)-5-(2,3,4,5-tetramethoxy-phenyl)-1H-[1,2,3]triazole |
| 146 | 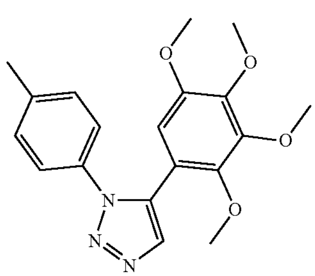 | 1-(4-methyl-phenyl)-5-(2,3,4,5-tetramethoxy-phenyl)-1H-[1,2,3]triazole |

TABLE 1-continued

| Compound No. | Structure | Chemical Name |
|---|---|---|
| 147 | 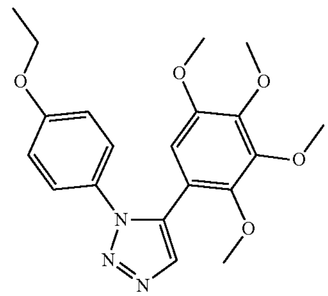 [SMILES: CCOc1ccc(-n2nncc2-c2cc(OC)c(OC)c(OC)c2OC)cc1] | 1-(4-ethoxy-phenyl)-5-(2,3,4,5-tetramethoxy-phenyl)-1H-[1,2,3]triazole |
| 148 | 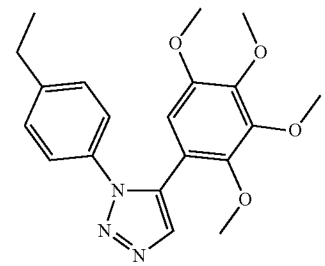 [SMILES: CCc1ccc(-n2nncc2-c2cc(OC)c(OC)c(OC)c2OC)cc1] | 1-(4-ethyl-phenyl)-5-(2,3,4,5-tetramethoxy-phenyl)-1H-[1,2,3]triazole |
| 149 | 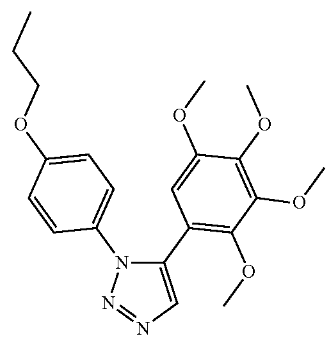 [SMILES: CCCOc1ccc(-n2nncc2-c2cc(OC)c(OC)c(OC)c2OC)cc1] | 1-(4-propoxy-phenyl)-5-(2,3,4,5-tetramethoxy-phenyl)-1H-[1,2,3]triazole |
| 150 | 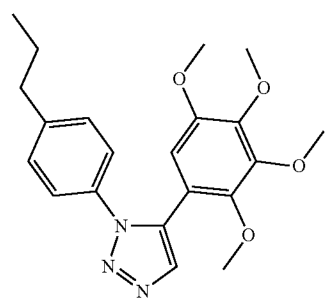 [SMILES: CCCc1ccc(-n2nncc2-c2cc(OC)c(OC)c(OC)c2OC)cc1] | 1-(4-propyl-phenyl)-5-(2,3,4,5-tetramethoxy-phenyl)-1H-[1,2,3]triazole |
| 151 | 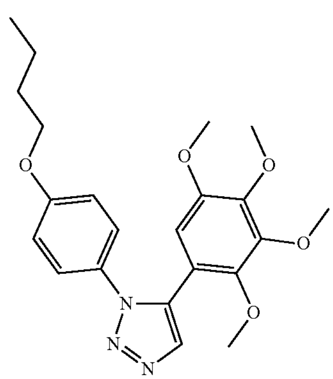 [SMILES: CCCCOc1ccc(-n2nncc2-c2cc(OC)c(OC)c(OC)c2OC)cc1] | 1-(4-butoxy-phenyl)-5-(2,3,4,5-tetramethoxy-phenyl)-1H-[1,2,3]triazole |

TABLE 1-continued

| Compound No. | Structure | Chemical Name |
|---|---|---|
| 152 | 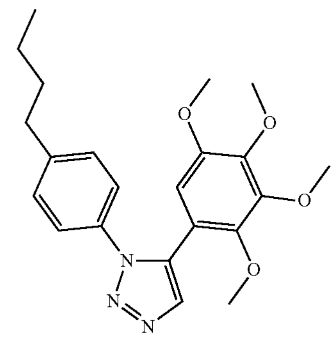 [SMILES: CCCCc1ccc(-n2nncc2-c2cc(OC)c(OC)c(OC)c2OC)cc1] | 1-(4-butyl-phenyl)-5-(2,3,4,5-tetramethoxy-phenyl)-1H-[1,2,3]triazole |
| 153 | 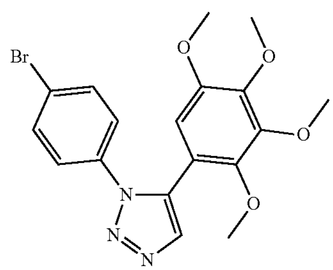 | 1-(4-bromo-phenyl)-5-(2,3,4,5-tetramethoxy-phenyl)-1H-[1,2,3]triazole |
| 154 | 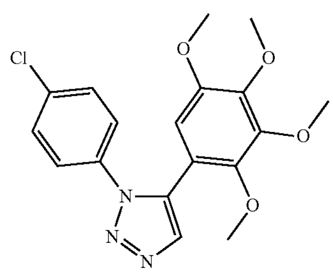 [SMILES: COc1cc(-c2cnnn2-c2ccc(Cl)cc2)c(OC)c(OC)c1OC] | 1-(4-chloro-phenyl)-5-(2,3,4,5-tetramethoxy-phenyl)-1H-[1,2,3]triazole |
| 155 | 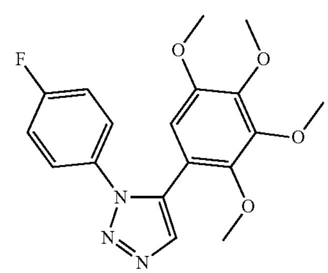 [SMILES: COc1cc(-c2cnnn2-c2ccc(F)cc2)c(OC)c(OC)c1OC] | 1-(4-fluoro-phenyl)-5-(2,3,4,5-tetramethoxy-phenyl)-1H-[1,2,3]triazole |
| 156 | 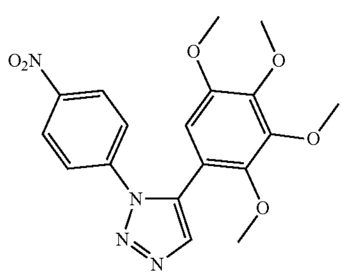 [SMILES: COc1cc(-c2cnnn2-c2ccc([N+](=O)[O-])cc2)c(OC)c(OC)c1OC] | 1-(4-nitro-phenyl)-5-(2,3,4,5-tetramethoxy-phenyl)-1H-[1,2,3]triazole |

TABLE 1-continued

| Compound No. | Structure | Chemical Name |
|---|---|---|
| 157 | 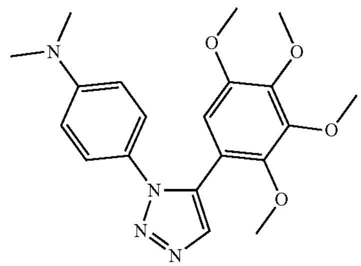 | 1-[4-(N,N-dimethylamino)-phenyl]-5-(2,3,4,5-tetramethoxy-phenyl)-1H-[1,2,3]triazole |
| 158 | 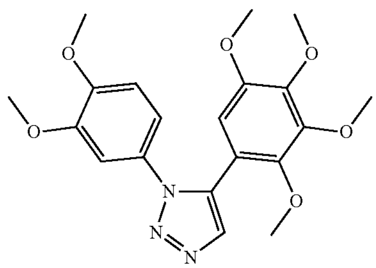 | 1-(3,4-dimethoxy-phenyl)-5-(2,3,4,5-tetramethoxy-phenyl)-1H-[1,2,3]triazole |
| 159 | 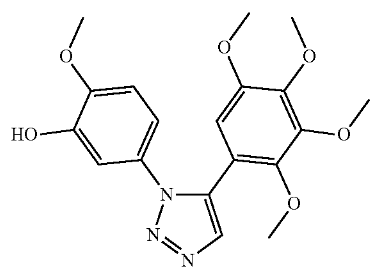 [SMILES: COc1ccc(-n2nncc2-c2cc(OC)c(OC)c(OC)c2OC)cc1O] | 1-(3-hydroxy-4-methoxy-phenyl)-5-(2,3,4,5-tetramethoxy-phenyl)-1H-[1,2,3]triazole |
| 160 | 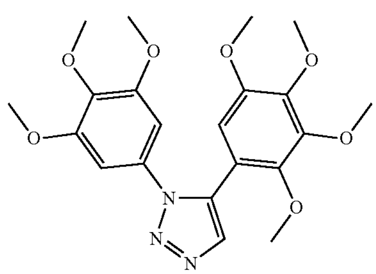 | 1-(3,4,5-trimethoxy-phenyl)-5-(2,3,4,5-tetramethoxy-phenyl)-1H-[1,2,3]triazole |
| 161 | 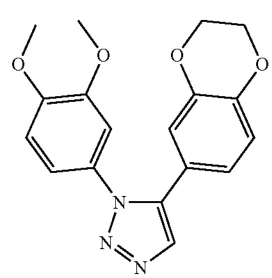 [SMILES: COc1ccc(-n2nncc2-c2ccc3c(c2)OCCO3)cc1OC] | 1-(3,4-trimethoxy-phenyl)-5-(2,3-dihydro-benzo[1,4]dioxin-6-yl)-1H-[1,2,3]triazole |

TABLE 1-continued

| Compound No. | Structure | Chemical Name |
|---|---|---|
| 162 | 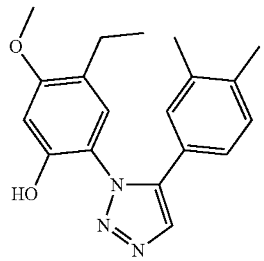 [SMILES: CCc1cc(-n2nncc2-c2ccc(C)c(C)c2)c(O)cc1OC] | 1-(2-hydroxy-4-methoxy-5-ethyl-phenyl)-5-(3,4-dimethyl-phenyl)-1H-[1,2,3]triazole |
| 163 | 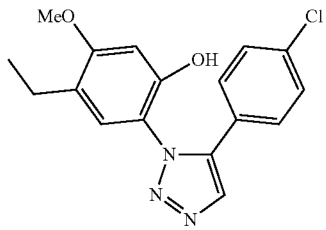 [SMILES: CCc1cc(-n2nncc2-c2ccc(Cl)cc2)c(O)cc1OC] | 1-(2-hydroxy-4-methoxy-5-ethyl-phenyl)-5-(4-chloro-phenyl)-1H-[1,2,3]triazole |
| 164 | 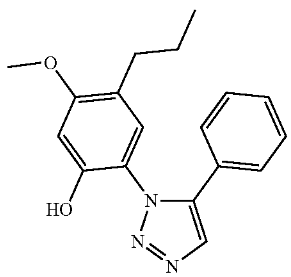 [SMILES: CCCc1cc(-n2nncc2-c2ccccc2)c(O)cc1OC] | 1-(2-hydroxy-4-methoxy-5-propyl-phenyl)-5-phenyl-1H-[1,2,3]triazole |
| 165 | 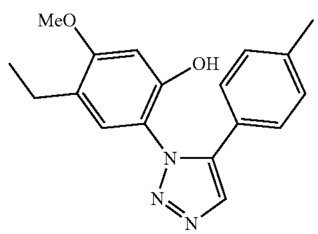 [SMILES: CCc1cc(-n2nncc2-c2ccc(C)cc2)c(O)cc1OC] | 1-(2-hydroxy-4-methoxy-5-ethyl-phenyl)-5-(4-methyl-phenyl)-1H-[1,2,3]triazole |
| 166 | 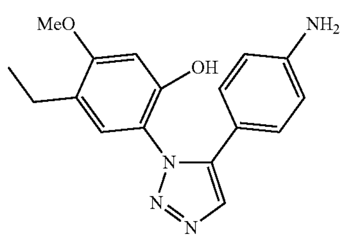 [SMILES: CCc1cc(-n2nncc2-c2ccc(N)cc2)c(O)cc1OC] | 1-(2-hydroxy-4-methoxy-5-ethyl-phenyl)-5-(4-amino-phenyl)-1H-[1,2,3]triazole |
| 167 | 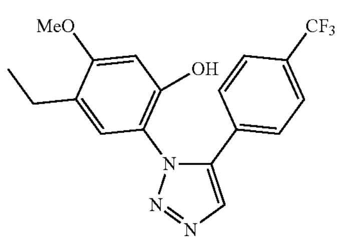 [SMILES: CCc1cc(-n2nncc2-c2ccc(C(F)(F)F)cc2)c(O)cc1OC] | 1-(2-hydroxy-4-methoxy-5-ethyl-phenyl)-5-(4-trifluoromethyl-phenyl)-1H-[1,2,3]triazole |

TABLE 1-continued

| Compound No. | Structure | Chemical Name |
|---|---|---|
| 168 | 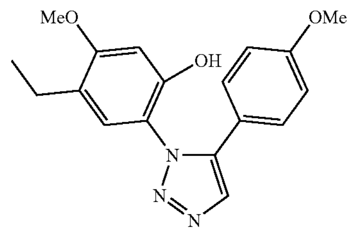 [SMILES: CCc1cc(-n2nncc2-c2ccc(OC)cc2)c(O)cc1OC] | 1-(2-hydroxy-4-methoxy-5-ethyl-phenyl)-5-(4-methoxy-phenyl)-1H-[1,2,3]triazole |
| 169 | 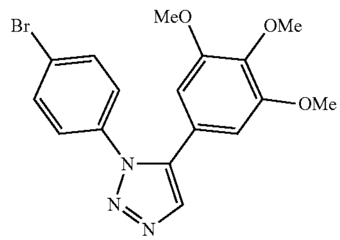 [SMILES: COc1cc(-c2cnnn2-c2ccc(Br)cc2)cc(OC)c1OC] | 1-(4-bromo-phenyl)-5-(3,4,5-trimethoxy-phenyl)-1H-[1,2,3]triazole |
| 170 | 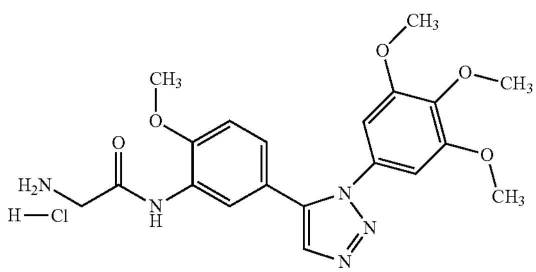 | 2-amino-N-(2-methoxy-5-(1-(3,4,5-trimethoxyphenyl)-1H-1,2,3-triazol-5-yl)phenyl)acetamide hydrochloride |
| 171 | 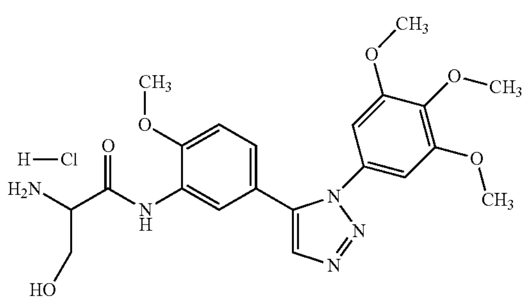 | 2-amino-3-hydroxy-N-(2-methoxy-5-(1-(3,4,5-trimethoxyphenyl)-1H-1,2,3-triazol-5-yl)phenyl)propanamide hydrochloride |
| 172 | 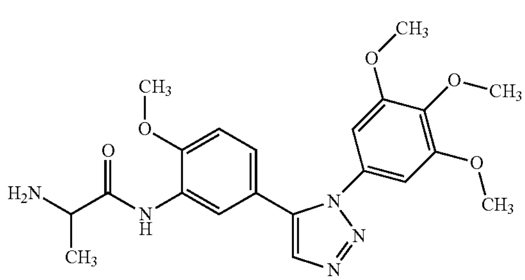 [SMILES: COc1ccc(-c2cnnn2-c2cc(OC)c(OC)c(OC)c2)cc1NC(=O)C(C)N] | 2-amino-N-(2-methoxy-5-(1-(3,4,5-trimethoxyphenyl)-1H-1,2,3-triazol-5-yl)phenyl)propanamide |

| Compound No. | Structure | Chemical Name |
|---|---|---|
| 173 | 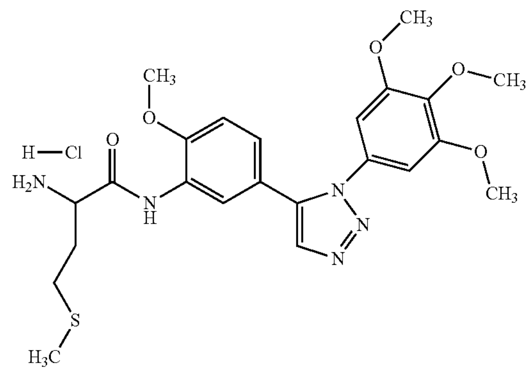 | 2-amino-N-(2-methoxy-5-(1-(3,4,5-trimethoxyphenyl)-1H-1,2,3-triazol-5-yl)phenyl)-4-(methylthio)butanamide hydrochloride |
| 174 | 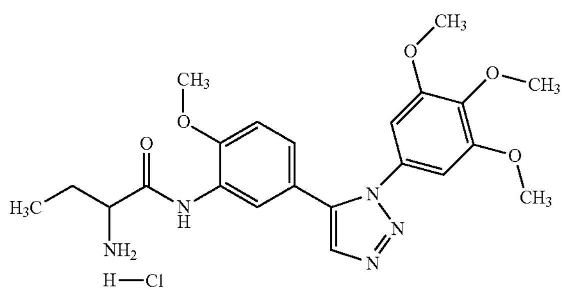 | 2-amino-N-(2-methoxy-5-(1-(3,4,5-trimethoxyphenyl)-1H-1,2,3-triazol-5-yl)phenyl)butanamide hydrochloride |
| 175 | 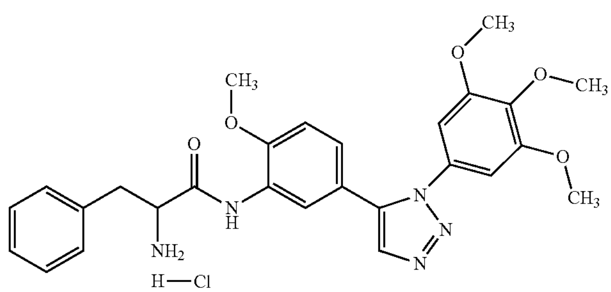 | 2-amino-N-(2-methoxy-5-(1-(3,4,5-trimethoxyphenyl)-1H-1,2,3-triazol-5-yl)phenyl)-3-phenylpropanamide hydrochloride |
| 176 | 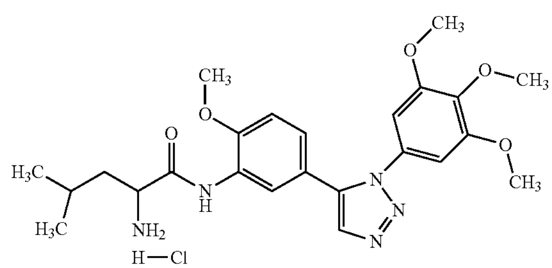 | 2-amino-N-(2-methoxy-5-(1-(3,4,5-trimethoxyphenyl)-1H-1,2,3-triazol-5-yl)phenyl)-4-methylpentanamide hydrochloride |
| 177 | 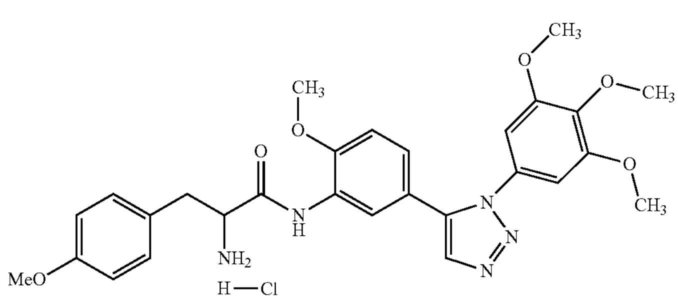 | 2-amino-N-(2-methoxy-5-(1-(3,4,5-trimethoxyphenyl)-1H-1,2,3-triazol-5-yl)phenyl)-3-(4-methoxyphenyl)propanamide hydrochloride |

TABLE 1-continued

| Compound No. | Structure | Chemical Name |
|---|---|---|
| 178 | 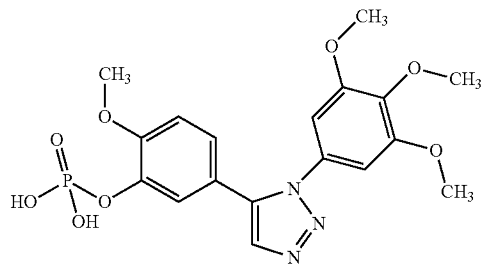 [SMILES: COc1ccc(-c2cnnn2-c2cc(OC)c(OC)c(OC)c2)cc1OP(=O)(O)O] | 2-methoxy-5-(1-(3,4,5-trimethoxyphenyl)-1H-1,2,3-triazol-5-yl)phenyl dihydrogen phosphate |
| 179 | 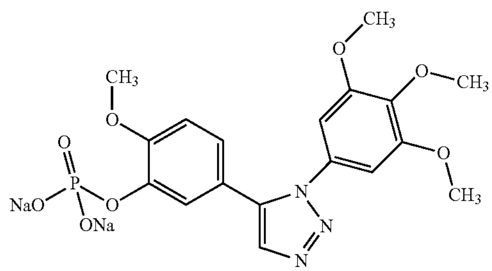 | sodium 2-methoxy-5-(1-(3,4,5-trimethoxyphenyl)-1H-1,2,3-triazol-5-yl)phenyl phosphate |
| 180 | 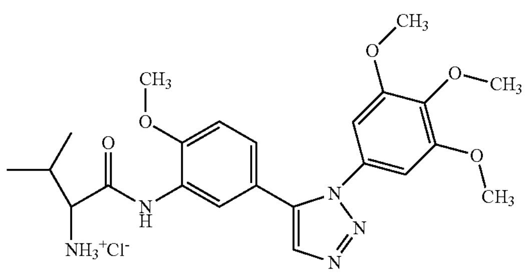 | 1-(2-methoxy-5-(1-(3,4,5-trimethoxyphenyl)-1H-1,2,3-triazol-5-yl)phenylamino)-3-methyl-1-oxobutan-2-aminium chloride |
| 181 | 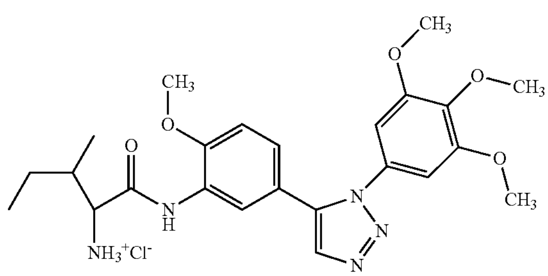 | 1-(2-methoxy-5-(1-(3,4,5-trimethoxyphenyl)-1H-1,2,3-triazol-5-yl)phenylamino)-3-methyl-1-oxopentan-2-aminium chloride |
| 182 | 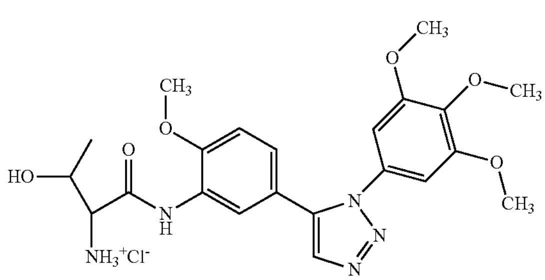 | 3-hydroxy-1-(2-methoxy-5-(1-(3,4,5-trimethoxyphenyl)-1H-1,2,3-triazol-5-yl)phenylamino)-1-oxobutan-2-aminium chloride |

TABLE 1-continued

| Compound No. | Structure | Chemical Name |
|---|---|---|
| 183 | 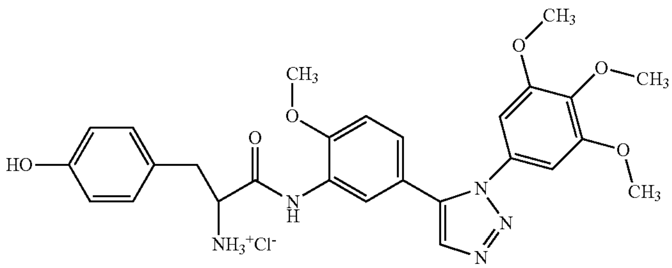 | 3-(4-hydroxyphenyl)-1-(2-methoxy-5-(1-(3,4,5-trimethoxyphenyl)-1H-1,2,3-triazol-5-yl)phenylamino)-1-oxopropan-2-aminium chloride |
| 184 | 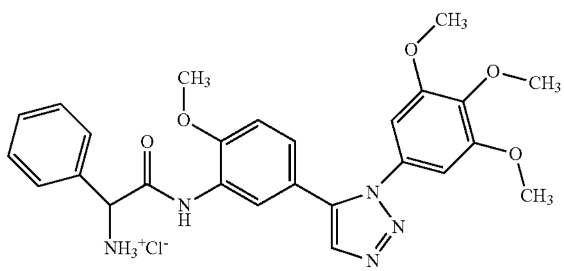 | 2-(2-methoxy-5-(1-(3,4,5-trimethoxyphenyl)-1H-1,2,3-triazol-5-yl)phenylamino)-2-oxo-1-phenylethanaminium chloride |
| 185 | 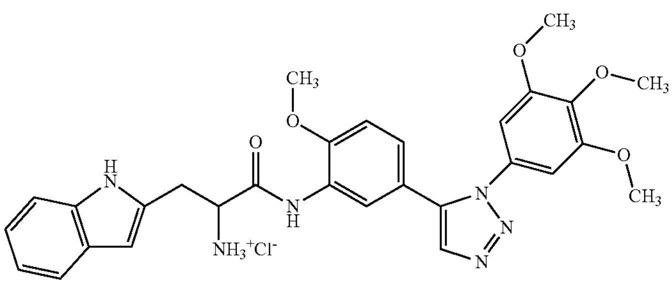 | 3-(1H-indol-2-yl)-1-(2-methoxy-5-(1-(3,4,5-trimethoxyphenyl)-1H-1,2,3-triazol-5-yl)phenylamino)-1-oxopropan-2-aminium chloride |
| 186 | 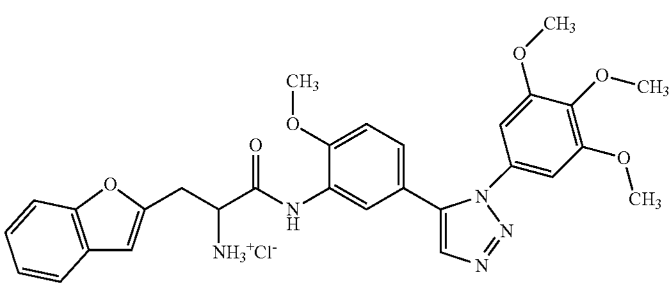 | 3-(benzofuran-2-yl)-1-(2-methoxy-5-(1-(3,4,5-trimethoxyphenyl)-1H-1,2,3-triazol-5-yl)phenylamino)-1-oxopropan-2-aminium chloride |
| 187 | 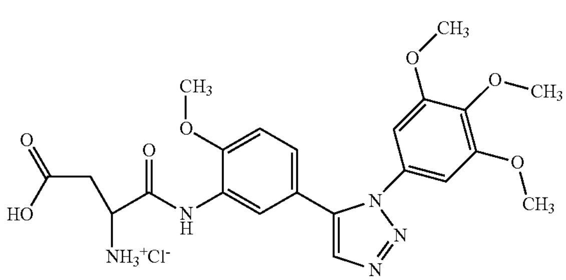 | 3-carboxy-1-(2-methoxy-5-(1-(3,4,5-trimethoxyphenyl)-1H-1,2,3-triazol-5-yl)phenylamino)-1-oxopropan-2-aminium chloride |

TABLE 1-continued

| Compound No. | Structure | Chemical Name |
|---|---|---|
| 188 | 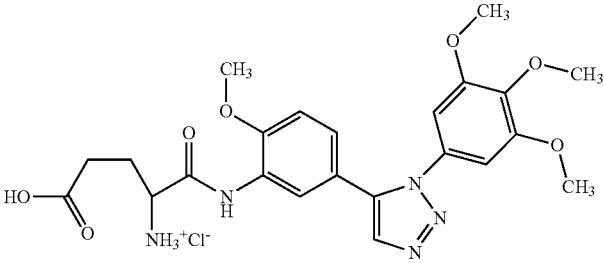 | 4-carboxy-1-(2-methoxy-5-(1-(3,4,5-trimethoxyphenyl)-1H-1,2,3-triazol-5-yl)phenylamino)-1-oxobutan-2-aminium chloride |
| 189 | 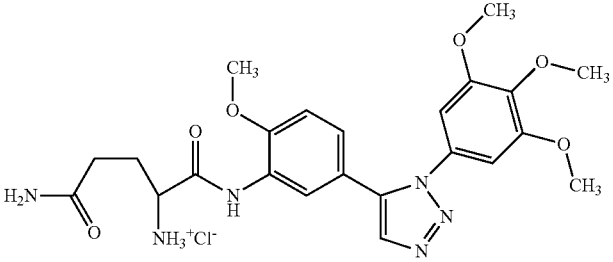 | 5-amino-1-(2-methoxy-5-(1-(3,4,5-trimethoxyphenyl)-1H-1,2,3-triazol-5-yl)phenylamino)-1,5-dioxopentan-2-aminium chloride |
| 190 | 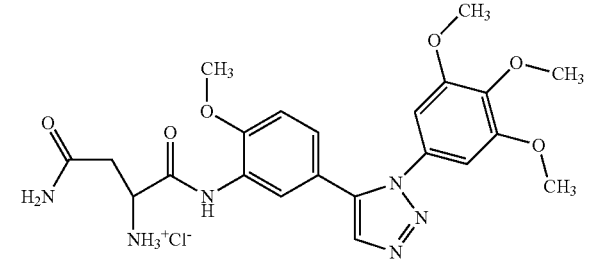 | 4-amino-1-(2-methoxy-5-(1-(3,4,5-trimethoxyphenyl)-1H-1,2,3-triazol-5-yl)phenylamino)-1,4-dioxobutan-2-aminium chloride |
| 191 | 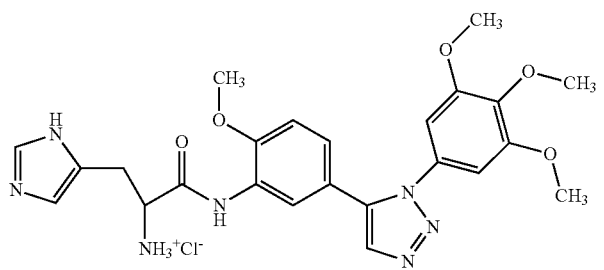 | 3-(1H-imidazol-5-yl)-1-(2-methoxy-5-(1-(3,4,5-trimethoxyphenyl)-1H-1,2,3-triazol-5-yl)phenylamino)-1-oxopropan-2-aminium chloride |
| 192 | 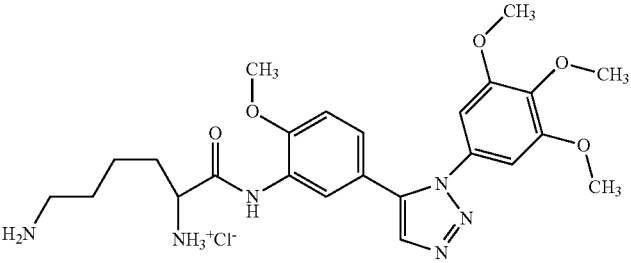 | 6-amino-1-(2-methoxy-5-(1-(3,4,5-trimethoxyphenyl)-1H-1,2,3-triazol-5-yl)phenylamino)-1-oxohexan-2-aminium chloride |

TABLE 1-continued

| Compound No. | Structure | Chemical Name |
|---|---|---|
| 193 | 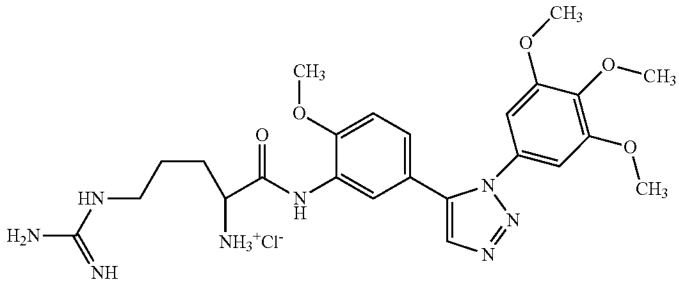 | 5-guanidino-1-(2-methoxy-5-(1-(3,4,5-trimethoxyphenyl)-1H-1,2,3-triazol-5-yl)phenylamino)-1-oxopentan-2-aminium chloride |
| 194 | 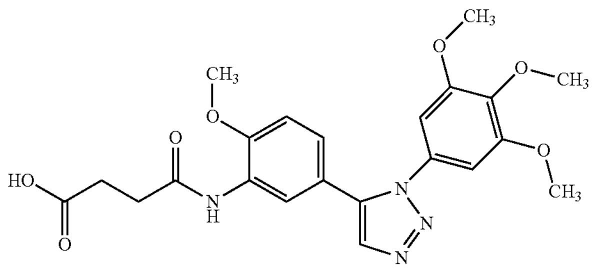 [SMILES: COc1ccc(-c2cnnn2-c2cc(OC)c(OC)c(OC)c2)cc1NC(=O)CCC(=O)O] | 4-(2-methoxy-5-(1-(3,4,5-trimethoxyphenyl)-1H-1,2,3-triazol-5-yl)phenylamino)-4-oxobutanoic acid |
| 195 | 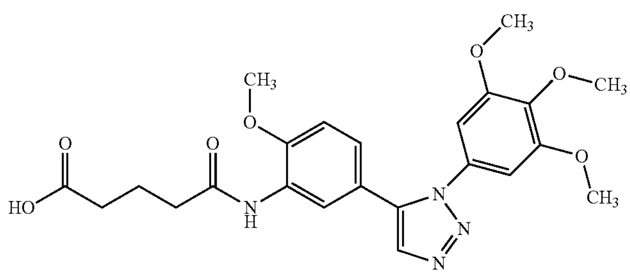 [SMILES: COc1ccc(-c2cnnn2-c2cc(OC)c(OC)c(OC)c2)cc1NC(=O)CCCC(=O)O] | 5-(2-methoxy-5-(1-(3,4,5-trimethoxyphenyl)-1H-1,2,3-triazol-5-yl)phenylamino)-5-oxopentanoic acid |
| 196 | 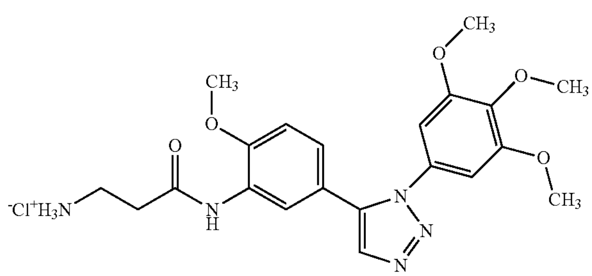 | 3-(2-methoxy-5-(1-(3,4,5-trimethoxyphenyl)-1H-1,2,3-triazol-5-yl)phenylamino)-3-oxopropan-1-aminium chloride |
| 197 | 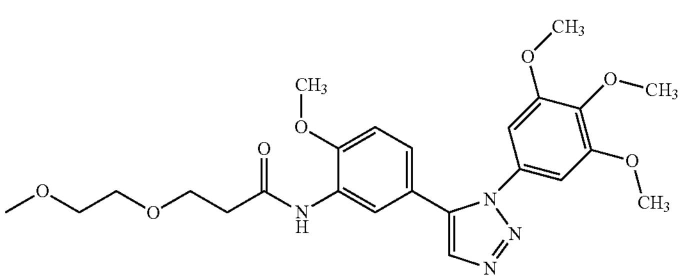 | N-(2-methoxy-5-(1-(3,4,5-trimethoxyphenyl)-1H-1,2,3-triazol-5-yl)phenyl)-3-(2-methoxyethoxy)propanamide |

TABLE 1-continued

| Compound No. | Structure | Chemical Name |
|---|---|---|
| 198 | 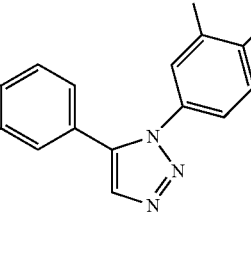 | 3-(2-PEG)-N-(2-methoxy-5-(1-(3,4,5-trimethoxyphenyl)-1H-1,2,3-triazol-5-yl)phenyl)butyramide |
| 199 | 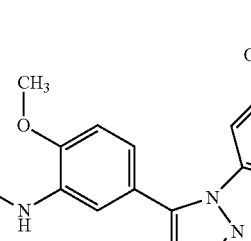 | N-(2-methoxy-5-(1-(3,4,5-trimethoxyphenyl)-1H-1,2,3-triazol-5-yl)phenyl)-3-(2-(methylamino)ethylamino)propanamide |
| 200 | 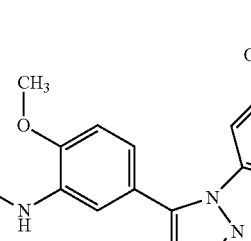 | 3-PEG-N-(2-methoxy-5-(1-(3,4,5-trimethoxyphenyl)-1H-1,2,3-triazol-5-yl)phenylamino)-2-oxoethyl)butyramide |
| 201 | 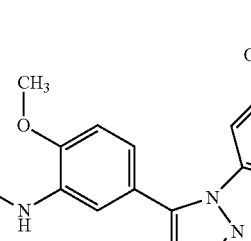 | 4-(2-(2-methoxy-5-(1-(3,4,5-trimethoxyphenyl)-1H-1,2,3-triazol-5-yl)phenylamino)-2-oxoethylamino)-4-oxobutanoic acid |
| 202 | 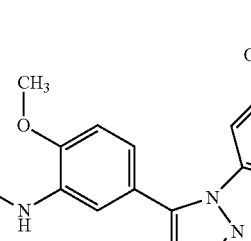 | 2-methoxyethyl 2-methoxy-5-(1-(3,4,5-trimethoxyphenyl)-1H-1,2,3-triazol-5-yl)phenylcarbamate |

TABLE 1-continued

| Compound No. | Structure | Chemical Name |
|---|---|---|
| 203 | 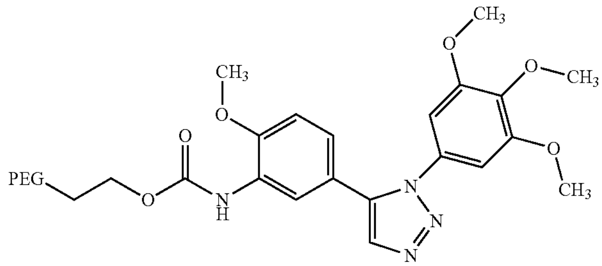 | PEG-2-methoxy-5-(1-(3,4,5-trimethoxyphenyl)-1H-1,2,3-triazol-5-yl)phenylcarbamate |
| 204 | 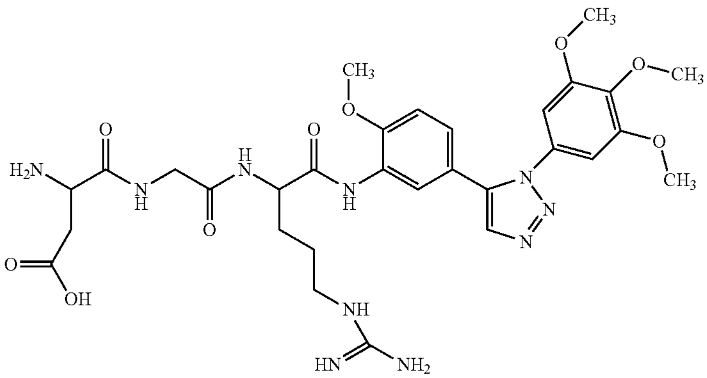 [SMILES: COc1ccc(-c2cnnn2-c2cc(OC)c(OC)c(OC)c2)cc1NC(=O)C(CCCNC(=N)N)NC(=O)CNC(=O)C(N)CC(=O)O] | 3-amino-4-(5-guanidino-1-(2-methoxy-5-(1-(3,4,5-trimethoxyphenyl)-1H-1,2,3-triazol-5-yl)phenylamino)-1-oxopentan-2-ylamino)-2-oxoethylamino)-4-oxobutanoic acid |
| 205 | 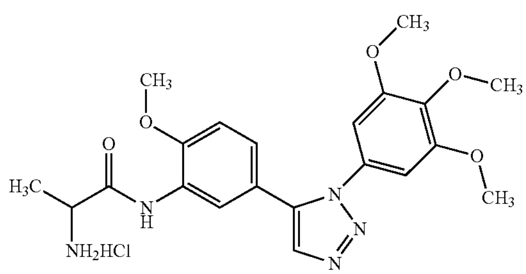 | 2-amino-N-(2-methoxy-5-(1-(3,4,5-trimethoxyphenyl)-1H-1,2,3-triazol-5-yl)phenyl)propanamide hydrochloride |
| 1b | 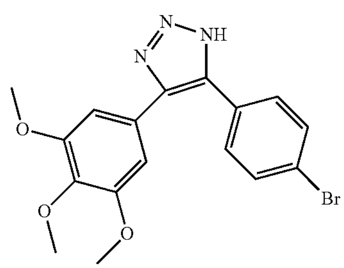 [SMILES: COc1cc(-c2nn[nH]c2-c2ccc(Br)cc2)cc(OC)c1OC] | 4-(3,4,5-trimethoxy-phenyl)-5-(4-bromo-phenyl)-1H-[1,2,3]triazole |
| 2b | 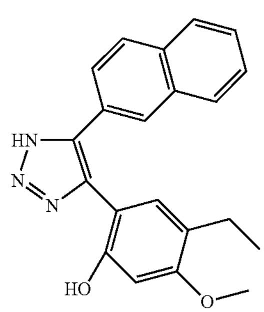 [SMILES: CCc1cc(-c2nn[nH]c2-c2ccc3ccccc3c2)c(O)cc1OC] | 4-ethyl-5-methoxy-2-(5-(naphthalen-2-yl)-1H-1,2,3-triazol-4-yl)phenol |

TABLE 1-continued

| Compound No. | Structure | Chemical Name |
|---|---|---|
| 3b | 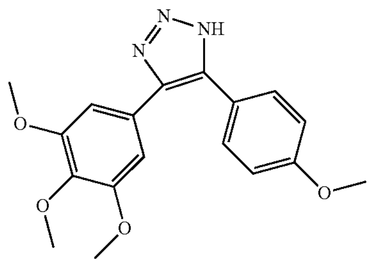 | 5-(4-methoxyphenyl)-4-(3,4,5-trimethoxyphenyl)-1H-1,2,3-triazole |
| 4b | 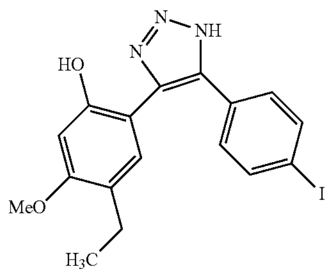 [SMILES: CCc1cc(-c2nn[nH]c2-c2ccc(I)cc2)c(O)cc1OC] | 4-ethyl-2-(5-(4-iodophenyl)-1H-1,2,3-triazol-4-yl)-5-methoxyphenol |
| 5b | 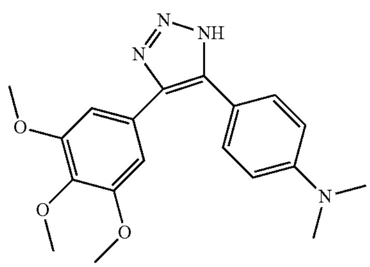 | N,N-dimethyl-4-(4-(3,4,5-trimethoxyphenyl)-1H-1,2,3-triazol-5-yl)aniline |
| 6b | 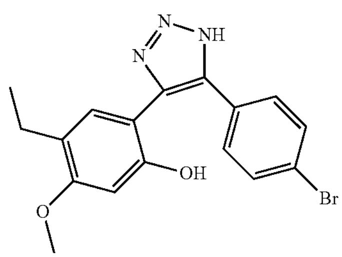 [SMILES: CCc1cc(-c2nn[nH]c2-c2ccc(Br)cc2)c(O)cc1OC] | 2-(5-(4-bromophenyl)-1H-1,2,3-triazol-4-yl)-4-ethyl-5-methoxyphenol |
| 7b | 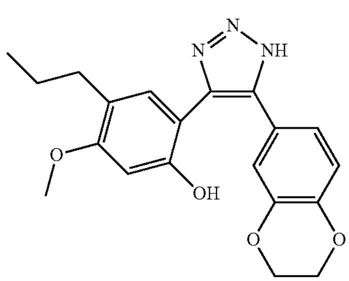 [SMILES: CCCc1cc(-c2nn[nH]c2-c2ccc3c(c2)OCCO3)c(O)cc1OC] | 2-(5-(2,3-dihydrobenzo[b][1,4]dioxin-6-yl)-1H-1,2,3-triazol-4-yl)-5-methoxy-4-propylphenol |
| 8b | 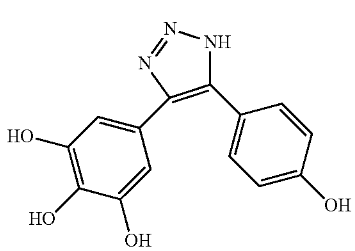 [SMILES: Oc1ccc(-c2[nH]nnc2-c2cc(O)c(O)c(O)c2)cc1] | 5-(5-(4-hydroxyphenyl)-1H-1,2,3-triazol-4-yl)benzene-1,2,3-triol |

TABLE 1-continued

| Compound No. | Structure | Chemical Name |
| --- | --- | --- |
| 9b | 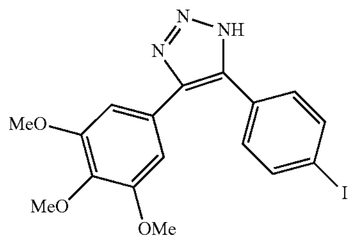 [SMILES: COc1cc(-c2nn[nH]c2-c2ccc(I)cc2)cc(OC)c1OC] | 5-(4-iodophenyl)-4-(3,4,5-trimethoxyphenyl)-1H-1,2,3-triazole |
| 10b | 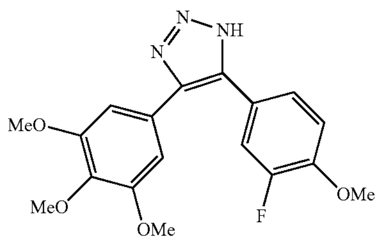 [SMILES: COc1ccc(-c2[nH]nnc2-c2cc(OC)c(OC)c(OC)c2)cc1F] | 5-(3-fluoro-4-methoxyphenyl)-4-(3,4,5-trimethoxyphenyl)-1H-1,2,3-triazole |
| 11b | 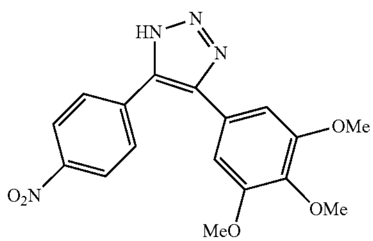 [SMILES: COc1cc(-c2nn[nH]c2-c2ccc([N+](=O)[O-])cc2)cc(OC)c1OC] | 5-(4-nitrophenyl)-4-(3,4,5-trimethoxyphenyl)-1H-1,2,3-triazole |
| 12b | 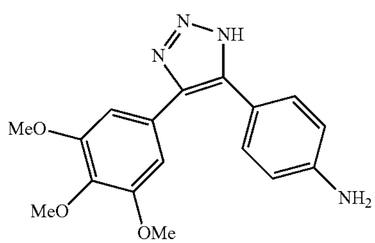 [SMILES: COc1cc(-c2nn[nH]c2-c2ccc(N)cc2)cc(OC)c1OC] | 4-(4-(3,4,5-trimethoxyphenyl)-1H-1,2,3-triazol-5-yl)aniline |
| 13b | 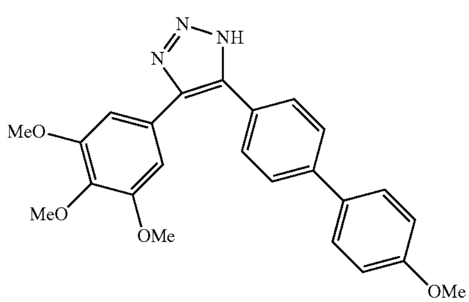 [SMILES: COc1ccc(-c2ccc(-c3[nH]nnc3-c3cc(OC)c(OC)c(OC)c3)cc2)cc1] | 5-(4'-methoxybiphenyl-4-yl)-4-(3,4,5-trimethoxyphenyl)-1H-1,2,3-triazole |
| 14b | 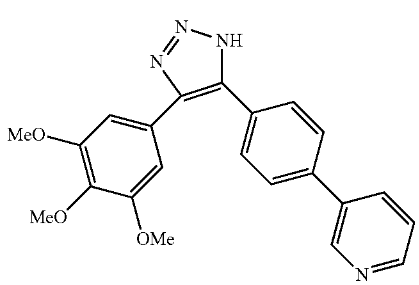 [SMILES: COc1cc(-c2nn[nH]c2-c2ccc(-c3cccnc3)cc2)cc(OC)c1OC] | 3-(4-(4-(3,4,5-trimethoxyphenyl)-1H-1,2,3-triazol-5-yl)phenyl)pyridine |

TABLE 1-continued

| Compound No. | Structure | Chemical Name |
|---|---|---|
| 15b | 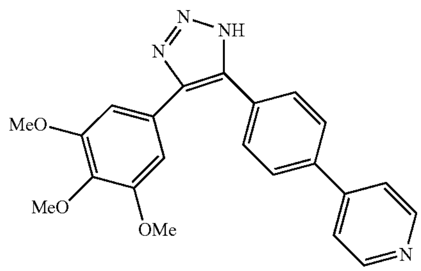 [SMILES: COc1cc(-c2nn[nH]c2-c2ccc(-c3ccncc3)cc2)cc(OC)c1OC] | 4-(4-(4-(3,4,5-trimethoxyphenyl)-1H-1,2,3-triazol-5-yl)phenyl)pyridine |
| 16b | 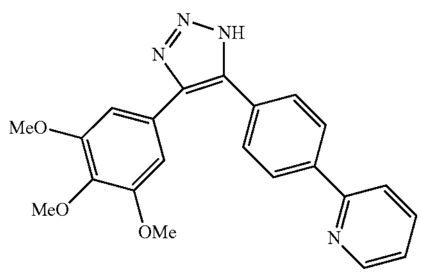 [SMILES: COc1cc(-c2nn[nH]c2-c2ccc(-c3ccccn3)cc2)cc(OC)c1OC] | 2-(4-(4-(3,4,5-trimethoxyphenyl)-1H-1,2,3-triazol-5-yl)phenyl)pyridine |
| 17b | 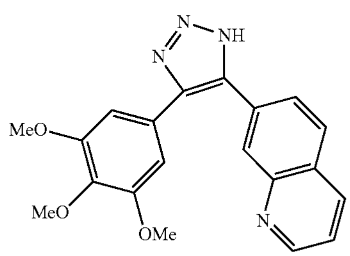 [SMILES: COc1cc(-c2nn[nH]c2-c2ccc3cccnc3c2)cc(OC)c1OC] | 7-(4-(3,4,5-trimethoxyphenyl)-1H-1,2,3-triazol-5-yl)quinoline |
| 18b | 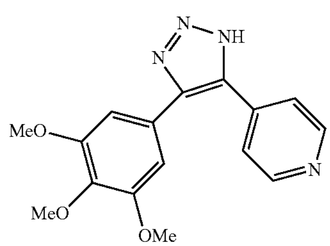 [SMILES: COc1cc(-c2nn[nH]c2-c2ccncc2)cc(OC)c1OC] | 4-(4-(3,4,5-trimethoxyphenyl)-1H-1,2,3-triazol-5-yl)pyridine |
| 19b | 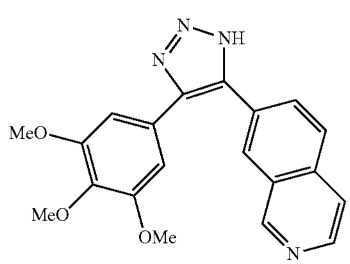 [SMILES: COc1cc(-c2nn[nH]c2-c2ccc3ccncc3c2)cc(OC)c1OC] | 7-(4-(3,4,5-trimethoxyphenyl)-1H-1,2,3-triazol-5-yl)isoquinoline |
| 20b | 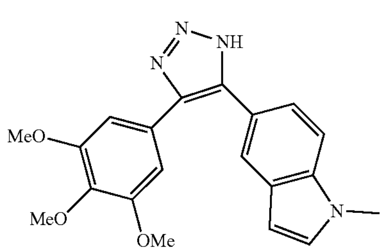 [SMILES: COc1cc(-c2nn[nH]c2-c2ccc3c(ccn3C)c2)cc(OC)c1OC] | 1-methyl-5-(4-(3,4,5-trimethoxyphenyl)-1H-1,2,3-triazol-5-yl)-1H-indole |

TABLE 1-continued

| Compound No. | Structure | Chemical Name |
| --- | --- | --- |
| 21b | 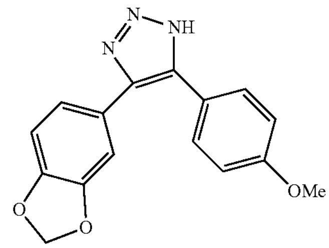 [SMILES: COc1ccc(-c2[nH]nnc2-c2ccc3c(c2)OCO3)cc1] | 4-(benzo[d][1,3]dioxol-5-yl)-5-(4-methoxyphenyl)-1H-1,2,3-triazole |
| 22b | 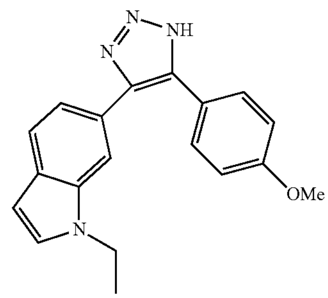 [SMILES: CCn1ccc2ccc(-c3nn[nH]c3-c3ccc(OC)cc3)cc21] | 1-ethyl-6-(5-(4-methoxyphenyl)-1H-1,2,3-triazole-4-yl)-1H-indole |
| 23b | 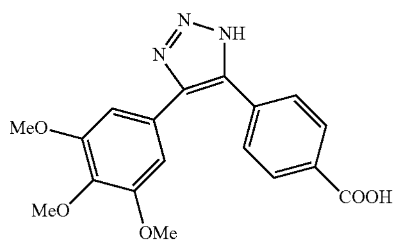 [SMILES: COc1cc(-c2nn[nH]c2-c2ccc(C(=O)O)cc2)cc(OC)c1OC] | 4-(4-(3,4,5-trimethoxyphenyl)-1H-1,2,3-triazol-5-yl)benzoic acid |
| 24b | 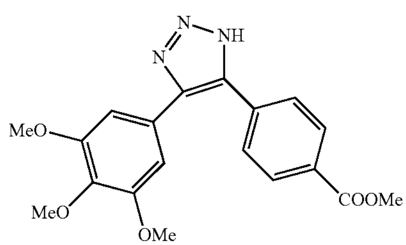 [SMILES: COC(=O)c1ccc(-c2[nH]nnc2-c2cc(OC)c(OC)c(OC)c2)cc1] | methyl 4-(4-(3,4,5-trimethoxyphenyl)-1H-1,2,3-triazol-5-yl)benzoate |
| 25b | 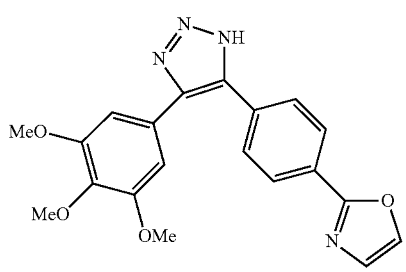 [SMILES: COc1cc(-c2nn[nH]c2-c2ccc(-c3ncco3)cc2)cc(OC)c1OC] | 2-(4-(4-(3,4,5-trimethoxyphenyl)-1H-1,2,3-triazol-5-yl)phenyl)oxazole |
| 26b | 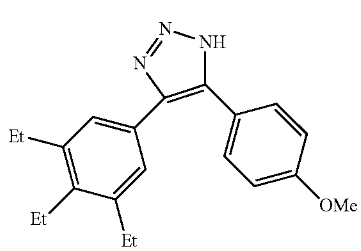 [SMILES: CCc1cc(-c2nn[nH]c2-c2ccc(OC)cc2)cc(CC)c1CC] | 5-(4-methoxyphenyl)-4-(3,4,5-trimethoxyphenyl)-1H-1,2,3-triazole |

| Compound No. | Structure | Chemical Name |
|---|---|---|
| 27b | 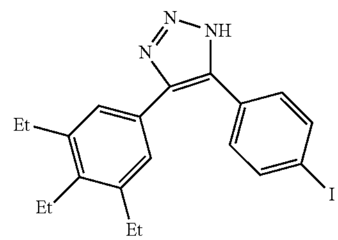 [SMILES: CCc1cc(-c2nn[nH]c2-c2ccc(I)cc2)cc(CC)c1CC] | 5-(4-iodophenyl)-4-(3,4,5-triethylphenyl)-1H-1,2,3-triazole |
| 28b | 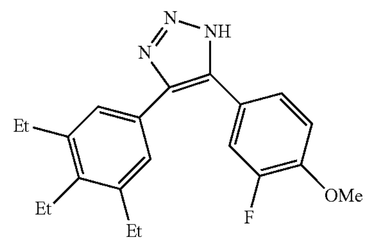 [SMILES: CCc1cc(-c2nn[nH]c2-c2ccc(OC)c(F)c2)cc(CC)c1CC] | 5-(3-fluoro-4-methoxyphenyl)-4-(3,4,5-triethylphenyl)-1H-1,2,3-triazole |
| 29b | 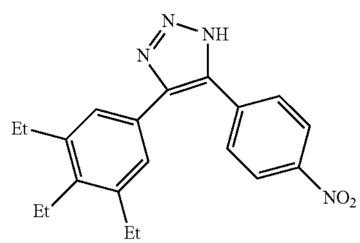 [SMILES: CCc1cc(-c2nn[nH]c2-c2ccc([N+](=O)[O-])cc2)cc(CC)c1CC] | 5-(4-nitrophenyl)-4-(3,4,5-triethylphenyl)-1H-1,2,3-triazole |
| 30b | 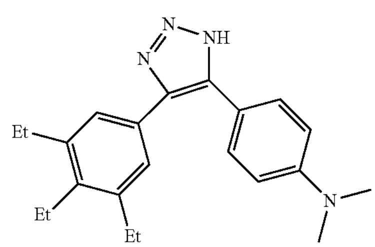 [SMILES: CCc1cc(-c2nn[nH]c2-c2ccc(N(C)C)cc2)cc(CC)c1CC] | N,N-dimethyl-4-(4-(3,4,5-triethylphenyl)-1H-1,2,3-triazol-5-yl)aniline |
| 31b | 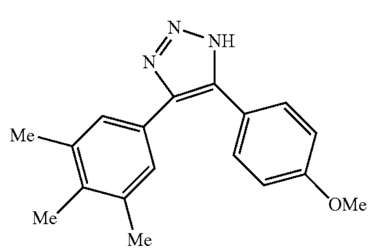 [SMILES: COc1ccc(-c2[nH]nnc2-c2cc(C)c(C)c(C)c2)cc1] | 5-(4-methoxyphenyl)-4-(3,4,5-trimethylphenyl)-1H-1,2,3-triazole |
| 32b | 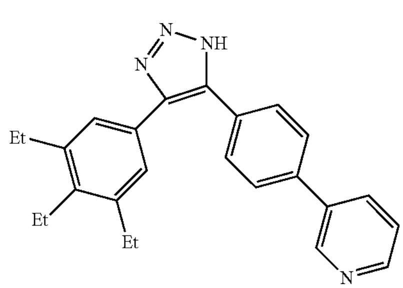 [SMILES: CCc1cc(-c2nn[nH]c2-c2ccc(-c3cccnc3)cc2)cc(CC)c1CC] | 3-(4-(4-(3,4,5-triethylphenyl)-1H-1,2,3-triazol-5-yl)phenyl)pyridine |

TABLE 1-continued

| Compound No. | Structure | Chemical Name |
| --- | --- | --- |
| 33b | 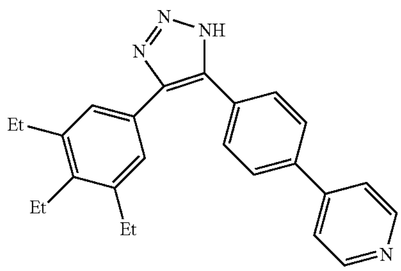 [SMILES: CCc1cc(-c2nn[nH]c2-c2ccc(-c3ccncc3)cc2)cc(CC)c1CC] | 4-(4-(4-(3,4,5-triethylphenyl)-1H-1,2,3-triazol-5-yl)phenyl)pyridine |
| 34b | 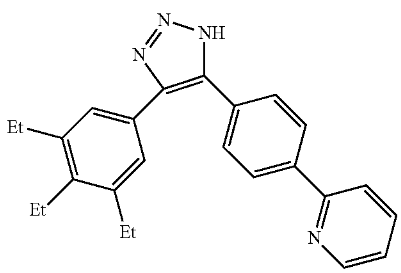 [SMILES: CCc1cc(-c2nn[nH]c2-c2ccc(-c3ccccn3)cc2)cc(CC)c1CC] | 2-(4-(4-(3,4,5-triethylphenyl)-1H-1,2,3-triazol-5-yl)phenyl)pyridine |
| 35b | 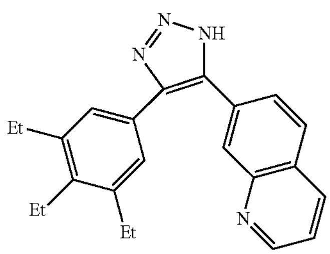 [SMILES: CCc1cc(-c2nn[nH]c2-c2ccc3cccnc3c2)cc(CC)c1CC] | 7-(4-(3,4,5-triethylphenyl)-1H-1,2,3-triazol-5-yl)quinoline |
| 36b | 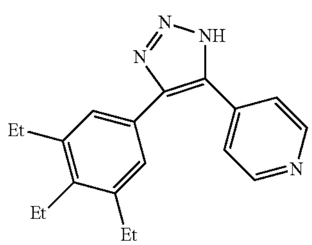 [SMILES: CCc1cc(-c2nn[nH]c2-c2ccncc2)cc(CC)c1CC] | 4-(4-(3,4,5-triethylphenyl)-1H-1,2,3-triazol-5-yl)pyridine |
| 37b | 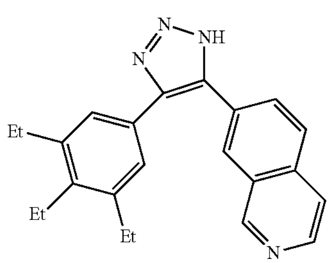 [SMILES: CCc1cc(-c2nn[nH]c2-c2ccc3ccncc3c2)cc(CC)c1CC] | 7-(4-(3,4,5-triethylphenyl)-1H-1,2,3-triazol-5-yl)isoquinoline |
| 38b | 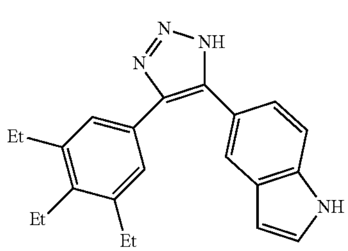 [SMILES: CCc1cc(-c2nn[nH]c2-c2ccc3[nH]ccc3c2)cc(CC)c1CC] | 5-(4-(3,4,5-triethylphenyl)-1H-1,2,3-triazol-5-yl)-1H-indole |

TABLE 1-continued

| Compound No. | Structure | Chemical Name |
|---|---|---|
| 39b | 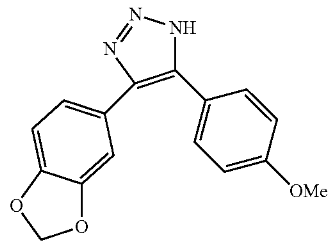 [SMILES: COc1ccc(-c2[nH]nnc2-c2ccc3c(c2)OCO3)cc1] | 4-(benzo[d][1,3]dioxol-5-yl)-5-(4-methoxyphenyl)-1H-1,2,3-triazole |
| 40b | 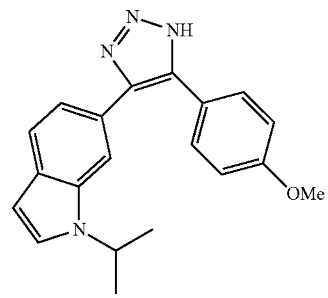 [SMILES: COc1ccc(-c2[nH]nnc2-c2ccc3ccn(C(C)C)c3c2)cc1] | 1-isopropyl-6-(5-(4-methoxyphenyl)-1H-1,2,3-triazol-4-yl)-1H-indole |
| 41b | 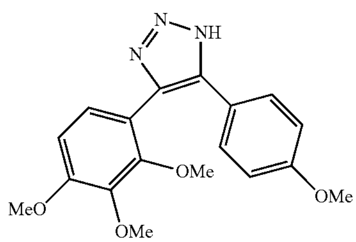 [SMILES: COc1ccc(-c2[nH]nnc2-c2ccc(OC)c(OC)c2OC)cc1] | 5-(4-methoxyphenyl)-4-(2,3,4-trimethoxyphenyl)-1H-1,2,3-triazole |
| 42b | 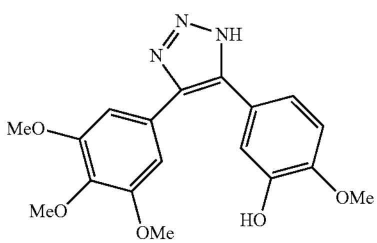 [SMILES: COc1ccc(-c2[nH]nnc2-c2cc(OC)c(OC)c(OC)c2)cc1O] | 2-methoxy-5-(4-(3,4,5-trimethoxyphenyl)-1H-1,2,3-triazol-5-yl)phenol |
| 43b | 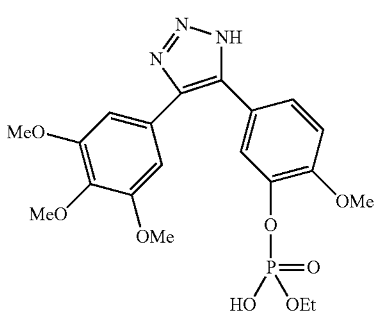 [SMILES: CCOP(=O)(O)Oc1cc(-c2[nH]nnc2-c2cc(OC)c(OC)c(OC)c2)ccc1OC] | ethyl 2-methoxy-5-(4-(3,4,5-trimethoxyphenyl)-1H-1,2,3-triazol-5-yl)phenyl hydrogen phosphate |
| 44b | 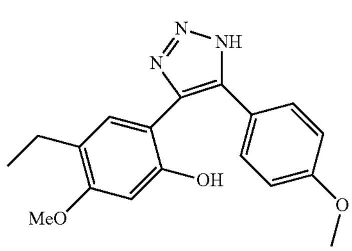 [SMILES: CCc1cc(-c2nn[nH]c2-c2ccc(OC)cc2)c(O)cc1OC] | 4-ethyl-2-(5-(4-methoxyphenyl)-1H-1,2,3-triazol-4-yl)-5-methoxyphenol |

TABLE 1-continued

| Compound No. | Structure | Chemical Name |
| --- | --- | --- |
| 45b | 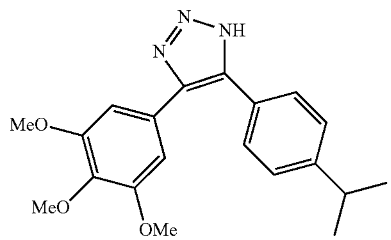 [SMILES: COc1cc(-c2nn[nH]c2-c2ccc(C(C)C)cc2)cc(OC)c1OC] | 5-(4-isopropylphenyl)-4-(3,4,5-trimethoxyphenyl)-1H-1,2,3-triazole |
| 46b | 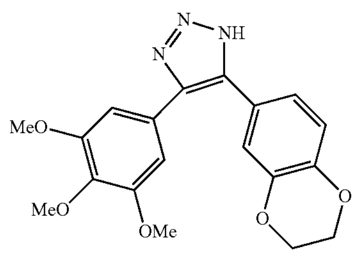 [SMILES: COc1cc(-c2nn[nH]c2-c2ccc3c(c2)OCCO3)cc(OC)c1OC] | 5-(2,3-dihydrobenzo[b][1,4]dioxin-6-yl)-4-(3,4,5-trimethoxyphenyl)-1H-1,2,3-triazole |
| 47b | 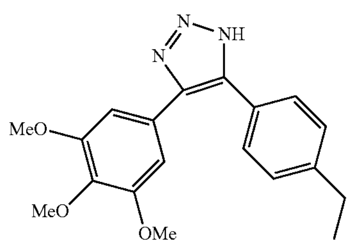 [SMILES: CCc1ccc(-c2[nH]nnc2-c2cc(OC)c(OC)c(OC)c2)cc1] | 5-(4-ethylphenyl)-4-(3,4,5-trimethoxyphenyl)-1H-1,2,3-triazole |
| 48b | 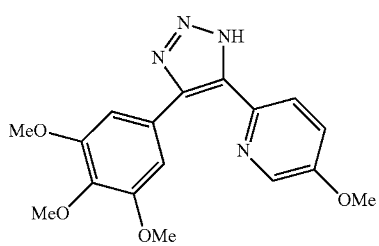 [SMILES: COc1ccc(-c2[nH]nnc2-c2cc(OC)c(OC)c(OC)c2)nc1] | 5-methoxy-2-(4-(3,4,5-trimethoxyphenyl)-1H-1,2,3-triazol-5-yl)pyridine |
| 49b | 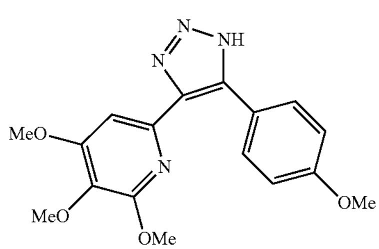 [SMILES: COc1ccc(-c2[nH]nnc2-c2cc(OC)c(OC)c(OC)n2)cc1] | 6-(5-(4-methoxyphenyl)-1H-1,2,3-triazol-4-yl)-2,3,4-trimethoxypyridine |
| 50b | 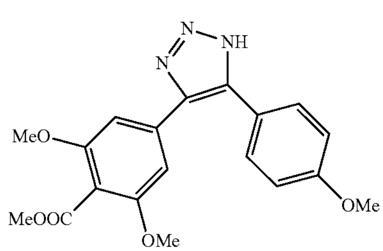 [SMILES: COC(=O)c1c(OC)cc(-c2nn[nH]c2-c2ccc(OC)cc2)cc1OC] | methyl 2,6-dimethoxy-4-(5-(4-methoxyphenyl)-1H-1,2,3-triazol-4-yl)benzoate |

TABLE 1-continued

| Compound No. | Structure | Chemical Name |
|---|---|---|
| 51b | 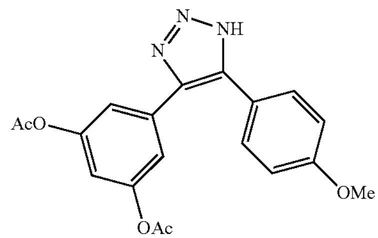 [SMILES: COc1ccc(-c2[nH]nnc2-c2cc(OC(C)=O)cc(OC(C)=O)c2)cc1] | 5-(5-(4-methoxyphenyl)-1H-1,2,3-triazol-4-yl)-1,3-phenylene diacetate |
| 52b | 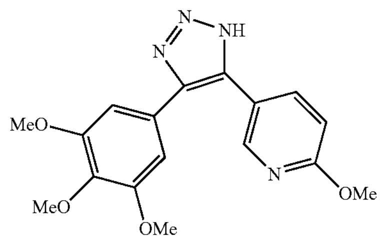 [SMILES: COc1ccc(-c2[nH]nnc2-c2cc(OC)c(OC)c(OC)c2)cn1] | 2-methoxy-5-(4-(3,4,5-trimethoxyphenyl)-1H-1,2,3-triazol-5-yl)pyridine |
| 53b | 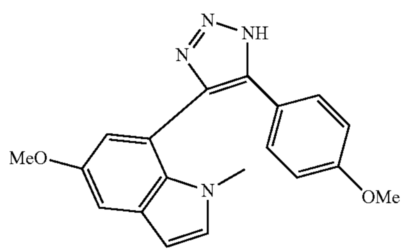 [SMILES: COc1ccc(-c2[nH]nnc2-c2cc(OC)cc3ccn(C)c23)cc1] | 5-methoxy-7-(5-(4-methoxyphenyl)-1H-1,2,3-triazol-4-yl)-1-methyl-1H-indole |
| 54b | 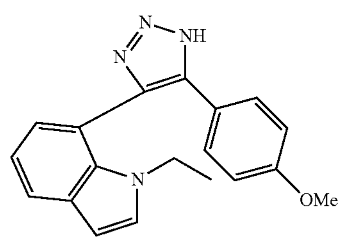 [SMILES: CCn1ccc2cccc(-c3nn[nH]c3-c3ccc(OC)cc3)c21] | 1-ethyl-7-(5-(4-methoxyphenyl)-1H-1,2,3-triazol-4-yl)-1H-indole |
| 55b | 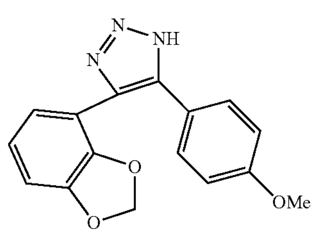 [SMILES: COc1ccc(-c2[nH]nnc2-c2cccc3c2OCO3)cc1] | 4-(benzo[d][1,3]dioxol-4-yl)-5-(4-methoxyphenyl)-1H-1,2,3-triazole |
| 56b | 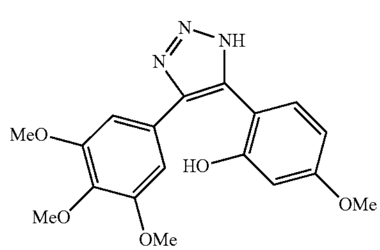 [SMILES: COc1ccc(-c2[nH]nnc2-c2cc(OC)c(OC)c(OC)c2)c(O)c1] | 5-methoxy-2-(4-(3,4,5-trimethoxyphenyl)-1H-1,2,3-triazol-5-yl)phenol |

TABLE 1-continued

| Compound No. | Structure | Chemical Name |
|---|---|---|
| 57b | 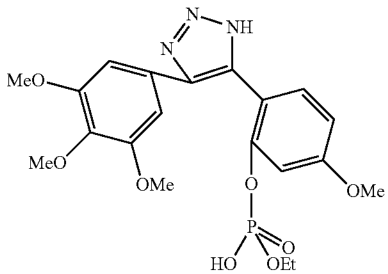 [SMILES: CCOP(=O)(O)Oc1cc(OC)ccc1-c1[nH]nnc1-c1cc(OC)c(OC)c(OC)c1] | ethyl 5-methoxy-2-(4-(3,4,5-trimethoxyphenyl)-1H-1,2,3-triazol-5-yl)phenyl hydrogen phosphate |
| 58b | 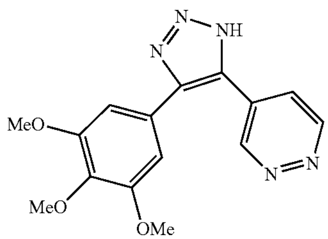 [SMILES: COc1cc(-c2nn[nH]c2-c2ccnnc2)cc(OC)c1OC] | 4-(4-(3,4,5-trimethoxyphenyl)-1H-1,2,3-triazol-5-yl)pyridazine |
| 59b | 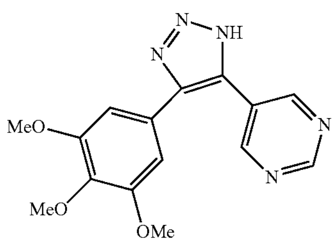 [SMILES: COc1cc(-c2nn[nH]c2-c2cncnc2)cc(OC)c1OC] | 5-(4-(3,4,5-trimethoxyphenyl)-1H-1,2,3-triazol-5-yl)pyrimidine |
| 60b | 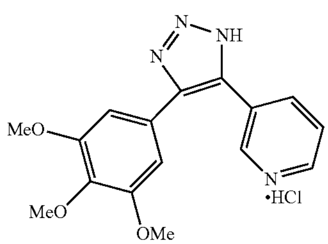 [SMILES: COc1cc(-c2nn[nH]c2-c2cccnc2)cc(OC)c1OC ; Cl] | 3-(4-(3,4,5-trimethoxyphenyl)-1H-1,2,3-triazol-5-yl)pyridine hydrochloride |
| 61b | 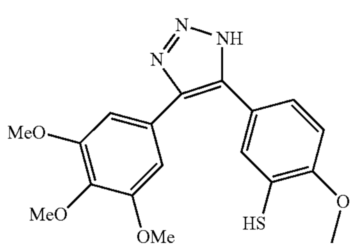 [SMILES: COc1ccc(-c2[nH]nnc2-c2cc(OC)c(OC)c(OC)c2)cc1S] | 2-methoxy-5-(4-(3,4,5-trimethoxyphenyl)-1H-1,2,3-triazol-5-yl)benzenethiol |
| 62b | 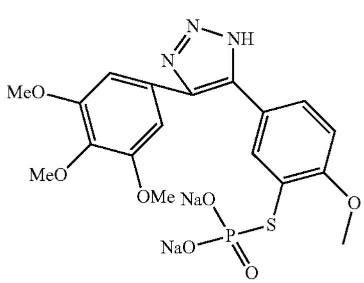 | sodium S-2-methoxy-5-(4-(3,4,5-trimethoxyphenyl)-1H-1,2,3-triazol-5-yl)phenyl phosphorothioate |

TABLE 1-continued

| Compound No. | Structure | Chemical Name |
|---|---|---|
| 63b | 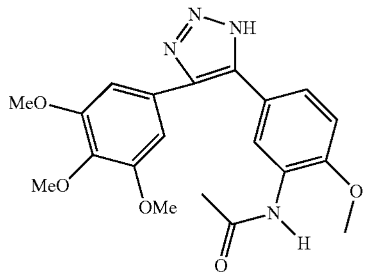 [SMILES: COc1ccc(-c2[nH]nnc2-c2cc(OC)c(OC)c(OC)c2)cc1NC(C)=O] | N-(2-methoxy-5-(4-(3,4,5-trimethoxyphenyl)-1H-1,2,3-triazol-5-yl)phenyl)acetamide |
| 64b | 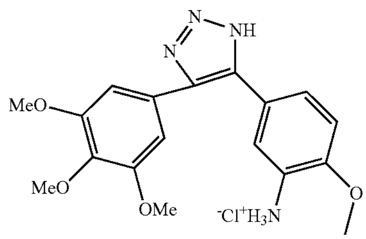 | 2-methoxy-5-(4-(3,4,5-trimethoxyphenyl)-1H-1,2,3-triazol-5-yl)benzenaminium chloride |
| 65b | 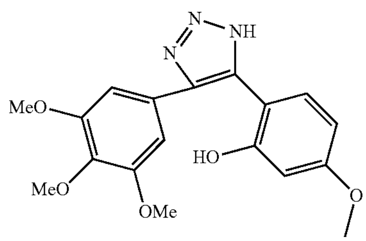 [SMILES: COc1ccc(-c2[nH]nnc2-c2cc(OC)c(OC)c(OC)c2)c(O)c1] | 5-methoxy-2-(4-(3,4,5-trimethoxyphenyl)-1H-1,2,3-triazol-5-yl)phenol |
| 66b | 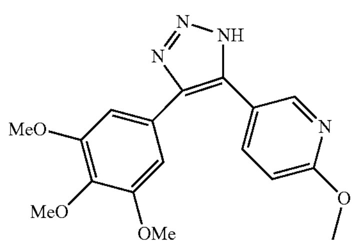 [SMILES: COc1ccc(-c2[nH]nnc2-c2cc(OC)c(OC)c(OC)c2)cn1] | 2-methoxy-5-(4-(3,4,5-trimethoxyphenyl)-1H-1,2,3-triazol-5-yl)pyridine |
| 67b | 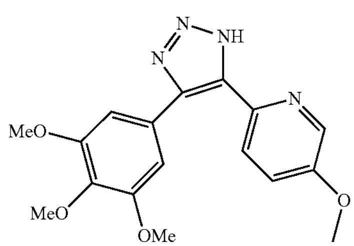 [SMILES: COc1ccc(-c2[nH]nnc2-c2cc(OC)c(OC)c(OC)c2)nc1] | 5-methoxy-2-(4-(3,4,5-trimethoxyphenyl)-1H-1,2,3-triazol-5-yl)pyridine |
| 68b | 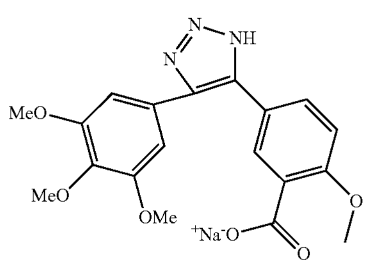 | sodium 2-methoxy-5-(4-(3,4,5-trimethoxyphenyl)-1H-1,2,3-triazol-5-yl)benzoate |

TABLE 1-continued

| Compound No. | Structure | Chemical Name |
|---|---|---|
| 69b | 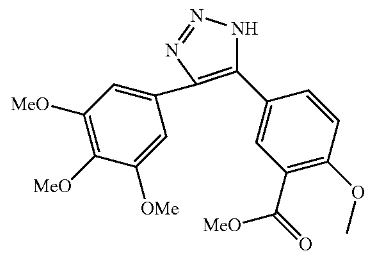 [SMILES: COC(=O)c1cc(-c2[nH]nnc2-c2cc(OC)c(OC)c(OC)c2)ccc1OC] | methyl 2-methoxy-5-(4-(3,4,5-trimethoxyphenyl)-1H-1,2,3-triazol-5-yl)benzoate |
| 70b | 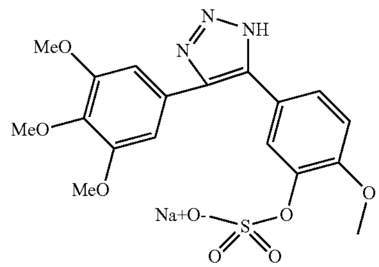 | sodium 2-methoxy-5-(4-(3,4,5-trimethoxyphenyl)-1H-1,2,3-triazol-5-yl)phenyl sulfate |
| 71b | 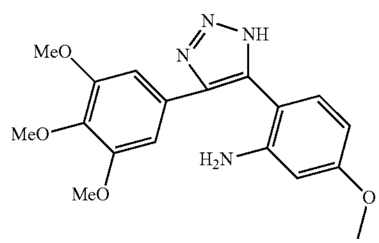 [SMILES: COc1ccc(-c2[nH]nnc2-c2cc(OC)c(OC)c(OC)c2)c(N)c1] | 5-methoxy-2-(4-(3,4,5-trimethoxyphenyl)-1H-1,2,3-triazol-5-yl)aniline |
| 72b | 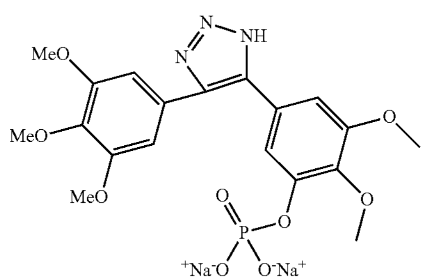 | sodium 2,3-dimethoxy-5-(4-(3,4,5-trimethoxyphenyl)-1H-1,2,3-triazol-5-yl)phenyl phosphate |
| 73b | 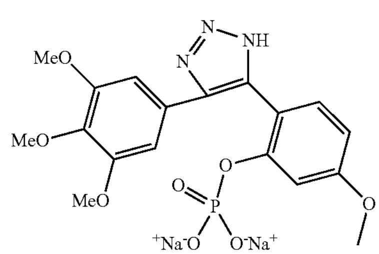 | sodium 5-methoxy-2-(4-(3,4,5-trimethoxyphenyl)-1H-1,2,3-triazol-5-yl)phenyl phosphate |
| 74b | 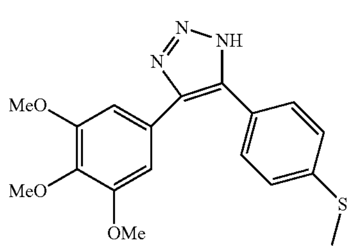 [SMILES: COc1cc(-c2nn[nH]c2-c2ccc(SC)cc2)cc(OC)c1OC] | 5-(4-(methylthio)phenyl)-4-(3,4,5-trimethoxyphenyl)-1H-1,2,3-triazole |

TABLE 1-continued

| Compound No. | Structure | Chemical Name |
|---|---|---|
| 75b | 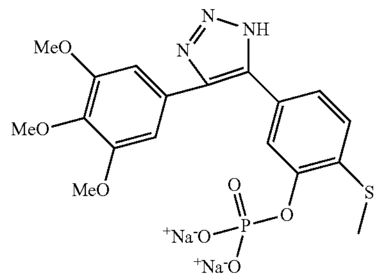 | sodium 2-(methylthio)-5-(4-(3,4,5-trimethoxyphenyl)-1H-1,2,3-triazol-5-yl)phenyl phosphate |
| 76b | 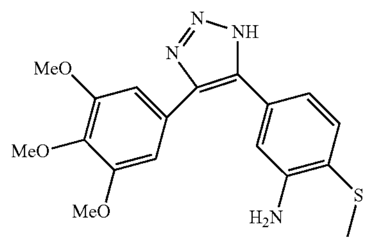 [SMILES: COc1cc(-c2nn[nH]c2-c2ccc(SC)c(N)c2)cc(OC)c1OC] | 2-(methylthio)-5-(4-(3,4,5-trimethoxyphenyl)-1H-1,2,3-triazol-5-yl)aniline |
| 77b | 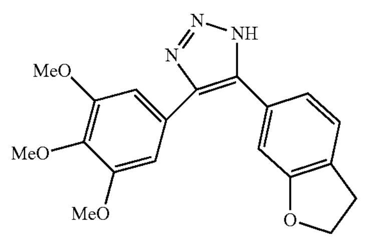 [SMILES: COc1cc(-c2nn[nH]c2-c2ccc3c(c2)OCC3)cc(OC)c1OC] | 5-(2,3-dihydrobenzofuran-6-yl)-4-(3,4,5-trimethoxyphenyl)-1H-1,2,3-triazole |
| 78b | 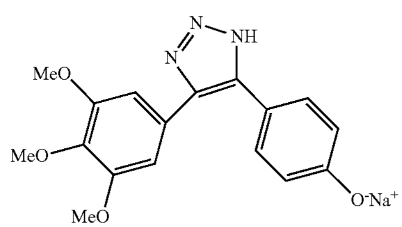 | sodium 4-(4-(3,4,5-trimethoxyphenyl)-1H-1,2,3-triazol-5-yl)phenolate |
| 79b | 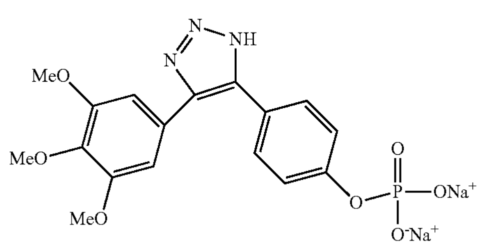 | monosodium monosodium(II) mono(4-(4-(3,4,5-trimethoxyphenyl)-1H-1,2,3-triazol-5-yl)phenyl phosphate) |
| 80b | 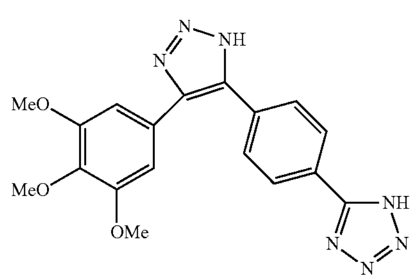 [SMILES: COc1cc(-c2nn[nH]c2-c2ccc(-c3nnn[nH]3)cc2)cc(OC)c1OC] | 5-(4-(4-(3,4,5-trimethoxyphenyl)-1H-1,2,3-triazol-5-yl)phenyl)-1H-tetrazole |

TABLE 1-continued

| Compound No. | Structure | Chemical Name |
|---|---|---|
| 81b | 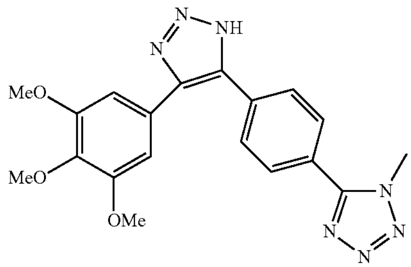 [SMILES: COc1cc(-c2nn[nH]c2-c2ccc(-c3nnnn3C)cc2)cc(OC)c1OC] | 1-methyl-5-(4-(4-(3,4,5-trimethoxyphenyl)-1H-1,2,3-triazol-5-yl)phenyl)-1H-tetrazole |
| 82b | 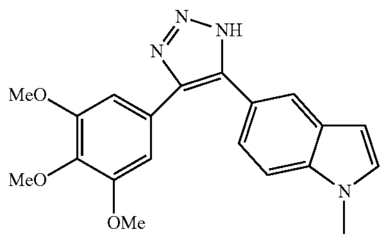 [SMILES: COc1cc(-c2nn[nH]c2-c2ccc3c(ccn3C)c2)cc(OC)c1OC] | 1-methyl-5-(4-(3,4,5-trimethoxyphenyl)-1H-1,2,3-triazol-5-yl)-1H-indole |
| 83b | 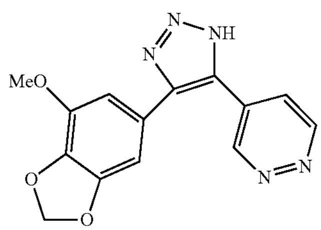 [SMILES: COc1cc(-c2nn[nH]c2-c2ccnnc2)cc2c1OCO2] | 4-(4-(7-methoxybenzo[d][1,3]dioxol-5-yl)-1H-1,2,3-triazol-5-yl)pyridazine |
| 84b | 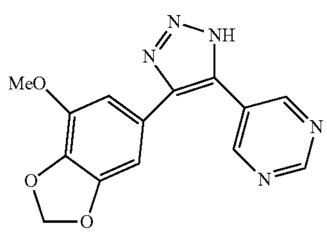 [SMILES: COc1cc(-c2nn[nH]c2-c2cncnc2)cc2c1OCO2] | 5-(4-(7-methoxybenzo[d][1,3]dioxol-5-yl)-1H-1,2,3-triazol-5-yl)pyrimidine |
| 85b | 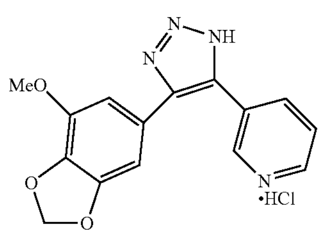 [SMILES: COc1cc(-c2nn[nH]c2-c2cccnc2)cc2c1OCO2 ; Cl] | 3-(4-(7-methoxybenzo[d][1,3]dioxol-5-yl)-1H-1,2,3-triazol-5-yl)pyridine hydrochloride |
| 86b | 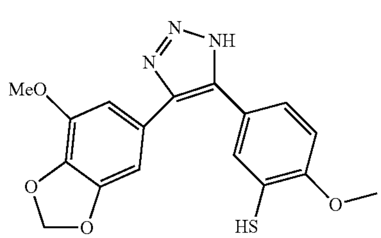 [SMILES: COc1ccc(-c2[nH]nnc2-c2cc(OC)c3c(c2)OCO3)cc1S] | 2-methoxy-5-(4-(7-methoxybenzo[d][1,3]dioxol-5-yl)-1H-1,2,3-triazol-5-yl)benzenethiol |

TABLE 1-continued

| Compound No. | Structure | Chemical Name |
|---|---|---|
| 87b | 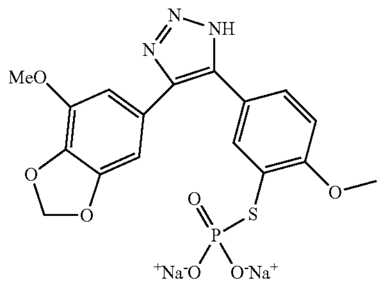 | sodium S-2-methoxy-5-(4-(7-methoxybenzo[d][1,3]dioxol-5-yl)-1H-1,2,3-triazol-5-yl)phenyl phosphorothioate |
| 88b | 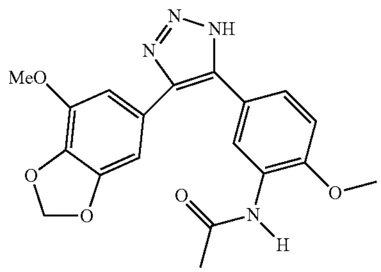 [SMILES: COc1ccc(-c2[nH]nnc2-c2cc(OC)c3c(c2)OCO3)cc1NC(C)=O] | N-(2-methoxy-5-(4-(7-methoxybenzo[d][1,3]dioxol-5-yl)-1H-1,2,3-triazol-5-yl)phenyl)acetamide |
| 89b | 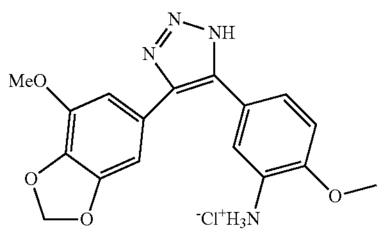 | 2-methoxy-5-(4-(7-methoxybenzo[d][1,3]dioxol-5-yl)-1H-1,2,3-triazol-5-yl)benzenaminium chloride |
| 90b | 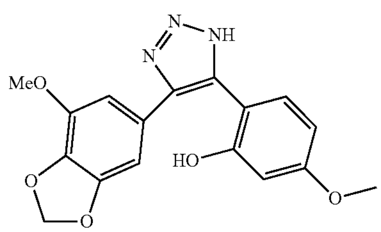 [SMILES: COc1ccc(-c2[nH]nnc2-c2cc(OC)c3c(c2)OCO3)c(O)c1] | 5-methoxy-2-(4-(7-methoxybenzo[d][1,3]dioxol-5-yl)-1H-1,2,3-triazol-5-yl)phenol |
| 91b | 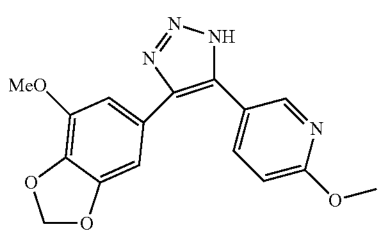 [SMILES: COc1ccc(-c2[nH]nnc2-c2cc(OC)c3c(c2)OCO3)cn1] | 2-methoxy-5-(4-(7-methoxybenzo[d][1,3]dioxol-5-yl)-1H-1,2,3-triazol-5-yl)pyridine |
| 92b | 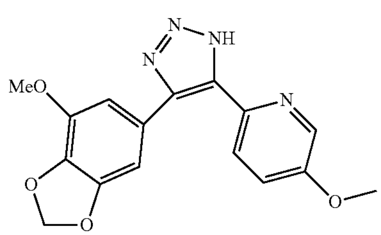 [SMILES: COc1ccc(-c2[nH]nnc2-c2cc(OC)c3c(c2)OCO3)nc1] | 5-methoxy-2-(4-(7-methoxybenzo[d][1,3]dioxol-5-yl)-1H-1,2,3-triazol-5-yl)pyridine |

TABLE 1-continued

| Compound No. | Structure | Chemical Name |
|---|---|---|
| 93b | 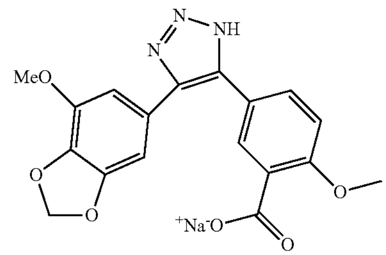 | sodium 2-methoxy-5-(4-(7-methoxybenzo[d][1,3]dioxol-5-yl)-1H-1,2,3-triazol-5-yl)benzoate |
| 94b | 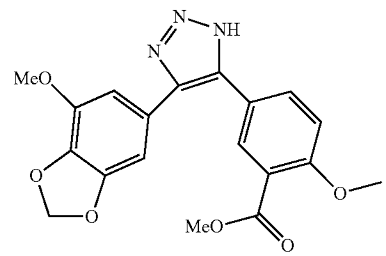 | methyl 2-methoxy-5-(4-(7-methoxybenzo[d][1,3]dioxol-5-yl)-1H-1,2,3-triazol-5-yl)benzoate |
| 95b | 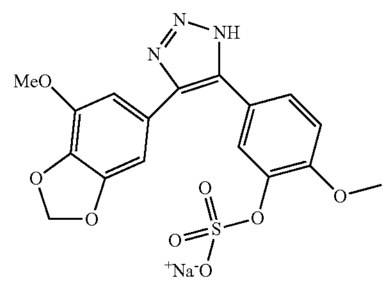 | sodium 2-methoxy-5-(4-(7-methoxybenzo[d][1,3]dioxol-5-yl)-1H-1,2,3-triazol-5-yl)phenyl sulfate |
| 96b | 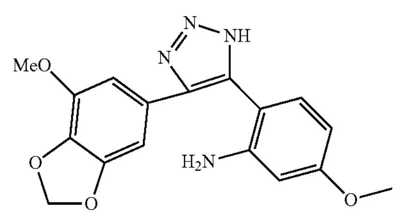 [SMILES: COc1ccc(-c2[nH]nnc2-c2cc(OC)c3c(c2)OCO3)c(N)c1] | 5-methoxy-2-(4-(7-methoxybenzo[d][1,3]dioxol-5-yl)-1H-1,2,3-triazol-5-yl)aniline |
| 97b | 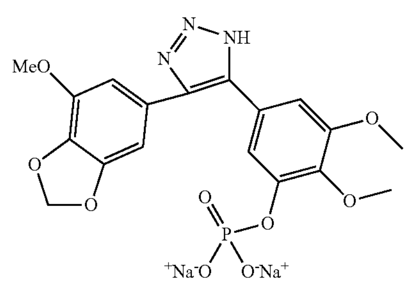 | sodium 2,3-dimethoxy-5-(4-(7-methoxybenzo[d][1,3]dioxol-5-yl)-1H-1,2,3-triazol-5-yl)phenyl phosphate |
| 98b | 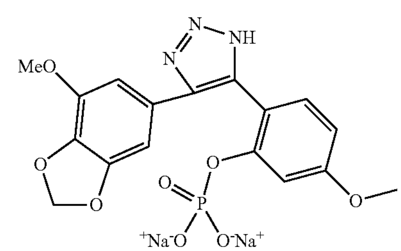 | sodium 5-methoxy-2-(4-(7-methoxybenzo[d][1,3]dioxol-5-yl)-1H-1,2,3-triazol-5-yl)phenyl phosphate |

| Compound No. | Structure | Chemical Name |
| --- | --- | --- |
| 99b | 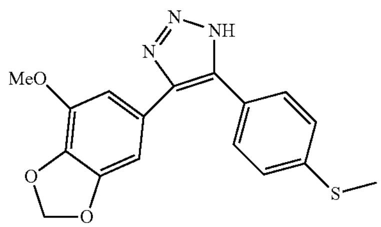 [SMILES: COc1cc(-c2nn[nH]c2-c2ccc(SC)cc2)cc2c1OCO2] | 4-(7-methoxybenzo[d][1,3]dioxol-5-yl)-5-(4-(methylthio)phenyl)-1H-1,2,3-triazole |
| 100b | 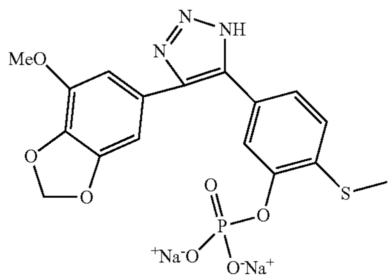 | sodium 5-(4-(7-methoxybenzo[d][1,3]dioxol-5-yl)-1H-1,2,3-triazol-5-yl)-2-(methylthio)phenyl phosphate |
| 101b | 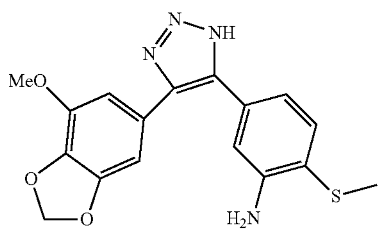 [SMILES: COc1cc(-c2nn[nH]c2-c2ccc(SC)c(N)c2)cc2c1OCO2] | 5-(4-(7-methoxybenzo[d][1,3]dioxol-5-yl)-1H-1,2,3-triazol-5-yl)-2-(methylthio)aniline |
| 102b | 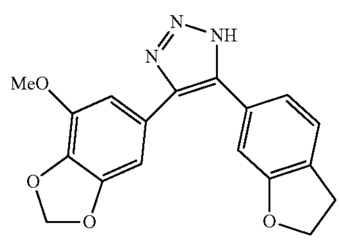 [SMILES: COc1cc(-c2nn[nH]c2-c2ccc3c(c2)OCC3)cc2c1OCO2] | 5-(2,3-dihydrobenzofuran-6-yl)-4-(7-methoxybenzo[d][1,3]dioxol-5-yl)-1H-1,2,3-triazole |
| 103b | 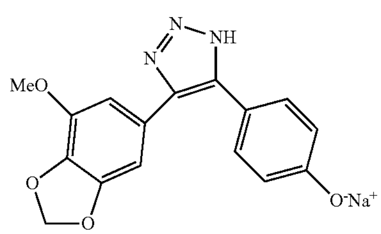 | sodium 4-(4-(7-methoxybenzo[d][1,3]dioxol-5-yl)-1H-1,2,3-triazol-5-yl)phenolate |
| 104b | 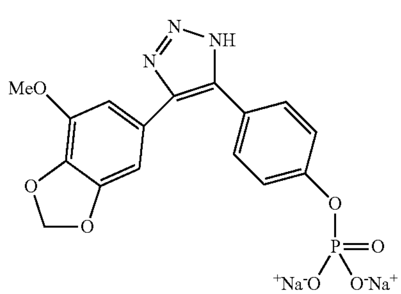 | sodium 4-(4-(7-methoxybenzo[d][1,3]dioxol-5-yl)-1H-1,2,3-triazol-5-yl)phenyl phosphate |

TABLE 1-continued

| Compound No. | Structure | Chemical Name |
|---|---|---|
| 105b | 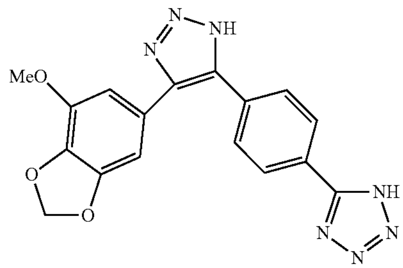 [SMILES: COc1cc(-c2nn[nH]c2-c2ccc(-c3nnn[nH]3)cc2)cc2c1OCO2] | 5-(4-(4-(7-methoxybenzo[d][1,3]dioxol-5-yl)-1H-1,2,3-triazol-5-yl)phenyl)-1H-tetrazole |
| 106b | 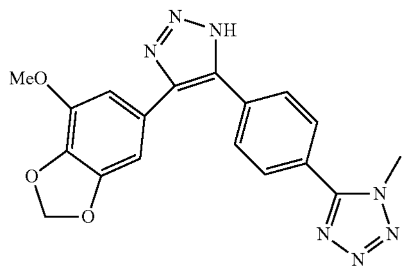 [SMILES: COc1cc(-c2nn[nH]c2-c2ccc(-c3nnnn3C)cc2)cc2c1OCO2] | 5-(4-(4-(7-methoxybenzo[d][1,3]dioxol-5-yl)-1H-1,2,3-triazol-5-yl)phenyl)-1-methyl-1H-tetrazole |
| 107b | 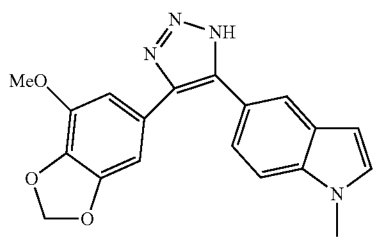 [SMILES: COc1cc(-c2nn[nH]c2-c2ccc3c(ccn3C)c2)cc2c1OCO2] | 5-(4-(7-methoxybenzo[d][1,3]dioxol-5-yl)-1H-1,2,3-triazol-5-yl)-1-methyl-1H-indole |
| 108b | 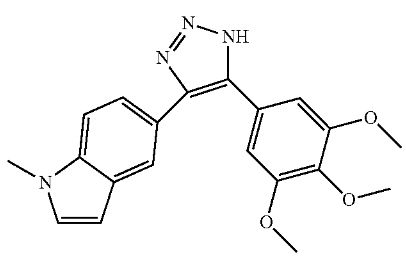 | 1-methyl-5-(5-(3,4,5-trimethoxyphenyl)-1H-1,2,3-triazol-4-yl)-1H-indole |
| 109b | 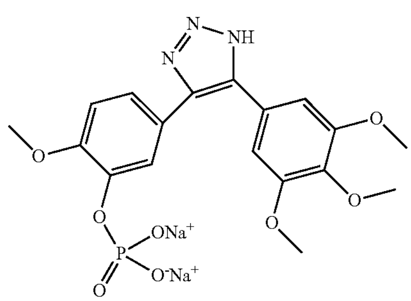 | monosodium monosodium(II) mono(2-methoxy-5-(5-(3,4,5-trimethoxyphenyl)-1H-1,2,3-triazol-4-yl)phenyl phosphate) |
| 110b | 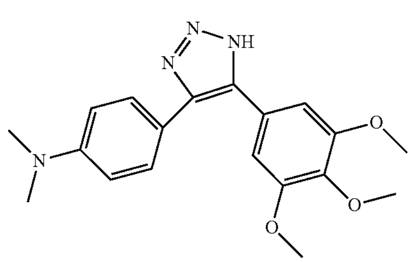 | N,N-dimethyl-4-(5-(3,4,5-trimethoxyphenyl)-1H-1,2,3-triazol-4-yl)aniline |

TABLE 1-continued

| Compound No. | Structure | Chemical Name |
|---|---|---|
| 111b | 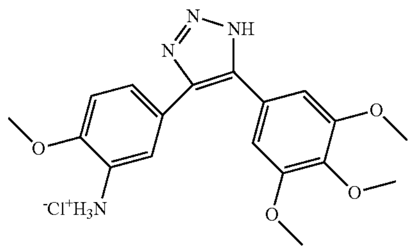 | 2-methoxy-5-(5-(3,4,5-trimethoxyphenyl)-1H-1,2,3-triazol-4-yl)benzenaminium chloride |
| 112b | 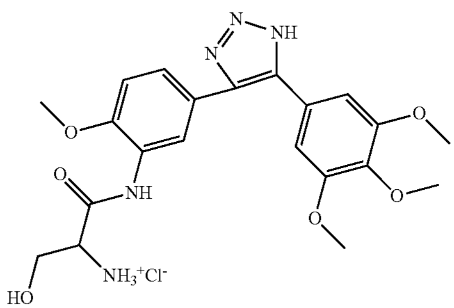 | 3-hydroxy-1-(2-methoxy-5-(5-(3,4,5-trimethoxyphenyl)-1H-1,2,3-triazol-4-yl)phenylamino)-1-oxopropan-2-aminium chloride |
| 113b | 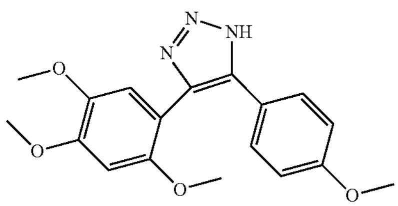 | 5-(4-methoxyphenyl)-4-(2,4,5-trimethoxyphenyl)-1H-1,2,3-triazole |
| 114b | 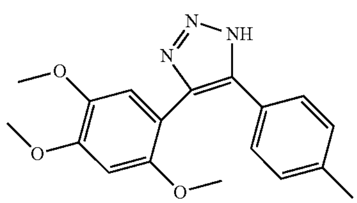 | 5-p-tolyl-4-(2,4,5-trimethoxyphenyl)-1H-1,2,3-triazole |
| 115b | 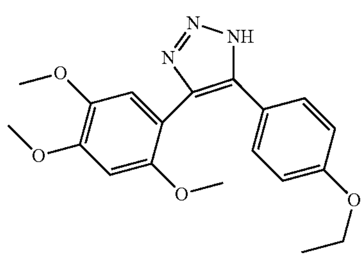 [SMILES: CCOc1ccc(-c2[nH]nnc2-c2cc(OC)c(OC)cc2OC)cc1] | 5-(4-ethoxyphenyl)-4-(2,4,5-trimethoxyphenyl)-1H-1,2,3-triazole |
| 116b | 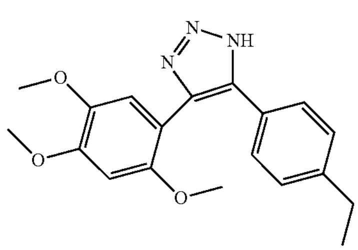 [SMILES: CCc1ccc(-c2[nH]nnc2-c2cc(OC)c(OC)cc2OC)cc1] | 5-(4-ethylphenyl)-4-(2,4,5-trimethoxyphenyl)-1H-1,2,3-triazole |

TABLE 1-continued

| Compound No. | Structure | Chemical Name |
|---|---|---|
| 117b | 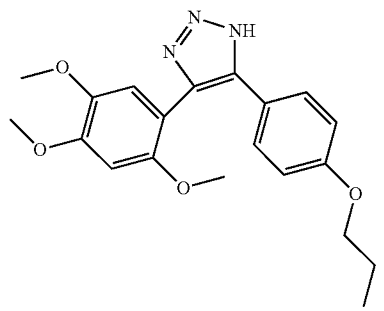 [SMILES: CCCOc1ccc(-c2[nH]nnc2-c2cc(OC)c(OC)cc2OC)cc1] | 5-(4-propoxyphenyl)-4-(2,4,5-trimethoxyphenyl)-1H-1,2,3-triazole |
| 118b | 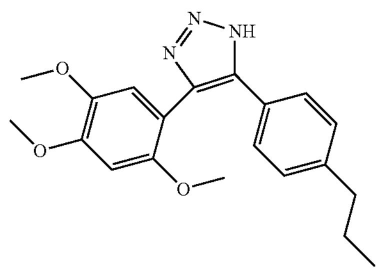 [SMILES: CCCc1ccc(-c2[nH]nnc2-c2cc(OC)c(OC)cc2OC)cc1] | 5-(4-propylphenyl)-4-(2,4,5-trimethoxyphenyl)-1H-1,2,3-triazole |
| 119b | 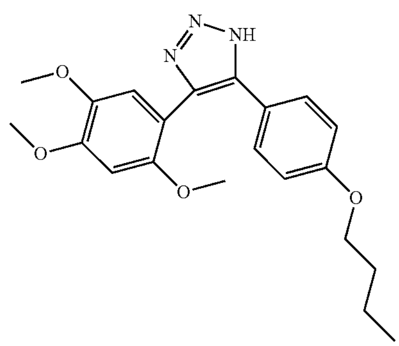 [SMILES: CCCCOc1ccc(-c2[nH]nnc2-c2cc(OC)c(OC)cc2OC)cc1] | 5-(4-butoxyphenyl)-4-(2,4,5-trimethoxyphenyl)-1H-1,2,3-triazole |
| 120b | 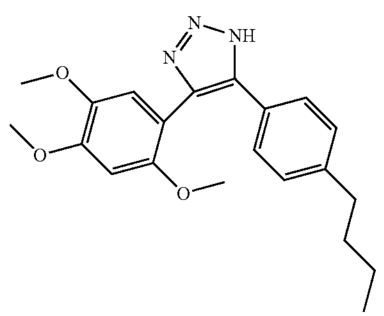 [SMILES: CCCCc1ccc(-c2[nH]nnc2-c2cc(OC)c(OC)cc2OC)cc1] | 5-(4-butylphenyl)-4-(2,4,5-trimethoxyphenyl)-1H-1,2,3-triazole |
| 121b | 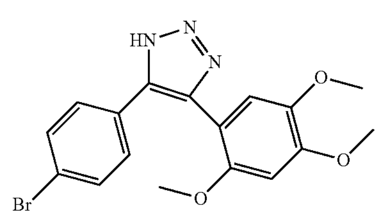 [SMILES: COc1cc(OC)c(-c2nn[nH]c2-c2ccc(Br)cc2)cc1OC] | 5-(4-bromophenyl)-4-(2,4,5-trimethoxyphenyl)-1H-1,2,3-triazole |

TABLE 1-continued

| Compound No. | Structure | Chemical Name |
| --- | --- | --- |
| 122b | 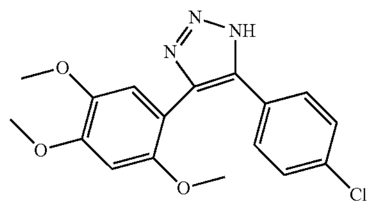 [SMILES: COc1cc(OC)c(-c2nn[nH]c2-c2ccc(Cl)cc2)cc1OC] | 5-(4-chlorophenyl)-4-(2,4,5-trimethoxyphenyl)-1H-1,2,3-triazole |
| 123b | 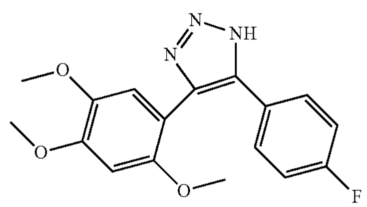 [SMILES: COc1cc(OC)c(-c2nn[nH]c2-c2ccc(F)cc2)cc1OC] | 5-(4-fluorophenyl)-4-(2,4,5-trimethoxyphenyl)-1H-1,2,3-triazole |
| 124b | 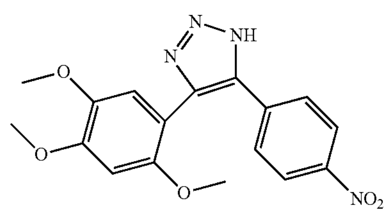 [SMILES: COc1cc(OC)c(-c2nn[nH]c2-c2ccc([N+](=O)[O-])cc2)cc1OC] | 5-(4-nitrophenyl)-4-(2,4,5-trimethoxyphenyl)-1H-1,2,3-triazole |
| 125b | 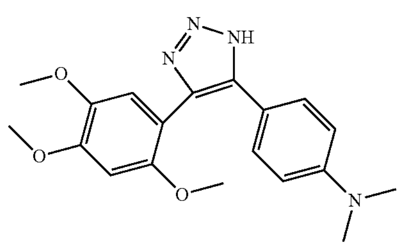 | N,N-dimethyl-4-(4-(2,4,5-trimethoxyphenyl)-1H-1,2,3-triazol-5-yl)aniline |
| 126b | 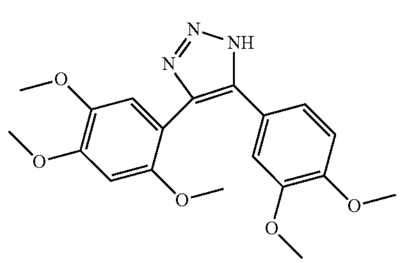 | 5-(3,4-dimethoxyphenyl)-4-(2,4,5-trimethoxyphenyl)-1H-1,2,3-triazole |
| 127b | 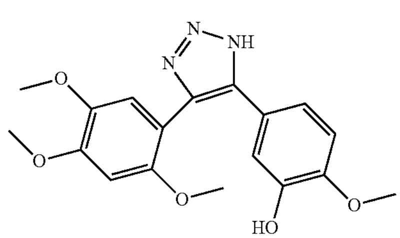 | 2-methoxy-5-(4-(2,4,5-trimethoxyphenyl)-1H-1,2,3-triazol-5-yl)phenol |

TABLE 1-continued

| Compound No. | Structure | Chemical Name |
|---|---|---|
| 128b | 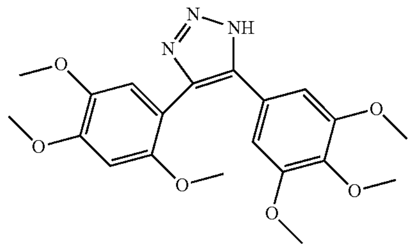 | 4-(2,4,5-trimethoxyphenyl)-5-(3,4,5-trimethoxyphenyl)-1H-1,2,3-triazole |
| 129b | 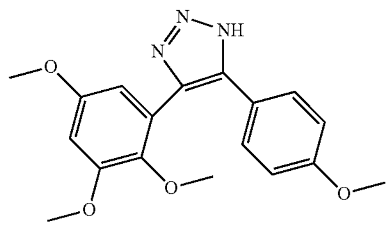 | 5-(4-methoxyphenyl)-4-(2,3,5-trimethoxyphenyl)-1H-1,2,3-triazole |
| 130b | 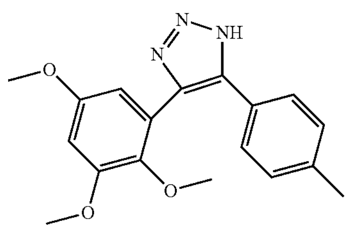 | 5-p-tolyl-4-(2,3,5-trimethoxyphenyl)-1H-1,2,3-triazole |
| 131b | 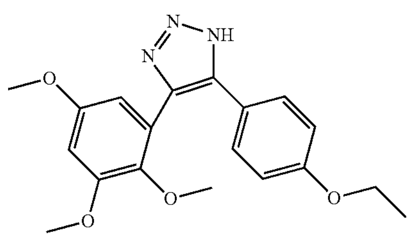 [SMILES: CCOc1ccc(-c2[nH]nnc2-c2cc(OC)cc(OC)c2OC)cc1] | 5-(4-ethoxyphenyl)-4-(2,3,5-trimethoxyphenyl)-1H-1,2,3-triazole |
| 132b | 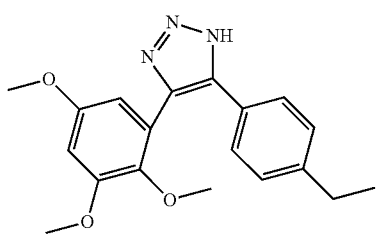 [SMILES: CCc1ccc(-c2[nH]nnc2-c2cc(OC)cc(OC)c2OC)cc1] | 5-(4-ethylphenyl)-4-(2,3,5-trimethoxyphenyl)-1H-1,2,3-triazole |
| 133b | 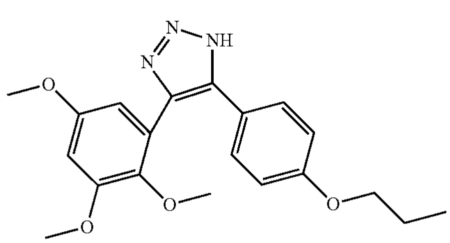 [SMILES: CCCOc1ccc(-c2[nH]nnc2-c2cc(OC)cc(OC)c2OC)cc1] | 5-(4-propoxyphenyl)-4-(2,3,5-trimethoxyphenyl)-1H-1,2,3-triazole |

TABLE 1-continued

| Compound No. | Structure | Chemical Name |
|---|---|---|
| 134b | 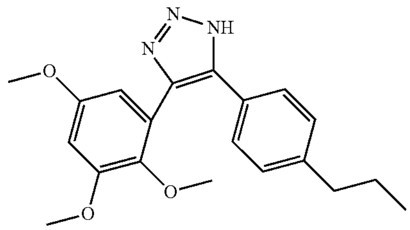 [SMILES: CCCc1ccc(-c2[nH]nnc2-c2cc(OC)cc(OC)c2OC)cc1] | 5-(4-propylphenyl)-4-(2,3,5-trimethoxyphenyl)-1H-1,2,3-triazole |
| 135b | 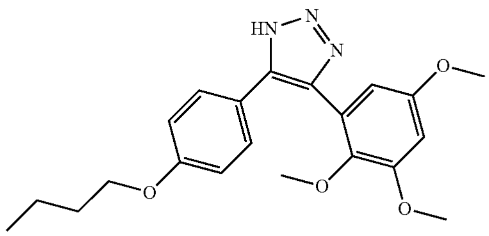 [SMILES: CCCCOc1ccc(-c2[nH]nnc2-c2cc(OC)cc(OC)c2OC)cc1] | 5-(4-butoxyphenyl)-4-(2,3,5-trimethoxyphenyl)-1H-1,2,3-triazole |
| 136b | 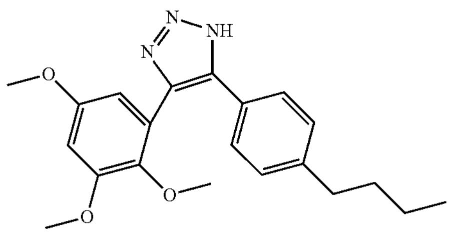 [SMILES: CCCCc1ccc(-c2[nH]nnc2-c2cc(OC)cc(OC)c2OC)cc1] | 5-(4-butylphenyl)-4-(2,3,5-trimethoxyphenyl)-1H-1,2,3-triazole |
| 137b | 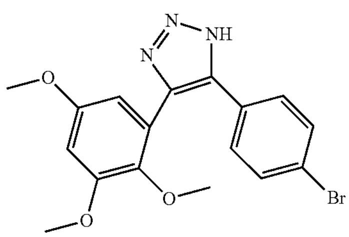 [SMILES: COc1cc(OC)c(OC)c(-c2nn[nH]c2-c2ccc(Br)cc2)c1] | 5-(4-bromophenyl)-4-(2,3,5-trimethoxyphenyl)-1H-1,2,3-triazole |
| 138b | 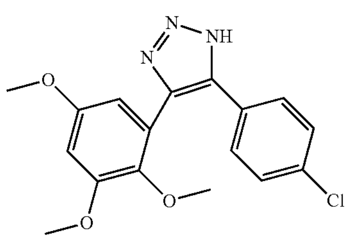 [SMILES: COc1cc(OC)c(OC)c(-c2nn[nH]c2-c2ccc(Cl)cc2)c1] | 5-(4-chlorophenyl)-4-(2,3,5-trimethoxyphenyl)-1H-1,2,3-triazole |
| 139b | 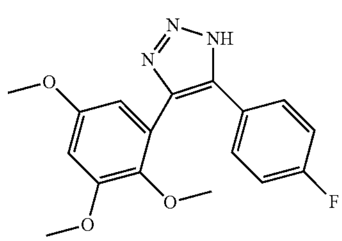 [SMILES: COc1cc(OC)c(OC)c(-c2nn[nH]c2-c2ccc(F)cc2)c1] | 5-(4-fluorophenyl)-4-(2,3,5-trimethoxyphenyl)-1H-1,2,3-triazole |

TABLE 1-continued

| Compound No. | Structure | Chemical Name |
|---|---|---|
| 140b | 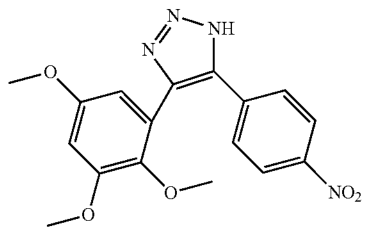 [SMILES: COc1cc(OC)c(OC)c(-c2nn[nH]c2-c2ccc([N+](=O)[O-])cc2)c1] | 5-(4-nitrophenyl)-4-(2,3,5-trimethoxyphenyl)-1H-1,2,3-triazole |
| 141b | 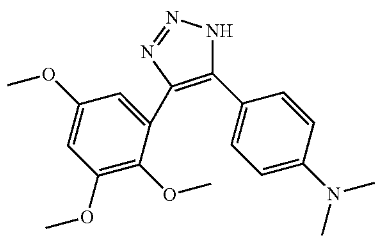 | N,N-dimethyl-4-(4-(2,3,5-trimethoxyphenyl)-1H-1,2,3-triazol-5-yl)aniline |
| 142b | 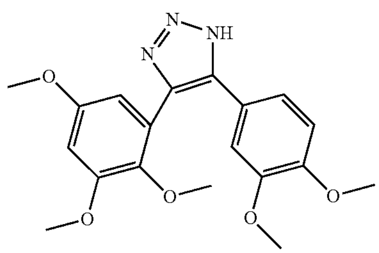 | 5-(3,4-dimethoxyphenyl)-4-(2,3,5-trimethoxyphenyl)-1H-1,2,3-triazole |
| 143b | 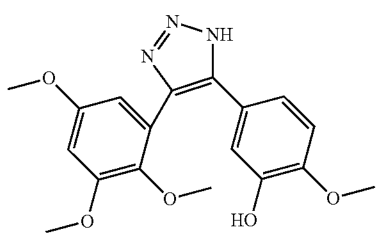 | 2-methoxy-5-(4-(2,3,5-trimethoxyphenyl)-1H-1,2,3-triazol-5-yl)phenol |
| 144b | 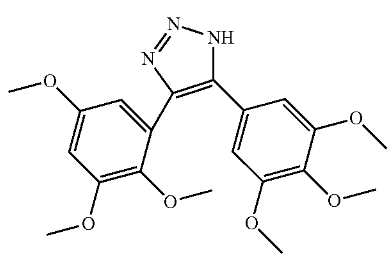 | 4-(2,3,5-trimethoxyphenyl)-5-(3,4,5-trimethoxyphenyl)-1H-1,2,3-triazole |
| 145b | 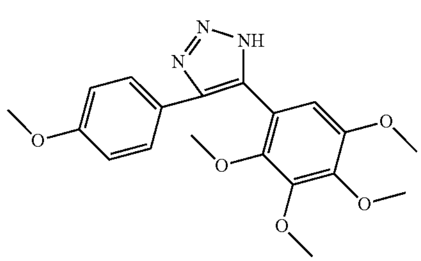 | 4-(4-methoxyphenyl)-5-(2,3,4,5-tetramethoxyphenyl)-1H-1,2,3-triazole |

TABLE 1-continued

| Compound No. | Structure | Chemical Name |
|---|---|---|
| 146b | 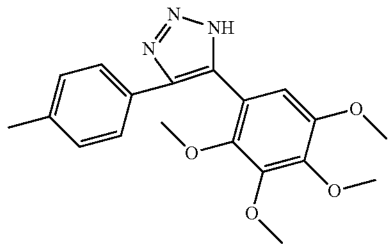 | 5-(2,3,4,5-tetramethoxyphenyl)-4-p-tolyl-1H-1,2,3-triazole |
| 147b | 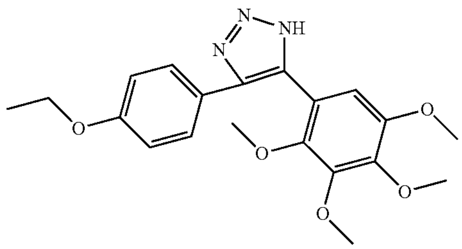 [SMILES: CCOc1ccc(-c2nn[nH]c2-c2cc(OC)c(OC)c(OC)c2OC)cc1] | 4-(4-ethoxyphenyl)-5-(2,3,4,5-tetramethoxyphenyl)-1H-1,2,3-triazole |
| 148b | 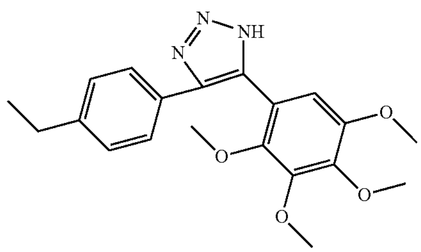 [SMILES: CCc1ccc(-c2nn[nH]c2-c2cc(OC)c(OC)c(OC)c2OC)cc1] | 4-(4-ethylphenyl)-5-(2,3,4,5-tetramethoxyphenyl)-1H-1,2,3-triazole |
| 149b | 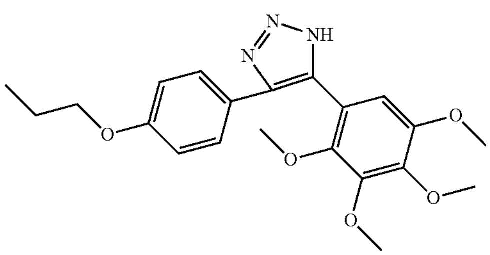 [SMILES: CCCOc1ccc(-c2nn[nH]c2-c2cc(OC)c(OC)c(OC)c2OC)cc1] | 4-(4-propoxyphenyl)-5-(2,3,4,5-tetramethoxyphenyl)-1H-1,2,3-triazole |
| 150b | 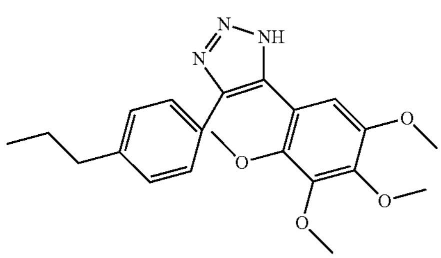 [SMILES: CCCc1ccc(-c2nn[nH]c2-c2cc(OC)c(OC)c(OC)c2OC)cc1] | 4-(4-propylphenyl)-5-(2,3,4,5-tetramethoxyphenyl)-1H-1,2,3-triazole |
| 151b | 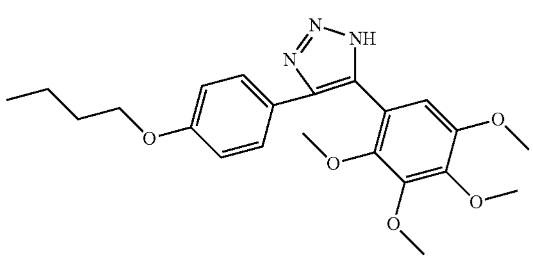 [SMILES: CCCCOc1ccc(-c2nn[nH]c2-c2cc(OC)c(OC)c(OC)c2OC)cc1] | 4-(4-butoxyphenyl)-5-(2,3,4,5-tetramethoxyphenyl)-1H-1,2,3-triazole |

TABLE 1-continued

| Compound No. | Structure | Chemical Name |
|---|---|---|
| 152b | 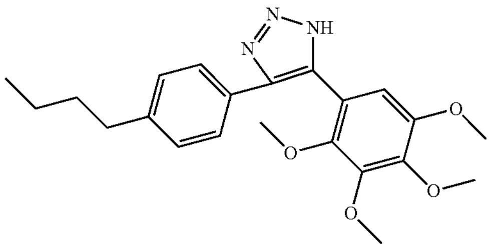 [SMILES: CCCCc1ccc(-c2nn[nH]c2-c2cc(OC)c(OC)c(OC)c2OC)cc1] | 4-(4-butylphenyl)-5-(2,3,4,5-tetramethoxyphenyl)-1H-1,2,3-triazole |
| 153b | 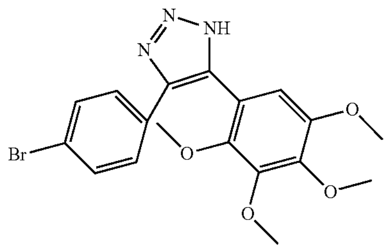 [SMILES: COc1cc(-c2[nH]nnc2-c2ccc(Br)cc2)c(OC)c(OC)c1OC] | 4-(4-bromophenyl)-5-(2,3,4,5-tetramethoxyphenyl)-1H-1,2,3-triazole |
| 154b | 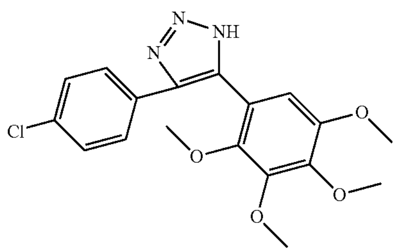 [SMILES: COc1cc(-c2[nH]nnc2-c2ccc(Cl)cc2)c(OC)c(OC)c1OC] | 4-(4-chlorophenyl)-5-(2,3,4,5-tetramethoxyphenyl)-1H-1,2,3-triazole |
| 155b | 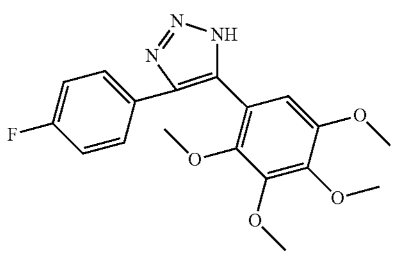 [SMILES: COc1cc(-c2[nH]nnc2-c2ccc(F)cc2)c(OC)c(OC)c1OC] | 4-(4-fluorophenyl)-5-(2,3,4,5-tetramethoxyphenyl)-1H-1,2,3-triazole |
| 156b | 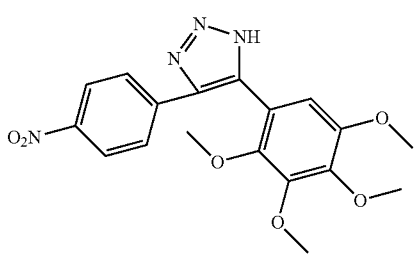 [SMILES: COc1cc(-c2[nH]nnc2-c2ccc([N+](=O)[O-])cc2)c(OC)c(OC)c1OC] | 4-(4-nitrophenyl)-5-(2,3,4,5-tetramethoxyphenyl)-1H-1,2,3-triazole |
| 157b | 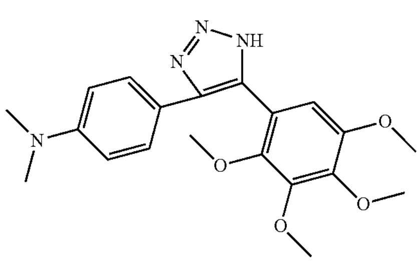 | N,N-dimethyl-4-(5-(2,3,4,5-tetramethoxyphenyl)-1H-1,2,3-triazol-4-yl)aniline |

TABLE 1-continued

| Compound No. | Structure | Chemical Name |
|---|---|---|
| 158b | 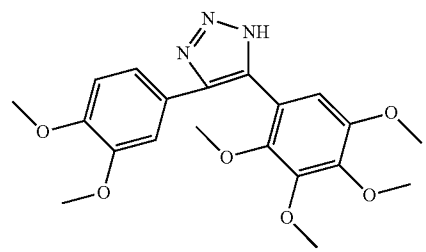 | 4-(3,4-dimethoxyphenyl)-5-(2,3,4,5-tetramethoxyphenyl)-1H-1,2,3-triazole |
| 159b | 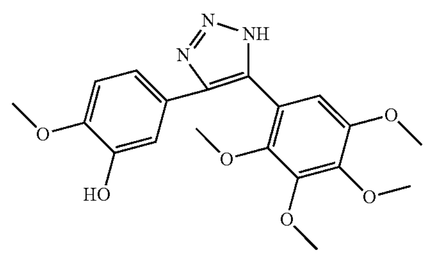 | 2-methoxy-5-(5-(2,3,4,5-tetramethoxyphenyl)-1H-1,2,3-triazol-4-yl)phenol |
| 160b | 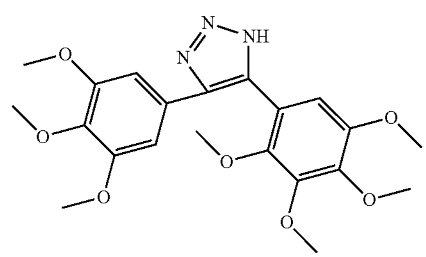 | 5-(2,3,4,5-tetramethoxyphenyl)-4-(3,4,5-trimethoxyphenyl)-1H-1,2,3-triazole |
| 161b | 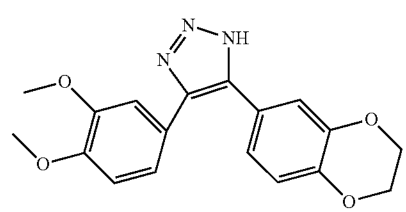 [SMILES: COc1ccc(-c2nn[nH]c2-c2ccc3c(c2)OCCO3)cc1OC] | 5-(2,3-dihydrobenzo[b][1,4]dioxin-6-yl)-4-(3,4-dimethoxyphenyl)-1H-1,2,3-triazole |
| 162b | 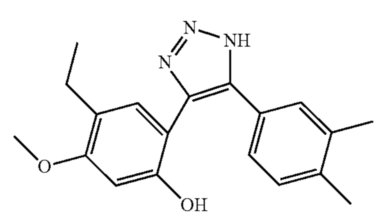 | 2-(5-(3,4-dimethylphenyl)-1H-1,2,3-triazol-4-yl)-4-ethyl-5-methoxyphenol |
| 163b | 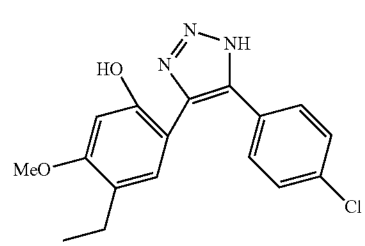 [SMILES: CCc1cc(-c2nn[nH]c2-c2ccc(Cl)cc2)c(O)cc1OC] | 2-(5-(4-chlorophenyl)-1H-1,2,3-triazol-4-yl)-4-ethyl-5-methoxyphenol |

TABLE 1-continued

| Compound No. | Structure | Chemical Name |
|---|---|---|
| 164b | 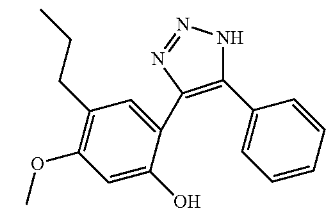 [SMILES: CCCc1cc(-c2nn[nH]c2-c2ccccc2)c(O)cc1OC] | 5-methoxy-2-(5-phenyl-1H-1,2,3-triazol-4-yl)-4-propylphenol |
| 165b | 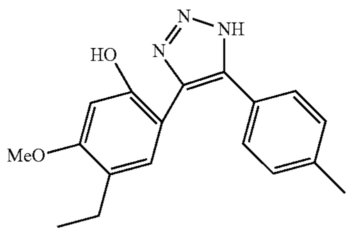 [SMILES: CCc1cc(-c2nn[nH]c2-c2ccc(C)cc2)c(O)cc1OC] | 4-ethyl-5-methoxy-2-(5-p-tolyl-1H-1,2,3-triazol-4-yl)phenol |
| 166b | 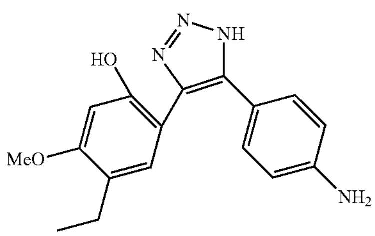 [SMILES: CCc1cc(-c2nn[nH]c2-c2ccc(N)cc2)c(O)cc1OC] | 2-(5-(4-aminophenyl)-1H-1,2,3-triazol-4-yl)-4-ethyl-5-methoxyphenol |
| 167b | 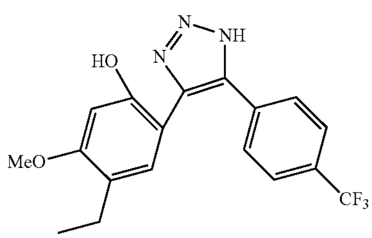 [SMILES: CCc1cc(-c2nn[nH]c2-c2ccc(C(F)(F)F)cc2)c(O)cc1OC] | 4-ethyl-5-methoxy-2-(5-(4-(trifluoromethyl)phenyl)-1H-1,2,3-triazol-4-yl)phenol |
| 168b | 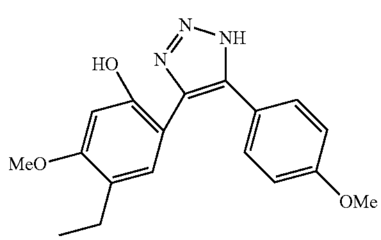 [SMILES: CCc1cc(-c2nn[nH]c2-c2ccc(OC)cc2)c(O)cc1OC] | 4-ethyl-5-methoxy-2-(5-(4-methoxyphenyl)-1H-1,2,3-triazol-4-yl)phenol |
| 169b | 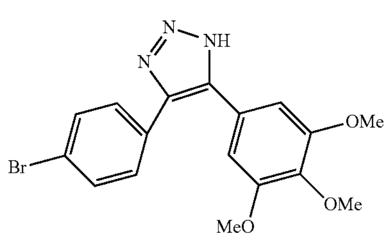 [SMILES: COc1cc(-c2[nH]nnc2-c2ccc(Br)cc2)cc(OC)c1OC] | 4-(4-bromophenyl)-5-(3,4,5-trimethoxyphenyl)-1H-1,2,3-triazole |

TABLE 1-continued

| Compound No. | Structure | Chemical Name |
|---|---|---|
| 170b | 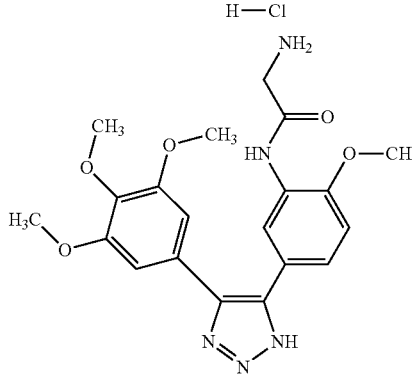 | 2-amino-N-(2-methoxy-5-(4-(3,4,5-trimethoxyphenyl)-1H-1,2,3-triazol-5-yl)phenyl)acetamide hydrochloride |
| 171b | 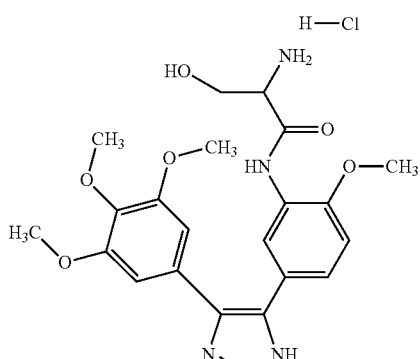 | 2-amino-3-hydroxy-N-(2-methoxy-5-(4-(3,4,5-trimethoxyphenyl)-1H-1,2,3-triazol-5-yl)phenyl)propanamide hydrochloride |
| 172b | 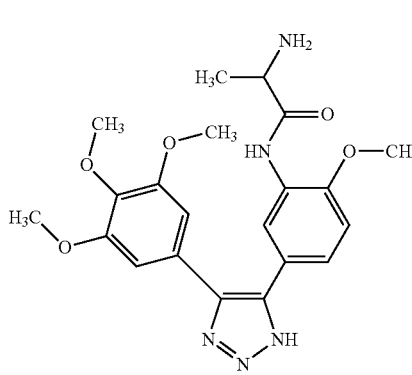 | 2-amino-N-(2-methoxy-5-(4-(3,4,5-trimethoxyphenyl)-1H-1,2,3-triazol-5-yl)phenyl)propanamide |
| 173b | 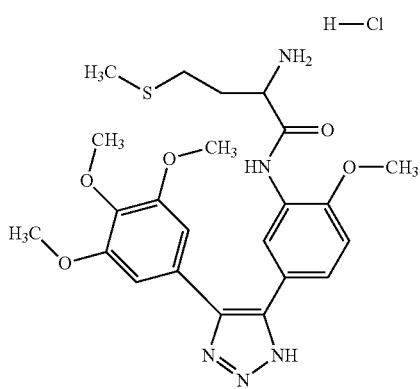 | 2-amino-N-(2-methoxy-5-(4-(3,4,5-trimethoxyphenyl)-1H-1,2,3-triazol-5-yl)phenyl)-4-(methylthio)butanamide hydrochloride |

TABLE 1-continued

| Compound No. | Structure | Chemical Name |
|---|---|---|
| 174b | 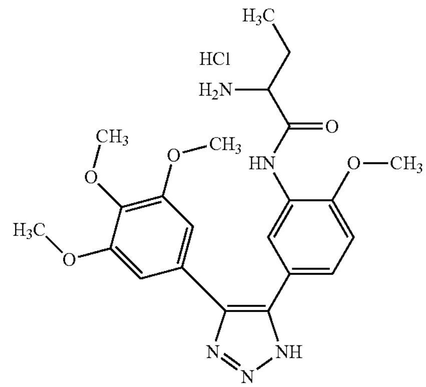 | 2-amino-N-(2-methoxy-5-(4-(3,4,5-trimethoxyphenyl)-1H-1,2,3-triazol-5-yl)phenyl)butanamide hydrochloride |
| 175b | 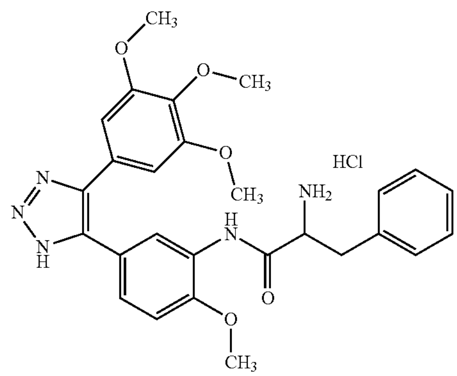 [SMILES: COc1ccc(-c2[nH]nnc2-c2cc(OC)c(OC)c(OC)c2)cc1NC(=O)C(N)Cc1ccccc1 ; Cl] | 2-amino-N-(2-methoxy-5-(4-(3,4,5-trimethoxyphenyl)-1H-1,2,3-triazol-5-yl)phenyl)-3-phenylpropanamide hydrochloride |
| 176b | 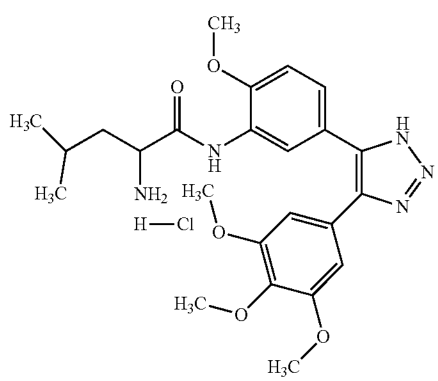 | 2-amino-N-(2-methoxy-5-(4-(3,4,5-trimethoxyphenyl)-1H-1,2,3-triazol-5-yl)phenyl)-4-methylpentanamide hydrochloride |
| 177b | 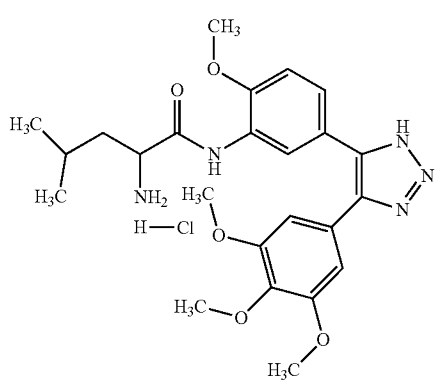 | 2-amino-N-(2-methoxy-5-(4-(3,4,5-trimethoxyphenyl)-1H-1,2,3-triazol-5-yl)phenyl)-4-methylpentanamide hydrochloride |

TABLE 1-continued

| Compound No. | Structure | Chemical Name |
|---|---|---|
| 178b | 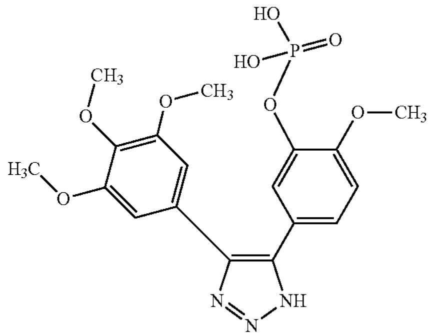 | 2-methoxy-5-(4-(3,4,5-trimethoxyphenyl)-1H-1,2,3-triazol-5-yl)phenyl dihydrogen phosphate |
| 179b | 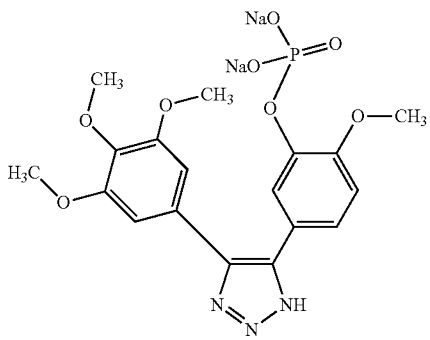 | sodium 2-methoxy-5-(4-(3,4,5-trimethoxyphenyl)-1H-1,2,3-triazol-5-yl)phenyl phosphate |
| 180b | 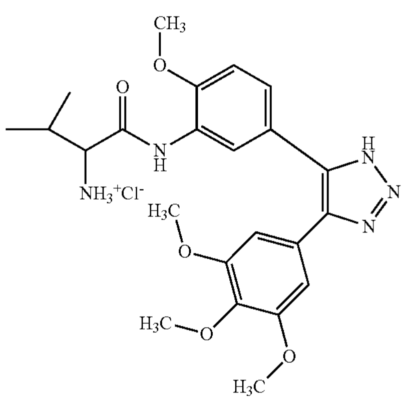 | 1-(2-methoxy-5-(4-(3,4,5-trimethoxyphenyl)-1H-1,2,3-triazol-5-yl)phenylamino)-3-methyl-1-oxobutan-2-aminium chloride |
| 181b | 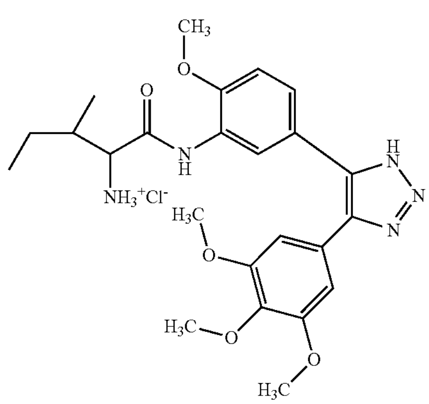 | 1-(2-methoxy-5-(4-(3,4,5-trimethoxyphenyl)-1H-1,2,3-triazol-5-yl)phenylamino)-3-methyl-1-oxopentan-2-aminium chloride |

TABLE 1-continued

| Compound No. | Structure | Chemical Name |
|---|---|---|
| 182b | 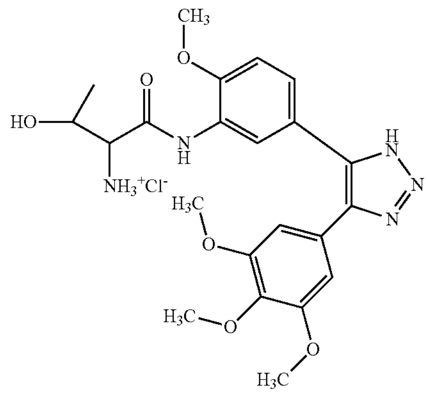 | 3-hydroxy-1-(2-methoxy-5-(4-(3,4,5-trimethoxyphenyl)-1H-1,2,3-triazol-5-yl)phenylamino)-1-oxobutan-2-aminium chloride |
| 183b | 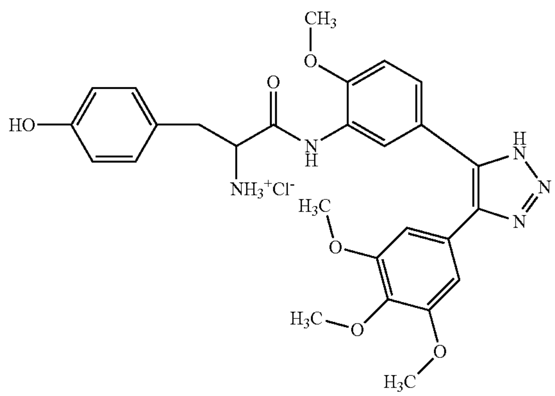 | 3-(4-hydroxyphenyl)-1-(2-methoxy-5-(4-(3,4,5-trimethoxyphenyl)-1H-1,2,3-triazol-5-yl)phenylamino)-1-oxopropan-2-aminium chloride |
| 184b | 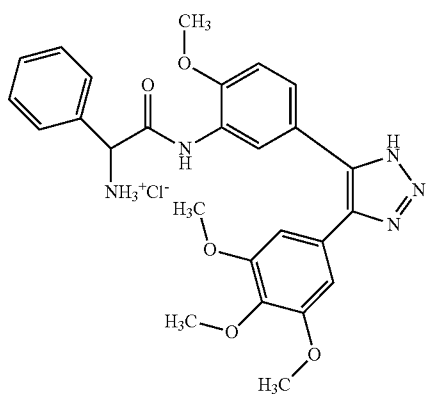 | 2-(2-methoxy-5-(4-(3,4,5-trimethoxyphenyl)-1H-1,2,3-triazol-5-yl)phenylamino)-2-oxo-1-phenylethanaminium chloride |
| 185b | 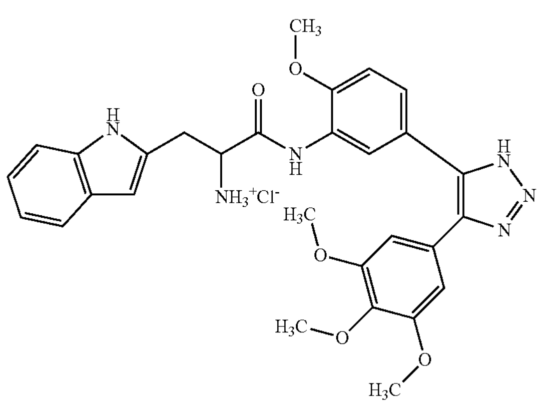 | 3-(1H-indol-2-yl)-1-(2-methoxy-5-(4-(3,4,5-trimethoxyphenyl)-1H-1,2,3-triazol-5-yl)phenylamino)-1-oxopropan-2-aminium chloride |

TABLE 1-continued

| Compound No. | Structure | Chemical Name |
|---|---|---|
| 186b | 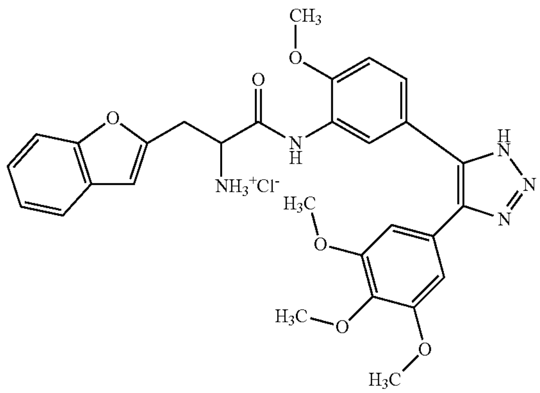 | 3-(benzofuran-2-yl)-1-(2-methoxy-5-(4-(3,4,5-trimethoxyphenyl)-1H-1,2,3-triazol-2-yl)phenylamino)-1-oxopropan-2-aminium chloride |
| 187b | 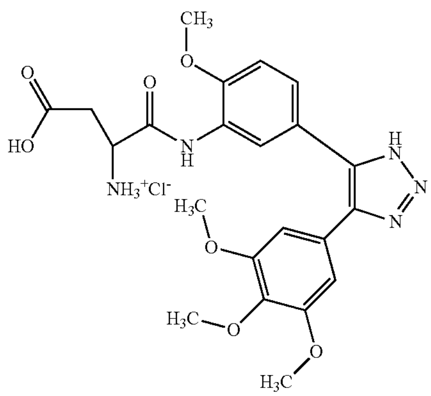 | 3-carboxy-1-(2-methoxy-5-(4-(3,4,5-trimethoxyphenyl)-1H-1,2,3-triazol-5-yl)phenylamino)-1-oxopropan-2-aminium chloride |
| 188b | 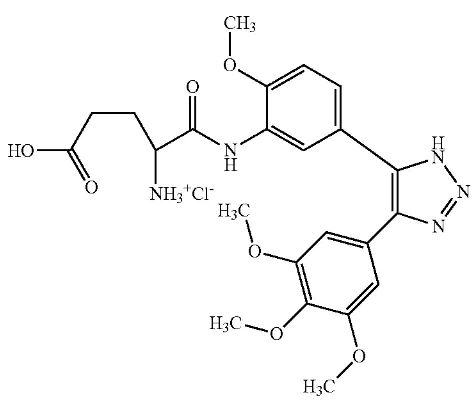 | 4-carboxy-1-(2-methoxy-5-(4-(3,4,5-trimethoxyphenyl)-1H-1,2,3-triazol-5-yl)phenylamino)-1-oxobutan-2-aminium chloride |
| 189b | 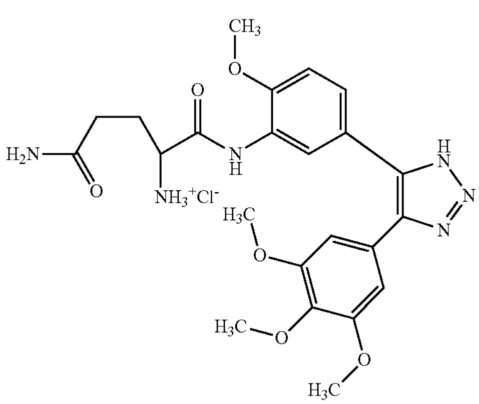 | 5-amino-1-(2-methoxy-5-(4-(3,4,5-trimethoxyphenyl)-1H-1,2,3-triazol-5-yl)phenylamino)-1,5-dioxopentan-2-aminium chloride |

TABLE 1-continued

| Compound No. | Structure | Chemical Name |
|---|---|---|
| 190b | 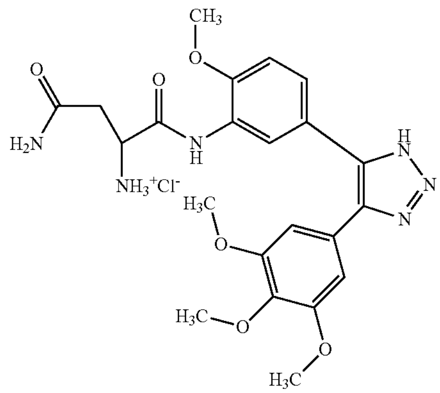 | 4-amino-1-(2-methoxy-5-(4-(3,4,5-trimethoxyphenyl)-1H-1,2,3-triazol-5-yl)phenylamino)-1,4-dioxobutan-2-aminium chloride |
| 191b | 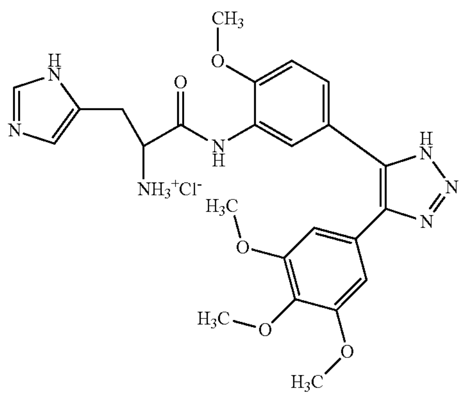 | 3-(1H-imidazol-5-yl)-1-(2-methoxy-5-(4-(3,4,5-trimethoxyphenyl)-1H-1,2,3-triazol-5-yl)phenylamino)-1-oxopropan-2-aminium chloride |
| 192b | 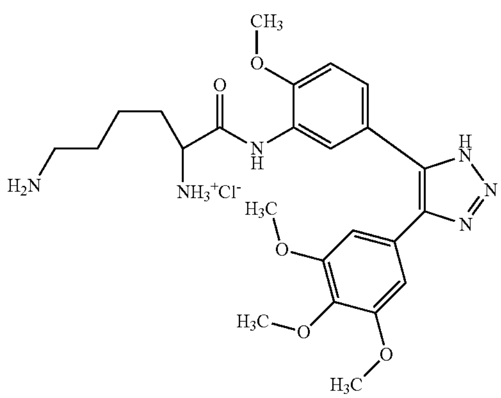 | 6-amino-1-(2-methoxy-5-(4-(3,4,5-trimethoxyphenyl)-1H-1,2,3-triazol-5-yl)phenylamino)-1-oxohexan-2-aminium chloride |
| 193b | 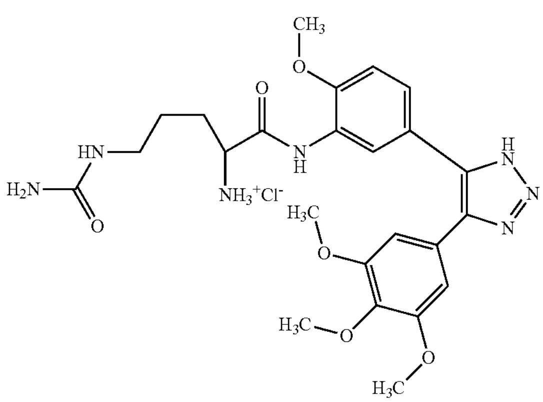 | 5-guanidino-1-(2-methoxy-5-(4-(3,4,5-trimethoxyphenyl)-1H-1,2,3-triazol-5-yl)phenylamino)-1-oxopentan-2-aminium chloride |

TABLE 1-continued

| Compound No. | Structure | Chemical Name |
| --- | --- | --- |
| 194b | 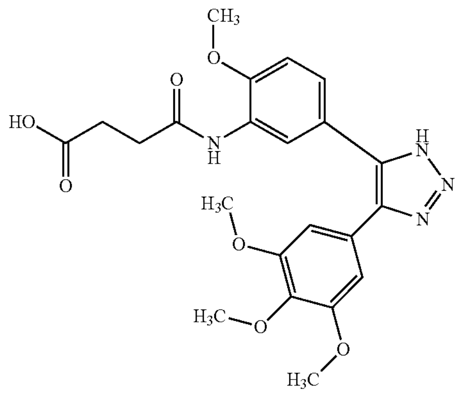 [SMILES: COc1ccc(-c2[nH]nnc2-c2cc(OC)c(OC)c(OC)c2)cc1NC(=O)CCC(=O)O] | 4-(2-methoxy-5-(4-(3,4,5-trimethoxyphenyl)-1H-1,2,3-triazol-5-yl)phenylamino)-4-oxobutanoic acid |
| 195b | 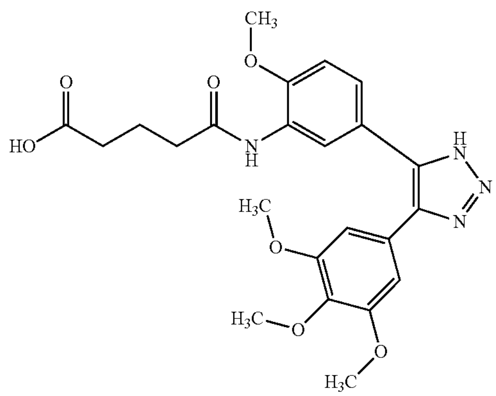 [SMILES: COc1ccc(-c2[nH]nnc2-c2cc(OC)c(OC)c(OC)c2)cc1NC(=O)CCCC(=O)O] | 5-(2-methoxy-5-(4-(3,4,5-trimethoxyphenyl)-1H-1,2,3-triazol-5-yl)phenylamino)-5-oxopentanoic acid |
| 196b | 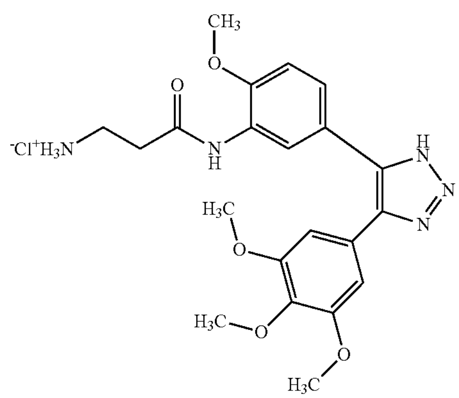 | 3-(2-methoxy-5-(4-(3,4,5-trimethoxyphenyl)-1H-1,2,3-triazol-5-yl)phenylamino)-3-oxopropan-1-aminium chloride |
| 197b | 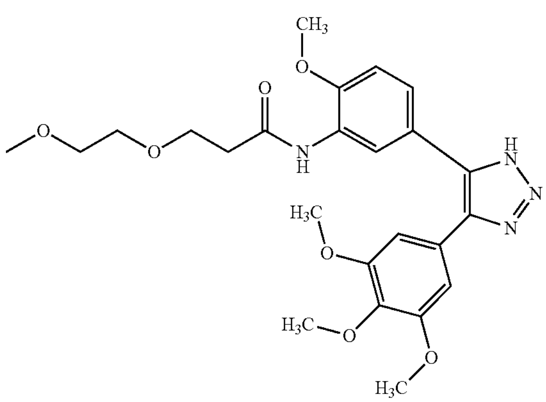 [SMILES: COCCOCCC(=O)Nc1cc(-c2[nH]nnc2-c2cc(OC)c(OC)c(OC)c2)ccc1OC] | N-(2-methoxy-5-(4-(3,4,5-trimethoxyphenyl)-1H-1,2,3-triazol-5-yl)phenyl)-3-(2-methoxyethoxy)propanamide |

TABLE 1-continued

| Compound No. | Structure | Chemical Name |
|---|---|---|
| 198b | 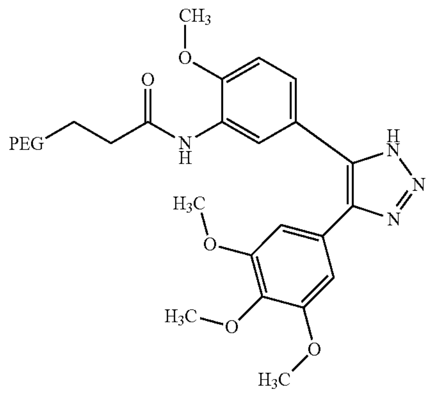 | 3-(2-PEG)-N-(2-methoxy-5-(4-(3,4,5-trimethoxyphenyl)-1H-1,2,3-triazol-5-yl)phenyl)butyramide |
| 199b | 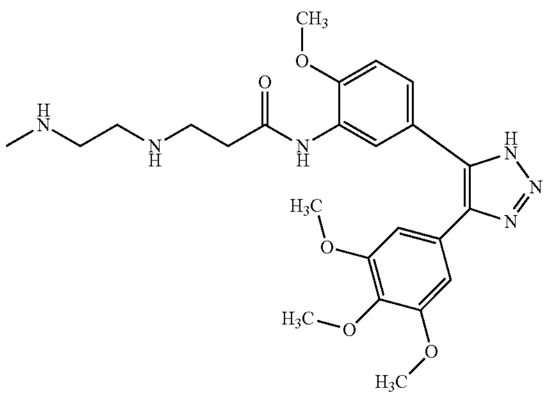 [SMILES: CNCCNCCC(=O)Nc1cc(-c2[nH]nnc2-c2cc(OC)c(OC)c(OC)c2)ccc1OC] | N-(2-methoxy-5-(4-(3,4,5-trimethoxyphenyl)-1H-1,2,3-triazol-5-yl)phenyl)-3-(2-(methylamino)ethylamino)propanamide |
| 200b | 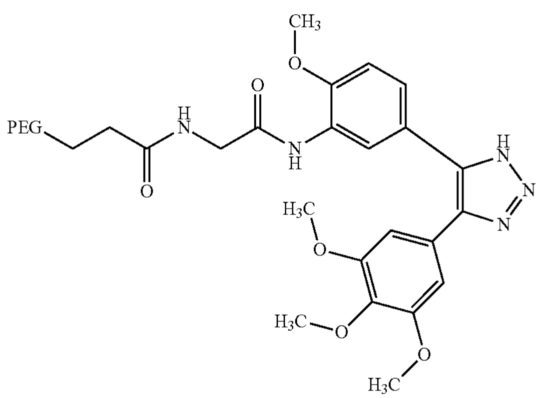 | 3-PEG-N-(2-methoxy-5-(4-(3,4,5-trimethoxyphenyl)-1H-1,2,3-triazol-5-yl)phenylamino)-2-oxoethyl)butyramide |
| 201b | 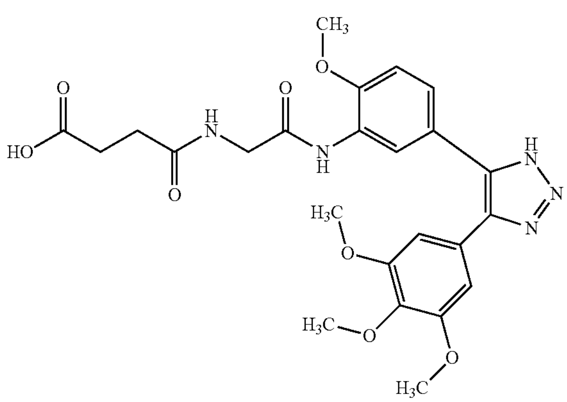 [SMILES: COc1ccc(-c2[nH]nnc2-c2cc(OC)c(OC)c(OC)c2)cc1NC(=O)CNC(=O)CCC(=O)O] | 4-(2-(2-methoxy-5-(4-(3,4,5-trimethoxyphenyl)-1H-1,2,3-triazol-5-yl)phenylamino)-2-oxoethylamino)-4-oxobutanoic acid |

TABLE 1-continued

| Compound No. | Structure | Chemical Name |
| --- | --- | --- |
| 202b | 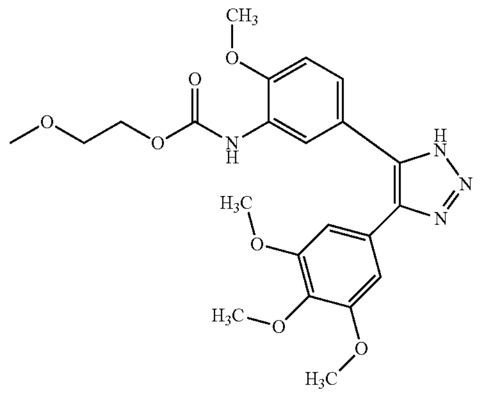 [SMILES: COCCOC(=O)Nc1cc(-c2[nH]nnc2-c2cc(OC)c(OC)c(OC)c2)ccc1OC] | 2-methoxyethyl 2-methoxy-5-(4-(3,4,5-trimethoxyphenyl)-1H-1,2,3-triazol-5-yl)phenylcarbamate |
| 203b | 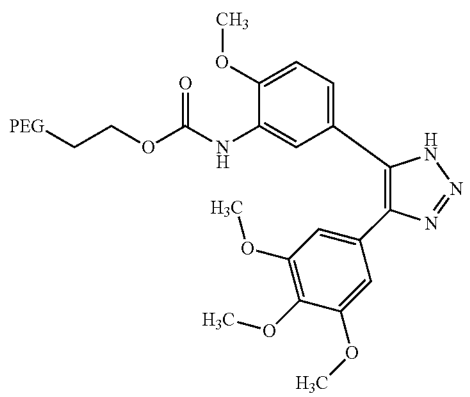 | PEG-2-methoxy-5-(4-(3,4,5-trimethoxyphenyl)-1H-1,2,3-triazol-5-yl)phenylcarbamate |
| 204b | 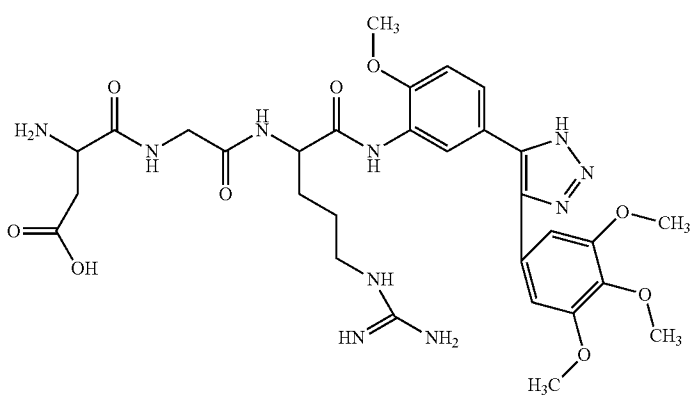 [SMILES: COc1ccc(-c2[nH]nnc2-c2cc(OC)c(OC)c(OC)c2)cc1NC(=O)C(CCCNC(=N)N)NC(=O)CNC(=O)C(N)CC(=O)O] | 3-amino-4-(2-(5-guanidino-1-(2-methoxy-5-(4-(3,4,5-trimethoxyphenyl)-1H-1,2,3-triazol-5-yl)phenylamino)-1-oxopentan-2-ylamino)-2-oxoethylamino)-4-oxobutanoic acid |
| 205b | 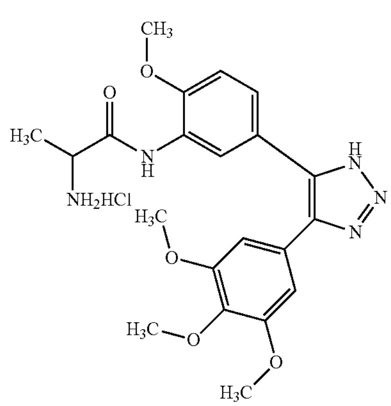 | 2-amino-N-(2-methoxy-5-(4-(3,4,5-trimethoxyphenyl)-1H-1,2,3-triazol-5-yl)phenyl)propanamide hydrochloride |

Methods of Making the Compounds of the Invention

The compounds of the invention can be made by the methods described herein in Example 1. Typically, an aromatic amine compound (a) is treated with a nitrite salt, such as sodium nitrite, in HCl and water followed by treatment with an azide salt, such as sodium azide, to form an aromatic azide (b). The aromatic azide (b) is then heated with an alkyne which is substituted with an aromatic group (c) to form the [1,2,3]triazole ring (I) (see scheme I).

Scheme I: Method of making the compounds of the invention.

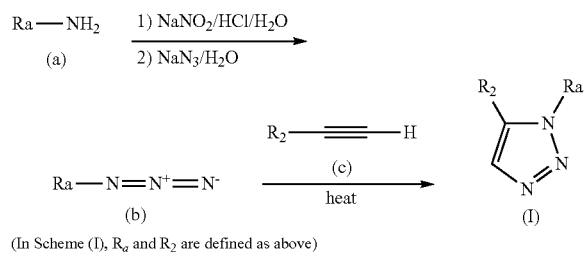

(In Scheme (I), $R_a$ and $R_2$ are defined as above)

Other methods of preparing 1,2,3-triazoles are described in Pati, Hari, N., et al., (2005). "Synthesis and biological evaluation of cis-combretastatin analogs and their novel 1,2,3-triazole derivatives." *Heterocycl. Commun.*, 11(2), 117-120, which is incorporated by reference herein in its entirety. In general, Wittig reagents are reacted with substituted benzaldehydes and then 1,2,3-triazoles are produced according to scheme II below.

Scheme II: Method of making the compounds of the invention.

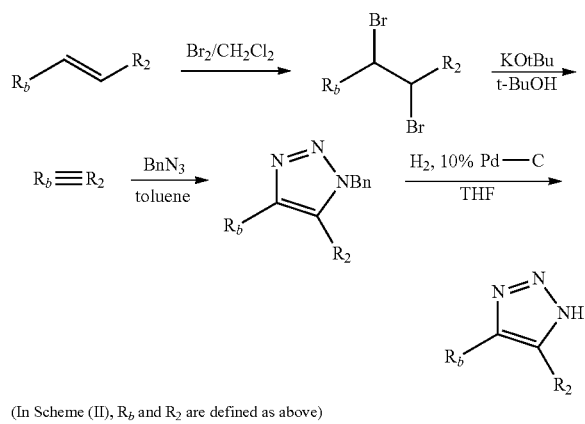

(In Scheme (II), $R_b$ and $R_2$ are defined as above)

Methods of Treatment and Prevention

In one embodiment, the invention provides a method of inhibiting tubulin polymerization in a cell, comprising contacting the cell with an effective amount of a compound of any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, and prodrug thereof, or a pharmaceutical composition comprising a compound of any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, and prodrug thereof. Inhibition of tubulin polymerization can be determined by determining the $IC_{50}$ for tubulin polymerization inhibition for a compound as described above, or by using the methods described in Examples 3, 4 and 5, herein.

In another embodiment, the invention provides a method of treating a proliferative disorder, such as cancer, in a subject in need thereof, comprising administering to the subject an effective amount of a compound of any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, and prodrug thereof, or a pharmaceutical composition comprising a compound of any one of formulas (I) through (XIX), (IA) through (XIA), (XVIIA) through (XIXA), (IB) through (XIB), (XVIIB) through (XIXB), or Table 1, or a pharmaceutically acceptable salt, solvate, clathrate, and prodrug thereof. Such patients may be treatment naïve or may experience partial or no response to conventional therapies.

Responsiveness to treatment with the compounds of the invention in the case of proliferative disorders, can be measured by reduction in the extent or severity of the symptoms associated with the disease or disorder and/or an increase in the longevity and/or quality of life of the subject compared with the absence of the treatment. Responsiveness to treatment with the compounds of the invention in the case of cancer, can be measured by a reduction in tumor mass, a reduction in the rate of tumor growth, a reduction in metastasis, a reduction in the severity of the symptoms associated with the cancer and/or an increase in the longevity of the subject compared with the absence of the treatment.

Combination Therapies

The invention also provides methods of preventing, treating, managing, or ameliorating a proliferative disorder, such as cancer, or one or more symptoms thereof, said methods comprising administering to a subject in need thereof one or more compounds of the invention and one or more other therapies (e.g., one or more prophylactic or therapeutic agents that are currently being used, have been used, are known to be useful or in development for use in the prevention, treatment or amelioration of a proliferative disorder, such as cancer, or one or more symptoms associated with said proliferative disorder).

The prophylactic or therapeutic agents of the combination therapies of the invention can be administered sequentially or concurrently. In a specific embodiment, the combination therapies of the invention comprise one or more compounds and at least one other therapy (e.g., another prophylactic or therapeutic agent) which has the same mechanism of action as said compounds (e.g., a therapeutic agent that inhibits tubulin polymerization). In another specific embodiment, the combination therapies of the invention comprise one or more compounds of the invention and at least one other therapy (e.g., another prophylactic or therapeutic agent) which has a different mechanism of action than said compounds. In certain embodiments, the combination therapies of the present invention improve the prophylactic or therapeutic effect of one or more compounds of the invention by functioning together with the compounds to have an additive or synergistic effect. In certain embodiments, the combination therapies of the present invention reduce the side effects associated with the therapies (e.g., prophylactic or therapeutic agents). In certain embodiments, the combination therapies of the present invention reduce the effective dosage of one or more of the therapies.

The prophylactic or therapeutic agents of the combination therapies can be administered to a subject, preferably a human subject, in the same pharmaceutical composition. In alternative embodiments, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more compounds of the invention is administered to a subject, preferably a human, to prevent, treat, manage, or ameliorate a proliferative disorder, such as cancer, or one or more symptom thereof. In accordance with the invention, pharmaceutical compositions of the invention may also comprise one or more other agents (e.g., prophylactic or therapeutic agents that are currently being used, have been used, or are known to be useful in the prevention, treatment or amelioration of a proliferative disorder or a symptom thereof).

The invention provides methods for preventing, managing, treating or ameliorating a proliferative disorder, such as cancer, or one or more symptoms thereof in a subject refractory (either completely or partially) to existing agent therapies for such a proliferative disorder, said methods comprising administering to said subject a dose of an effective amount of one or more compounds of the invention and a dose of an effective amount of one or more therapies (e.g., one or more prophylactic or therapeutic agents useful for the prevention, treatment, management, or amelioration of a proliferative disorder or a symptom thereof). The invention also provides methods for preventing, treating, managing, or ameliorating a proliferative disorder or a symptom thereof by administering one or more compounds of the invention in combination with any other therapy(ies) to patients who have proven refractory to other therapies but are no longer on these therapies.

The compounds of the invention and/or other therapies can be administered to a subject by any route known to one of skill in the art. Examples of routes of administration include, but are not limited to, parenteral, e.g., intravenous, intradermal, subcutaneous, oral (e.g., inhalation), intranasal, transdermal (topical), transmucosal, and rectal administration.

Agents Useful in Combination with Compounds of the Invention

Anticancer agents that can be co-administered with the compounds of the invention include Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds of the invention.

Other anti-cancer agents that can be employed in combination with the compounds of the invention include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs that can be employed in combination with the compounds of the invention include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred anticancer drugs are 5-fluorouracil and leucovorin.

Other chemotherapeutic agents that can be employed in combination with the compounds of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with the compounds of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with the compounds of the invention include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-0Y-007 (National Health Research Institutes), and SSR-250411 (Sanofi).

Pharmaceutical Compositions

The present invention provides compositions for the treatment, prophylaxis, and amelioration of proliferative disorders, such as cancer. In a specific embodiment, a composition comprises one or more compounds of the invention, or a pharmaceutically acceptable salt, solvate, clathrate, hydrate or prodrug thereof. In another embodiment, a composition of the invention comprises one or more prophylactic or therapeutic agents other than a compound of the invention, or a pharmaceutically acceptable salt, solvate, clathrate, hydrate, prodrug thereof. In another embodiment, a composition of the invention comprises one or more compounds of the invention, or a pharmaceutically acceptable salt, solvate, clathrate, hydrate or prodrug thereof, and one or more other prophylactic or therapeutic agents. In another embodiment, the composition comprises a compound of the invention, or a pharmaceutically acceptable salt, solvate, clathrate, hydrate, or prodrug thereof, and a pharmaceutically acceptable carrier, diluent or excipient.

In a preferred embodiment, a composition of the invention is a pharmaceutical composition or a single unit dosage form. Pharmaceutical compositions and dosage forms of the invention comprise one or more active ingredients in relative amounts and formulated in such a way that a given pharmaceutical composition or dosage form can be used to treat or prevent proliferative disorders, such as cancer. Preferred pharmaceutical compositions and dosage forms comprise a compound of formulas (I) through (XIX), (IA) through (XIA), (XVIIA) through (XIXA), (IB) through (XIB), (XVIIB) through (XIXB), or Table 1, or a pharmaceutically acceptable prodrug, salt, solvate, clathrate, hydrate, or prodrug thereof, optionally in combination with one or more additional active agents.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formulas (I) through (XIX), (IA) through (XIA), (XVIIA) through (XIXA), (IB) through (XIB), (XVIIB) through (XIXB), or Table 1, or a pharmaceutically acceptable salt, solvate, hydrate, clathrate, or prodrug thereof, in spheroids which further comprise microcrystalline cellulose and, optionally, hydroxypropylmethyl-cellulose coated with a mixture of ethyl cellulose and hydroxypropylmethylcellulose. Such extended release formulations can be prepared according to U.S. Pat. No. 6,274,171, the entirety of which is incorporated herein by reference.

A specific controlled-release formulation of this invention comprises from about 6% to about 40% a compound of formulas (I) through (XIX), (IA) through (XIA), (XVIIA) through (XIXA), (IB) through (XIB), (XVIIB) through (XIXB), or Table 1, or a pharmaceutically acceptable salt, solvate, hydrate, clathrate, or prodrug thereof, by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays; aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Dosage & Frequency of Administration

The amount of the compound or composition of the invention which will be effective in the prevention, treatment, management, or amelioration of a proliferative disorder, such as cancer, or one or more symptoms thereof, will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the *Physician's Desk Reference* (57th ed., 2003).

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention for the conditions described herein lie within the range of from about 0.01 mg to about 1000 mg per day, given as a single once every one to four weeks, or once-a-day dose or as divided doses throughout a day. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different proliferative disorders, as will be readily known by those of ordinary skill in the art. Similarly, amounts sufficient to prevent, manage, treat or ameliorate such proliferative disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate a proliferative disorders, such as cancer, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a proliferative disorders, such as cancer, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, 1 mg to 2.5 mg.

The dosages of prophylactic or therapeutic agents other than compounds of the invention, which have been or are currently being used to prevent, treat, manage, or proliferative disorders, such as cancer, or one or more symptoms thereof can be used in the combination therapies of the invention. Preferably, dosages lower than those which have been or are currently being used to prevent, treat, manage, or ameliorate a proliferative disorder, or one or more symptoms thereof, are used in the combination therapies of the invention. The recommended dosages of agents currently used for the prevention, treatment, management, or amelioration of a proliferative disorders, such as cancer, or one or more symptoms thereof, can obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J., which are incorporated herein by reference in its entirety.

In certain embodiments, when the compounds of the invention are administered in combination with another therapy, the therapies (e.g., prophylactic or therapeutic agents) are administered simultaneously, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies (e.g., prophylactic or therapeutic agents) are administered within the same patent visit.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophyladic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing, treating, managing, or ameliorating a proliferative disorders, such as cancer, or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

Other Embodiments

The compounds of the invention may be used as research tools (for example, to evaluate the mechanism of action of new drug agents, to isolate new drug discovery targets using affinity chromatography, as antigens in an ELISA or ELISA-like assay, or as standards in in vitro or in vivo assays). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Experimental Rationale

Without wishing to be bound by theory, it is believed that the compounds of this invention inhibit tubulin polymerization and, therefore, can be used to inhibit undesirable cellular proliferation in disorders such as cancer. The examples that follow demonstrate these properties.

Materials and General Methods

Reagents and solvents used below can be obtained from commercial sources such as Aldrich Chemical Co. (Milwaukee, Wis., USA). $^1$H-NMR and $^{13}$C-NMR spectra were recorded on a Varian 300 MHz NMR spectrometer. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

Example 1

Synthesis of Representative Exemplary Compounds of this Invention

Compound 3: 1-(3,4,5-trimethoxy-phenyl)-5-(4-methoxy-phenyl)-1H-[1,2,3]triazole

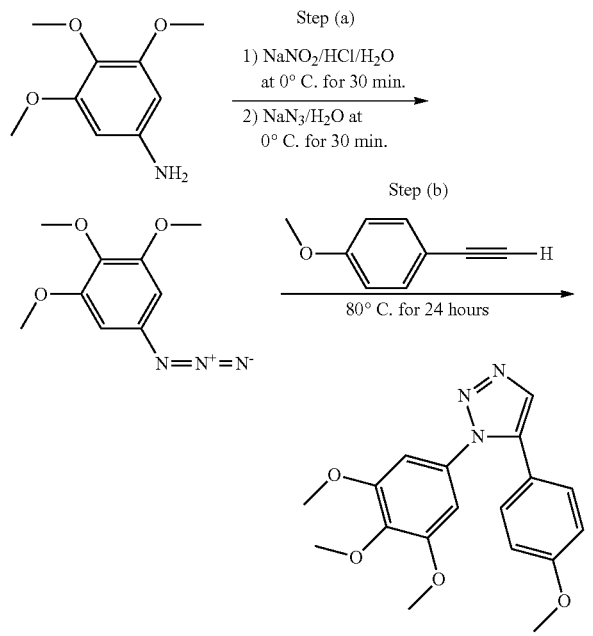

Step (a): Synthesis of 3,4,5-Trimethoxyphenyl azide 3,4,5-Trimethoxyaniline (1.83 g; 10 mmol) is added to a 100 mL flask containing water (20 mL) and HCl (conc. aqueous solution, 5 mL). The solution is chilled to 0° C. and a solution of sodium nitrite (830 mg; 12 mmol) in water (5 mL) is added. The solution is stirred at 0° C. for 30 minutes, and then a solution of sodium azide (1.3 g; 20 mmol) in water (5 mL) is added. After another 30 minutes of stirring, dichloromethane is added (20 mL) and the organic phase was collected and filtered through a plug of silica, dried over magnesium sulfate and the solvent was evaporated to give approximately two grams of 3,4,5-trimethoxyphenyl azide.

$^1$H-NMR (CDCl$_3$) δ (ppm) 6.21 (s, 2H); 3.82 (s, 6H); 3.80 (s, 3H)

Step (b): Synthesis of 1-(3,4,5-trimethoxy-phenyl)-5-(4-methoxy-phenyl)-1H-[1,2,3]triazole To a scintillation vial was added 4-ethynyl anisole (660 mg.; 5 mmol) and 3,4,5-trimethoxyphenyl azide (1.05 g.; 5 mmol) and the mixture was heated at 80° C. for 24 hours. The crude mixture was purified by column chromatography to give 1-(3,4,5-trimethoxy-phenyl)-5-(4-methoxy-phenyl)-1H-[1,2,3]triazole.

$^1$H-NMR (CDCl$_3$) δ (ppm) 7.80 (s, 1H); 7.19 (d, 2H); 6.88 (d, 2H); 6.58 (s, 2H); 3.88 (s, 3H); 3.81 (s, 3H); 3.72 (s, 6H)

Expected MH+ mass ion=342, observed 342.1

Compound 5: 1-(3,4,5-trimethoxy-phenyl)-5-[4-(N,N-dimethylamino)-phenyl]-1H-[1,2,3]triazole

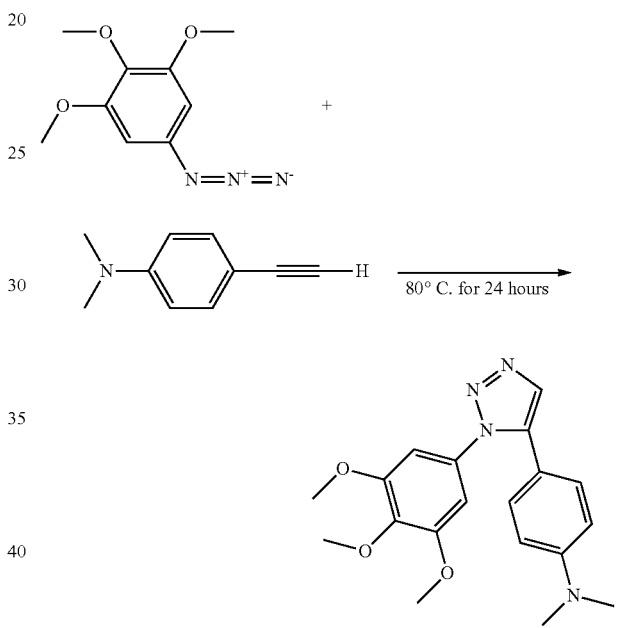

To a scintillation vial was added (4-ethynyl phenyl)-dimethyl amine (660 5 mmol) and 3,4,5-trimethoxyphenyl azide (1.05 g.; 5 mmol) and the mixture was heated at 80° C. for 24 hours. The crude mixture was purified by column chromatography to give 1-(3,4,5-trimethoxy-phenyl)-5-[4-(N,N-dimethylamino)-phenyl]-1H-[1,2,3]triazole.

$^1$H-NMR (CDCl$_3$) δ (ppm) 7.78 (s, 1H); 7.11 (d; 2H); 6.64 (d, 2H); 6.62 (s, 2H); 3.87 (s, 3H); 3.75 (s, 6H); 2.99 (s, 6H).

Compound 216: PEG-2-methoxy-5-(1-(3,4,5-trimethoxyphenyl)-1H-1,2,3-triazol-5-yl)phenylcarbamate

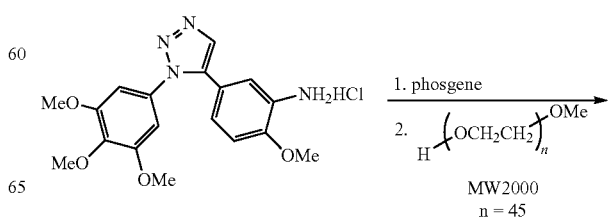

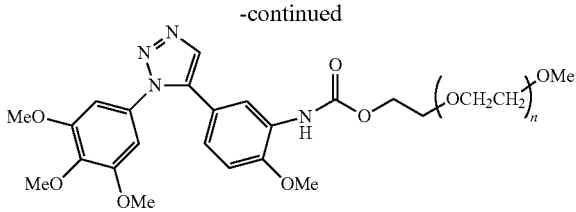

A solution of 1-(3,4,5-trimethoxy-phenyl)-5-(3-amino-4-methoxy-phenyl)-1H-[1,2,3]triazole hydrochloride (300 mg) and triethylamine (0.22 mL, 1.60 mmol) in dichloromethane (3 mL) is added slowly to a solution of triphosgene (77 mg, 0.26 mmol) in dichloromethane (5 mL) at 0° C. under nitrogen atmosphere. The reaction mixture is stirred for 30 min at room temperature, and then cooled to 0° C. before the addition of PEG (1.53 g, 0.76 mmol) and triethylamine (0.12 mL, 0.77 mmol) in 2 ml of dichloromethane. The resulting reaction mixture is stirred for 3 h. and washed with NaHCO$_3$ solution. The aqueous layer is extracted with dichloromethane (2×), and the combined organic layers are washed with saturated NaCl solution, dried over Na$_2$SO$_4$ and evaporated. The crude product is purified by silica gel column chromatography (20% MeOH in EA) to give desired product PEG-2-methoxy-5-(1-(3,4,5-trimethoxyphenyl)-1H-1,2,3-triazol-5-yl)phenylcarbamate.

Synthesis of Amino-acid Derivatives tert-butyl 2-(2-methoxy-5-(1-(3,4,5-trimethoxyphenyl)-1H-1,2,3-triazol-5-yl)phenylamino)-2-oxoethylcarbamate (2)

To a solution of N-t-Boc-glycine (357 mg, 2 mmol) and N-methyl-imidazole (0.162 mL, 2 mmol) in THF (16 mL) cooled with ice methanesulfonyl chloride (0.158 mL, 2 mmol) is added. Ice bath is removed, compound 1 (0.4 g) is added as a solid, followed by thriethylamine (0.144 mL, 2.02 mmol), and the reaction mixture is stirred at 40-50° C. overnight. A resulted solution is decanted from a solid, a flask rinsed with EtOAc, and a combined organic solution is washed with saturated ammonium chloride solution, then twice with water, brine and dried over anhydrous sodium sulfate. The solution is filtered out through a celite pad, concentrated and the residue is dissolved in 2-propanol (3 mL) with heating, and hexane (1-2 mL) is added drop-wise to start precipitation. In 1 hour a solid is filtered out, washed with 1:1 Hexane:ether mixture (10 ml X$_2$) and vacuum-dried to give compound 2.

2-amino-N-(2-methoxy-5-(1-(3,4,5-trimethoxyphenyl)-1H-1,2,3-triazol-5-yl)phenyl)acetamide hydrochloride (3)

To a solution of 2 in THF (6 mL) a 1M solution of HCl in ethanol (17 mL) is added, and a resulted solution is stirred overnight at room temperature to form a suspension with

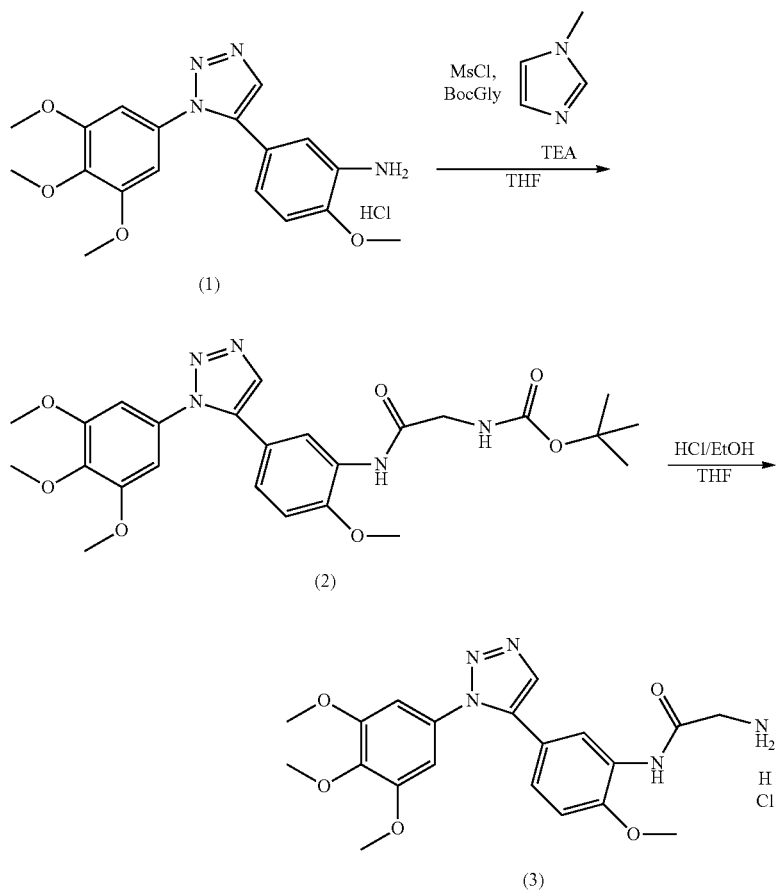

product partly precipitated out. The reaction mixture is concentrated under reduced pressure keeping temperature below 45° C. to ~10 mL volume. A solid is filtered out, washed with ether (5 ml×2), hexane (5 mL) and vacuum-dried to give compound 3.

Example 2

Cytotoxicity of Compounds of the Invention

The in vitro cytotoxicity of the compounds of the invention was determined in the following human cell lines: HL-60, HL-60-TX1000 (MDR), MES-SA and MES-SA/DX5 (uterine sarcoma). MES-SA is a model of uterine sarcoma, and the cells are sensitive to a number of chemotherapeutic agents including doxorubicin, dactinomycin, mitomycin C, taxol and bleomycin. The MES-SA/Dx5 cell line was established in the presence of increasing concentrations of doxorubicin. The cells express high levels of mdr-1 mRNA and p-glycoprotein and exhibit cross resistance to more than fifteen chemotherapeutic agents including taxol, etoposide, mitomycin C, colchicine, vinblastine, dactinomycin, 5-fluorouracil, methotrexate and so on. All cells except HL-60-TX1000 were purchased from ATCC. HL-60, a model of myeloid leukemia, was from ATCC and HL60/TX1000 was a gift from Dr. Bhalla of Emory University School of Medicine. HL-60/TX1000 was isolated in vitro by subculturing HL-60 in progressively higher concentration of Taxol. HL-60/TX1000 cells over-express mdr-1 mRNA and p-glycoprotein, as determined by western blot and immunofluorescence labeling with antiPGP antibodies The cell lines were maintained in RPMI1640 (GIBCO) supplemented with 10% FCS, 100 units/mL penicillin, 100 ug/ml streptomycin, and 2 mM L-glutamine. Cells were split every third day and diluted to a concentration of $2 \times 10^5$ cells/mL one day before the experiment was performed. All experiments were performed on exponentially growing cell cultures. Cell densities were $2.5 \times 10^4$ cells/mL in all experiments.

Test compounds were prepared by dissolving the compounds at a concentration of 10 mM in 100% DMSO. Final concentrations 10, 1, 0.1, 0.01 and 0.001 µM were obtained by diluting the stock solution directly into the tissue culture medium. Cells were incubated with varying concentrations of test compounds for 72 hours and the $IC_{50}$ was determined by MTS (i.e. 3-(4,5-dimethylthiazol-2-yl)-2,5-diphenyl tetrazolium bromide) assay. $IC_{50}$ in this context stands for the concentration of a compound required to inhibit 50% tumor cell growth. $IC_{50}$s of compounds 3 and 5 and Taxol are listed in Table 2 for each cell line. Surprisingly, Compounds 3 and 5 exhibited lower $IC_{50}$s for multidrug resistant cell lines HL-60-MDR and MES-SA/DX5 than for non-multidrug resistant cell lines HL-60 and MES-SA. In contrast, Taxol exhibited an $IC_{50}$ of 2 nM against HL-60 cells and 5 nM against and MES-SA cells but has an $IC_{50}$ of 1,000 nM against multi-drug resistant cell line HL-60-TX1000 and 5,000 nM against multi-drug resistant cell line MES-SA/DX5.

TABLE 2

In vitro cytotoxicity of compounds of the invention.

| Cell Line | Compound 3 | Compound 5 | Taxol |
|---|---|---|---|
| HL-60 | 53 nM | 41.5 nM | 2 nM |
| HL-60-TX1000 | 20 nM | 7.5 nM | 1000 nM |
| MES-SA | 52 nM | 68.5 nM | 5 nM |
| MES-SA/DX5 | 37 nM | 29 nM | 5,000 nM |

Example 3

Cell Cycle Analysis

MDA-435 cells are cultured in 6-well plates at $1 \times 10^6$ cells/well and are untreated (negative control), treated with Taxol (positive control), or treated with a compound of the invention at 37° C. for 20 h. The cells are detached with 1× trypsin and washed one time with PBS. Cycle TEST PLUS kit (BD PharMingen, Cat #340242) is used to stain the cells. Cell cycle is analyzed with FACScomp program (BS PharMingen).

Example 4

Inhibition of Tubulin Polymerization by Compounds of the Invention

Material and Methods: Wild-type Chinese Hamster Ovary cells (WT CHO) cells are maintained in Ham's F-12 medium supplemented with 10% fetal bovine serum (FBS; HyClone, Logan, Utah). Cells of low density (~20%) growing on 2-well chambered cover-slips (Labtek (Campbell, Calif.) or Fisher Scientific) are transfected with a mammalian expression vector encoding α-tubulin-YFP (Clontech, Palo Alto, Calif.) with the use of FuGENE 6 (Roche Molecular Biochemicals, Indianapolis, Ind.), according to the manufacturer's instructions. Twenty-four hours after transfection, the cells are cultured in 400 µg/ml G418 (Invitrogen, Carlsbad, Calif.)-containing selection medium for 2 weeks. Living cells are examined using a fluorescent microscope for α-tubulin-YFP expression. Cells in single colonies containing microtubules labeled with α-tubulin-YFP are lifted and expanded in G418-containing medium. Expression of α-tubulin-YFP is confirmed by the presence of the tubulin-YFP labeled microtubule pattern identical to immunostained microtubule pattern of non-transfected cells, as well as by subjecting the cells to Western blot analysis using an anti-GFP antibody (Roche Molecular Biochemicals, Basel, Switzerland) and confirming the correct mass of the α-tubulin-YFP chimeric protein. Expressed tubulin-YFP is detected as a single band in Western blots. The tubulin-YFP expressing cell lines (referred as CHO-α-tubulin-YFP cells) are used in the studies described below. Similar methods are used to generate MCF-7 cell lines stably expressing α-tubulin-YFP (referred as MCF7-α-tubulin-YFP cells).

CHO-α-tubulin-YFP or MCF7-α-tubulin-YFP cells are cultured in 2-well chambered cover-slips (Labtek (Campbell, Calif.) or Fisher Scientific) for 24 hours before treatment with a compound of the invention. For comparison of the effects of treatment on α-tubulin-YFP labeled microtubules with the compounds of the invention, CHO-α-tubulin-YFP or MCF7-α-tubulin-YFP cells are treated with the a compound of the invention, Taxol or equivalent concentrations of DMSO-containing media for various time periods before imaging. Tubulin-YFP fluorescence in living cells or fixed cells is captured using a standard filter for FITC and objectives of 20× or 60× magnification on a Nikon TE300 microscope with a Leica DC50 color digital camera (Leica, Bannockburn, Ill.) or a CoolSnap HQ monochrome CCD camera (Photonetrics, Tucson, Ariz.). The Leica DC50 and CoolSnapHQ cameras are controlled with Leica DC50 software and MetaVue/MetaMorph software, respectively (Universal Imaging Corp, Downingtown, Pa.). Inspection of the cells shows a typical microtubule network in cells treated with DMSO alone, whereas microtubule bundle formation can be seen with Taxol, and a disperse pattern of cytoplasmic tubulin-YFP is expected with compounds of the invention indicating microtubulin depolymerization.

Example 5

Microtubule Disruption in Cells Resistant to the Depolymerization Effects of Colchicine and Vincristine The effects of compounds of the invention on microtubules can be studied in CV-1 cells. The microtubules of CV-1 cells are known to be resistant to the depolymerizing effects of colchicine and vincristine. CV-1 cells are treated with 500 nM of a compound of the invention, or vincristine or colchicines. At 24, 48 and 72 hr the cells are fixed and stained to examine microtubule structure. In cells treated with compounds of the invention, microtubule structures are expected to be diminished compared to untreated cells. Disorganized but clear microtubule structures are typically found in cells treated with either vincristine or colchicines.

Example 6

Anti-Tumor Activity Against Human Tumor Cells Line in Nude Mouse Xenograft Models The human tumor cell line, MDA-MB-435S (ATCC #HTB-129; G. Ellison, et al., *Mol. Pathol.* 55:294-299, 2002), is obtained from the American Type Culture Collection (ATCC; Manassas, Va., USA). The human tumor cell line, RERF-LC-Al (RCB0444; S. Kyoizumi, et al., *Cancer. Res.* 45:3274-3281, 1985), is obtained from the Riken Cell Bank (RCB; Tsukuba, Ibaraki, Japan). The cell lines are cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100×MEM non-essential amino acids. FBS is obtained from ATCC and all other reagents are obtained from Invitrogen Corp. (Carlsbad, Calif., USA). Approximately 4-5×10(6) cells that had been cryopreserved in liquid nitrogen are rapidly thawed at 37° C. and transferred to a 175 cm$^2$ tissue culture flask containing 50 ml of growth media and then incubated at 37° C. in a 5% CO$_2$ incubator. The growth media is replaced every 2-3 days until the flask is 90% confluent, typically in 5-7 days. To passage and expand the cell line, a 90% confluent flask is washed with 10 mL of room temperature phosphate buffered saline (PBS) and the cells are disassociated by adding 5 mL 1× Trypsin-EDTA (Invitrogen) and incubating at 37° C. until the cells detached from the surface of the flask. To inactivate the trypsin, 5 mL of growth media is added and then the contents of the flask are centrifuged to pellet the cells. The supernatant is aspirated and the cell pellet is resuspended in 10 mL of growth media and the cell number is determined using a hemocytometer. Approximately 1-3× 10(6) cells per flask are seeded into 175 cm$^2$ flasks containing 50 mL of growth media and incubated at 37° C. in a 5% CO$_2$ incubator. When the flasks reached 90% confluence, the above passaging process is repeated until sufficient cells are obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 7 and 19 weeks of age at implantation. To implant MDA-MB-435S tumor cells into nude mice, the cells are trypsinized as above, washed in PBS and resuspended at a concentration of 50×10 (6) cells/mL in PBS. Using a 27 gauge needle and 1 cc syringe, 0.1 mL of the cell suspension is injected into the corpus adiposum of nude mice. The corpus adiposum is a fat body located in the ventral abdominal vicera in the right quadrant of the abdomen at the juncture of the os coxae (pelvic bone) and the os femoris (femur). To implant RERF-LC-Al tumor cells into nude mice, the cells are trypsinized as above, washed in PBS and resuspended at a concentration of 50×10(6) cells/mL in 50% non-supplemented RPMI Media 1640 and 50% Matrigel Basement Membrane Matrix (#354234; BD Biosciences; Bedford, Mass., USA). Using a 27 gauge needle and 1 cc syringe, 0.1 mL of the cell suspension is injected subcutaneously into the flank of nude mice.

Tumors are then permitted to develop in vivo until they reached approximately 100-200 mm$^3$ in volume, which typically required 2-3 weeks following implantation. Tumor volumes (V) are calculated by caliper measurement of the width (W), length (L) and thickness (T) of tumors using the following formula: V=0.5326×(L×W×T). Animals were randomized into treatment groups so that the average tumor volumes of each group were similar at the start of dosing.

Stock solutions of test articles are prepared by dissolving the appropriate amounts of each compound in dimethyl sulfoxide (DMSO) by sonication in an ultrasonic water bath. Stock solutions are prepared at the start of the study, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare formulations for daily dosing, DMSO stock solutions are diluted 1:10 with 20% Cremophore RH40. The final formulation for dosing contained 10% DMSO, 18% Cremophore RH40, 3.6% dextrose, 68.4% water and the appropriate amount of test article (e.g., a compound of the invention or a control compounds such as paclitaxel). Animals are intravenously (i.v.) injected with this solution at 10 ml per kg body weight on a schedule of 3 days per week (Monday, Wednesday, Friday, with no dosing on Saturday and Sunday) for a total of 9-10 doses.

Treatment with compounds of the invention at, for example, 6.25, 12.5 and 25 mg/kg body weigh are expected to decreased the growth rate and/or cause tumor regression of MDA-MB-435S melanoma cells or of RERF-LC-Al lung tumor cells in nude mice. Treatment with 7.5 mg/kg of paclitaxel typically results in decreased tumor growth compared to animals treated with vehicle alone. Overt toxicity of Compound 3, as shown by the minimal effect on body weights, should be minimal with the compounds of the invention.

Example 7

Necrosis in a Nude Mouse Tumor Model

Mouse mammary carcinoma cell line, EMT6 (ATCC #CRL-2755), are obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100×MEM non-essential amino acids. FBS is obtained from ATCC and all other reagents are obtained from Invitrogen Corp. (Carlsbad, Calif., USA). Approximately 4-5×10(6) cells that have been cryopreserved in liquid nitrogen are rapidly thawed at 37° C. and transferred to a 175 cm² tissue culture flask containing 50 ml of growth media and then incubated at 37° C. in a 5% $CO_2$ incubator. The growth media is replaced every 2-3 days until the flask became 90% confluent, typically in 5-7 days. To passage and expand the cell line, a 90% confluent flask is washed with 10 ml of room temperature phosphate buffered saline (PBS) and the cells are disassociated by adding 5 ml 1× Trypsin-EDTA (Invitrogen) and incubating at 37° C. until the cells detached from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1-3×10(6) cells per flask are seeded into 175 cm² flasks containing 50 ml of growth media and incubated at 37° C. in a 5% $CO_2$ incubator. When the flasks reach 90% confluence, the above passaging process is repeated until sufficient cells are obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of 10×10(6) cells/ml in PBS. Using a 27 gauge needle and 1 cc syringe, 0.1 ml of the cell suspension is injected subcutaneously into the flank of each nude mouse.

Tumors are then permitted to develop in vivo until the majority reached 75-125 mm³ in tumor volume, which typically required 1 week following implantation. Animals with oblong, very small or large tumors are discarded, and only animals carrying tumors that display consistent growth rates are selected for studies. Tumor volumes (V) are calculated by caliper measurement of the width (W), length (L) and thickness (T) of tumors using the following formula: V=0.5236× (L×W×T). Animals are randomized into treatment groups so that each group has median tumor volumes of ~100 mm³ at the start of dosing.

To formulate compounds of the invention in DRD, a stock solution of the test article is prepared by dissolving an appropriate amount of the compound in dimethyl sulfoxide (DMSO) by sonication in an ultrasonic water bath. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare a DRD formulation for dosing, the DMSO stock solution is diluted 1:10 with 20% Cremophore RH40. The final DRD formulation for dosing contains 10% DMSO, 18% Cremophore RH40, 3.6% dextrose, 68.4% water and the appropriate amount of test article.

Tumor-bearing animals are given a single intravenous (i.v.) bolus injections of either DRD vehicle or a compound of the invention formulated in DRD, both at 10 mL per kg body weight. Then, 4-24 hr after drug treatment, tumors are excised, cut in half and fixed overnight in 10% neutral-buffered formalin. Each tumor is embedded in paraffin with the cut surfaces placed downwards in the block, and rough cut until a complete section is obtained. From each tumor, 5 µM serial sections are prepared and stained with hematoxylin and eosin. Slides are evaluated manually using light microscopy with a 10×10 square gridded reticle. The percentage of necrosis in a tumor is quantified at 200× magnification by scoring the total number of grid squares containing necrosis and the total number of grid squares containing viable tumor cells.

It is expected that compounds of the invention will rapidly increase cell necrosis after injection (e.g. single bolus injection of 25 mg/kg body weight) relative to baseline necrosis observed in vehicle treated tumors, as would be expected for a vascular targeting mechanism of action. Such rapid onset of necrosis is consistent with there being a loss of blood flow to tumors resulting in hypoxia and tumor cell death.

Example 8

Vascular Disrupting Activities in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100×MEM non-essential amino acids. FBS is obtained from ATCC and all other reagents are obtained from Invitrogen Corp. (Carlsbad, Calif., USA). Approximately 4-5×10⁶ cells that have been cryopreserved in liquid nitrogen are rapidly thawed at 37° C. and transferred to a 175 cm² tissue culture flask containing 50 mL of growth media and then incubated at 37° C. in a 5% $CO_2$ incubator. The growth media is replaced every 2-3 days until the flask becomes 90% confluent, typically in 5-7 days. To passage and expand the cell line, a 90% confluent flask is washed with 10 mL of room temperature phosphate buffered saline (PBS) and the cells are disassociated by adding 5 mL 1× Trypsin-EDTA (Invitrogen) and incubating at 37° C. until the cells detach from the surface of the flask. To inactivate the trypsin, 5 mL of growth media is added and then the contents of the flask are centrifuged to pellet the cells. The supernatant is aspirated and the cell pellet is resuspended in 10 mL of growth media and the cell number determined using a hemocytometer. Approximately 1-3×10⁶ cells per flask are seeded into 175 cm² flasks containing 50 mL of growth media and incubated at 37° C. in a 5% $CO_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of 10×10⁶ cells/mL in PBS. Using a 27 gauge needle and 1 cc syringe, 0.1 mL of the cell suspension is injected subcutaneously into the flank of each nude mouse.

For the Evans Blue dye assay, tumors are permitted to develop in vivo until the majority reach 40-90 mm³ in tumor volume (to minimize the extent of tumor necrosis), which typically requires 4-6 days following implantation. Animals with visibly necrotic, oblong, very small or very large tumors are discarded and only animals carrying tumors that display consistent growth rates are selected for use. Tumor volumes (V) are calculated by caliper measurement of the width (W), length (L) and thickness (T) of tumors using the following formula: V=0.5236×(L×W×T). Animals are randomized into treatment groups so that at the start of dosing each group has median tumor volumes of ~125 mm³ or ~55 mm³ for Evans Blue dye assays.

To formulate compounds of the invention for dosing, the appropriate amount of compound is dissolved in 5% dextrose in water (D5W; Abbott Laboratories, North Chicago, Ill., USA). Vehicle-treated animals are dosed with D5W.

To conduct the Evans Blue dye assay, tumor-bearing animals are dosed with vehicle or test article at 0 hr, and then i.v. injected with 100 µL of a 1% (w/v) Evan's Blue dye (Sigma #E-2129; St. Louis, Mo., USA) solution in 0.9% NaCl at +1 hr. Tumors are excised at +4 hr, weighed and the tissue disassociated by incubation in 50 µL 1 N KOH at 60° C. for 16 hr. To extract the dye, 125 µL of a 0.6 N phosphoric acid and 325 µL acetone is added, and the samples vigorously vortexed and then microcentrifuged at 3000 RPM for 15 min to pellet cell debris. The optical absorbance of 200 µL of supernatant is then measured at 620 nM in a Triad spectrophotometer (Dynex Technologies, Chantilly, Va., USA). Background $OD_{620}$ values from similarly sized groups of vehicle or test article-treated animals that have not been injected with dye are subtracted as background. $OD_{620}$ values are then normalized for tumor weight and dye uptake is calculated relative to vehicle-treated tumors.

To examine the vascular disrupting activity of compounds of the invention, the Evans Blue dye assay is employed as a measurement of tumor blood volume (Graff et al., Eur J Cancer 36:1433-1440, 2000). Evans Blue dye makes a complex with serum albumin by electrostatic interaction between the sulphonic acid group of the dye and the terminal cationic nitrogens of the lysine residues in albumin. The dye leaves the circulation very slowly, principally by diffusion into extravascular tissues while still bound to albumin. Albumin-dye complex taken up by tumors is located in the extracellular space of non-necrotic tissue, and intracellular uptake and uptake in necrotic regions is negligible. The amount of dye present in a tumor is a measurement of the tumor blood volume and microvessel permeability. Compounds of the invention are expected to substantially decrease tumor dye uptake relative to vehicle-treated animals. Such a decrease in dye penetration into the tumor is consistent with there being a loss of blood flow to tumors due to blockage of tumor vasculature, consistent with a vascular disrupting mechanism of action.

All publications, patent applications, patents, and other documents cited herein are incorporated by reference in their entirety. In case of conflict, the present specification, including definitions, will control. In addition, the materials, methods, and examples are illustrative only and not intended to be limiting in any way.

We claim:

1. A compound represented by structural formula (V):

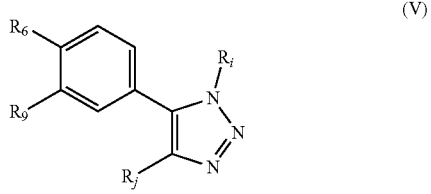

(V)

or a pharmaceutically acceptable salt thereof, wherein:

one of $R_i$ or $R_j$ is —H and the other is

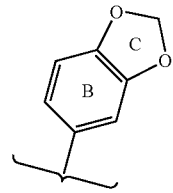

$R_6$ is a halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$;

$R_7$ and $R_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_9$ is —H, halo, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, cyano, nitro, guanadino, a haloalkyl, a haloalkoxy, a heteroalkyl, —OR$_7$, —NR$_{10}$R$_{11}$, —C(O)R$_7$, —C(O)OR$_7$, —OC(O)R$_7$, —C(O)NR$_{10}$R$_{11}$, —NR$_8$C(O)R$_7$, —OP(O)(OR$_7$)$_2$, —SP(O)(OR$_7$)$_2$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$; or $R_6$ and $R_9$ together form —OCH$_2$O— or —OCH$_2$CH$_2$O—;

$R_{10}$ and $R_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl; and Ring B is optionally substituted with one to three substituents; and Ring C is optionally substituted with one or two substituents.

p is 1 or 2.

2. The compound of claim 1, wherein the compound is represented by formula (IVA):

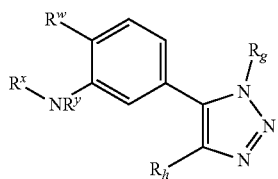

(IVA)

or a pharmaceutically acceptable salt thereof, wherein:
one of $R_g$ or $R_h$ is —H and the other is

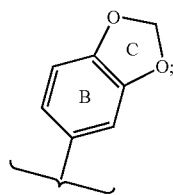

$R^x$ is $(R^{aa})_m$, —$R^{aa}$—C(O)(CH$_2$)$_n$C(O)OH, —C(O)(CH$_2$)$_n$C(O)OH, —C(O)YR$^z$, —C(O)NH—$R^{aa}$, or —$(R^{aa})_q$C(O)(Y$_1$);
$R^y$ is —H or lower alkyl;
$R^w$ is —H, an alkyl, an alkenyl, an alkynyl, cyano, a haloalkyl, an alkoxy, a haloalkoxy, a halo, an amino, an alkylamino, a dialkylamino, —OP(O)(OR$_7$)$_2$, —SP(O)(OR$_7$)$_2$, nitro, an alkyl ester, or hydroxyl;
$R^{aa}$ is an amino acid residue or an amino acid residue analog;
Y is CH$_2$, O, or NH;
$R^z$ is Alk-NH$_2$, Alk-C(O)OH, Het, or Y$_1$;
Alk is an optionally substituted alkylene;
Het is an optionally substituted heteroalkyl;
Y$_1$ is a water soluble polymer with a molecular weight less than 60,000 daltons;
n is 1, 2, 3, or 4;
m is an integer from 1 to 10;
q is 0 or 1;
Ring B is optionally substituted with one to three substituents; and
Ring C is optionally substituted with one or two substituents.

3. The compound of claim 2, wherein the compound is represented by structural formula (VA):

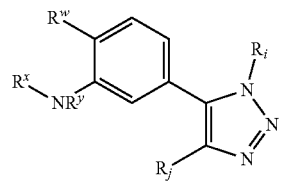

(VA)

or a pharmaceutically acceptable salt thereof, wherein:
one of $R_i$ or $R_j$ is —H and the other is

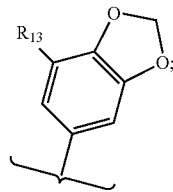

$R_{13}$ is —H, an alkyl, an alkoxy, a halo, nitro, cyano, —OH, —NH$_2$, an alkyl amino, or a dialkyl amino.

4. The compound of claim 1, wherein the compound is represented by formula (IVB):

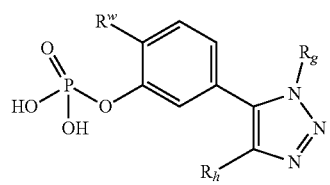

(IVB)

or a pharmaceutically acceptable salt thereof, wherein:
one of $R_g$ or $R_h$ is —H and the other is

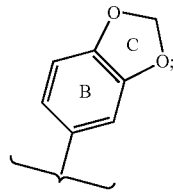

$R^w$ is —H, an alkyl, an alkenyl, an alkynyl, cyano, a haloalkyl, an alkoxy, a haloalkoxy, a halo, an amino, an alkylamino, a dialkylamino, —OP(O)(OR$_7$)$_2$, —SP(O)(OR$_7$)$_2$, nitro, an alkyl ester, or hydroxyl;
$R_7$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;
Ring B is optionally substituted with one to three substituents; and
Ring C is optionally substituted with one or two substituents.

* * * * *